(12) United States Patent
Galley et al.

(10) Patent No.: US 8,802,673 B2
(45) Date of Patent: Aug. 12, 2014

(54) HETEROCYCLIC AMINE DERIVATIVES

(75) Inventors: Guido Galley, Rheinfelden (DE); Roger David Norcross, Olsberg (CH); Philippe Pflieger, Schwoben (FR)

(73) Assignee: Hoffmann-La Roche Inc, Nutley, NJ (US)

( * ) Notice: Subject to any disclaimer, the term of this patent is extended or adjusted under 35 U.S.C. 154(b) by 111 days.

(21) Appl. No.: 13/424,406

(22) Filed: Mar. 20, 2012

(65) Prior Publication Data

US 2012/0245172 A1     Sep. 27, 2012

(30) Foreign Application Priority Data

Mar. 24, 2011   (EP) .................................... 11159566

(51) Int. Cl.
| | | |
|---|---|---|
| *C07D 413/12* | (2006.01) | |
| *C07D 265/30* | (2006.01) | |
| *C07D 403/12* | (2006.01) | |
| *C07D 417/12* | (2006.01) | |
| *C07D 401/12* | (2006.01) | |
| *C07D 211/26* | (2006.01) | |
| *C07D 413/14* | (2006.01) | |
| *C07D 207/09* | (2006.01) | |

(52) U.S. Cl.
CPC ............ *C07D 401/12* (2013.01); *C07D 413/12* (2013.01); *C07D 403/12* (2013.01); *C07D 417/12* (2013.01); *C07D 211/26* (2013.01); *C07D 265/30* (2013.01); *C07D 413/14* (2013.01); *C07D 207/09* (2013.01)
USPC ..................... 514/235.8; 514/237.8; 544/120; 544/122; 544/123; 544/124; 544/162

(58) Field of Classification Search
CPC ........................... C07D 413/12; C07D 265/30
USPC ........................ 544/120, 122, 123, 124, 162; 514/235.8, 237.8
See application file for complete search history.

(56) References Cited

U.S. PATENT DOCUMENTS

2009/0124618 A1 *   5/2009   Watanabe et al. .......... 514/235.5

FOREIGN PATENT DOCUMENTS

| WO | 2006/028290 | 3/2006 |
|---|---|---|
| WO | 2009/016088 | 5/2009 |
| WO | 2011/023795 | 3/2011 |
| WO | 2012/016879 | 9/2012 |
| WO | 2012/004375 | 12/2012 |

OTHER PUBLICATIONS

Revel, F.G. et al., PNAS 108(20):8485-8490 ( 2011).
Guari et al., Tetrahedron Letters 40:3789-3790 ( 1999).
(International Search Report for PCT/EP2012/054939 May 7, 2012).
Psychopharmacology Series, vol. 1 Earl Usdin and Merton Sandler, vol. 1 ( 1976).
Premont et al., Proc. Natl. Acad. Sci. USA 98:9474-9475 ( 2001).
Branchek et al., Curr. Opin. Pharmacol. 3:90-97 ( 2003).
McCormack et al., J. Neurosci. 6:94-101 ( 1986).
Deutch et al., Neurotransmitters in Fundamental Neuroscience:193-234 ( 1999).
Lindemann et al., Trends in Pharmacol. Sci. 26:274-281 ( 2005).
Lindemann et al., Genomics 85:372-385 ( 2005).
Parker et al., J. Pharmacol. Exp. Ther. 245:199-210 ( 1988).
Wong et al., Nat. Rev. Neurosci.:343-351 ( 2001).
Castellanos et al., Nat. Rev. Neurosci. 3:617-628 ( 2002).
Carlsson et al., Annu. Rev. Pharmacol. Toxicol. 41:237-260 ( 2001).
Mousseau et al., Prog. Brain Res. 106:285-291 ( 1995).
Dyck, L.E., Life Sci. 44:1149-1156 ( 1989).
Tuite et al., Expert Opin. Investig. Drugs 12:1335-1352 ( 2003).

* cited by examiner

Primary Examiner — Rebecca Anderson

(57) ABSTRACT

The present invention relates to compounds of formula I

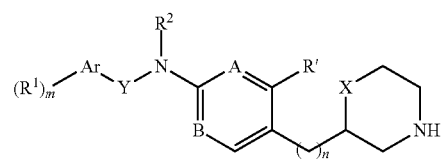

wherein A, B, X, Y, Ar, $R^1$, $R^2$, R', m and n are as defined herein and to pharmaceutical active acid addition salts thereof, which have a good affinity to the trace amine associated receptors TAAR1, so that they can be used for the treatment of depression, anxiety disorders and bipolar disorder.

30 Claims, No Drawings

HETEROCYCLIC AMINE DERIVATIVES

PRIORITY TO RELATED APPLICATION(S)

This application claims the benefit of European Patent Application No. 11159566.6, filed Mar. 24, 2011, which is hereby incorporated by reference in its entirety.

BACKGROUND OF THE INVENTION

Some of the physiological effects (i.e. cardiovascular effects, hypotension, induction of sedation) which have been reported for compounds which may bind to adrenergic receptors (WO02/076950, WO97/12874 or EP 0717 037) may be considered to be undesirable side effects in the case of medicaments aimed at treating diseases of the central nervous system as described above. Therefore it is desirable to obtain medicaments having selectivity for the TAAR1 receptor vs adrenergic receptors.

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlaps with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "crossreacting" with their receptor systems [9,12,13]. This view changed significantly with the identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1-4) highly conserved between human and rodents. TAs activate TAAR1 via Gαs. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

Therefore, there is a broad interest to increase the knowledge about trace amine associated receptors.

REFERENCES USED

1 Deutch, A. Y. and Roth, R. H. (1999) Neurotransmitters. In *Fundamental Neuroscience* (2$^{nd}$ edn) (Zigmond, M. J., Bloom, F. E., Landis, S. C., Roberts, J. L, and Squire, L. R., eds.), pp. 193-234, Academic Press;

2 Wong, M. L. and Licinio, J. (2001) Research and treatment approaches to depression. *Nat. Rev. Neurosci.* 2, 343-351;

3 Carlsson, A. et al. (2001) Interactions between monoamines, glutamate, and GABA in schizophrenia: new evidence. *Annu. Rev. Pharmacol. Toxicol.* 41, 237-260;

4 Tuite, P. and Riss, J. (2003) Recent developments in the pharmacological treatment of Parkinson's disease. *Expert Opin. Investig. Drugs* 12, 1335-1352, 5 Castellanos, F. X. and Tannock, R. (2002) Neuroscience of attention-deficit/hyperactivity disorder: the search for endophenotypes. *Nat. Rev. Neurosci.* 3, 617-628;

6 Usdin, Earl; Sandler, Merton; Editors. *Psychopharmacology Series, Vol.* 1: *Trace Amines and the Brain. [Proceedings of a Study Group at the 14th Annual Meeting of the American College of Neuropsychopharmacology*, San Juan, Puerto Rico] (1976);

7 Lindemann, L. and Hoener, M. (2005) A renaissance in trace amines inspired by a novel GPCR family. *Trends in Pharmacol. Sci.* 26, 274-281;

8 Branchek, T. A. and Blackburn, T. P. (2003) Trace amine receptors as targets for novel therapeutics: legend, myth and fact. *Curr. Opin. Pharmacol.* 3, 90-97;

9 Premont, R. T. et al. (2001) Following the trace of elusive amines. *Proc. Natl. Acad. Sci. U.S.A.* 98, 9474-9475;

10 Mousseau, D. D. and Butterworth, R. F. (1995) A high-affinity [3H] tryptamine binding site in human brain. *Prog. Brain Res.* 106, 285-291;

11 McCormack, J. K. et al. (1986) Autoradiographic localization of tryptamine binding sites in the rat and dog central nervous system. *J. Neurosci.* 6, 94-101;

12 Dyck, L. E. (1989) Release of some endogenous trace amines from rat striatal slices in the presence and absence of a monoamine oxidase inhibitor. *Life Sci.* 44, 1149-1156;

13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;

14 Lindemann, L. et al. (2005) Trace amine associated receptors form structurally and functionally distinct subfamilies of novel G protein-coupled receptors. *Genomics* 85, 72-385.

SUMMARY OF THE INVENTION

The present invention provides compounds of formula I

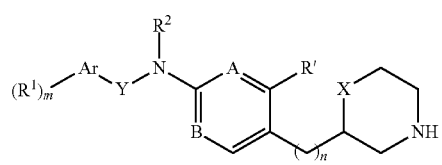

wherein $R^1$ is hydrogen, lower alkyl, halogen, lower alkyl substituted by halogen, lower alkoxy, lower alkoxy substituted by halogen, cyano, nitro, $C_{3-6}$-cycloalkyl, —$CH_2$—$C_{3-6}$-cycloalkyl,
—O—$CH_2$—$C_{3-6}$-cycloalkyl, —O—$(CH_2)_2$—O-lower alkyl, $S(O)_2CH_3$, $SF_5$, —C(O)NH-lower alkyl, phenyl, —O-pyrimidinyl, optionally substituted by lower alkoxy substituted by halogen, or is benzyl, oxetanyl or furanyl;

m is 1 or 2;

Ar is aryl or heteroaryl, selected from the group consisting of phenyl, naphthyl, pyrimidinyl, pyridinyl, benzothiazolyl, quinolinyl, quinazolinyl, benzo[d][1.3]dioxolyl, 5,6,7,8-tetrahydro-quinazolinyl, pyrazolyl, pyrazinyl, pyridazinyl, or 1,3,4-oxadiazolyl;

Y is a bond, —$CH_2$—, —$CH_2CH_2$—, —$CH(CF_3)$— and —$CH(CH_3)$—;

$R^2$ is hydrogen or lower alkyl;

A is CR or N; and R is hydrogen, cyano, halogen or lower alkyl;

R' is hydrogen or halogen; with the proviso that when R' is halogen, A is CH;

B is CH or N;

n is 0, 1 or 2; and

X is a bond, —$CH_2$— or —O—;

or pharmaceutical active acid addition salts thereof.

The invention includes all racemic mixtures, all their corresponding enantiomers and/or optical isomers. In addition, all tautomeric forms of compounds of formula I are also encompassed by the present invention.

Compounds of formula I have a good affinity to the trace amine associated receptors (TAARs), especially for TAAR1. The compounds show selectivity for TAAR1 receptor over adrenergic receptors, in particular good selectivity vs the human and rat alpha1 and alpha2 adrenergic receptors.

The compounds can be used for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The present invention provides new compounds of formula I and their pharmaceutically acceptable salts, pharmaceutical compositions containing compounds of the invention, and the treatment of diseases related to the biological function of the trace amine associated receptors. The invention also provides methods for the manufacture of the compounds and compositions of the invention. The invention also provides methods for the control or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, diabetes, anxiety and attention deficit hyperactivity disorder (ADHD).

DETAILED DESCRIPTION OF THE INVENTION

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a lower alkyl group as defined above which is attached via an oxygen atom.

As used herein, the term "lower alkyl substituted by halogen" denotes a lower alkyl group as defined above, wherein at least one hydrogen atom is replaced by halogen, for example $CF_3$, $CHF_2$, $CH_2F$, $CH_2CF_3$, $CH_2CH_2CF_3$, $CH_2CF_2CF_3$ and the like.

As used herein, the term "lower alkoxy substituted by halogen" denotes a lower alkoxy group as defined above wherein at least one hydrogen atom in the lower alkyl residue is replaced by halogen.

The term "halogen" denotes chlorine, iodine, fluorine and bromine.

The term "cycloalkyl" is an alkylene ring, containing from 3 to 6 carbon ring atoms.

The term "aryl", denotes an aromatic carbocyclic ring such as phenyl or naphthyl, preferably phenyl.

The term "heteroaryl" refers to an aromatic 5 to 6 membered monocyclic ring or 9 to 10 membered bicyclic ring which contains 1, 2 or 3 heteroatoms selected from nitrogen, oxygen and/or sulphur, such as pyrimidinyl, pyridinyl, benzothiazolyl, quinolinyl, quinazolinyl, benzo[d][1.3]dioxolyl, 5,6,7,8-tetrahydro-quinazolinyl, pyrazolyl, pyrazinyl, pyridazinyl, or 1,3,4-oxadiazolyl;

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "pharmaceutically acceptable carrier" such as pharmaceutically acceptable carrier, excipient, etc., means pharmacologically acceptable and substantially non-tonic to the subject to which the particular compound is administered.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

One embodiment of the present invention are compounds of formula IA

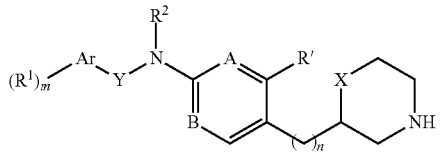

wherein
$R^1$ is hydrogen, lower alkyl, halogen, lower alkyl substituted by halogen, lower alkoxy, lower alkoxy substituted by halogen, cyano, nitro, $C_{3-6}$-cycloalkyl, $S(O)_2CH_3$ or phenyl;
m is 1 or 2;
Ar is aryl or heteroaryl, selected from the group consisting of phenyl, naphthyl, pyrimidinyl, pyridinyl, benzothiazolyl, quinolinyl, quinazolinyl, benzo[d][1.3]dioxolyl, 5,6,7,8-tetrahydro-quinazolinyl, pyrazolyl and 1,3,4-oxadiazolyl;
Y is a bond, —$CH_2$—, —$CH_2CH_2$—, —$CH(CF_3)$— or —$CH(CH_3)$—;
$R^2$ is hydrogen or lower alkyl;
A is CR or N; and R is hydrogen, cyano, halogen or lower alkyl;
B is CH or N;
n is 0, 1 or 2; and
X is a bond, —$CH_2$— or —O—;
or a pharmaceutical active acid addition salt thereof.

One further embodiment of the invention are compounds of formula I, wherein A is CR, and B is CH.

An embodiment of the invention provides compounds of formula I, wherein Y is a bond and Ar is phenyl or naphthyl, for example the following compounds
(RS)-(4-Chloro-phenyl)-(4-morpholin-2-yl-phenyl)-amine;
((S)-4-Morpholin-2-yl-phenyl)-naphthalen-2-yl-amine;
(S)-4-Chloro-2-fluoro-N-(4-(morpholin-2-yl)phenyl)aniline;
(4-Chloro-phenyl)-methyl-((S)-4-morpholin-2-yl-phenyl)-amine;
(RS)-(4-Chloro-phenyl)-(2-methyl-4-morpholin-2-yl-phenyl)-amine;
[5-(3,4-Dimethoxy-phenyl)-pyrimidin-2-yl]-((S)-4-morpholin-2-yl-phenyl)-amine; and
[5-(3,4-Dimethoxy-phenyl)-pyrimidin-2-yl]-((R)-4-morpholin-2-yl-phenyl)-amine.

An embodiment of the invention provides further compounds of formula I, wherein Y is a bond and Ar is pyridinyl, pyrimidinyl, pyrazolyl, benzothiazolyl, quinolinyl, quinazolinyl, benzo[d][1.3]dioxolyl, 5,6,7,8-tetrahydroquinazolinyl, pyrazinyl, pyridazinyl or 1,3,4-oxadiazolyl, for example the following compounds
(RS)-(4,6-Dimethyl-pyrimidin-2-yl)-(4-pyrrolidin-3-yl-phenyl)-amine;
(RS)-(5-Chloro-pyridin-2-yl)-(4-morpholin-2-yl-phenyl)-amine;
(RS)-(5-Chloro-pyrimidin-2-yl)-(4-morpholin-2-yl-phenyl)-amine;
(RS)-(5-Bromo-pyrimidin-2-yl)-(4-morpholin-2-yl-phenyl)-amine;
(S)-5-Bromo-N-(4-(morpholin-2-yl)phenyl)pyridin-2-amine;
(S)—N-(4-(Morpholin-2-yl)phenyl)-5-(trifluoromethyl)pyridin-2-amine;
(5-Methoxy-pyrimidin-2-yl)-((S)-4-morpholin-2-yl-phenyl)-amine;
(5-Fluoro-pyrimidin-2-yl)-((S)-4-morpholin-2-yl-phenyl)-amine;
(5-Ethyl-pyrimidin-2-yl)-((S)-4-morpholin-2-yl-phenyl)-amine;
2-((S)-4-Morpholin-2-yl-phenylamino)-pyrimidine-5-carbonitrile;
(5-Cyclopropyl-pyrimidin-2-yl)-((S)-4-morpholin-2-yl-phenyl)-amine;
(5-Methyl-pyrimidin-2-yl)-((S)-4-morpholin-2-yl-phenyl)-amine;
((S)-4-Morpholin-2-yl-phenyl)-(5-trifluoromethyl-pyrimidin-2-yl)-amine;
((S)-4-Morpholin-2-yl-phenyl)-(5-propyl-pyrimidin-2-yl)-amine;
(6-Chloro-benzothiazol-2-yl)-((S)-4-morpholin-2-yl-phenyl)-amine;
(5-Ethoxy-pyrimidin-2-yl)-((S)-4-morpholin-2-yl-phenyl)-amine;
(5-Chloro-pyridin-2-yl)-((S)-4-morpholin-2-yl-phenyl)-amine;
(S)-4-Methoxy-N-(4-(morpholin-2-yl)phenyl)pyridin-2-amine;
(S)-6-Chloro-5-fluoro-N-(4-(morpholin-2-yl)phenyl)pyridin-3-amine;
(S)—N-(4-(Morpholin-2-yl)phenyl)-3-(trifluoromethyl)pyridin-2-amine;
(S)—N-(4-(Morpholin-2-yl)phenyl)-4-(trifluoromethyl)pyridin-2-amine;
(S)-5-Fluoro-N-(4-(morpholin-2-yl)phenyl)pyridin-3-amine;
((S)-4-Morpholin-2-yl-phenyl)-quinolin-2-yl-amine;
(S)-6-Chloro-N-(4-(morpholin-2-yl)phenyl)quinolin-2-amine;
(S)-2-Methyl-N-(4-(morpholin-2-yl)phenyl)quinolin-8-amine;
(S)—N-(4-(Morpholin-2-yl)phenyl)-2,8-bis(trifluoromethyl)quinolin-4-amine;
(S)-6-Chloro-N-(4-(morpholin-2-yl)phenyl)quinazolin-4-amine;
(S)-8-Chloro-N-(4-(morpholin-2-yl)phenyl)quinolin-2-amine;
(S)-5-Bromo-N-(4-(morpholin-2-yl)phenyl)quinolin-2-amine;
(S)-4-Chloro-N-(4-(morpholin-2-yl)phenyl)quinolin-2-amine;
(2-Fluoro-pyridin-3-yl)-((S)-4-morpholin-2-yl-phenyl)-amine;
(S)-5-Bromo-3-methyl-N-(4-(morpholin-2-yl)phenyl)pyridin-2-amine;
(S)-5-Bromo-3-fluoro-N-(4-(morpholin-2-yl)phenyl)pyridin-2-amine;
(S)-3,5-Dichloro-N-(4-(morpholin-2-yl)phenyl)pyridin-2-amine;
(S)-3,5-Dibromo-N-(4-(morpholin-2-yl)phenyl)pyridin-2-amine;
(S)-5-Bromo-4-methyl-N-(4-(morpholin-2-yl)phenyl)pyridin-2-amine;
(S)-2,5-Dichloro-N-(4-(morpholin-2-yl)phenyl)pyridin-4-amine;
(S)-4-Bromo-5-methyl-N-(4-(morpholin-2-yl)phenyl)pyridin-2-amine;
(S)—N-(4-(Morpholin-2-yl)phenyl)benzo[d][1,3]dioxol-5-amine;
(S)-5-Bromo-N-(4-(morpholin-2-yl)phenyl)quinolin-8-amine;

(R)-6-Chloro-N-(4-(morpholin-2-yl)phenyl)pyridin-3-amine;
(R)-5-Ethyl-N-(4-(morpholin-2-yl)phenyl)pyrimidin-2-amine;
(R)-5-Chloro-N-(4-(morpholin-2-yl)phenyl)pyridin-2-amine;
(S)-6-Chloro-5-ethoxy-N-(4-(morpholin-2-yl)phenyl)pyridin-3-amine;
(5-Ethyl-4-methyl-pyrimidin-2-yl)-((S)-4-morpholin-2-yl-phenyl)-amine;
(5-Isopropyl-4-methyl-pyrimidin-2-yl)-((S)-4-morpholin-2-yl-phenyl)-amine;
((S)-4-Morpholin-2-yl-phenyl)-(5,6,7,8-tetrahydro-quinazolin-2-yl)-amine;
((S)-4-Morpholin-2-yl-phenyl)-(5-nitro-pyrimidin-2-yl)-amine;
(RS)-5-Bromo-N-(2-methyl-4-(morpholin-2-yl)phenyl)pyridin-2-amine;
(S)-5-Chloro-3-fluoro-N-(4-(morpholin-2-yl)phenyl)pyridin-2-amine;
(5-Methanesulfonyl-pyrimidin-2-yl)-((S)-4-morpholin-2-yl-phenyl)-amine;
(RS)-(5-Chloro-pyridin-2-yl)-(2-methyl-4-morpholin-2-yl-phenyl)-amine;
(RS)-(5-Chloro-pyrimidin-2-yl)-(2-methyl-4-morpholin-2-yl-phenyl)-amine;
(S)-5-Chloro-N-(4-(morpholin-2-yl)phenyl)-4-(trifluoromethyl)pyridin-2-amine;
(S)-5-Chloro-4-methyl-N-(4-(morpholin-2-yl)phenyl)pyridin-2-amine;
(RS)-5-Chloro-4-methyl-N-(2-methyl-4-(morpholin-2-yl)phenyl)pyridin-2-amine;
(RS)-5-Bromo-4-methyl-N-(2-methyl-4-(morpholin-2-yl)phenyl)pyridin-2-amine;
(5-Cyclopropyl-pyrimidin-2-yl)-((R)-4-morpholin-2-yl-phenyl)-amine;
(RS)-5-Cyclopropyl-N-(2-methyl-4-(morpholin-2-yl)phenyl)pyrimidin-2-amine;
(RS)-5-Ethyl-N-(2-methyl-4-(morpholin-2-yl)phenyl)pyrimidin-2-amine;
(RS)-5-Bromo-N-(2-methyl-4-(morpholin-2-yl)phenyl)pyrimidin-2-amine;
((R)-4-Morpholin-2-yl-phenyl)-(5-propyl-pyrimidin-2-yl)-amine;
(5-Bromo-pyrimidin-2-yl)-((R)-4-morpholin-2-yl-phenyl)-amine;
((R)-4-Morpholin-2-yl-phenyl)-(5-trifluoromethyl-pyrimidin-2-yl)-amine;
(RS)-5-Chloro-N-(2-fluoro-4-(morpholin-2-yl)phenyl)pyrimidin-2-amine;
(RS)-5-Ethyl-N-(2-fluoro-4-(morpholin-2-yl)phenyl)pyrimidin-2-amine;
(RS)-5-Cyclopropyl-N-(2-fluoro-4-(morpholin-2-yl)phenyl)pyrimidin-2-amine;
(RS)-5-Chloro-N-(2-fluoro-4-(morpholin-2-yl)phenyl)pyridin-2-amine;
(RS)-(5-Ethoxy-pyrimidin-2-yl)-(2-fluoro-4-morpholin-2-yl-phenyl)-amine;
(RS)-(2-Fluoro-4-morpholin-2-yl-phenyl)-(5-propyl-pyrimidin-2-yl)-amine;
(RS)-(5-Bromo-pyrimidin-2-yl)-(2-fluoro-4-morpholin-2-yl-phenyl)-amine;
(R)-5-Chloro-N-(4-(morpholin-2-yl)phenyl)pyrimidin-2-amine;
(S)-5-Chloro-N-(4-(morpholin-2-yl)phenyl)pyrimidin-2-amine;
(5-Ethoxy-pyrimidin-2-yl)-((R)-4-morpholin-2-yl-phenyl)-amine;
(5-Ethyl-pyrimidin-2-yl)-((R)-2-methyl-4-morpholin-2-yl-phenyl)-amine;
(5-Ethyl-pyrimidin-2-yl)-((S)-2-methyl-4-morpholin-2-yl-phenyl)-amine;
(5-Cyclopropyl-pyrimidin-2-yl)-((R)-2-methyl-4-morpholin-2-yl-phenyl)-amine;
(5-Cyclopropyl-pyrimidin-2-yl)-((S)-2-methyl-4-morpholin-2-yl-phenyl)-amine;
(5-Ethyl-pyrimidin-2-yl)-((S)-4-piperidin-3-yl-phenyl)-amine;
(S)—N-(4-(Morpholin-2-yl)phenyl)-5-phenyl-1H-pyrazol-3-amine;
(5-Ethoxy-pyrimidin-2-yl)-((S)-4-piperidin-3-yl-phenyl)-amine;
(S)—N-(4-(Morpholin-2-yl)phenyl)-5-phenyl-1,3,4-oxadiazol-2-amine;
(5-Ethyl-pyrimidin-2-yl)-((R)-2-fluoro-4-morpholin-2-yl-phenyl)-amine;
(5-Ethyl-pyrimidin-2-yl)-((S)-2-fluoro-4-morpholin-2-yl-phenyl)-amine;
(5-Cyclopropyl-pyrimidin-2-yl)-((R)-2-fluoro-4-morpholin-2-yl-phenyl)-amine;
(5-Cyclopropyl-pyrimidin-2-yl)-((S)-2-fluoro-4-morpholin-2-yl-phenyl)-amine;
(RS)-(2-Fluoro-4-morpholin-2-yl-phenyl)-(5-trifluoromethyl-pyrimidin-2-yl)-amine;
(5-Isopropoxy-pyrimidin-2-yl)-((S)-4-morpholin-2-yl-phenyl)-amine;
(5-Isopropoxy-pyrimidin-2-yl)-((R)-4-morpholin-2-yl-phenyl)-amine;
(S)-5-(Cyclopropylmethoxy)-N-(4-(morpholin-2-yl)phenyl)pyrimidin-2-amine;
(R)-5-(Cyclopropylmethoxy)-N-(4-(morpholin-2-yl)phenyl)pyrimidin-2-amine;
(5-Bromo-pyrimidin-2-yl)-((R)-2-fluoro-4-morpholin-2-yl-phenyl)-amine;
(5-Bromo-pyrimidin-2-yl)-((S)-2-fluoro-4-morpholin-2-yl-phenyl)-amine;
((R)-2-Fluoro-4-morpholin-2-yl-phenyl)-(5-propyl-pyrimidin-2-yl)-amine;
((S)-2-Fluoro-4-morpholin-2-yl-phenyl)-(5-propyl-pyrimidin-2-yl)-amine;
(5-Chloro-pyrimidin-2-yl)-((R)-2-fluoro-4-morpholin-2-yl-phenyl)-amine;
(5-Chloro-pyrimidin-2-yl)-((S)-2-fluoro-4-morpholin-2-yl-phenyl)-amine;
(5-Ethoxy-pyrimidin-2-yl)-((R)-2-fluoro-4-morpholin-2-yl-phenyl)-amine;
(5-Ethoxy-pyrimidin-2-yl)-((S)-2-fluoro-4-morpholin-2-yl-phenyl)-amine;
((R)-2-Fluoro-4-morpholin-2-yl-phenyl)-(5-trifluoromethyl-pyrimidin-2-yl)-amine;
((S)-2-Fluoro-4-morpholin-2-yl-phenyl)-(5-trifluoromethyl-pyrimidin-2-yl)-amine;
((S)-4-Morpholin-2-yl-phenyl)-[5-(2,2,2-trifluoro-ethoxy)-pyrimidin-2-yl]-amine;
((R)-4-Morpholin-2-yl-phenyl)-[5-(2,2,2-trifluoro-ethoxy)-pyrimidin-2-yl]-amine;
[5-(2-Methoxy-ethoxy)-pyrimidin-2-yl]-((S)-4-morpholin-2-yl-phenyl)-amine;
[5-(2-Methoxy-ethoxy)-pyrimidin-2-yl]-((R)-4-morpholin-2-yl-phenyl)-amine;
(RS)-(1-Methyl-1H-pyrazol-3-yl)-(4-morpholin-2-yl-phenyl)-amine;

(RS)-(4-Bromo-1-methyl-1H-pyrazol-3-yl)-(4-morpholin-2-yl-phenyl)-amine;
((R)-2-Fluoro-4-morpholin-2-yl-phenyl)-[5-(2,2,2-trifluoro-ethoxy)-pyrimidin-2-yl]-amine;
((S)-2-Fluoro-4-morpholin-2-yl-phenyl)-[5-(2,2,2-trifluoro-ethoxy)-pyrimidin-2-yl]-amine;
(RS)-(1-Cyclopropylmethyl-1H-pyrazol-3-yl)-(4-morpholin-2-yl-phenyl)-amine;
(5-Furan-2-yl-pyrimidin-2-yl)-((S)-4-morpholin-2-yl-phenyl)-amine;
(5-Furan-2-yl-pyrimidin-2-yl)-((R)-4-morpholin-2-yl-phenyl)-amine;
(RS)—N-(2-Chloro-4-(morpholin-2-yl)phenyl)-5-cyclopropylpyrimidin-2-amine;
(RS)-[1-(2,2-Difluoro-ethyl)-1H-pyrazol-3-yl]-(4-morpholin-2-yl-phenyl)-amine;
((R)-2-Fluoro-4-morpholin-2-yl-phenyl)-[5-(2-methoxy-ethoxy)-pyrimidin-2-yl]-amine;
((S)-2-Fluoro-4-morpholin-2-yl-phenyl)-[5-(2-methoxy-ethoxy)-pyrimidin-2-yl]-amine;
((S)-4-Morpholin-2-yl-phenyl)-(2-trifluoromethyl-pyrimidin-5-yl)-amine;
((R)-4-Morpholin-2-yl-phenyl)-(2-trifluoromethyl-pyrimidin-5-yl)-amine;
(RS)-(4-Morpholin-2-yl-phenyl)-(1H-pyrazol-3-yl)-amine;
(5-Methyl-pyrazin-2-yl)-((S)-4-morpholin-2-yl-phenyl)-amine;
(5-Methyl-pyrazin-2-yl)-((R)-4-morpholin-2-yl-phenyl)-amine;
2-((S)-4-Morpholin-2-yl-phenylamino)-pyrimidine-5-carboxylic acid methylamide;
2-((R)-4-Morpholin-2-yl-phenylamino)-pyrimidine-5-carboxylic acid methylamide;
(6-Methyl-pyridazin-3-yl)-((S)-4-morpholin-2-yl-phenyl)-amine;
(1-Benzyl-1H-pyrazol-3-yl)-((S)-4-morpholin-2-yl-phenyl)-amine;
(1-Benzyl-1H-pyrazol-3-yl)-((R)-4-morpholin-2-yl-phenyl)-amine;
((S)-4-Morpholin-2-yl-phenyl)-(1-phenyl-1H-pyrazol-3-yl)-amine;
((R)-4-Morpholin-2-yl-phenyl)-(1-phenyl-1H-pyrazol-3-yl)-amine;
((S)-4-Morpholin-2-yl-phenyl)-(5-oxetan-3-yl-pyridin-2-yl)-amine;
((R)-2-Methyl-4-morpholin-2-yl-phenyl)-(5-trifluoromethyl-pyrimidin-2-yl)-amine;
((S)-2-Methyl-4-morpholin-2-yl-phenyl)-(5-trifluoromethyl-pyrimidin-2-yl)-amine;
((R)-2-Chloro-4-morpholin-2-yl-phenyl)-(5-trifluoromethyl-pyrimidin-2-yl)-amine;
((S)-2-Chloro-4-morpholin-2-yl-phenyl)-(5-trifluoromethyl-pyrimidin-2-yl)-amine;
(R)—N-(2-Chloro-4-(morpholin-2-yl)phenyl)-5-cyclopropylpyrimidin-2-amine;
(S)—N-(2-Chloro-4-(morpholin-2-yl)phenyl)-5-cyclopropylpyrimidin-2-amine;
((R)-4-Morpholin-2-yl-phenyl)-[4-(2,2,2-trifluoro-ethoxy)-pyrimidin-2-yl]-amine;
(R)—N-(4-(Morpholin-2-yl)phenyl)-4-(trifluoromethyl)pyrimidin-2-amine;
(R)-5-(5-(Difluoromethoxy)pyrimidin-2-yloxy)-N-(4-(morpholin-2-yl)phenyl)pyrimidin-2-amine;
(R)—N-(2-Chloro-4-(morpholin-2-yl)phenyl)-5-(5-(difluoromethoxy)pyrimidin-2-yloxy)pyrimidin-2-amine;
(R)—N-(4-(Morpholin-2-yl)phenyl)pyrimidin-2-amine;
((R)-4-Morpholin-2-yl-phenyl)-quinazolin-2-yl-amine;
(4-Methyl-6-trifluoromethyl-pyrimidin-2-yl)-((R)-4-morpholin-2-yl-phenyl)-amine;
(R)-5-(Difluoromethoxy)-N-(4-(morpholin-2-yl)phenyl)pyrimidin-2-amine;
(4-Chloro-6-methoxy-pyrimidin-2-yl)-((R)-4-morpholin-2-yl-phenyl)-amine;
2-((R)-4-Morpholin-2-yl-phenylamino)-pyrimidine-4-carbonitrile;
(4,6-Dimethyl-pyrimidin-2-yl)-((R)-4-morpholin-2-yl-phenyl)-amine;
(4,6-Dimethoxy-pyrimidin-2-yl)-((R)-4-morpholin-2-yl-phenyl)-amine;
((R)-2-Chloro-4-morpholin-2-yl-phenyl)-[5-(2,2,2-trifluoro-ethoxy)-pyrimidin-2-yl]-amine;
(R)-3-Chloro-N-(4-(morpholin-2-yl)phenyl)-5-(trifluoromethyl)pyridin-2-amine;
(S)-2,5-Dichloro-N-(4-(morpholin-2-yl)phenyl)pyrimidin-4-amine;
((S)-4-Morpholin-2-yl-phenyl)-[4-(2,2,2-trifluoro-ethoxy)-pyrimidin-2-yl]-amine;
[5-Fluoro-4-(2,2,2-trifluoro-ethoxy)-pyrimidin-2-yl]-((R)-4-morpholin-2-yl-phenyl)-amine;
(4-Cyclopropyl-pyrimidin-2-yl)-((R)-4-morpholin-2-yl-phenyl)-amine;
(4-Cyclopropyl-5-fluoro-pyrimidin-2-yl)-((R)-4-morpholin-2-yl-phenyl)-amine;
(4-Pentafluorosulfanyl-phenyl)-((R)-4-morpholin-2-yl-phenyl)-amine;
(R)-5-Cyclopropyl-N-(3-fluoro-4-(morpholin-2-yl)phenyl)pyrimidin-2-amine;
((S)-3-Chloro-4-morpholin-2-yl-phenyl)-(5-cyclopropyl-pyrimidin-2-yl)-amine;
((R)-3-Chloro-4-morpholin-2-yl-phenyl)-(5-cyclopropyl-pyrimidin-2-yl)-amine;
(S)-5-Cyclopropyl-N-(3-fluoro-4-(morpholin-2-yl)phenyl)pyrimidin-2-amine;
(R)—N-(3-Fluoro-4-(morpholin-2-yl)phenyl)-5-(trifluoromethyl)pyrimidin-2-amine;
(S)—N-(3-Fluoro-4-(morpholin-2-yl)phenyl)-5-(trifluoromethyl)pyrimidin-2-amine;
(R)—N-(4-(Morpholin-2-yl)phenyl)-6-(trifluoromethyl)pyrimidin-4-amine;
(R)-6-Chloro-N-(4-(morpholin-2-yl)phenyl)pyrimidin-4-amine;
(R)—N-(4-(morpholin-2-yl)phenyl)-2-(trifluoromethyl)pyrimidin-4-amine;
(R)—N-(4-(Morpholin-2-yl)phenyl)-5-(trifluoromethyl)pyrazin-2-amine;
((R)-3-Chloro-4-morpholin-2-yl-phenyl)-(5-chloro-pyrimidin-2-yl)-amine;
((R)-3-Chloro-4-morpholin-2-yl-phenyl)-[5-(2,2,2-trifluoro-ethoxy)-pyrimidin-2-yl]-amine;
((R)-3-Chloro-4-morpholin-2-yl-phenyl)-(5-trifluoromethyl-pyrimidin-2-yl)-amine;
(R)-5-Chloro-N-(4-(morpholin-2-yl)phenyl)pyrazin-2-amine;
(R)-6-Chloro-N-(4-(morpholin-2-yl)phenyl)pyrazin-2-amine;
(R)—N-(3-Fluoro-4-(morpholin-2-yl)phenyl)-5-(2,2,2-trifluoroethoxy)pyrimidin-2-amine;
(R)—N-(3-Fluoro-4-(morpholin-2-yl)phenyl)-4-(2,2,2-trifluoroethoxy)pyrimidin-2-amine;
(R)-5-Fluoro-N-(3-fluoro-4-(morpholin-2-yl)phenyl)-4-(2,2,2-trifluoroethoxy)pyrimidin-2-amine;
(R)-5-Chloro-N-(3-fluoro-4-(morpholin-2-yl)phenyl)pyrimidin-2-amine; and ((R)-3-Chloro-4-morpholin-2-yl-phenyl)-[4-(2,2,2-trifluoro-ethoxy)-pyrimidin-2-yl]-amine.

An embodiment of the invention provides compounds of formula I, wherein Y is —CH₂—, —CH₂CH₂—, —CH(CF₃)— or —CH(CH₃)— and Ar is phenyl or naphthyl, for example the following compounds

[(RS)-1-(4-Chloro-phenyl)-2,2,2-trifluoro-ethyl]-[(RS)-4-(2-pyrrolidin-3-yl-ethyl)-phenyl]-amine;
(RS)-[1-(4-Chloro-phenyl)-2,2,2-trifluoro-ethyl]-[(RS)-4-(2-piperidin-3-yl-ethyl)-phenyl]-amine;
(RS)-(4-Chloro-benzyl)-(4-morpholin-2-yl-phenyl)-amine;
((S)-4-Morpholin-2-yl-phenyl)-phenethyl-amine;
(4-Methoxy-benzyl)-((S)-4-morpholin-2-yl-phenyl)-amine;
(4-Methyl-benzyl)-((S)-4-morpholin-2-yl-phenyl)-amine;
4-[((S)-4-Morpholin-2-yl-phenylamino)-methyl]-benzonitrile;
((S)-4-Morpholin-2-yl-phenyl)-(4-trifluoromethyl-benzyl)-amine;
((S)-4-Morpholin-2-yl-phenyl)-(4-trifluoromethoxy-benzyl)-amine;
(3,4-Dichloro-benzyl)-((S)-4-morpholin-2-yl-phenyl)-amine;
(4-Fluoro-benzyl)-((S)-4-morpholin-2-yl-phenyl)-amine;
[2-(4-Chloro-phenyl)-ethyl]-((S)-4-morpholin-2-yl-phenyl)-amine;
(4-Chloro-2-fluoro-benzyl)-((S)-4-morpholin-2-yl-phenyl)-amine;
(4-Ethyl-benzyl)-((S)-4-morpholin-2-yl-phenyl)-amine;
(4-Bromo-benzyl)-((S)-4-morpholin-2-yl-phenyl)-amine; and
[(RS)-1-(4-Chloro-phenyl)-ethyl]-((S)-4-morpholin-2-yl-phenyl)-amine.

A further embodiment of the invention provides compounds of formula I, wherein Y is —CH₂—, —CH₂CH₂—, —CH(CF₃)— or —CH(CH₃)— and Ar is furyl, pyridinyl, pyrimidinyl, pyrazolyl, benzothiazolyl, quinolinyl, quinazolinyl, benzo[d][1.3]dioxolyl, 5,6,7,8-tetrahydroquinazolinyl or 1,3,4-oxadiazoly, for example the following compounds

[(RS)-1-(5-Bromo-pyridin-2-yl)-2,2,2-trifluoro-ethyl]-((RS)-4-pyrrolidin-3-yl-phenyl)-amine;
(5-Bromo-pyridin-2-ylmethyl)-((S)-4-morpholin-2-yl-phenyl)-amine;
(6-Methoxy-pyridin-2-ylmethyl)-((S)-4-morpholin-2-yl-phenyl)-amine;
(S)—N-((6-Chloropyridin-3-yl)methyl)-4-(morpholin-2-yl) aniline;
(S)-4-(Morpholin-2-yl)-N-((6-(trifluoromethyl)pyridin-3-yl)methyl)aniline;
(5-Fluoro-pyridin-2-ylmethyl)-((S)-4-morpholin-2-yl-phenyl)-amine; and
(S)—N-((2-Chloroquinolin-3-yl)methyl)-4-(morpholin-2-yl)aniline.

One further embodiment of the invention provides compounds of formula I, wherein A is N, B is CH, Y is a bond and Ar is pyridinyl, pyrimidinyl, for example the following compounds (RS)-5-Chloro-N-(5-(morpholin-2-yl)pyridin-2-yl)pyridin-2-amine;
(RS)-5-Bromo-N-(5-(morpholin-2-yl)pyridin-2-yl)pyridin-2-amine;
(RS)-5-Cyclopropyl-N-(5-(morpholin-2-yl)pyridin-2-yl)pyrimidin-2-amine;
(R)-5-Bromo-N-(5-(morpholin-2-yl)pyridin-2-yl)pyridin-2-amine; and
(S)-5-Bromo-N-(5-(morpholin-2-yl)pyridin-2-yl)pyridin-2-amine.

One further embodiment of the invention provides compounds of formula I, wherein A is CR, B is N, Y is a bond and Ar is pyridinyl, for example the following compound (RS)—N-(5-Bromopyridin-2-yl)-3-methyl-5-(morpholin-2-yl)pyridin-2-amine.

The present compounds of formula I and their pharmaceutically acceptable salts can be prepared by methods known in the art, for example, by processes described below, which process comprises a) cleaving off the N-protecting group from compounds of formula

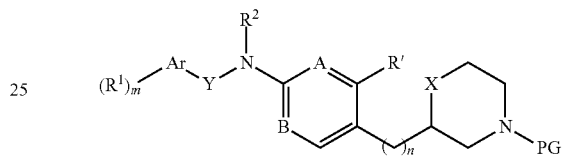

to obtain a compound of formula

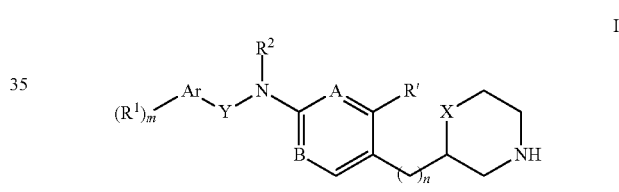

PG is a N-protecting group selected from —C(O)O-tert-butyl, and if desired, converting the compounds obtained into pharmaceutically acceptable acid addition salts.

The preparation of compounds of formula I of the present invention can be carried out in sequential or convergent synthetic routes. Syntheses of the compounds of the invention are shown in the following schemes 1-11 and in the description of 211 specific examples. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1 to 11, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

General Procedure
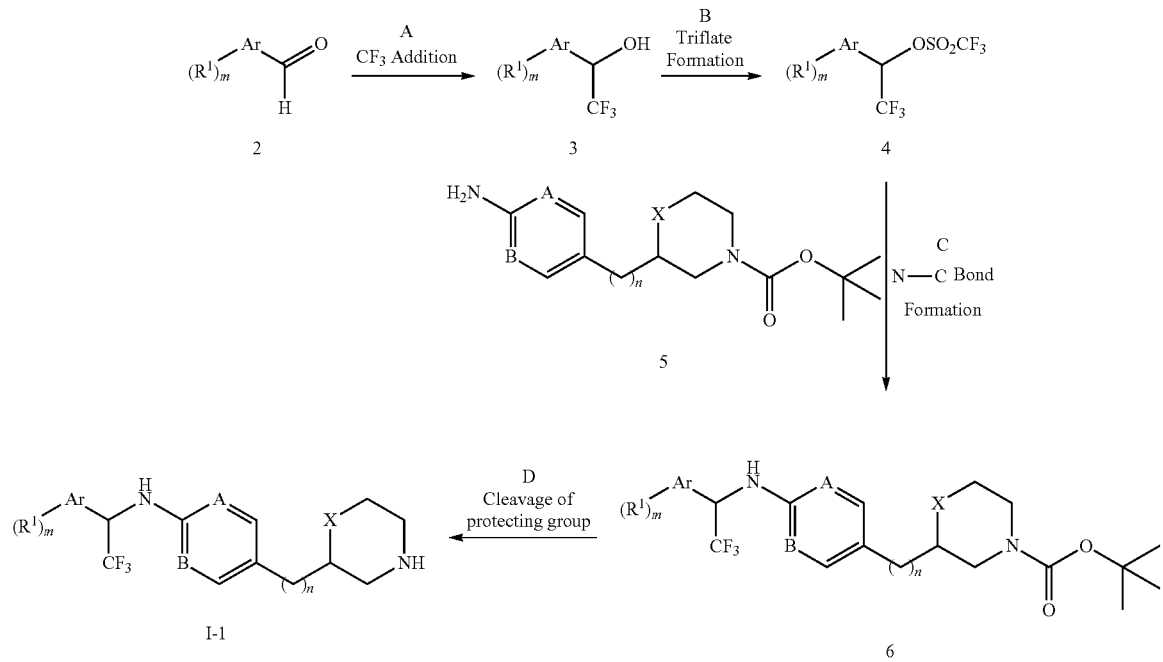
for example using:
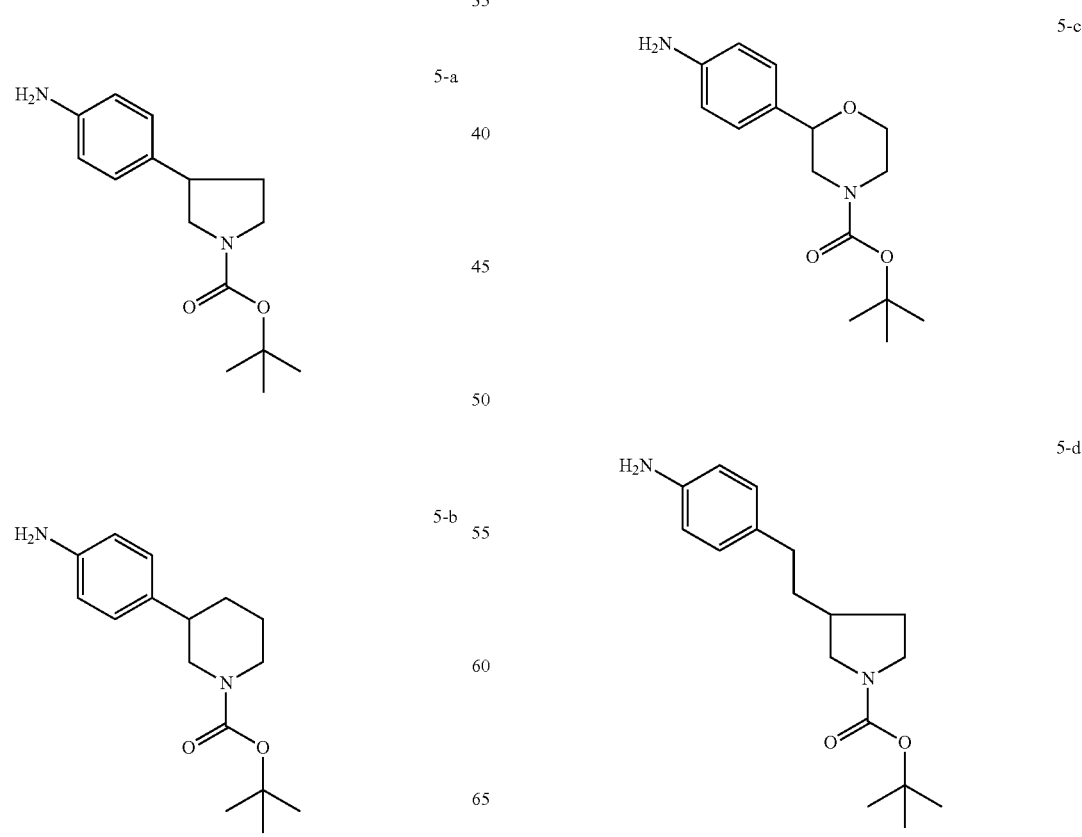

-continued

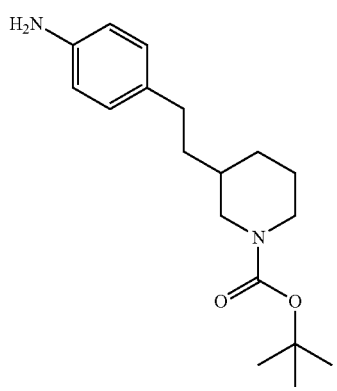
5-e

The substituents are as described above and Y is —CH(CF$_3$)—.

Step A:
Addition of a trifluoromethyl group to aromatic aldehyde 2 can be accomplished by treatment with (trifluoromethyl)trimethylsilane in the presence of a source of fluoride ion such as tetrabutylammonium fluoride.

Preferred conditions are using THF as solvent at 0° C. for 30 minutes and then at room temperature for 2 hours.

Step B:
Conversion of alcohol 3 to the corresponding triflate ester 4 can be can be accomplished by deprotonation with a base such as NaH, KOtBu, n-BuLi, LiHMDS, NaHMDS, KHMDS or LDA in non-protic organic solvents such as THF, dioxane, 1,2-dimethoxyethane, DMF, benzene, toluene or mixtures thereof at temperatures from −78° C. to 80° C. for 15 min-2 hrs followed by treatment with trifluoromethanesulfonyl chloride.

Preferred conditions are deprotonation at room temperature for 30 min using sodium hydride as base and diethyl ether as solvent, followed by treatment with trifluoromethanesulfonyl chloride at room temperature for 15 min.

Step C:
C—N bond formation can be accomplished by treatment of triflate 4 with aryl amine 5 in the presence of a base such as NaH, KOtBu, n-BuLi, LiHMDS, NaHMDS, KHMDS or LDA in non-protic organic solvents such as THF, dioxane, 1,2-dimethoxyethane, DMF, benzene, toluene or mixtures thereof at temperatures from −78° C. to 80° C. for 15 min-24 hours.

Examples of appropriate amines 5 include N-protected pyrrolidine derivatives such as 5-a [CAS 908334-28-1] or 5-d [Example 3(b)], piperidine derivatives such as 5-b [CAS 875798-79-1] or 5-e [Example 4], or morpholine derivatives such as 5-c [CAS 1002726-96-6].

Preferred conditions are deprotonation of amine 5 at room temperature for 15 min using sodium hydride as base and THF as solvent, followed by treatment with triflate 4 at room temperature overnight.

Step D:
Removal of the BOC N-protecting group can be effected with mineral acids such as HCl, H$_2$SO$_4$ or H$_3$PO$_4$ or organic acids such as CF$_3$COOH, CHCl$_2$COOH, HOAc or p-toluenesulfonic acid in solvents such as CH$_2$Cl$_2$, CHCl$_3$, THF, MeOH, EtOH or H$_2$O at 0 to 80° C.

Preferred conditions are CF$_3$COOH in aqueous acetonitrile at 80° C. for 2 hours or 4 N HCl in dioxane and THF at 60° C. for 4 hours.

Scheme 2

For Y being a bond

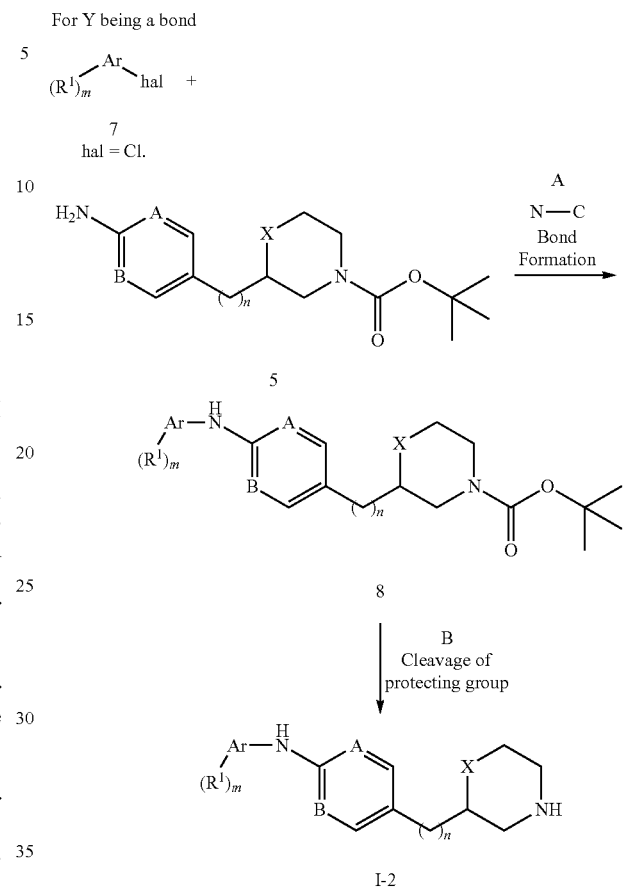

for example using:

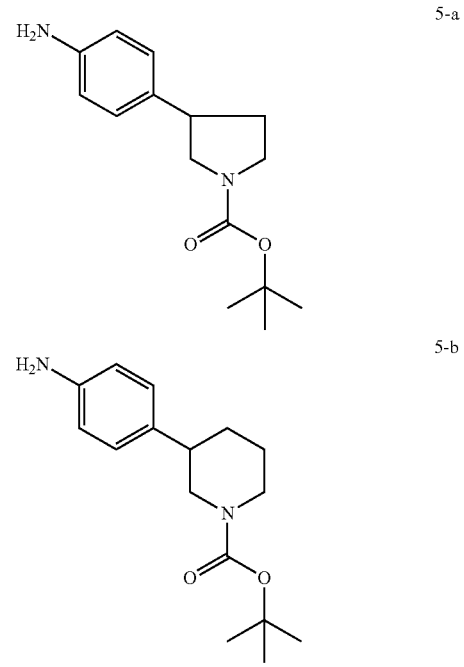

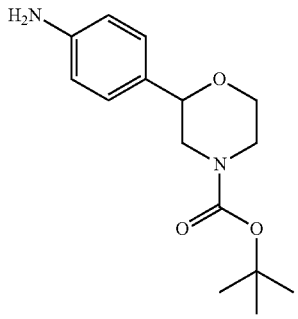

5-c

Scheme 3

For Y being —CH$_2$— or —CH$_2$CH$_2$—

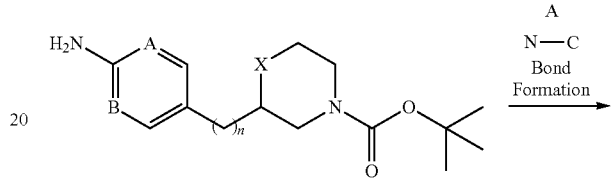

Y' = a bond or —CH$_2$—

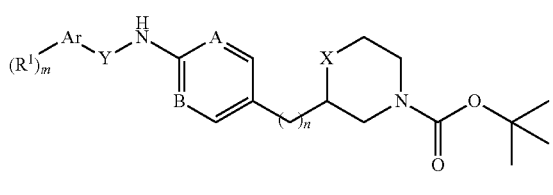

↓ B
Cleavage of protecting group

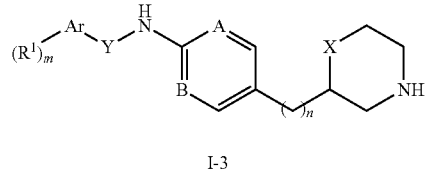

I-3 for example using:

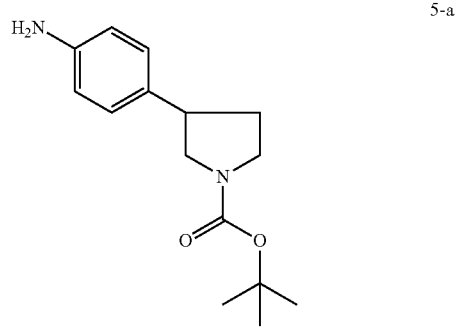

5-a

The substituents are as described above and Y is a bond.

Step A:

C—N bond formation can be accomplished by treatment of aryl halide 7 or heteroaryl halide 7 with aryl amine 5 in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Examples of appropriate amines 5 include N-protected pyrrolidine derivatives such as 5-a [CAS 908334-28-1], piperidine derivatives such as 5-b [CAS 875798-79-1], or morpholine derivatives such as 5-c [CAS 1002726-96-6].

Preferred conditions are catalytic tris(dibenzylidineacetone)dipalladium chloroform complex, catalytic 9,9-dimethyl-4,5-bis(diphenylphosphino)xanthene (xantphos)and caesium carbonate in dioxane in a sealed tube heated at 100° C. overnight according to a modification of the procedure of van Leeuwen and co-workers (*Tetrahedron. Lett.* 1999, 40, 3789-3790).

In case the aryl halide 7 or heteroaryl halide 7 is activated towards undergoing nucleophilic substitution due to the presence of electron withdrawing substitutuents, preferably by the presence of a trifluoromethylgroup, coupling with the aryl amine 5 can be achieved by reacting these compounds in the presence of a base such as diisopropylethylamine, triethylamine, potassium carbonate or sodium hydride in a solvent such as isopropanol, dioxane, dimethylacetamide or dimethylformamide at a temperature between 50° C. and 140° C. for 1 hour to 24 hours.

Preferred conditions are heating the mixture of 5 and 7 with diisopropylethylamine in isopropanol or dimethylacetamide at 80° C. for 18 hours.

Step B:

Removal of the BOC N-protecting group can be effected with mineral acids such as HCl, H$_2$SO$_4$ or H$_3$PO$_4$ or organic acids such as CF$_3$COOH, CHCl$_2$COOH, HOAc or p-toluenesulfonic acid in solvents such as CH$_2$Cl$_2$, CHCl$_3$, THF, MeOH, EtOH or H$_2$O at 0 to 80° C.

Preferred conditions are CF$_3$COOH in aqueous acetonitrile at 80° C. for 2 hours or 4 N HCl in dioxane and THF at 60° C. for 16 hours.

-continued

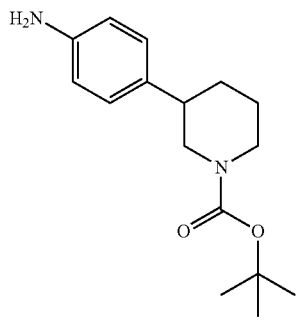

5-b

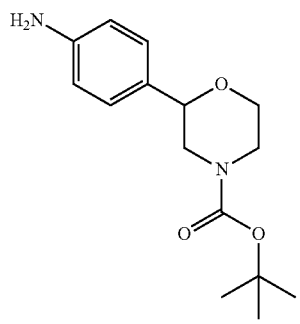

5-c

The substituents are as described above and Y is —CH$_2$— or —CH$_2$CH$_2$—.

Step A:

C—N bond formation can be accomplished by a reductive amination reaction involving treatment of aldehyde 9 with aryl amine 5 in the presence of a reducing agent such as NaBH$_4$, LiBH$_4$, NaBH(OAc)$_3$ or Na(CN)BH$_3$ in a solvent such as MeOH, EtOH, dichloromethane, 1,2-dichloroethane, THF, dioxane or mixtures thereof in the presence of an activating protic acid such as HCl or a carboxylic acid or an activating Lewis acid such as ZnCl$_2$ or Ti(OiPr)$_4$ at a temperature of −10 to 60° C. for 1-40 h.

Examples of appropriate amines 5 include N-protected pyrrolidine derivatives such as 5-a [CAS 908334-28-1], piperidine derivatives such as 5-b [CAS 875798-79-1], or morpholine derivatives such as 5-c [CAS 1002726-96-6].

Preferred conditions are sodium triacetoxyborohydride in acetic acid and THF at 60° C. for 3 hours.

Step B:

Removal of the BOC N-protecting group can be effected with mineral acids such as HCl, H$_2$SO$_4$ or H$_3$PO$_4$ or organic acids such as CF$_3$COOH, CHCl$_2$COOH, HOAc or p-toluenesulfonic acid in solvents such as CH$_2$Cl$_2$, CHCl$_3$, THF, MeOH, EtOH or H$_2$O at 0 to 80° C.

Preferred conditions are CF$_3$COOH in aqueous acetonitrile at 80° C. for 2 hours or 4 N HCl in dioxane and THF at 60° C. for 16 hours.

Scheme 4

For Y being a bond —CH$_2$—, —CH$_2$CH$_2$— or —CH$_2$(CH$_3$)—

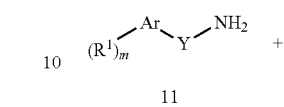

11

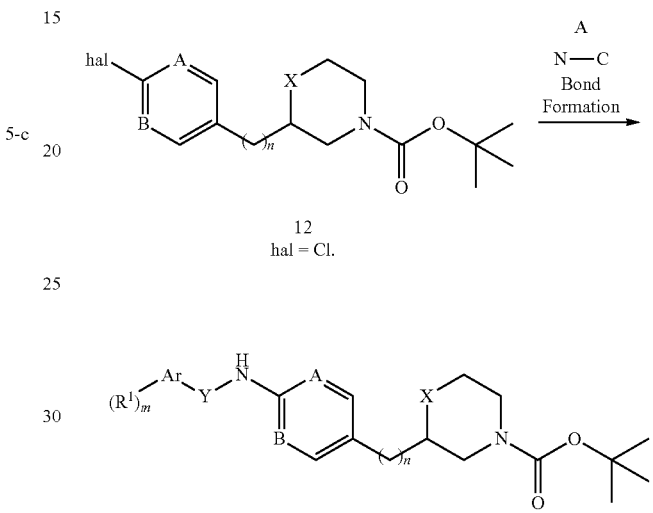

12
hal = Cl.

A
N—C Bond Formation

10

B
Cleavage of protecting group

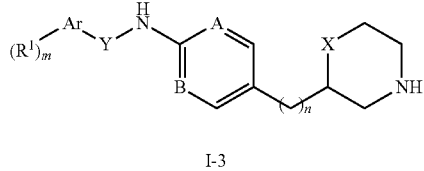

I-3 for example using:

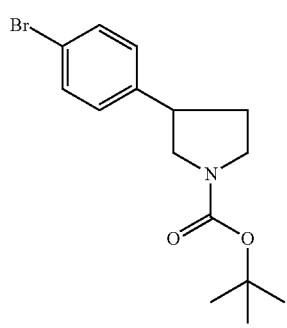

12-a

-continued

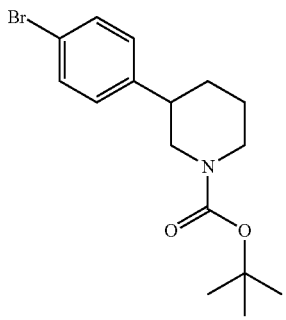

12-b

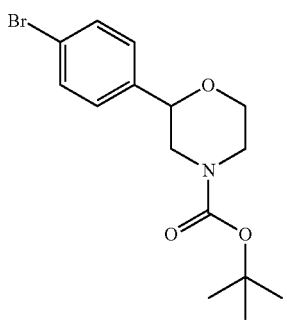

12-c

The substituents are as described above and Y is a bond, —CH$_2$—, —CH$_2$CH$_2$— or —CH(CH$_3$)—.

Step A:

C—N bond formation can be accomplished by treatment of amine 11 with aryl halide 12 in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Examples of appropriate aryl halides 12 include N-protected pyrrolidine derivatives such as 12-a [CAS 328546-99-2], piperidine derivatives such as 12-b [CAS 769944-73-2], or morpholine derivatives such as 12-c [CAS 1131220-82-0].

Preferred conditions are catalytic tris(dibenzylideneacetone)dipalladium(0), catalytic 2-di-tert-butylphosphino-2',4',6'-triisopropylbiphenyl and sodium tert-butoxide in dioxane in a sealed tube heated at 120° C. overnight.

Step B:

Removal of the BOC N-protecting group can be effected with mineral acids such as HCl, H$_2$SO$_4$ or H$_3$PO$_4$ or organic acids such as CF$_3$COOH, CHCl$_2$COOH, HOAc or p-toluenesulfonic acid in solvents such as CH$_2$Cl$_2$, CHCl$_3$, THF, MeOH, EtOH or H$_2$O at 0 to 80° C.

Preferred conditions are CF$_3$COOH in aqueous acetonitrile at 80° C. for 2 hours or 4 N HCl in dioxane and THF at 60° C. for 16 hours.

Scheme 5

For X being O, Y being a bond, A being C-lower alkyl, B being CH and n being 0

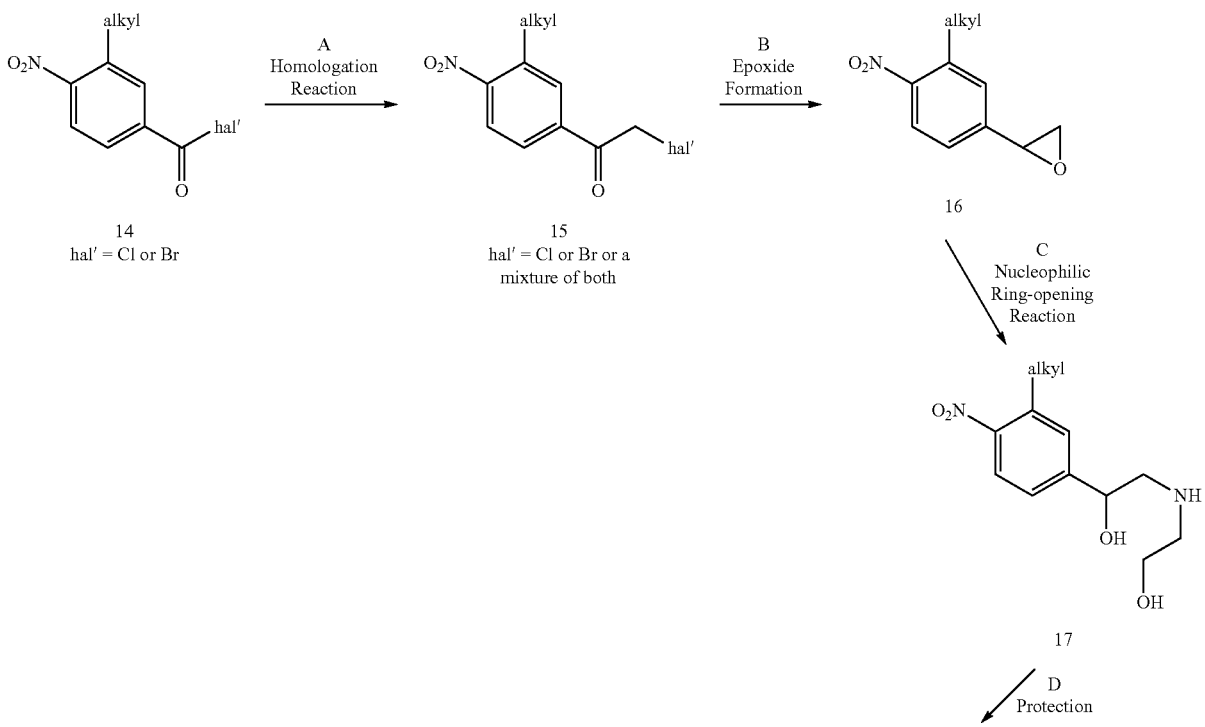

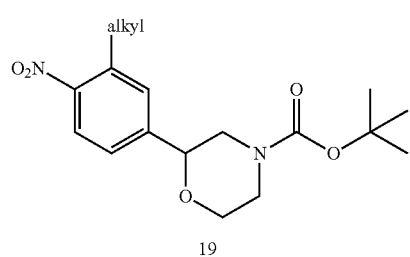

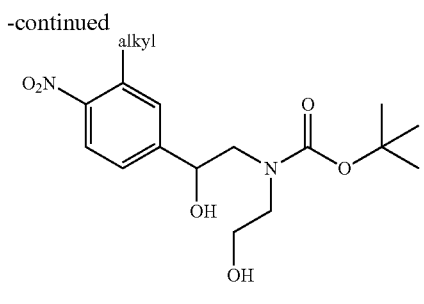

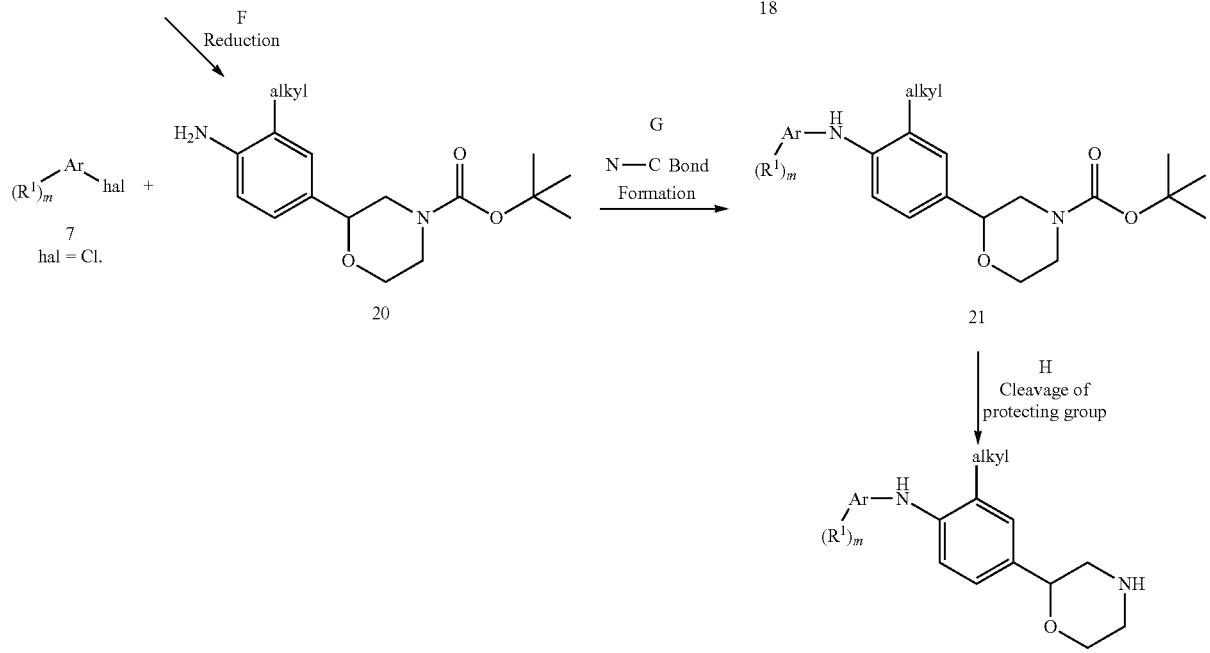

The substituents are as described above and X is O, Y is a bond, A is C-lower alkyl, B is CH, R' is hydrogen and n is 0.

Step A:

Alpha-halo ketones 15 can be obtained by a homologation reaction of an acyl halide 14 [e.g. hal'=chloro and alkyl=methyl, CAS 35675-46-8] involving sequential treatment first with (trimethylsilyl)diazomethane and then treatment with concentrated hydrobromic acid or hydrochloric acid. The reaction is carried out using a mixture of acetonitrile, THF and hexane as solvent at temperatures between 0° C. and room temperature.

Preferred conditions are mixing of reactants at 0-5° C. followed by allowing to react for 1 hour at room temperature for the first step, and mixing of reactants at 0-5° C. followed by allowing to react for 30 minutes at room temperature for the second step.

Step B:

Epoxide formation can be accomplished by a stepwise process involving reduction of alpha-halo ketones 15 by treatment with a reducing agent such as NaBH$_4$ or LiBH$_4$ in a solvent such as MeOH, EtOH, THF, dioxane, followed by cyclisation of the ensuing alpha-halo alcohol by treatment with a base such as sodium methoxide, sodium ethoxide, potassium tert-butoxide or caesium carbonate in the same solvent.

Preferred conditions are NaBH$_4$ in ethanol at 5° C. to room temperature for 1 hour followed by treatment with sodium methoxide at room temperature for 16 hours.

Step C:

Nucleophilic ring-opening can be accomplished by treatment of epoxide 16 with 2-aminoethanol, optionally in the presence of an organic base such as triethylamine, N,N-diisopropylethylamine or N-methylmorpholine in a non-protic polar organic solvent such as ether, THF, dioxane or TBME.

Preferred conditions are using excess 2-aminoethanol as base in THF at room temperature for 16 hours.

Step D:

Selective protection of the amino group of amino alcohol 17 can be effected by treatment with di-tert-butyl carbonate, optionally in the presence of an organic base such as triethylamine, N,N-diisopropylethylamine or N-methylmorpholine, in halogenated solvents such as dichloromethane or 1,2-dichloroethane or ethereal solvents such as diethyl ether, dioxane, THF or TBME.

Preferred conditions are THF in the absence of a base at room temperature for 16 hours.

Step E:

Cyclisation can be accomplished by a stepwise process involving sulphonate ester formation by treatment of diol 18 with one equivalent of methanesulfonyl chloride in the presence of an organic base such as triethylamine, N,N-diisopropylethylamine or N-methylmorpholine in ethereal solvents such as diethyl ether, dioxane, THF or TBME, followed by cyclisation by treatment with a non-nucleophilic base such as potassium tert-butoxide or potassium 2-methyl-2-butoxide in ethereal solvents such as diethyl ether, dioxane, THF or TBME.

Preferred conditions for the first step are triethylamine in THF mixing the reactants at 0-5° C. and then allowing to react for 1 hour at room temperature, then removal of the by-product triethylamine hydrochloride by filtration. Preferred conditions for the second step are potassium 2-methyl-2-butoxide in THF mixing the reactants at 0-5° C. and then allowing to react for 30 minutes at room temperature.

Step F:

Reduction of the nitro group of 19 can be effected by hydrogenation with hydrogen under normal or elevated pressure or by transfer hydrogenation using ammonium formate or cyclohexadiene as hydrogen source with a catalyst such as $PtO_2$, Pd—C or Raney nickel in solvents such as MeOH, EtOH, $H_2O$, dioxane, THF, HOAc, EtOAc $CH_2Cl_2$, $CHCl_3$, DMF or mixtures thereof. Preferred conditions are ammonium formate in the presence of palladium on charcoal in MeOH at 60° C. for 1 hour.

Step G:

C—N bond formation can be accomplished by treatment of an aryl halide 7 with aryl amine 20 in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium chloroform complex, catalytic 9,9-dimethyl-4,5-bis(diphenylphosphino)xanthene (xantphos)and caesium carbonate in dioxane in a sealed tube heated at 80° C. for 1 hour according to a modification of the procedure of van Leeuwen and co-workers (*Tetrahedron. Lett.* 1999, 40, 3789-3790).

Step H:

Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0 to 80° C.

Preferred conditions are $CF_3COOH$ in aqueous acetonitrile at 80° C. for 2 hours or 4 N HCl in dioxane and THF at 60° C. for 16 hours.

Scheme 6

For X being O, Y being a bond, A being N, B being CH, R' being hydrogen and n being 0

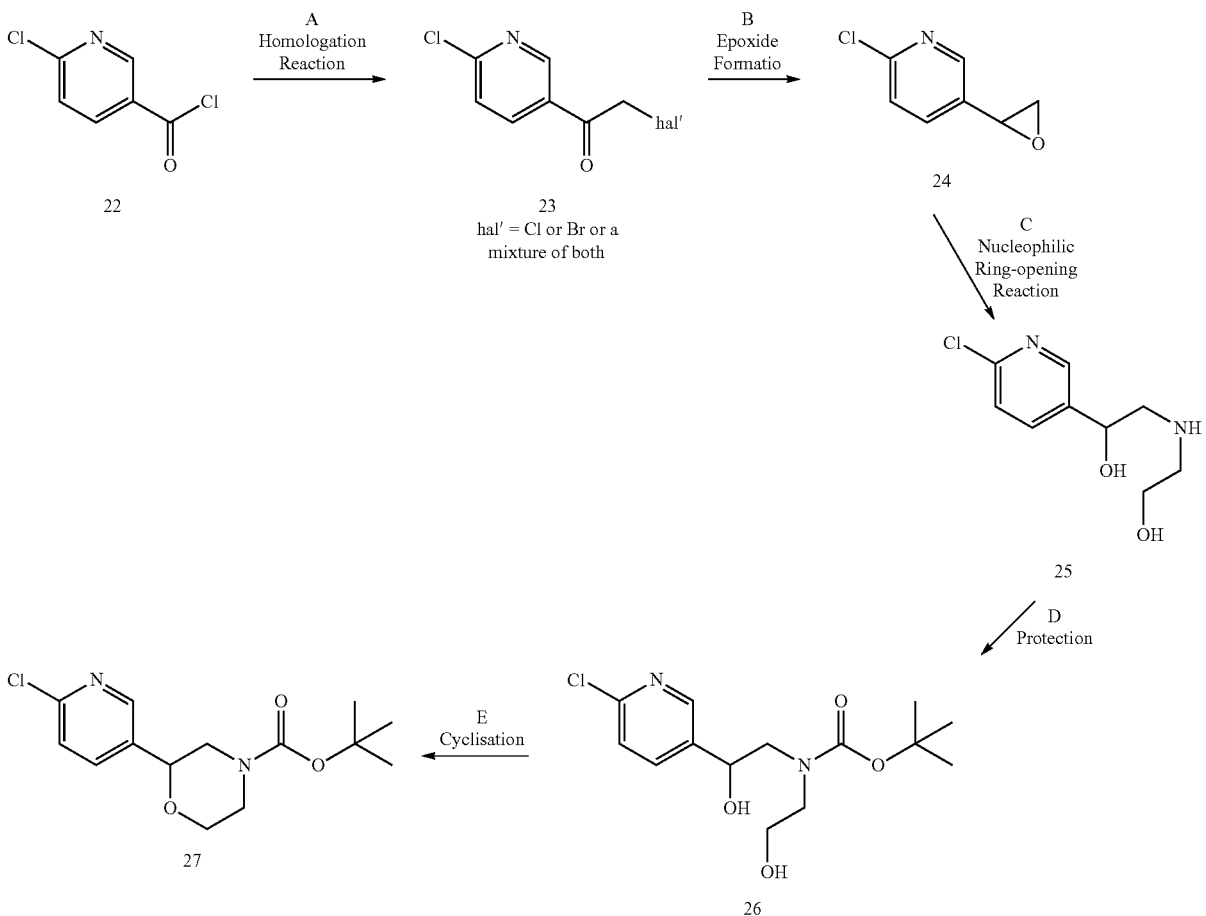

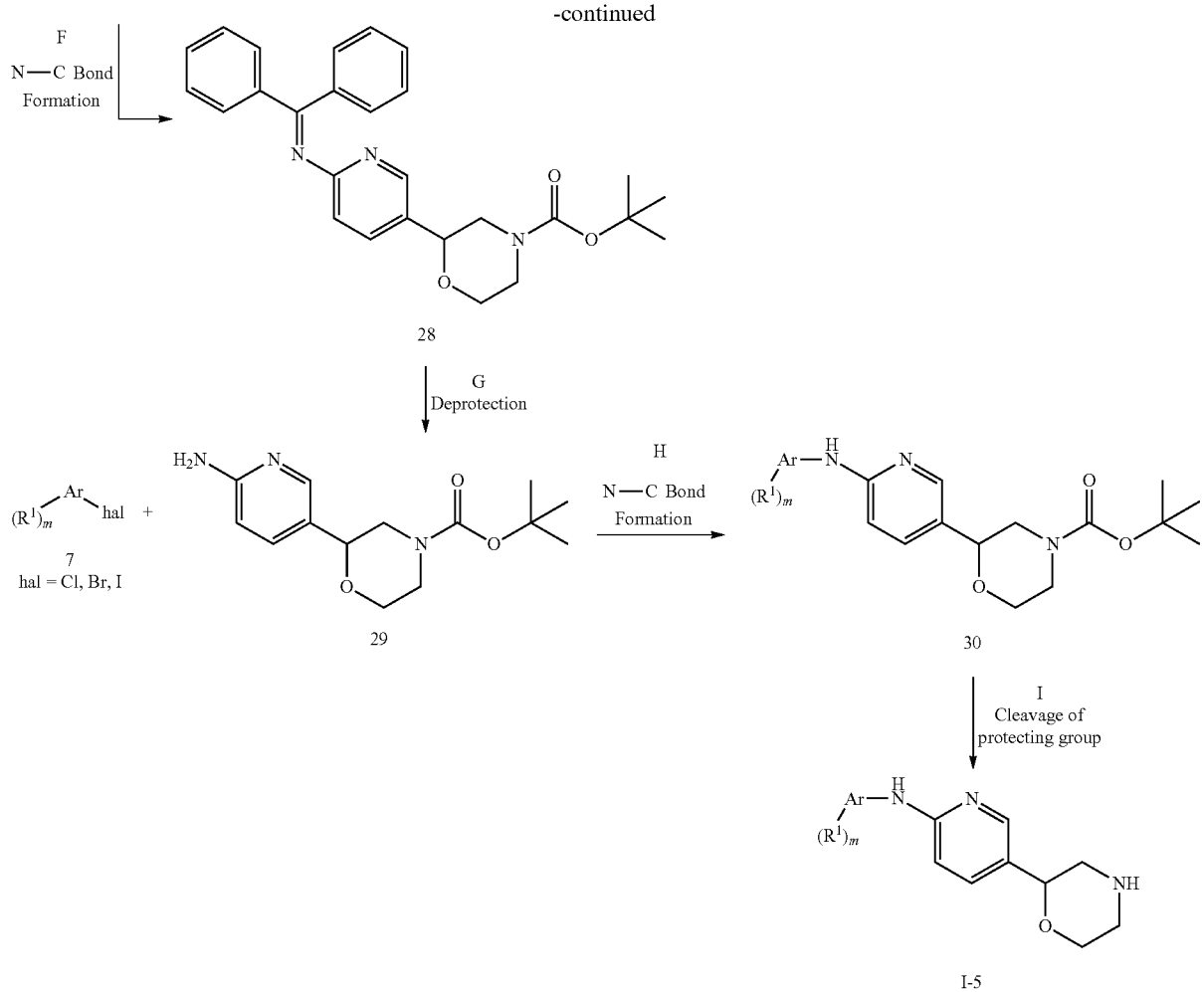

The substituents are as described above and X is O, Y is a bond, A is N, B is CH, R' is hydrogen and n is 0.

Step A:
Alpha-halo ketones 23 can be obtained by a homologation reaction of acyl chloride 22 [CAS 58757-38-3] involving sequential treatment first with (trimethylsilyl)diazomethane and then treatment with concentrated hydrobromic acid or hydrochloric acid. The reaction is carried out using a mixture of acetonitrile, THF and hexane as solvent at temperatures between 0° C. and room temperature.

Preferred conditions are mixing of reactants at 0-5° C. followed by allowing to react for 1 hour at room temperature for the first step, and mixing of reactants at 0-5° C. followed by allowing to react for 30 minutes at room temperature for the second step.

Step B:
Epoxide formation can be accomplished by a stepwise process involving reduction of alpha-halo ketones 23 by treatment with a reducing agent such as $NaBH_4$ or $LiBH_4$ in a solvent such as MeOH, EtOH, THF, dioxane, followed by cyclisation of the ensuing alpha-halo alcohol by treatment with a base such as sodium methoxide, sodium ethoxide, potassium tert-butoxide or caesium carbonate in the same solvent.

Preferred conditions are $NaBH_4$ in ethanol at 5° C. to room temperature for 1 hour followed by treatment with sodium methoxide at room temperature for 16 hours.

Step C:
Nucleophilic ring-opening can be accomplished by treatment of epoxide 24 with 2-aminoethanol, optionally in the presence of an organic base such as triethylamine, N,N-diisopropylethylamine or N-methylmorpholine in a non-protic polar organic solvent such as ether, THF, dioxane or TBME.

Preferred conditions are using excess 2-aminoethanol as base in THF at room temperature for 16 hours.

Step D:
Selective protection of the amino group of amino alcohol 25 can be effected by treatment with di-tert-butyl carbonate, optionally in the presence of an organic base such as triethylamine, N,N-diisopropylethylamine or N-methylmorpholine, in halogenated solvents such as dichloromethane or 1,2-dichloroethane or ethereal solvents such as diethyl ether, dioxane, THF or TBME.

Preferred conditions are THF in the absence of a base at room temperature for 16 hours.

Step E:
Cyclisation can be accomplished by a stepwise process involving sulphonate ester formation by treatment of diol 26 with one equivalent of methanesulfonyl chloride in the presence of an organic base such as triethylamine, N,N-diisopropylethylamine or N-methylmorpholine in ethereal solvents such as diethyl ether, dioxane, THF or TBME, followed by cyclisation by treatment with a non-nucleophilic base such as potassium tert-butoxide or potassium 2-methyl-2-butoxide in ethereal solvents such as diethyl ether, dioxane, THF or TBME.

Preferred conditions for the first step are triethylamine in THF mixing the reactants at 0-5° C. and then allowing to react for 2.5 hours at room temperature, then removal of the by-product triethylamine hydrochloride by filtration. Preferred conditions for the second step are potassium 2-methyl-2-butoxide in THF mixing the reactants at 0-5° C. and then allowing to react for 15 minutes at room temperature.

Step F:

C—N bond formation can be accomplished by treatment of 27 with benzophenone imine in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium(0), catalytic (R)-(+)-2,2'-bis(diphenylphosphino)-1,1'-binaphthyl and sodium tert-butoxide in dioxane at 100° C. for 16 hours.

Step G:

Removal of the nitrogen protecting group of 28 can be effected by hydrogenation with hydrogen under normal or elevated pressure or by transfer hydrogenation using ammonium formate or cyclohexadiene as hydrogen source with a catalyst such as $PtO_2$, Pd—C or Raney nickel in solvents such as MeOH, EtOH, $H_2O$, dioxane, THF, HOAc, EtOAc $CH_2Cl_2$, $CHCl_3$, DMF or mixtures thereof.

Preferred conditions are ammonium formate in the presence of palladium on charcoal in MeOH at 60° C. for 1 hour.

Step H:

C—N bond formation can be accomplished by treatment of an aryl halide 7 with aryl amine 29 in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium chloroform complex, catalytic 9,9-dimethyl-4,5-bis(diphenylphosphino)xanthene (xantphos) and caesium carbonate in dioxane in a sealed tube heated at 100° C. for 16 hours according to a modification of the procedure of van Leeuwen and co-workers (*Tetrahedron. Lett.* 1999, 40, 3789-3790).

Step I:

Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0 to 80° C.

Preferred conditions are $CF_3COOH$ in aqueous acetonitrile at 80° C. for 2 hours or 4 N HCl in dioxane and THF at 60° C. for 16 hours.

Scheme 7

For X being O, Y being a bond, A being C-alkyl, B being N and n being 0

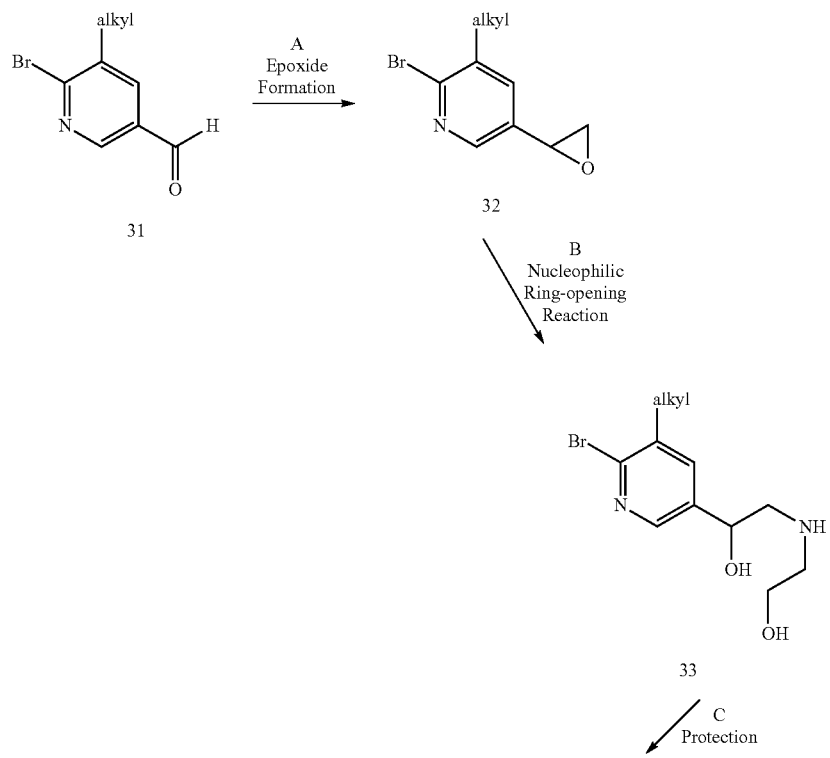

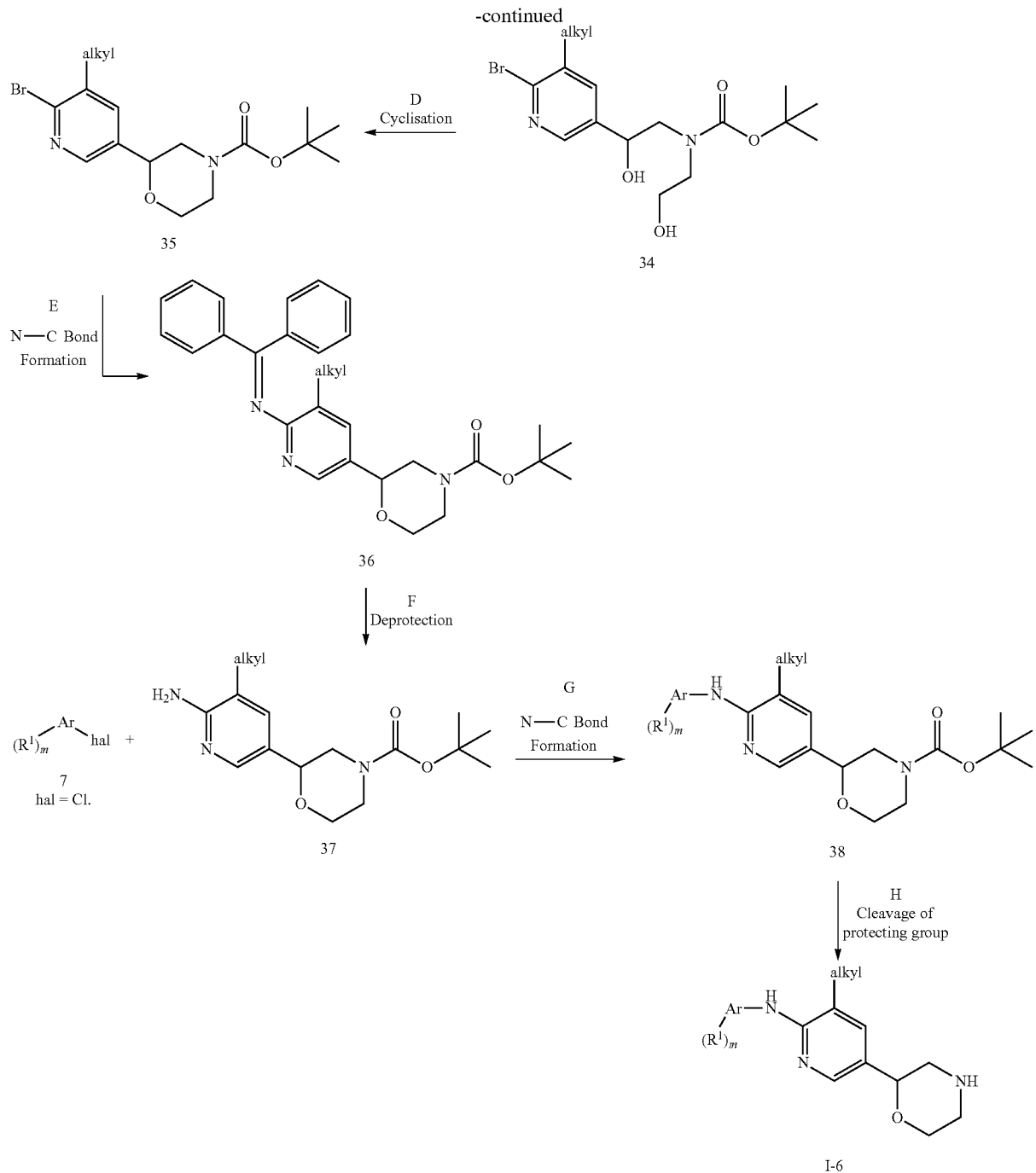

The substituents are as described above and X is O, Y is a bond, A is C-alkyl, B is N, R' is hydrogen and n is 0.

Step A:
Epoxide formation can be accomplished by a Corey-Tchaikovsky reaction of aldehydes 31 [e.g. alkyl=methyl, CAS 885167-81-7] by treatment with trimethylsulfonium iodide in the presence of a base such as sodium hydride in a non-protic polar organic solvent such as DMSO or DMF.

Preferred conditions are sodium hydride in DMSO at 0° C. for 30 minutes and then at room temperature for 16 hours.

Step B:
Nucleophilic ring-opening can be accomplished by treatment of epoxide 32 with 2-aminoethanol, optionally in the presence of an organic base such as triethylamine, N,N-diisopropylethylamine or N-methylmorpholine in a non-protic polar organic solvent such as ether, THF, dioxane or TBME. Preferred conditions are using excess 2-aminoethanol as base in THF at room temperature for 16 hours.

Step C:
Selective protection of the amino group of amino alcohol 33 can be effected by treatment with di-tert-butyl carbonate, optionally in the presence of an organic base such as triethylamine, N,N-diisopropylethylamine or N-methylmorpholine, in halogenated solvents such as dichloromethane or 1,2-dichloroethane or ethereal solvents such as diethyl ether, dioxane, THF or TBME.

Preferred conditions are THF in the absence of a base at room temperature for 7 hours.

Step D:

Cyclisation can be accomplished by a stepwise process involving sulphonate ester formation by treatment of diol 34 with one equivalent of methanesulfonyl chloride in the presence of an organic base such as triethylamine, N,N-diisopropylethylamine or N-methylmorpholine in ethereal solvents such as diethyl ether, dioxane, THF or TBME, followed by cyclisation by treatment with a non-nucleophilic base such as potassium tert-butoxide or potassium 2-methyl-2-butoxide in ethereal solvents such as diethyl ether, dioxane, THF or TBME.

Preferred conditions for the first step are triethylamine in THF mixing the reactants at 0-5° C. and then allowing to react for 15 minutes at room temperature, then removal of the by-product triethylamine hydrochloride by filtration. Preferred conditions for the second step are potassium 2-methyl-2-butoxide in THF mixing the reactants at 0-5° C. and then allowing to react for 10 minutes at room temperature.

Step E:

C—N bond formation can be accomplished by treatment of 35 with benzophenone imine in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium(0), catalytic (R)-(+)-2,2'-bis(diphenylphosphino)-1,1'-binaphthyl and sodium tert-butoxide in dioxane at 100° C. for 16 hours.

Step F:

Removal of the nitrogen protecting group of 36 can be effected by hydrogenation with hydrogen under normal or elevated pressure or by transfer hydrogenation using ammonium formate or cyclohexadiene as hydrogen source with a catalyst such as $PtO_2$, Pd—C or Raney nickel in solvents such as MeOH, EtOH, $H_2O$, dioxane, THF, HOAc, EtOAc $CH_2Cl_2$, $CHCl_3$, DMF or mixtures thereof.

Preferred conditions are ammonium formate in the presence of palladium on charcoal in MeOH at 80° C. for 2 hours.

Step G:

C—N bond formation can be accomplished by treatment of an aryl halide 7 with aryl amine 37 in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium chloroform complex, catalytic 9,9-dimethyl-4,5-bis(diphenylphosphino)xanthene (xantphos)and caesium carbonate in dioxane in a sealed tube heated at 100° C. for 16 hours according to a modification of the procedure of van Leeuwen and co-workers (*Tetrahedron. Lett.* 1999, 40, 3789-3790).

Step H:

Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0 to 80° C. Preferred conditions are $CF_3COOH$ in aqueous acetonitrile at 80° C. for 3 hours or 4 N HCl in dioxane and THF at 60° C. for 16 hours.

Scheme 8

For X being O, Y being a bond, A being C—F, B being CH, R' being hydrogen and n being 0

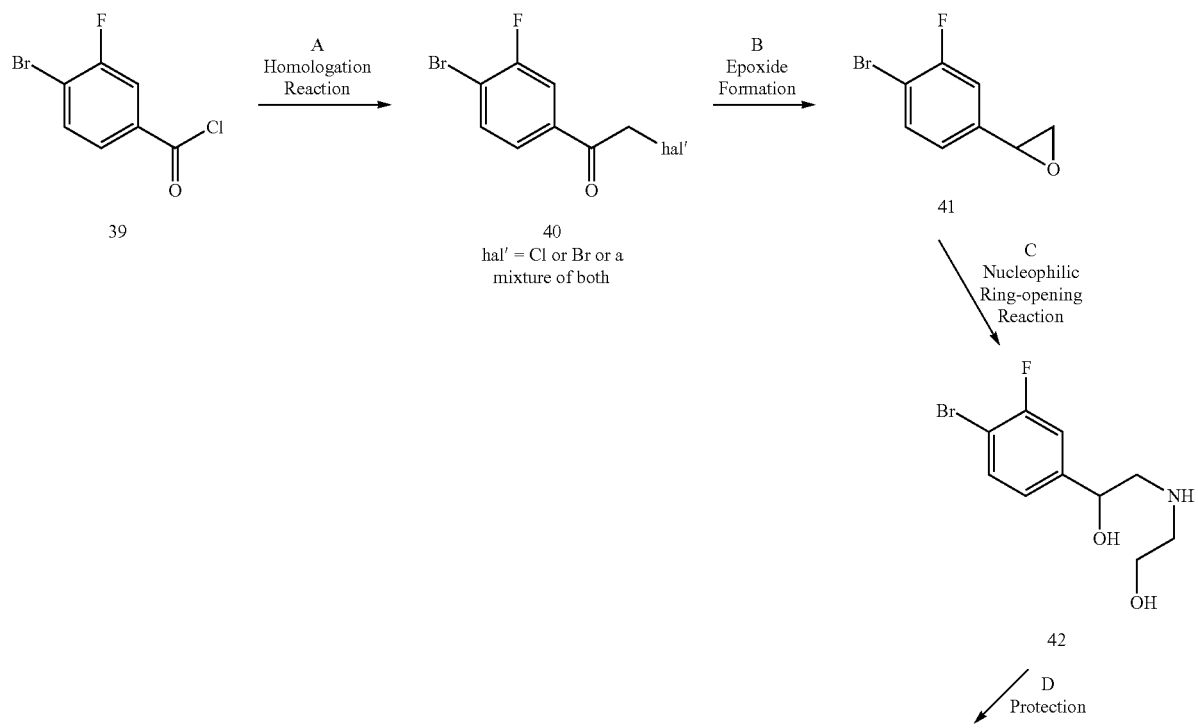

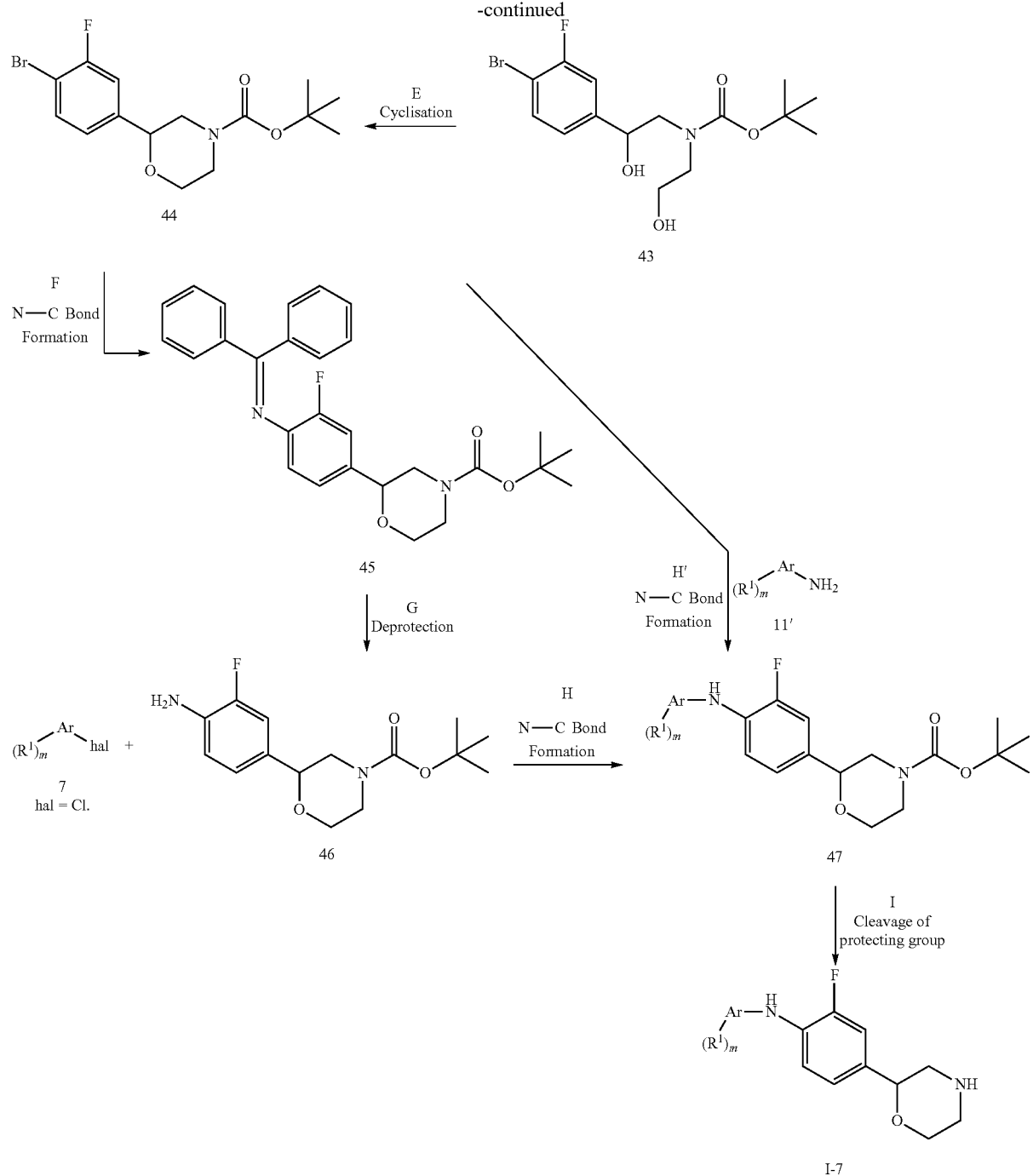

The substituents are as described above and X is O, Y is a bond, A is C—F, B is CH, R' is hydrogen and n is 0.

Step A:

Alpha-halo ketones 40 can be obtained by a homologation reaction of acyl chloride 39 [CAS 695188-21-7] involving sequential treatment first with (trimethylsilyl)diazomethane and then treatment with concentrated hydrobromic acid or hydrochloric acid. The reaction is carried out using a mixture of acetonitrile, THF and hexane as solvent at temperatures between 0° C. and room temperature.

Preferred conditions are mixing of reactants at 0-5° C. followed by allowing to react for 30 minutes at room temperature for the first step, and mixing of reactants at 0-5° C. followed by allowing to react for 1 hour at room temperature for the second step.

Step B:

Epoxide formation can be accomplished by a stepwise process involving reduction of alpha-halo ketones 40 by treatment with a reducing agent such as $NaBH_4$ or $LiBH_4$ in a solvent such as MeOH, EtOH, THF, dioxane, followed by cyclisation of the ensuing alpha-halo alcohol by treatment with a base such as sodium methoxide, sodium ethoxide, potassium tert-butoxide or caesium carbonate in the same solvent.

Preferred conditions are NaBH$_4$ in ethanol at 5° C. to room temperature for 1 hour followed by treatment with sodium methoxide at room temperature for 16 hours amd then at 40° C. for 1 hour.

Step C:

Nucleophilic ring-opening can be accomplished by treatment of epoxide 41 with 2-aminoethanol, optionally in the presence of an organic base such as triethylamine, N,N-diisopropylethylamine or N-methylmorpholine in a non-protic polar organic solvent such as ether, THF, dioxane or TBME.

Preferred conditions are using excess 2-aminoethanol as base in THF at room temperature for 16 hours.

Step D:

Selective protection of the amino group of amino alcohol 42 can be effected by treatment with di-tert-butyl carbonate, optionally in the presence of an organic base such as triethylamine, N,N-diisopropylethylamine or N-methylmorpholine, in halogenated solvents such as dichloromethane or 1,2-dichloroethane or ethereal solvents such as diethyl ether, dioxane, THF or TBME.

Preferred conditions are dichloromethane in the absence of a base at room temperature for 16 hours.

Step E:

Cyclisation can be accomplished by a stepwise process involving sulphonate ester formation by treatment of diol 43 with one equivalent of methanesulfonyl chloride in the presence of an organic base such as triethylamine, N,N-diisopropylethylamine or N-methylmorpholine in ethereal solvents such as diethyl ether, dioxane, THF or TBME, followed by cyclisation by treatment with a non-nucleophilic base such as potassium tert-butoxide or potassium 2-methyl-2-butoxide in ethereal solvents such as diethyl ether, dioxane, THF or TBME.

Preferred conditions for the first step are triethylamine in THF mixing the reactants at 0-5° C. and then allowing to react for 30 minutes at room temperature, then removal of the by-product triethylamine hydrochloride by filtration. Preferred conditions for the second step are potassium 2-methyl-2-butoxide in THF mixing the reactants at 0-5° C. and then allowing to react for 1 hour at room temperature.

Step F:

C—N bond formation can be accomplished by treatment of 44 with benzophenone imine in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium(0), catalytic (R)-(+)-2,2'-bis(diphenylphosphino)-1,1'-binaphthyl and sodium tert-butoxide in dioxane at 100° C. for 1 hour.

Step G:

Removal of the nitrogen protecting group of 45 can be effected by hydrogenation with hydrogen under normal or elevated pressure or by transfer hydrogenation using ammonium formate or cyclohexadiene as hydrogen source with a catalyst such as PtO$_2$, Pd—C or Raney nickel in solvents such as MeOH, EtOH, H$_2$O, dioxane, THF, HOAc, EtOAc CH$_2$Cl$_2$, CHCl$_3$, DMF or mixtures thereof.

Preferred conditions are ammonium formate in the presence of palladium on charcoal in MeOH at 60° C. for 1 hour.

Step H:

C—N bond formation can be accomplished by treatment of an aryl halide 7 with aryl amine 46 in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium chloroform complex, catalytic 9,9-dimethyl-4,5-bis(diphenylphosphino)xanthene (xantphos)and caesium carbonate in dioxane in a sealed tube heated at 120° C. for 2 hours according to a modification of the procedure of van Leeuwen and co-workers (*Tetrahedron. Lett.* 1999, 40, 3789-3790).

Step H':

C—N bond formation to afford bi-aryl amine 47 can alternatively be accomplished directly from aryl bromide 44 by treatment of aryl bromide 44 with an aryl amine 11' in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium(0), catalytic 2-di-tert-butylphosphino-2', 4',6'-triisopropylbiphenyl and sodium tert-butoxide in dioxane at 120° C. for 16 hours.

Step I:

Removal of the BOC N-protecting group can be effected with mineral acids such as HCl, H$_2$SO$_4$ or H$_3$PO$_4$ or organic acids such as CF$_3$COOH, CHCl$_2$COOH, HOAc or p-toluenesulfonic acid in solvents such as CH$_2$Cl$_2$, CHCl$_3$, THF, MeOH, EtOH or H$_2$O at 0 to 80° C.

Preferred conditions are CF$_3$COOH in aqueous acetonitrile at 80° C. for 3 hours or 4 N HCl in dioxane and THF at 60° C. for 16 hours.

Scheme 9

For X being O, Y being a bond, A being C—Cl, B being CH, R' being hydrogen and n being 0

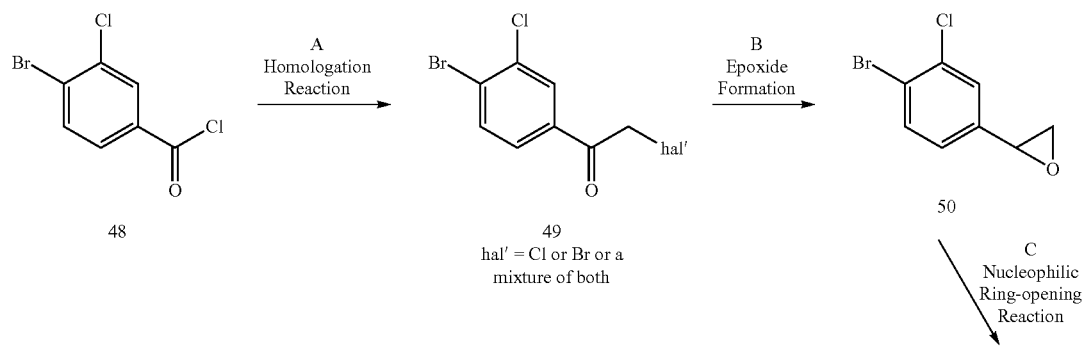

-continued
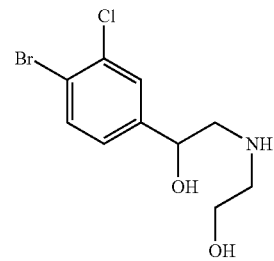
51
↓ D
Protection
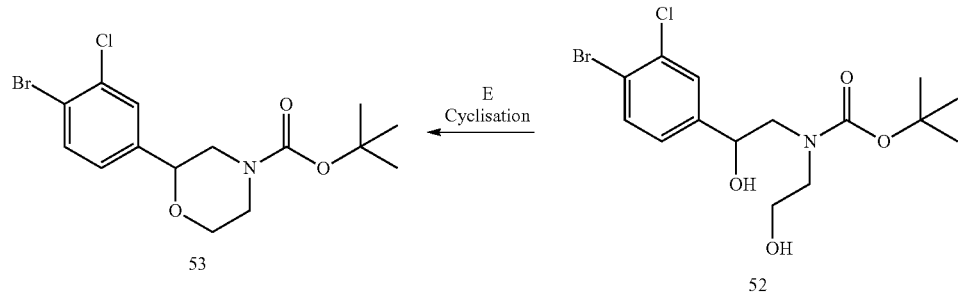
F
N—C Bond
Formation
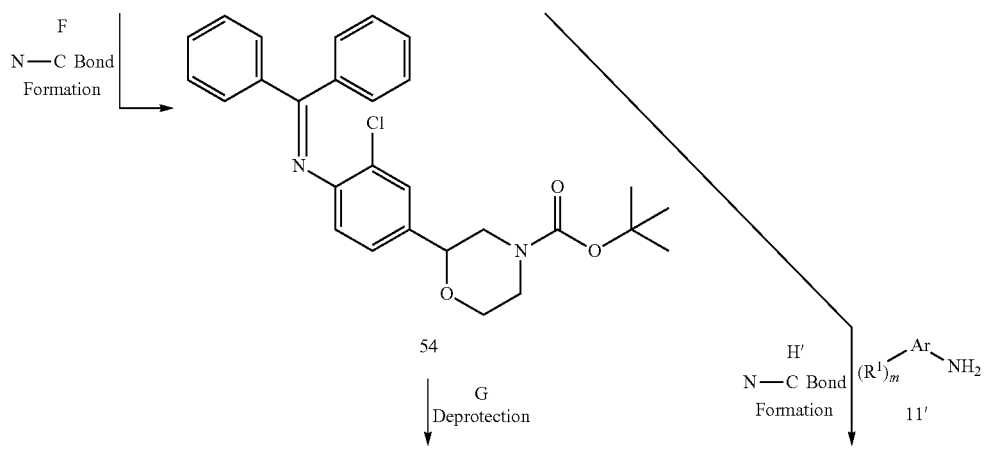
54
↓ G
Deprotection
H'
N—C Bond
Formation
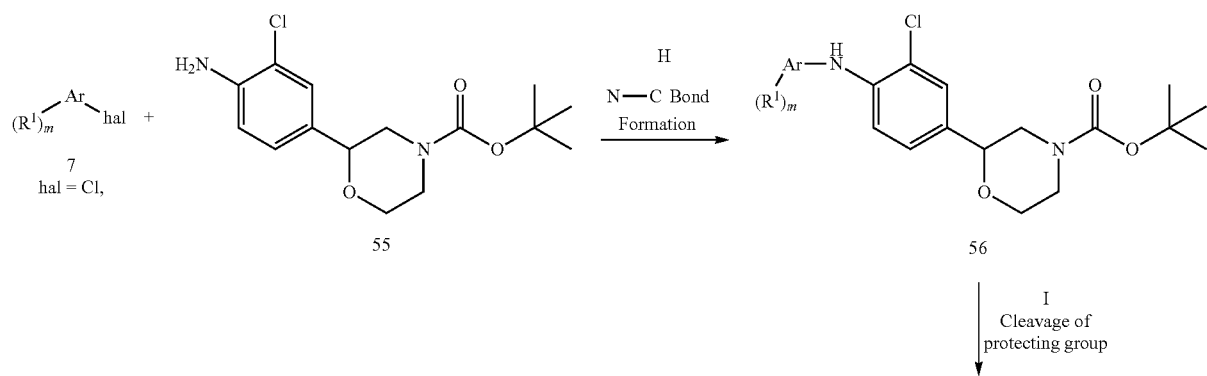
↓ I
Cleavage of
protecting group

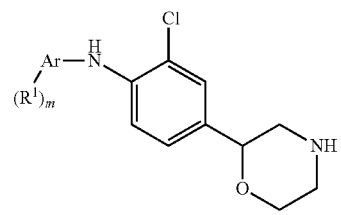

I-8

The substituents are as described above and X is O, Y is a bond, A is C—Cl, B is CH, R' is hydrogen and n is 0.

Step A:

Alpha-halo ketones 49 can be obtained by a homologation reaction of acyl chloride 48 [CAS 21900-32-3] involving sequential treatment first with (trimethylsilyl)diazomethane and then treatment with concentrated hydrobromic acid or hydrochloric acid. The reaction is carried out using a mixture of acetonitrile, THF and hexane as solvent at temperatures between 0° C. and room temperature.

Preferred conditions are mixing of reactants at 0-5° C. followed by allowing to react for 30 minutes at room temperature for the first step, and mixing of reactants at 0-5° C. followed by allowing to react for 30 min at room temperature for the second step.

Step B:

Epoxide formation can be accomplished by a stepwise process involving reduction of alpha-halo ketones 49 by treatment with a reducing agent such as $NaBH_4$ or $LiBH_4$ in a solvent such as MeOH, EtOH, THF, dioxane, followed by cyclisation of the ensuing alpha-halo alcohol by treatment with a base such as sodium methoxide, sodium ethoxide, potassium tert-butoxide or caesium carbonate in the same solvent.

Preferred conditions are $NaBH_4$ in ethanol at 5° C. to room temperature for 90 minutes followed by treatment with sodium methoxide at 50° C. for 4 hours.

Step C:

Nucleophilic ring-opening can be accomplished by treatment of epoxide 50 with 2-aminoethanol, optionally in the presence of an organic base such as triethylamine, N,N-diisopropylethylamine or N-methylmorpholine in a non-protic polar organic solvent such as ether, THF, dioxane or TBME.

Preferred conditions are using excess 2-aminoethanol as base in THF at room temperature for 7 hours.

Step D:

Selective protection of the amino group of amino alcohol 51 can be effected by treatment with di-tert-butyl carbonate, optionally in the presence of an organic base such as triethylamine, N,N-diisopropylethylamine or N-methylmorpholine, in halogenated solvents such as dichloromethane or 1,2-dichloroethane or ethereal solvents such as diethyl ether, dioxane, THF or TBME.

Preferred conditions are dichloromethane in the absence of a base at room temperature for 16 hours.

Step E:

Cyclisation can be accomplished by a stepwise process involving sulphonate ester formation by treatment of diol 52 with one equivalent of methanesulfonyl chloride in the presence of an organic base such as triethylamine, N,N-diisopropylethylamine or N-methylmorpholine in ethereal solvents such as diethyl ether, dioxane, THF or TBME, followed by cyclisation by treatment with a non-nucleophilic base such as potassium tert-butoxide or potassium 2-methyl-2-butoxide in ethereal solvents such as diethyl ether, dioxane, THF or TBME.

Preferred conditions for the first step are triethylamine in THF mixing the reactants at 0-5° C. and then allowing to react for 1 hour at room temperature, then removal of the by-product triethylamine hydrochloride by filtration. Preferred conditions for the second step are potassium 2-methyl-2-butoxide in THF mixing the reactants at 0-5° C. and then allowing to react for 30 minutes at room temperature.

Step F:

C—N bond formation can be accomplished by treatment of 53 with benzophenone imine in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium(0), catalytic (R)-(+)-2,2'-bis(diphenylphosphino)-1,1'-binaphthyl and sodium tert-butoxide in dioxane at 90° C. for 16 hours.

Step G:

Removal of the nitrogen protecting group of 54 can be effected by treatment with hydroxylamine hydrochloride in the presence of a base such as sodium acetate or sodium methoxide in solvents such as MeOH, EtOH, $H_2O$, dioxane, THF, HOAc, EtOAc $CH_2Cl_2$, $CHCl_3$, DMF or mixtures thereof Preferred conditions are hydroxylamine hydrochloride in the presence of sodium acetate in MeOH at 60° C. for 1 hour.

Step H:

C—N bond formation can be accomplished by treatment of an aryl halide 7 with aryl amine 55 in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium chloroform complex, catalytic 9,9-dimethyl-4,5-bis(diphenylphosphino)xanthene (xantphos)and caesium carbonate in dioxane in a sealed tube heated at 120° C. for 16 hours according to a modification of the procedure of van Leeuwen and co-workers (*Tetrahedron. Lett.* 1999, 40, 3789-3790).

Step H':

C—N bond formation to afford bi-aryl amine 56 can alternatively be accomplished directly from aryl bromide 53 by treatment of aryl bromide 53 with an aryl amine 11' in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium(0), catalytic 2-di-tert-butylphosphino-2',4',6'-triisopropylbiphenyl and sodium tert-butoxide in dioxane at 120° C. for 16 hours.

Step I:

Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0 to 80° C. Preferred conditions are $CF_3COOH$ in aqueous acetonitrile at 80° C. for 3 hours or 4 N HCl in dioxane and THF at 60° C. for 16 hours.

Scheme 10

For X being O, Y being a bond, A being CH, R' being F, B being CH and n being 0

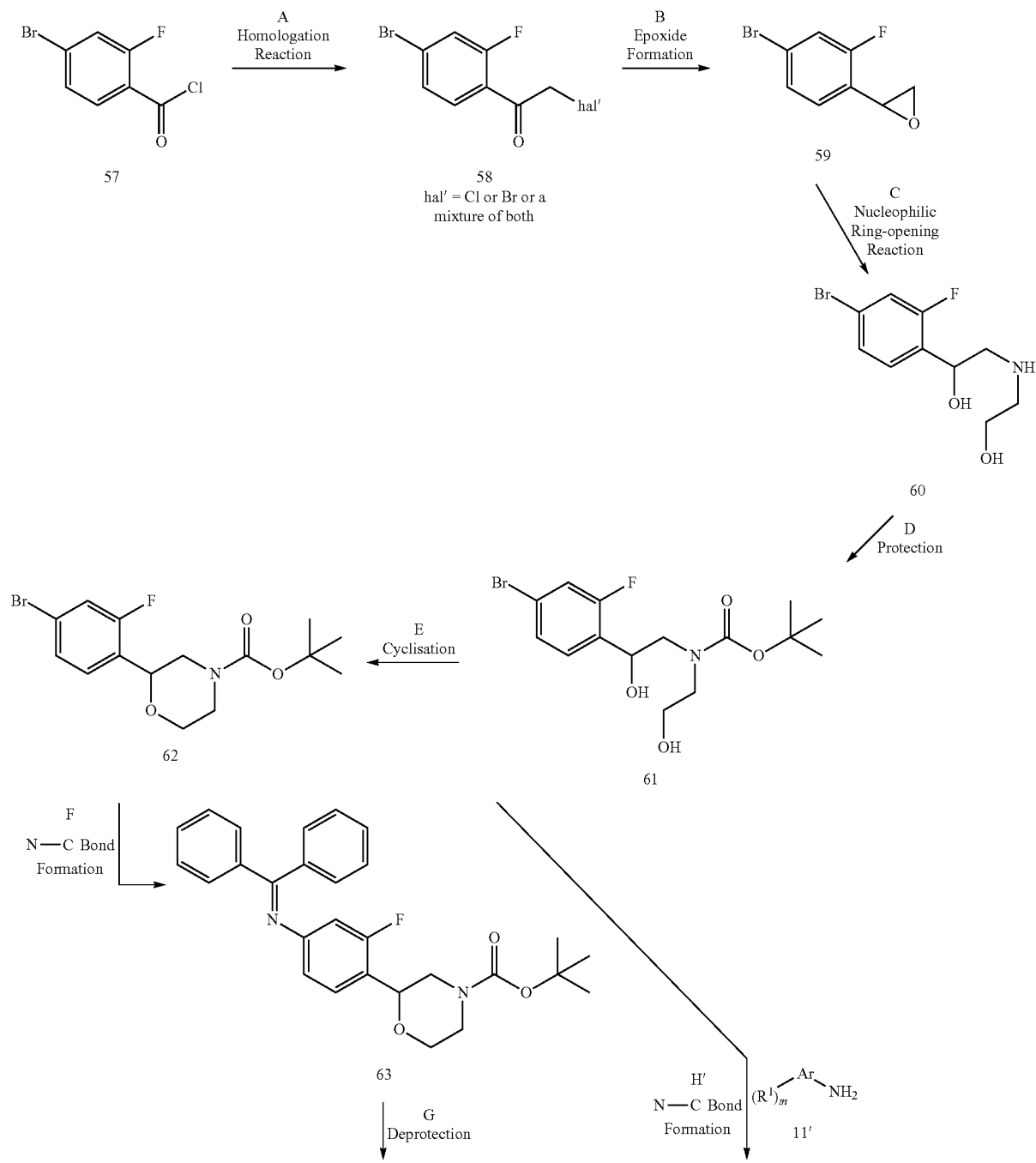

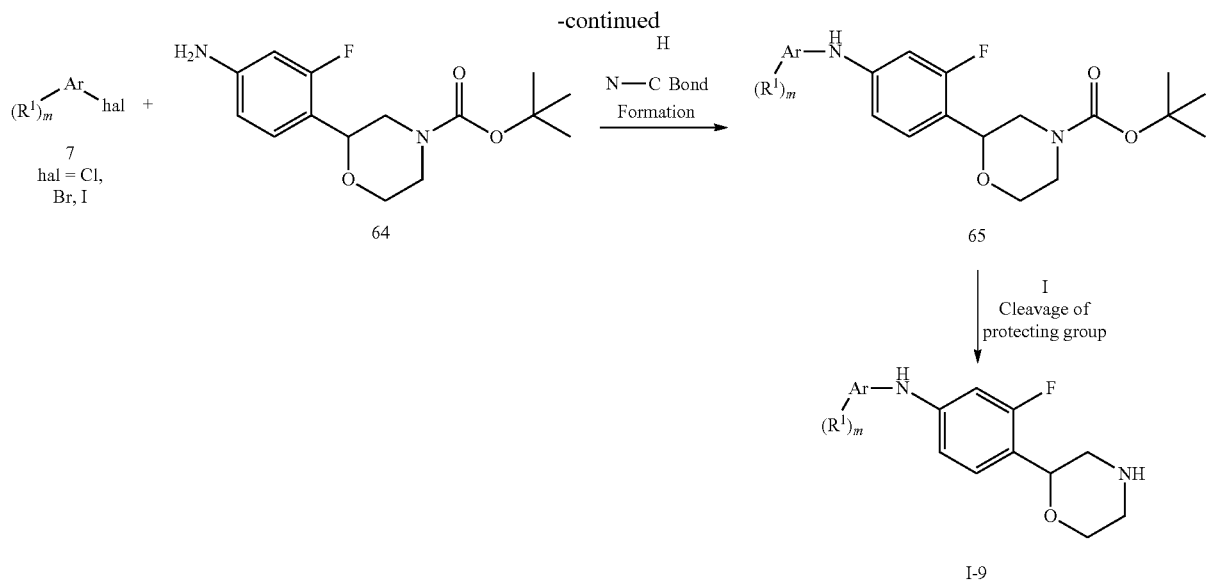

The substituents are as described above and X is O, Y is a bond, A is CH, R' is F, B is CH and n is 0.

Step A:
Alpha-halo ketones 58 can be obtained by a homologation reaction of acyl chloride 57 [CAS 151982-51-3] involving sequential treatment first with (trimethylsilyl)diazomethane and then treatment with concentrated hydrobromic acid or hydrochloric acid. The reaction is carried out using a mixture of acetonitrile, THF and hexane as solvent at temperatures between 0° C. and room temperature.

Preferred conditions are mixing of reactants at 0-5° C. followed by allowing to react for 30 minutes at room temperature for the first step, and mixing of reactants at 0-5° C. followed by allowing to react for 1 hour at room temperature for the second step.

Step B:
Epoxide formation can be accomplished by a stepwise process involving reduction of alpha-halo ketones 58 by treatment with a reducing agent such as $NaBH_4$ or $LiBH_4$ in a solvent such as MeOH, EtOH, THF, dioxane, followed by cyclisation of the ensuing alpha-halo alcohol by treatment with a base such as sodium methoxide, sodium ethoxide, potassium tert-butoxide or caesium carbonate in the same solvent.

Preferred conditions are $NaBH_4$ in ethanol at 5° C. to room temperature for 1 hour followed by treatment with sodium methoxide at room temperature for 16 hours.

Step C:
Nucleophilic ring-opening can be accomplished by treatment of epoxide 59 with 2-aminoethanol, optionally in the presence of an organic base such as triethylamine, N,N-diisopropylethylamine or N-methylmorpholine in a non-protic polar organic solvent such as ether, THF, dioxane or TBME.

Preferred conditions are using excess 2-aminoethanol as base in THF at room temperature for 16 hours.

Step D:
Selective protection of the amino group of amino alcohol 60 can be effected by treatment with di-tert-butyl carbonate, optionally in the presence of an organic base such as triethylamine, N,N-diisopropylethylamine or N-methylmorpholine, in halogenated solvents such as dichloromethane or 1,2-dichloroethane or ethereal solvents such as diethyl ether, dioxane, THF or TBME.

Preferred conditions are dichloromethane in the absence of a base at room temperature for 16 hours.

Step E:
Cyclisation can be accomplished by a stepwise process involving sulphonate ester formation by treatment of diol 61 with one equivalent of methanesulfonyl chloride in the presence of an organic base such as triethylamine, N,N-diisopropylethylamine or N-methylmorpholine in ethereal solvents such as diethyl ether, dioxane, THF or TBME, followed by cyclisation by treatment with a non-nucleophilic base such as potassium tert-butoxide or potassium 2-methyl-2-butoxide in ethereal solvents such as diethyl ether, dioxane, THF or TBME.

Preferred conditions for the first step are triethylamine in THF mixing the reactants at 0-5° C. and then allowing to react for 1 hour at room temperature, then removal of the by-product triethylamine hydrochloride by filtration. Preferred conditions for the second step are potassium 2-methyl-2-butoxide in THF mixing the reactants at 0-5° C. and then allowing to react for 20 minutes at room temperature.

Step F:
C—N bond formation can be accomplished by treatment of 62 with benzophenone imine in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium(0), catalytic (R)-(+)-2,2'-bis(diphenylphosphino)-1,1'-binaphthyl and sodium tert-butoxide in dioxane at 90° C. for 90 minutes.

Step G:
Removal of the nitrogen protecting group of 63 can be effected by treatment with hydroxylamine hydrochloride in the presence of a base such as sodium acetate or sodium methoxide in solvents such as MeOH, EtOH, $H_2O$, dioxane, THF, HOAc, EtOAc $CH_2Cl_2$, $CHCl_3$, DMF or mixtures thereof.

Preferred conditions are hydroxylamine hydrochloride in the presence of sodium acetate in MeOH at 50° C. for 16 hours.

Step H:

C—N bond formation can be accomplished by treatment of an aryl halide 7 with aryl amine 64 in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium chloroform complex, catalytic 9,9-dimethyl-4,5-bis(diphenylphosphino)xanthene (xantphos)and caesium carbonate in dioxane in a sealed tube heated at 120° C. for 3 hours according to a modification of the procedure of van Leeuwen and co-workers (*Tetrahedron. Lett.* 1999, 40, 3789-3790).

Step H':

C—N bond formation to afford bi-aryl amine 56 can alternatively be accomplished directly from aryl bromide 53 by treatment of aryl bromide 53 with an aryl amine 11' in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium(0), catalytic 2-di-tert-butylphosphino-2', 4',6'-triisopropylbiphenyl and sodium tert-butoxide in dioxane at 100° C. for 2 hours.

Step I:

Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0 to 80° C. Preferred conditions are $CF_3COOH$ in aqueous acetonitrile at 80° C. for 16 hours or 4 N HCl in dioxane and THF at 60° C. for 16 hours.

Scheme 11

For X being O, Y being a bond, A being CH, R' being Cl, B being CH and n being 0

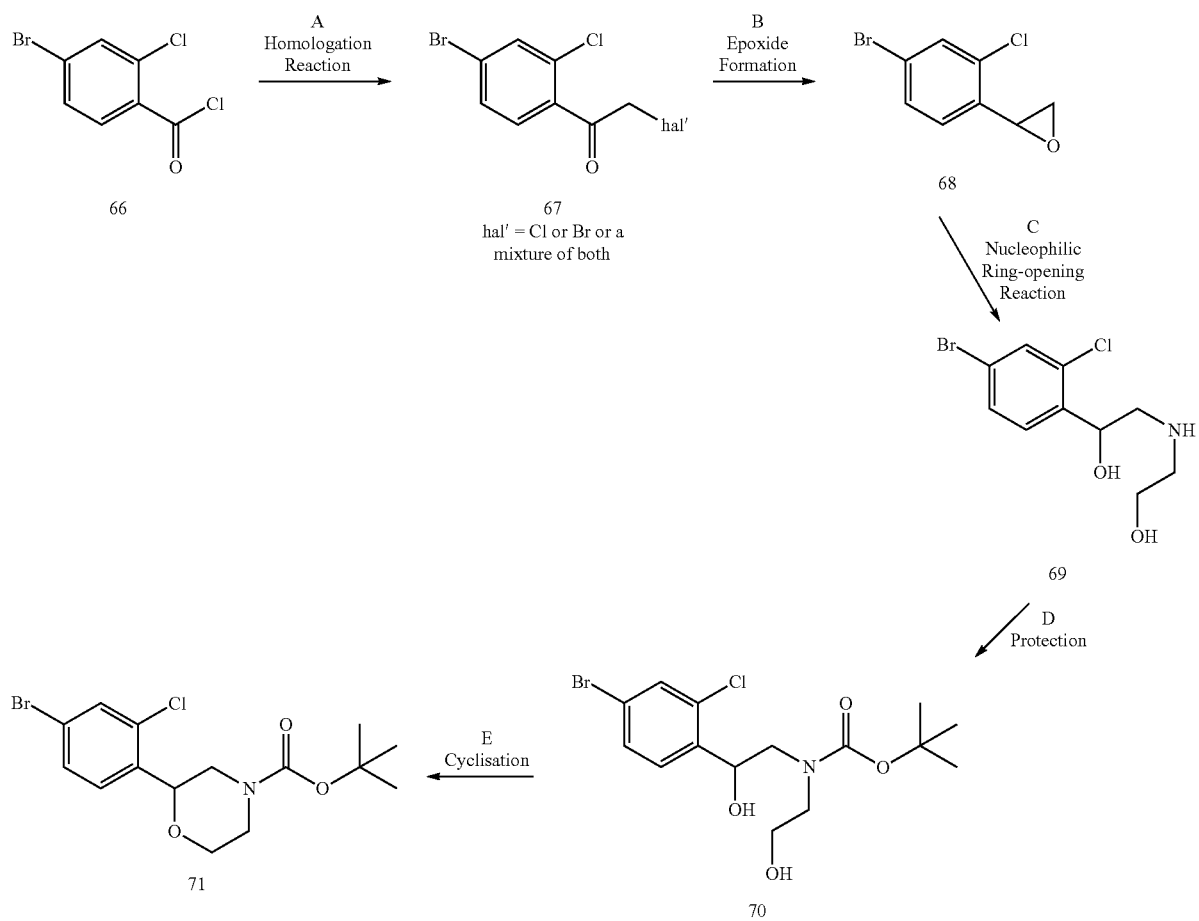

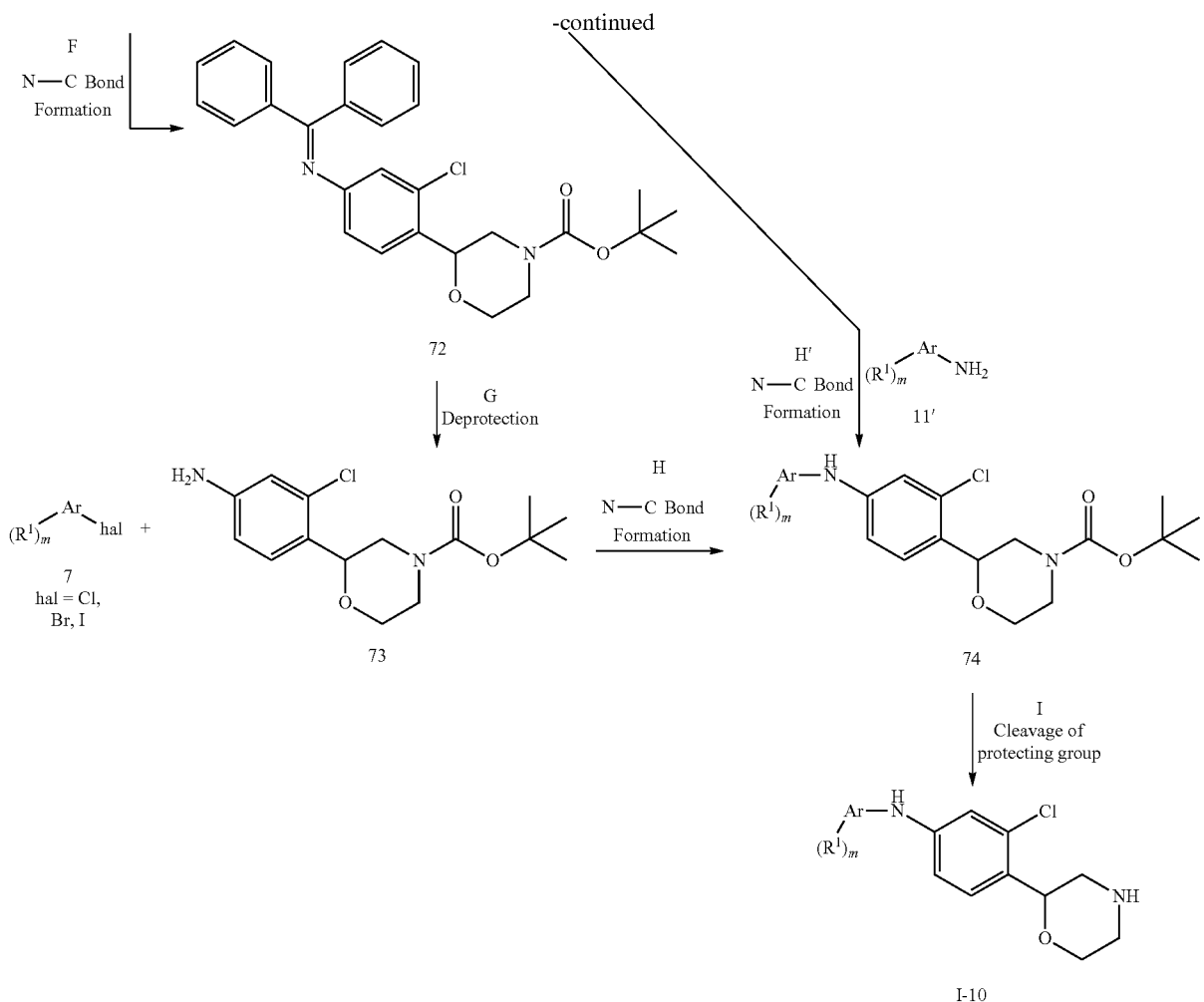

The substituents are as described above and X is O, Y is a bond, A is CH, R' is Cl, B is CH and n is 0.

Step A:

Alpha-halo ketones 67 can be obtained by a homologation reaction of acyl chloride 66 [CAS 21900-55-0] involving sequential treatment first with (trimethylsilyl)diazomethane and then treatment with concentrated hydrobromic acid or hydrochloric acid. The reaction is carried out using a mixture of acetonitrile, THF and hexane as solvent at temperatures between 0° C. and room temperature.

Preferred conditions are mixing of reactants at 0-5° C. followed by allowing to react for 30 minutes at room temperature for the first step, and mixing of reactants at 0-5° C. followed by allowing to react for 30 min at room temperature for the second step.

Step B:

Epoxide formation can be accomplished by a stepwise process involving reduction of alpha-halo ketones 67 by treatment with a reducing agent such as $NaBH_4$ or $LiBH_4$ in a solvent such as MeOH, EtOH, THF, dioxane, followed by cyclisation of the ensuing alpha-halo alcohol by treatment with a base such as sodium methoxide, sodium ethoxide, potassium tert-butoxide or caesium carbonate in the same solvent.

Preferred conditions are $NaBH_4$ in ethanol at 5° C. to room temperature for 90 minutes followed by treatment with sodium methoxide at 50° C. for 4 hours.

Step C:

Nucleophilic ring-opening can be accomplished by treatment of epoxide 68 with 2-aminoethanol, optionally in the presence of an organic base such as triethylamine, N,N-diisopropylethylamine or N-methylmorpholine in a non-protic polar organic solvent such as ether, THF, dioxane or TBME.

Preferred conditions are using excess 2-aminoethanol as base in THF at room temperature for 7 hours.

Step D:

Selective protection of the amino group of amino alcohol 69 can be effected by treatment with di-tert-butyl carbonate, optionally in the presence of an organic base such as triethylamine, N,N-diisopropylethylamine or N-methylmorpholine, in halogenated solvents such as dichloromethane or 1,2-dichloroethane or ethereal solvents such as diethyl ether, dioxane, THF or TBME.

Preferred conditions are dichloromethane in the absence of a base at room temperature for 16 hours.

Step E:

Cyclisation can be accomplished by a stepwise process involving sulphonate ester formation by treatment of diol 70 with one equivalent of methanesulfonyl chloride in the presence of an organic base such as triethylamine, N,N-diisopropylethylamine or N-methylmorpholine in ethereal solvents such as diethyl ether, dioxane, THF or TBME, followed by cyclisation by treatment with a non-nucleophilic base such as potassium tert-butoxide or potassium 2-methyl-2-butoxide in ethereal solvents such as diethyl ether, dioxane, THF or TBME.

Preferred conditions for the first step are triethylamine in THF mixing the reactants at 0-5° C. and then allowing to react for 1 hour at room temperature, then removal of the by-product triethylamine hydrochloride by filtration. Preferred conditions for the second step are potassium 2-methyl-2-butoxide in THF mixing the reactants at 0-5° C. and then allowing to react for 30 minutes at room temperature.

Step F:

C—N bond formation can be accomplished by treatment of 71 with benzophenone imine in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium(0), catalytic (R)-(+)-2,2'-bis(diphenylphosphino)-1,1'-binaphthyl and sodium tert-butoxide in dioxane at 90° C. for 16 hours.

Step G:

Removal of the nitrogen protecting group of 72 can be effected by treatment with hydroxylamine hydrochloride in the presence of a base such as sodium acetate or sodium methoxide in solvents such as MeOH, EtOH, $H_2O$, dioxane, THF, HOAc, EtOAc $CH_2Cl_2$, $CHCl_3$, DMF or mixtures thereof.

Preferred conditions are hydroxylamine hydrochloride in the presence of sodium acetate in MeOH at 60° C. for 1 hour.

Step H:

C—N bond formation can be accomplished by treatment of an aryl halide 7 with aryl amine 73 in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium chloroform complex, catalytic 9,9-dimethyl-4,5-bis(diphenylphosphino)xanthene (xantphos)and caesium carbonate in dioxane in a sealed tube heated at 120° C. for 16 hours according to a modification of the procedure of van Leeuwen and co-workers (*Tetrahedron. Lett.* 1999, 40, 3789-3790).

Step H':

C—N bond formation to afford bi-aryl amine 74 can alternatively be accomplished directly from aryl bromide 71 by treatment of aryl bromide 71 with an aryl amine 11' in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium(0), catalytic 2-di-tert-butylphosphino-2',4',6'-triisopropylbiphenyl and sodium tert-butoxide in dioxane at 100° C. for 2 hours.

Step I:

Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0 to 80° C.

Preferred conditions are $CF_3COOH$ in aqueous acetonitrile at 80° C. for 3 hours or 4 N HCl in dioxane and THF at 60° C. for 16 hours.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and can be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

Example 1

(RS)-(4,6-Dimethyl-pyrimidin-2-yl)-(4-pyrrolidin-3-yl-phenyl)-amine; hydrochloride

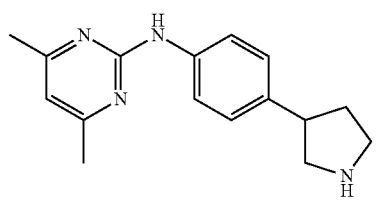 [SMILES: Cc1cc(C)nc(Nc2ccc(C3CCNC3)cc2)n1]

The title compound was obtained in analogy to example 5 using (RS)-3-(4-amino-phenyl)-pyrrolidine-1-carboxylic acid tert-butyl ester (CAS 908334-28-1) in place of (RS)-2-(4-amino-phenyl)-morpholine-4-carboxylic acid tert-butyl ester and 2-chloro-4,6-dimethylpyrimidine (CAS 4472-44-0) instead of 2,5-dichloropyridine in step (a). Light brown solid. MS (ISP): 271.3 ([$\{^{37}Cl\}$M+H]$^+$), 269.4 ([$\{^{35}Cl\}$M+H]$^+$).

Example 2

[(RS)-1-(5-Bromo-pyridin-2-yl)-2,2,2-trifluoro-ethyl]-((RS)-4-pyrrolidin-3-yl-phenyl)-amine

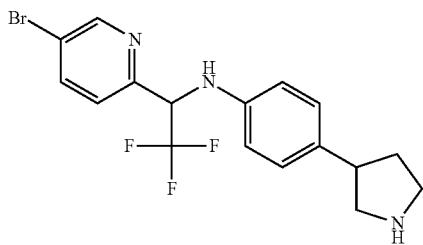 [SMILES: FC(F)(F)C(Nc1ccc(C2CCNC2)cc1)c1ccc(Br)cn1]

a) (RS)-1-(5-Bromo-pyridin-2-yl)-2,2,2-trifluoro-ethanol

To a cooled, stirred solution of 5-bromopyridine-2-carbaldehyde (3.72 g, CAS 31181-90-5) and (trifluoromethyl)trimethylsilane (3.56 ml) in THF (30 ml) at 0° C. was added dropwise tetrabutylammonium fluoride solution (1.0 ml, 1 M solution in THF). The reaction mixture was stirred at 0° C. for 30 min and then at room temperature for 2 hours. The mixture was then diluted with 1 N aq. HCl (20 ml) and stirring was continued for a further 2 hours. The mixture was diluted with water and extracted twice with ethyl acetate. The combined organic phases were dried over sodium sulfate and concentrated in vacuo. The residue was purified by column chromatography (SiO$_2$; gradient: heptane/EtOAc) to give (RS)-1-(5-bromo-pyridin-2-yl)-2,2,2-trifluoro-ethanol as a light yellow solid (3.35 g, 65%). MS (ISP): 258.0 ([{$^{81}$Br}M+H]$^+$), 256.1 ([{$^{79}$Br}M+H]$^+$).

b) Trifluoro-methanesulfonic acid (RS)-1-(5-bromo-pyridin-2-yl)-2,2,2-trifluoro-ethyl ester To a stirred suspension of sodium hydride (765 mg, 60% dispersion in mineral oil) in dry diethyl ether (20 ml) under an argon atmosphere at 0° C. was added dropwise a solution of (RS)-1-(5-bromo-pyridin-2-yl)-2,2,2-trifluoro-ethanol (3.06 g) in diethyl ether (10 ml) and the resulting mixture was stirred at room temperature for 30 min. Trifluoromethanesulfonyl chloride (1.4 ml) was added and stirring was continued for a further 15 min at room temperature. The reaction mixture was quenched by addition of 10% aq. sodium bicarbonate solution and the mixture was extracted with diethyl ether. The phases were separated and the organic phase was washed with saturared brine. The organic phase was separated, dried over sodium sulphate, and concentrated in vacuo. The reside was purified by Kugelrohr distillation (60° C. oven temperature, 0.3 mbar) to give trifluoro-methanesulfonic acid (RS)-1-(5-bromo-pyridin-2-yl)-2,2,2-trifluoro-ethyl ester (3.6 g, 78%) as a white solid. MS (EI): 389 ([{$^{81}$Br}M]$^+$), 387 ([{$^{79}$Br}M]$^+$), 320 ([{$^{81}$Br}M-CF$_3$]$^+$), 318 ([{$^{79}$Br}M-CF$_3$]$^+$), 256 ([{$^{81}$Br}M-CF$_3$—SO$_2$]$^+$), 254 ([{$^{79}$Br}M-CF$_3$—SO$_2$]$^+$), 240 ([{$^{81}$Br}M-OSO$_2$CF$_3$]$^+$), 238 ([{$^{79}$Br}M-OSO$_2$CF$_3$]).

c) (RS)-3-{4-[(RS)-1-(5-Bromo-pyridin-2-yl)-2,2,2-trifluoro-ethylamino]-phenyl}-pyrrolidine-1-carboxylic acid tert-butyl ester To a stirred solution of (RS)-3-(4-amino-phenyl)-pyrrolidine-1-carboxylic acid tert-butyl ester (50 mg, CAS 908334-28-1) in dry THF (0.1 ml) under an argon atmosphere was added sodium hydride (14 mg, 60% dispersion in mineral oil) and stirring was continued for 15 minutes. Trifluoro-methanesulfonic acid 1-(5-bromo-pyridin-2-yl)-2,2,2-trifluoro-ethyl ester (74 mg) was then added and the mixture was stirred overnight at room temperature. The reaction mixture was diluted with ethyl acetate and washed sequentially with water and with saturared brine. The organic phase was separated, dried over sodium sulphate, and concentrated in vacuo. The reside was purified by flash column chromatography (silical gel; gradient: heptane/EtOAc) to give (RS)-3-{4-[(RS)-1-(5-bromo-pyridin-2-yl)-2,2,2-trifluoro-ethylamino]-phenyl}-pyrrolidine-1-carboxylic acid tert-butyl ester (34 mg, 36%) as a yellow oil. MS (ISP): 501.9 ([{$^{81}$Br}M+H]$^+$), 500.2 ([{$^{79}$Br}M+H]$^+$), 446.2 ([{$^{81}$Br}M+H—C$_4$H$_8$]$^+$), 444.1 ([{$^{79}$Br}M+H—C$_4$H$_8$]$^+$).

d) [(RS)-1-(5-Bromo-pyridin-2-yl)-2,2,2-trifluoro-ethyl]-((RS)-4-pyrrolidin-3-yl-phenyl)-amine To a stirred solution of (RS)-3-{4-[(RS)-1-(5-bromo-pyridin-2-yl)-2,2,2-trifluoro-ethylamino]-phenyl}-pyrrolidine-1-carboxylic acid tert-butyl ester (27 mg) in THF (1 ml) was added dropwise a solution of hydrogen chloride in dioxane (0.20 ml, 4 M solution) and the mixture was heated at 60° C. for 4 hours. The mixture was then cooled to room temperature, diluted with ethyl acetate/THF (1:1), and washed sequentially with 2 N aq. sodium hydroxide solution and with saturated brine. The organic phase was separated, dried over sodium sulphate, and concentrated in vacuo. The reside was purified by flash column chromatography (silical gel; gradient: heptane/dichloromethane/methanol) to give [(RS)-1-(5-bromo-pyridin-2-yl)-2,2,2-trifluoro-ethyl]-((RS)-4-pyrrolidin-3-yl-phenyl)-amine (12 mg, 56%) as a yellow amorphous solid. MS (ISP): 402.1 ([{$^{81}$Br}M+H]$^+$), 400.1 ([{$^{79}$Br}M+H]$^+$).

Example 3

[(RS)-1-(4-Chloro-phenyl)-2,2,2-trifluoro-ethyl]-[(RS)-4-(2-pyrrolidin-3-yl-ethyl)-phenyl]-amine

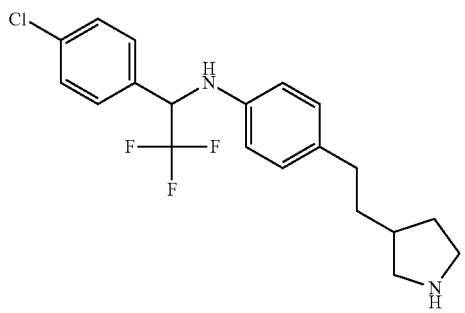 [SMILES: FC(F)(F)C(Nc1ccc(CCC2CCNC2)cc1)c1ccc(Cl)cc1]

a) (RS)-3-[(E)-2-(4-Nitro-phenyl)-vinyl]-pyrrolidine-1-carboxylic acid tert-butyl ester To a stirred solution of N,N-diisopropylamine (3.36 ml) in tetrahydrofuran (20 ml) at −78° C. was added dropwise a solution of n-butyllithium (14.9 ml, 1.6 M in hexane) and the reaction mixture was then warmed to 0° C. for 15 min. After re-cooling to −78° C., a solution of diethyl (4-nitrobenzyl) phosphonate (5.00 g, CAS 2609-49-6) in tetrahydrofuran (10 ml) was added dropwise. The mixture was stirred at −78° C. for 60 min and then a solution of (RS)-3-formyl-pyrrolidine-1-carboxylic acid tert-butyl ester (4.01 g, CAS 59379-02-1) in tetrahydrofuran (10 ml) was added dropwise over 30 min. The mixture was then allowed to warm to room temparature and stirring continued at room temperature for 18 hours. The mixture was then diluted with ethyl acetate and acidified to pH 6 by addition of aqueous hydrochloric acid (1 N). The mixture was washed sequentially with water and with saturated brine, dried over $Na_2SO_4$ and concentrated in vacuo. The residue was purified by flash column chromatography (silica gel, gradient: heptane/EtOAc) to yield (RS)-3-[(E)-2-(4-nitro-phenyl)-vinyl]-pyrrolidine-1-carboxylic acid tert-butyl ester (3.39 g, 58%) as a yellow oil.

b) (RS)-3-[2-(4-Amino-phenyl)-ethyl]-pyrrolidine-1-carboxylic acid tert-butyl ester To a solution of (RS)-3-formyl-pyrrolidine-1-carboxylic acid tert-butyl ester (3.39 g) in methanol (250 ml) was added palladium on charcoal (10%, 340 mg). The mixture was stirred vigorously under an atmosphere of hydogen for 7 hours. The catalyst was filtered off and the filtrate was evaporated. The crude product was purified by flash column chromatography (silica gel; gradient: heptane/EtOAc) to give (RS)-3-[2-(4-amino-phenyl)-ethyl]-pyrrolidine-1-carboxylic acid tert-butyl ester (2.44 g, 79%) as a yellow oil. MS (ISP): 291.2 ([M+H]$^+$).

c) (RS)-3-(2-{4-[(RS)-1-(4-Chloro-phenyl)-2,2,2-trifluoro-ethylamino]-phenyl}-ethyl)-pyrrolidine-1-carboxylic acid tert-butyl ester The title compound was obtained in analogy to example 2 step (c) using (RS)-3-[2-(4-amino-phenyl)-ethyl]-pyrrolidine-1-carboxylic acid tert-butyl ester instead of (RS)-3-(4-amino-phenyl)-pyrrolidine-1-carboxylic acid tert-butyl ester and trifluoro-methanesulfonic acid (RS)-1-(4-chloro-phenyl)-2,2,2-trifluoro-ethyl ester (CAS 1202576-95-1) instead of trifluoro-methanesulfonic acid (RS)-1-(5-bromo-pyridin-2-yl)-2,2,2-trifluoro-ethyl ester. Yellow oil. MS (ISP): 429.2 ([$^{37}$Cl]M+H—$C_4H_8$]$^+$), 427.1 ([$^{35}$Cl]M+H—$C_4H_8$]$^+$).

d) [(RS)-1-(4-Chloro-phenyl)-2,2,2-trifluoro-ethyl]-[(RS)-4-(2-pyrrolidin-3-yl-ethyl)-phenyl]-amine The title compound was obtained in analogy to example 2 step (d) using (RS)-3-(2-{4-[(RS)-1-(4-chloro-phenyl)-2,2,2-trifluoro-ethylamino]-phenyl}-ethyl)-pyrrolidine-1-carboxylic acid tert-butyl ester instead of (RS)-3-{4-[(RS)-1-(5-bromo-pyridin-2-yl)-2,2,2-trifluoro-ethylamino]-phenyl}-pyrrolidine-1-carboxylic acid tert-butyl ester. Off-white solid. MS (ISP): 385.2 ([$^{37}$Cl]M+H]$^+$), 383.2 ([$^{35}$Cl]M+H]$^+$).

Example 4

(RS)-[1-(4-Chloro-phenyl)-2,2,2-trifluoro-ethyl]-[(RS)-4-(2-piperidin-3-yl-ethyl)-phenyl]-amine

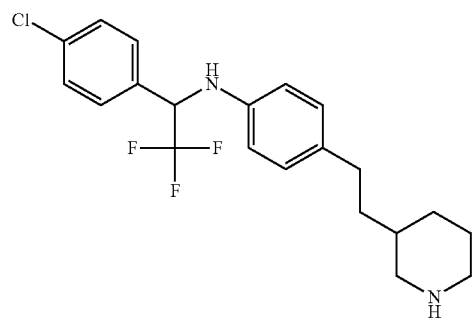 [SMILES: FC(F)(F)C(Nc1ccc(CCC2CCCNC2)cc1)c1ccc(Cl)cc1]

The title compound was obtained in analogy to example 3 using (RS)-3-formyl-piperidine-1-carboxylic acid tert-butyl ester (CAS 118156-93-7) instead of (RS)-3-formyl-pyrrolidine-1-carboxylic acid tert-butyl ester in step (a). Colourless amorphous solid. MS (ISP): 399.1 ([$^{37}$Cl]M+H]$^+$), 397.1 ([$^{35}$Cl]M+H]$^+$).

Example 5

(RS)-(5-Chloro-pyridin-2-yl)-(4-morpholin-2-yl-phenyl)-amine

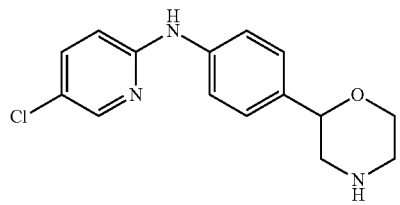

a) (RS)-2-[4-(5-Chloro-pyridin-2-ylamino)-phenyl]-morpholine-4-carboxylic acid tert-butyl ester (RS)-2-(4-Amino-phenyl)-morpholine-4-carboxylic acid tert-butyl ester (60 mg, CAS 1002726-96-6), 2,5-dichloropyridine (31.9 mg, CAS 16110-09-1) and cesium carbonate (105 mg) were combined with dioxane (2 ml) to give a yellow suspension. The mixture was degassed by bubbling argon into the mixture for several minutes. Xantphos (7.48 mg) and tris(dibenzylideneacetone)dipalladium chloroform complex (6.69 mg) were then added. The reaction mixture was then capped and stirred at 100° C. overnight. The crude reaction mixture was cooled to room temperature and filtered. The filtrate was concentrated in vacuo and the residue was purified by flash column chromatography (silica gel; gradient: 0% to 70% EtOAc in hexanes) to afford (RS)-2-[4-(5-chloro-pyridin-2-ylamino)-phenyl]-morpholine-4-carboxylic acid tert-butyl ester (52 mg, 62%) as a yellow amorphous solid. MS (ISP): 392.0 ([{$^{37}$Cl}M+H]$^+$), 390.1 ([{$^{35}$Cl}M+H]$^+$), 336.4 ([{$^{37}$Cl}M+H—C$_4$H$_8$]$^+$), 334.3 ([{$^{35}$Cl}M+H—C$_4$H$_8$]$^+$).

b) (RS)-(5-Chloro-pyridin-2-yl)-(4-morpholin-2-yl-phenyl)-amine

To a stirred solution of (RS)-2-[4-(5-chloro-pyridin-2-ylamino)-phenyl]-morpholine-4-carboxylic acid tert-butyl ester (50 mg) in THF (2 ml) was added dropwise a solution of hydrogen chloride in dioxane (0.26 ml, 4 M solution) and the mixture was heated at 60° C. overnight. The mixture was then cooled to room temperature and poured into 1 M aq. sodium hydroxide solution. The mixture was extracted twice with ethyl acetate and the combined organic layers were dried over Na$_2$SO$_4$, filtered and concentrated in vacuo. The residue was purified by column chromatography (Isolute® Flash-NH$_2$ from Separtis; gradient: heptane/ethyl acetate/methanol) to afford (RS)-(5-chloro-pyridin-2-yl)-(4-morpholin-2-yl-phenyl)-amine (19 mg, 51%) as a white solid. MS (ISP): 292.1 ([{$^{37}$Cl}M+H]$^+$), 290.1 ([{35Cl}M+H]$^+$).

Example 6

(RS)-(5-Chloro-pyrimidin-2-yl)-(4-morpholin-2-yl-phenyl)-amine

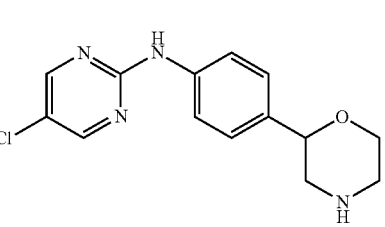

The title compound was obtained in analogy to example 5 using 2,5-dichloropyrimidine (CAS 22536-67-0) instead of 2,5-dichloropyridine in step (a). Yellow solid. MS (ISP): 293.1 ([{$^{37}$Cl}M+H]$^+$), 291.1 ([{$^{35}$Cl}M+H]$^+$).

Example 7

(RS)-(5-Bromo-pyrimidin-2-yl)-(4-morpholin-2-yl-phenyl)-amine

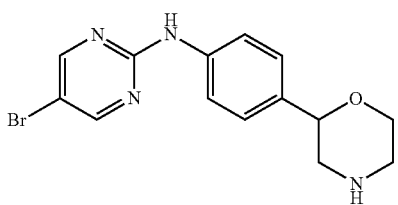

The title compound was obtained in analogy to example 5 using 2,5-dibromopyrimidine (CAS 32779-37-6) instead of 2,5-dichloropyridine in step (a). Yellow solid. MS (ISP): 337.1 ([{$^{81}$Br}M+H]$^+$), 335.1 ([{$^{79}$Br}M+H]$^+$).

Example 8

(RS)-(4-Chloro-phenyl)-(4-morpholin-2-yl-phenyl)-amine

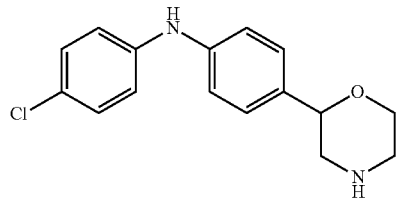 [SMILES: Clc1ccc(Nc2ccc(C3CNCCO3)cc2)cc1]

The title compound was obtained in analogy to example 5 using 1-bromo-4-chlorobenzene (CAS 106-39-8) instead of 2,5-dichloropyridine in step (a). White solid. MS (ISP): 291.1 ([{$^{37}$Cl}M+H]$^+$), 289.1 ([{$^{35}$Cl}M+H]$^+$).

Example 9

(RS)-(4-Chloro-benzyl)-(4-morpholin-2-yl-phenyl)-amine

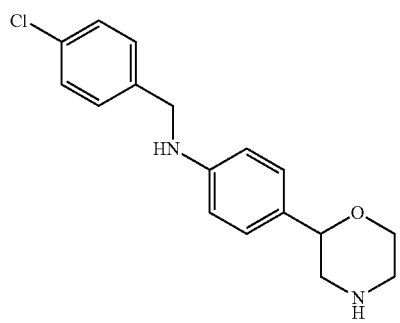 [SMILES: Clc1ccc(CNc2ccc(C3CNCCO3)cc2)cc1]

a) (RS)-2-[4-(4-Chloro-benzylamino)-phenyl]-morpholine-4-carboxylic acid tert-butyl ester To a mixture of (RS)-2-(4-amino-phenyl)-morpholine-4-carboxylic acid tert-butyl ester (60 mg, CAS 1002726-96-6), 4-chlorobenzaldehyde (33.3 mg) and AcOH (123 µl) in THF (2 ml) was added sodium triacetoxyborohydride (68.5 mg). The reaction mixture was then capped and the mixture was shaken at 60° C. for 3 h. The crude reaction mixture was then concentrated in vacuo and the residue was purified by flash column chromatography (silica gel; gradient: 0% to 65% EtOAc in hexanes) to afford (RS)-2-[4-(4-chloro-benzylamino)-phenyl]-morpholine-4-carboxylic acid tert-butyl ester (68 mg, 78%) as a colourless oil. MS (ISP): 405.4 ([{$^{37}$Cl}M+H]$^+$), 403.4 ([{$^{35}$Cl}M+H]$^+$).

b) (RS)-(4-Chloro-benzyl)-(4-morpholin-2-yl-phenyl)-amine

To a stirred solution of (RS)-2-[4-(4-chloro-benzylamino)-phenyl]-morpholine-4-carboxylic acid tert-butyl ester (68 mg) in THF (2 ml) was added dropwise a solution of hydrogen chloride in dioxane (0.34 ml, 4 M solution) and the mixture was heated at 60° C. overnight. The mixture was then cooled to room temperature and poured into 1 M aq. sodium hydroxide solution. The mixture was extracted twice with ethyl acetate and the combined organic layers were dried over Na₂SO₄, filtered and concentrated in vacuo. The residue was purified by column chromatography (Isolute® Flash-NH₂ from Separtis; gradient: heptane/ethyl acetate/methanol) to afford (RS)-(4-chloro-benzyl)-(4-morpholin-2-yl-phenyl)-amine (36 mg, 70%) as a white solid. MS (ISP): 305.1 ([{$^{37}$Cl}M+H]$^+$), 303.2 ([{$^{35}$Cl}M+H]$^+$).

Example 10

(S)-5-Bromo-N-(4-(morpholin-2-yl)phenyl)pyridin-2-amine

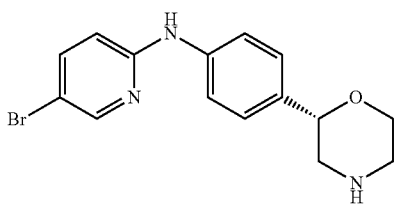

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2,5-dibromopyridine (CAS 624-28-2) instead of 2,5-dichloropyridine in step (a). Off-white solid. MS (ISP): 336.1 ([{$^{81}$Br}M+H]$^+$), 334.1 ([{$^{79}$Br}M+H]$^+$).

Example 11

(S)—N-(4-(Morpholin-2-yl)phenyl)-5-(trifluoromethyl)pyridin-2-amine

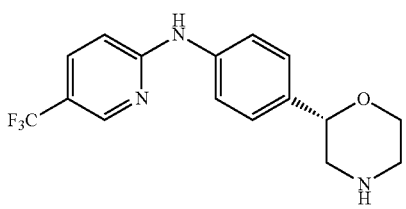 [SMILES: FC(F)(F)c1ccc(Nc2ccc([C@H]3CNCCO3)cc2)nc1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-bromo-5-(trifluoromethyl)pyridine (CAS 50488-42-1) instead of 2,5-dichloropyridine in step (a). Off-white solid. MS (ISP): 324.1 ([M+H]$^+$).

Example 12

(5-Methoxy-pyrimidin-2-yl)-((S)-4-morpholin-2-yl-phenyl)-amine

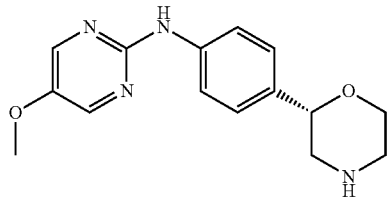 [SMILES: COc1cnc(Nc2ccc([C@H]3CNCCO3)cc2)nc1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-5-methoxypyrimidine (CAS 22536-65-8) instead of 2,5-dichloropyridine in step (a). Light yellow solid. MS (ISP): 287.1 ([M+H]$^+$).

Example 13

((S)-4-Morpholin-2-yl-phenyl)-phenethyl-amine

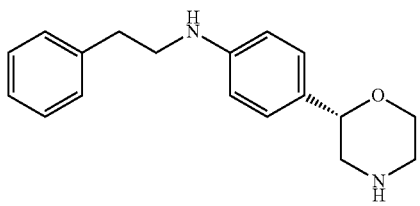 [SMILES: c1ccc(CCNc2ccc([C@H]3CNCCO3)cc2)cc1]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and phenylacetaldehyde instead of 4-chlorobenzaldehyde in step (a). Light brown solid. MS (ISP): 283.2 ([M+H]$^+$).

Example 14

(5-Fluoro-pyrimidin-2-yl)-((S)-4-morpholin-2-yl-phenyl)-amine

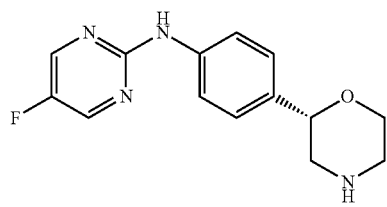 [SMILES: Fc1cnc(Nc2ccc([C@H]3CNCCO3)cc2)nc1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-5-fluoropyrimidine (CAS 62802-42-0) instead of 2,5-dichloropyridine in step (a). Off-white solid. MS (ISP): 275.3 ([M+H]$^+$).

Example 15

(5-Ethyl-pyrimidin-2-yl)-((S)-4-morpholin-2-yl-phenyl)-amine

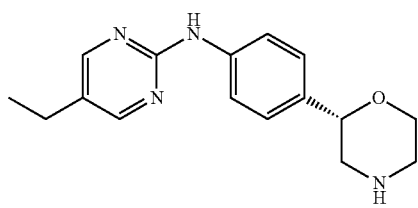 [SMILES: CCc1cnc(Nc2ccc([C@H]3CNCCO3)cc2)nc1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-5-ethylpyrimidine (CAS 111196-81-7) instead of 2,5-dichloropyridine in step (a). Yellow solid. MS (ISP): 285.3 ([M+H]$^+$).

Example 16

2-((S)-4-Morpholin-2-yl-phenylamino)-pyrimidine-5-carbonitrile

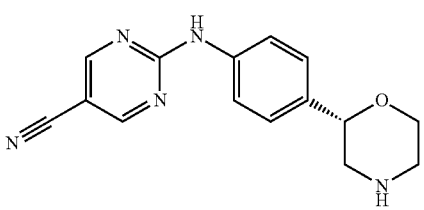 [SMILES: N#Cc1cnc(Nc2ccc([C@H]3CNCCO3)cc2)nc1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloropyrimidine-5-carbonitrile (CAS 1753-50-0) instead of 2,5-dichloropyridine in step (a). Yellow solid. MS (ISP): 282.1 ([M+H]$^+$).

Example 17

(5-Cyclopropyl-pyrimidin-2-yl)-((S)-4-morpholin-2-yl-phenyl)-amine

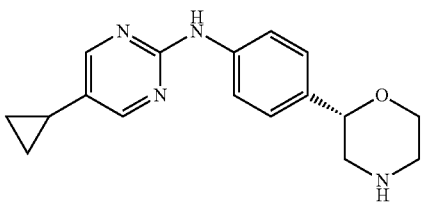 [SMILES: c1cc([C@H]2CNCCO2)ccc1Nc1ncc(C2CC2)cn1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-5-cyclopropylpyrimidine (CAS 166740-44-9) instead of 2,5-dichloropyridine in step (a). Yellow solid. MS (ISP): 297.4 ([M+H]$^+$).

Example 18

(5-Methyl-pyrimidin-2-yl)-((S)-4-morpholin-2-yl-phenyl)-amine

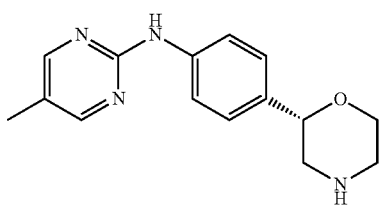 [SMILES: Cc1cnc(Nc2ccc([C@H]3CNCCO3)cc2)nc1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-5-methylpyrimidine (CAS 22536-61-4) instead of 2,5-dichloropyridine in step (a). Yellow solid. MS (ISP): 271.4 ([M+H]$^+$).

Example 19

((S)-4-Morpholin-2-yl-phenyl)-(5-trifluoromethyl-pyrimidin-2-yl)-amine

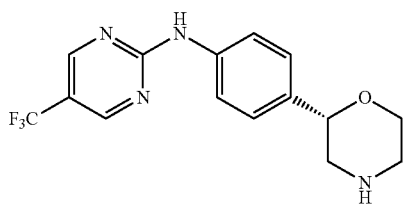

a) (S)-2-[4-(5-Trifluoromethyl-pyrimidin-2-ylamino)-phenyl]-morpholine-4-carboxylic acid tert-butyl ester To a 10 ml glass vial was added (S)-2-(4-bromo-phenyl)-morpholine-4-carboxylic acid tert-butyl ester (70 mg, CAS 1131220-37-5) and 5-trifluoromethyl-pyrimidin-2-ylamine (66.7 mg, CAS 69034-08-8) in dioxane (2 ml). The reaction mixture was purged with argon for 5 min. 2-Di-tert-butylphosphino-2',4',6'-triisopropylbiphenyl (14.3 mg), tris(dibenzylideneacetone)dipalladium(0) (7.49 mg) and sodium tert-butoxide (21.6 mg) were then added. The vial was capped and heated at 120° C. for 16 h. The reaction mixture was then filtered through sintered glass and the filtrate was concentrated in vacuo. The residue was purified by flash column chromatography (silica gel; gradient: 0% to 50% EtOAc in hexanes) to afford (S)-2-[4-(5-trifluoromethyl-pyrimidin-2-ylamino)-phenyl]-morpholine-4-carboxylic acid tert-butyl ester (94 mg, quant.) as an off-white solid. MS (ISP): 425.2 ([M+H]$^+$).

b) ((S)-4-Morpholin-2-yl-phenyl)-(5-trifluoromethyl-pyrimidin-2-yl)-amine

To a stirred solution of (S)-2-[4-(5-trifluoromethyl-pyrimidin-2-ylamino)-phenyl]-morpholine-4-carboxylic acid tert-butyl ester (87 mg) in THF (2 ml) was added dropwise a solution of hydrogen chloride in dioxane (0.77 ml, 4 M solution) and the mixture was heated at 60° C. overnight. The mixture was then cooled to room temperature and poured into 1 M aq. sodium hydroxide solution. The mixture was extracted twice with ethyl acetate and the combined organic layers were dried over $Na_2SO_4$, filtered and concentrated in vacuo. The residue was purified by column chromatography (Isolute® Flash-$NH_2$ from Separtis; gradient: heptane/ethyl acetate/methanol) to afford ((S)-4-morpholin-2-yl-phenyl)-(5-trifluoromethyl-pyrimidin-2-yl)-amine (41 mg, 62%) as a white solid. MS (ISP): 325.3 ([M+H]+).

Example 20

(4-Methoxy-benzyl)-((S)-4-morpholin-2-yl-phenyl)-amine

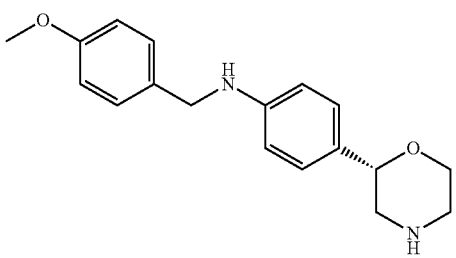 [SMILES: COc1ccc(CNc2ccc([C@H]3CNCCO3)cc2)cc1]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 4-methoxy-benzaldehyde instead of 4-chlorobenzaldehyde in step (a). Yellow solid. MS (ISP): 299.4 ([M+H]+).

Example 21

((S)-4-Morpholin-2-yl-phenyl)-(5-propyl-pyrimidin-2-yl)-amine

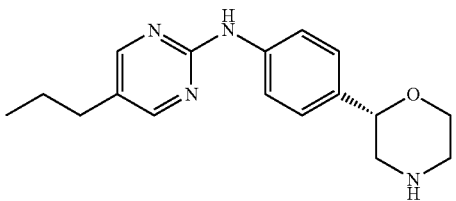 [SMILES: CCCc1cnc(Nc2ccc([C@H]3CNCCO3)cc2)nc1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-5-propylpyrimidine (CAS 219555-98-3) instead of 2,5-dichloropyridine in step (a). Off-white amorphous solid. MS (ISP): 299.4 ([M+H]+).

Example 22

(4-Methyl-benzyl)-((S)-4-morpholin-2-yl-phenyl)-amine

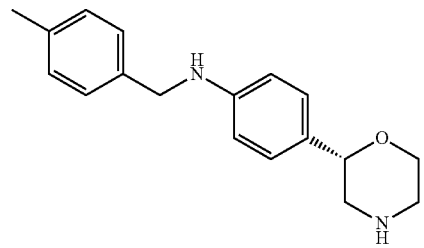 [SMILES: Cc1ccc(CNc2ccc([C@H]3CNCCO3)cc2)cc1]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 4-methyl-benzaldehyde instead of 4-chlorobenzaldehyde in step (a). Light yellow solid. MS (ISP): 283.4 ([M+H]+).

Example 23

4-[((S)-4-Morpholin-2-yl-phenylamino)-methyl]-benzonitrile

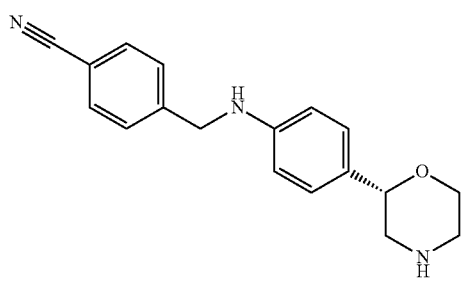 [SMILES: N#Cc1ccc(CNc2ccc([C@H]3CNCCO3)cc2)cc1]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 4-cyano-benzaldehyde instead of 4-chlorobenzaldehyde in step (a). White solid. MS (ISP): 294.2 ([M+H]+).

Example 24

((S)-4-Morpholin-2-yl-phenyl)-(4-trifluoromethyl-benzyl)-amine

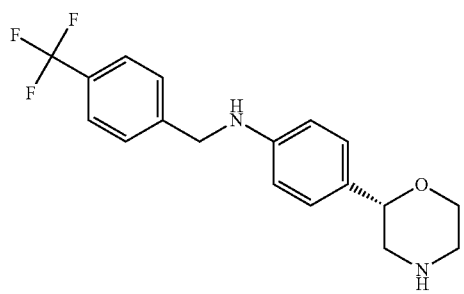 [SMILES: FC(F)(F)c1ccc(CNc2ccc([C@H]3CNCCO3)cc2)cc1]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 4-(trifluoromethyl)benzaldehyde instead of 4-chlorobenzaldehyde in step (a). Light yellow solid. MS (ISP): 337.4 ([M+H]$^+$).

Example 25

((S)-4-Morpholin-2-yl-phenyl)-(4-trifluoromethoxy-benzyl)-amine

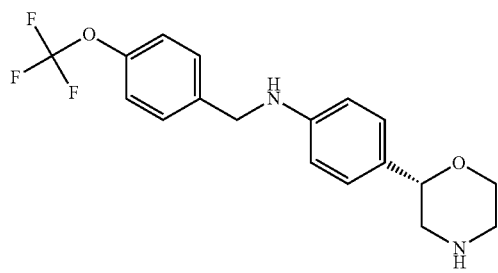 [SMILES: FC(F)(F)Oc1ccc(CNc2ccc([C@H]3CNCCO3)cc2)cc1]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 4-(trifluoromethoxy)benzaldehyde instead of 4-chlorobenzaldehyde in step (a). Light yellow solid. MS (ISP): 353.3 ([M+H]$^+$).

Example 26

(6-Chloro-benzothiazol-2-yl)-((S)-4-morpholin-2-yl-phenyl)-amine

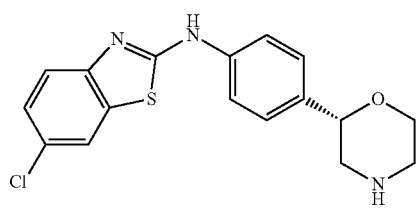 [SMILES: Clc1ccc2nc(Nc3ccc([C@H]4CNCCO4)cc3)sc2c1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2,6-dichlorobenzo[d]thiazole (CAS 3622-23-9) instead of 2,5-dichloropyridine in step (a). Off-white solid. MS (ISP): 348.2 ([$^{37}$Cl}M+H]$^+$), 346.0 ([$^{35}$Cl}M+H]$^+$).

Example 27

(5-Bromo-pyridin-2-ylmethyl)-((S)-4-morpholin-2-yl-phenyl)-amine

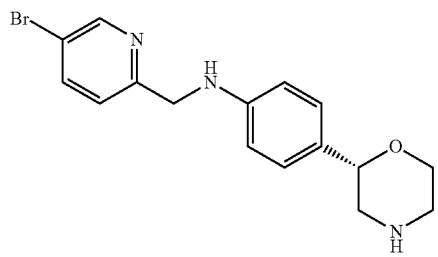 [SMILES: Brc1ccc(CNc2ccc([C@H]3CNCCO3)cc2)nc1]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 5-bromopicolinaldehyde instead of 4-chlorobenzaldehyde in step (a). Brown oil. MS (ISP): 350.1 ([$^{81}$Br}M+H]$^+$), 348.2 ([$^{79}$Br}M+H]$^+$).

Example 28

(6-Methoxy-pyridin-2-ylmethyl)-((S)-4-morpholin-2-yl-phenyl)-amine

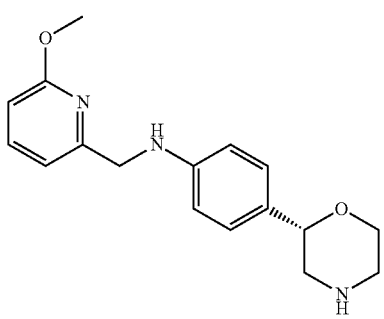 [SMILES: COc1cccc(CNc2ccc([C@H]3CNCCO3)cc2)n1]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 6-methoxypicolinaldehyde instead of 4-chlorobenzaldehyde in step (a). Colourless oil. MS (ISP): 300.2 ([M+H]$^+$).

Example 29

(5-Ethoxy-pyrimidin-2-yl)-((S)-4-morpholin-2-yl-phenyl)-amine

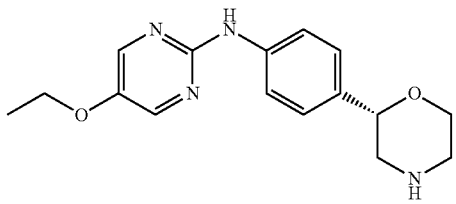 [SMILES: CCOc1cnc(Nc2ccc([C@H]3CNCCO3)cc2)nc1]

The title compound was obtained in analogy to example 19 using 2-amino-5-ethoxypyrimidine (CAS 39268-74-1) instead of 5-trifluoromethyl-pyrimidin-2-ylamine in step (a). Yellow solid. MS (ISP): 301.3 ([M+H]$^+$).

Example 30

(3,4-Dichloro-benzyl)-((S)-4-morpholin-2-yl-phenyl)-amine

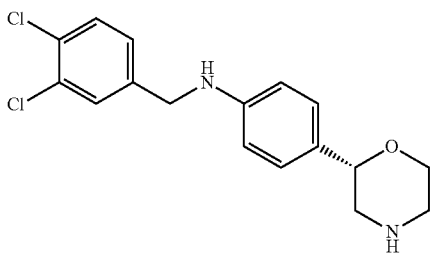 [SMILES: Clc1ccc(CNc2ccc([C@H]3CNCCO3)cc2)cc1Cl]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 3,4-dichlorobenzaldehyde instead of 4-chlorobenzaldehyde in step (a). Off-white solid. MS (ISP): 341.3 ([{$^{37}$Cl}M+H]$^+$), 339.2 ([{$^{37}$Cl$^{35}$Cl}M+H]$^+$), 337.3 ([{$^{35}$Cl}M+H]$^+$).

Example 31

(4-Fluoro-benzyl)-((S)-4-morpholin-2-yl-phenyl)-amine

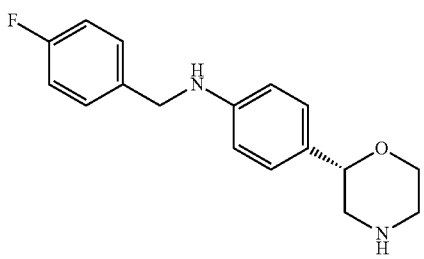 [SMILES: Fc1ccc(CNc2ccc([C@H]3CNCCO3)cc2)cc1]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 4-fluoro-benzaldehyde instead of 4-chlorobenzaldehyde in step (a). Off-white solid. MS (ISP): 287.2 ([M+H]$^+$).

Example 32

(S)—N-((6-Chloropyridin-3-yl)methyl)-4-(morpholin-2-yl)aniline

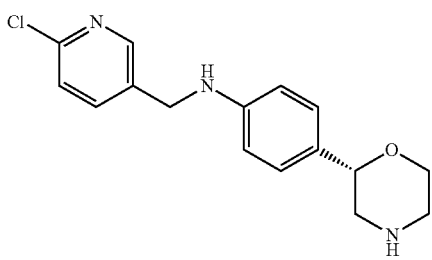 [SMILES: Clc1ccc(CNc2ccc([C@H]3CNCCO3)cc2)cn1]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 6-chloronicotinaldehyde instead of 4-chlorobenzaldehyde in step (a). White solid. MS (ISP): 306.1 ([{$^{37}$Cl}M+H]$^+$), 304.1 ([{$^{35}$Cl}M+H]$^+$).

Example 33

(S)-4-(Morpholin-2-yl)-N-((6-(trifluoromethyl)pyridin-3-yl)methyl)aniline

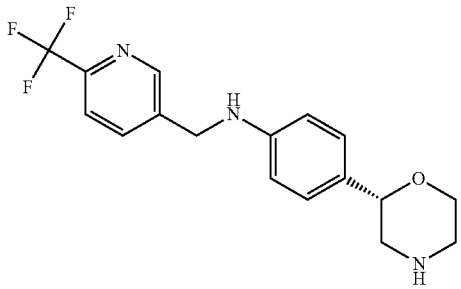 [SMILES: FC(F)(F)c1ccc(CNc2ccc([C@H]3CNCCO3)cc2)cn1]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 6-(trifluoromethyl)nicotinaldehyde instead of 4-chlorobenzaldehyde in step (a). White solid. MS (ISP): 338.1 ([M+H]$^+$).

Example 34

[2-(4-Chloro-phenyl)-ethyl]-((S)-4-morpholin-2-yl-phenyl)-amine

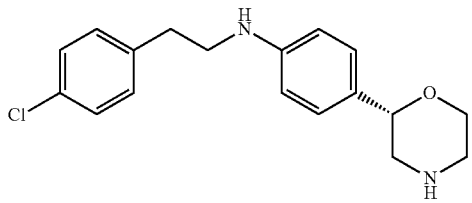 [SMILES: Clc1ccc(CCNc2ccc([C@H]3CNCCO3)cc2)cc1]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and (4-chloro-phenyl)-acetaldehyde instead of 4-chlorobenzaldehyde in step (a). Off-white solid. MS (ISP): 319.2 ([{$^{37}$Cl}M+H]$^+$), 317.2 ([{$^{35}$Cl}M+H]$^+$).

Example 35

(4-Chloro-2-fluoro-benzyl)-((S)-4-morpholin-2-yl-phenyl)-amine

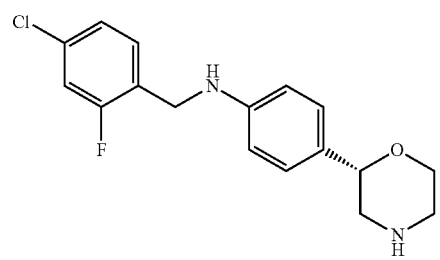 [SMILES: Fc1cc(Cl)ccc1CNc1ccc([C@H]2CNCCO2)cc1]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 4-chloro-2-fluorobenzaldehyde instead of 4-chlorobenzaldehyde in step (a). Off-white solid. MS (ISP): 323.3 ([{$^{37}$Cl}M+H]$^+$), 321.2 ([{$^{35}$Cl}M+H]$^+$).

Example 36

(4-Ethyl-benzyl)-((S)-4-morpholin-2-yl-phenyl)-amine

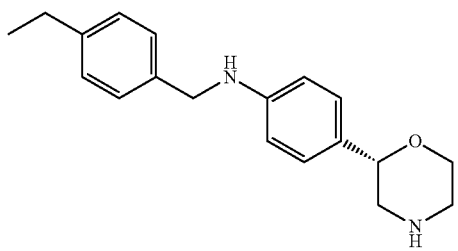 [SMILES: CCc1ccc(CNc2ccc([C@H]3CNCCO3)cc2)cc1]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 4-ethylbenzaldehyde instead of 4-chlorobenzaldehyde in step (a). Off-white solid. MS (ISP): 297.4 ([M+H]$^+$).

Example 37

(5-Fluoro-pyridin-2-ylmethyl)-((S)-4-morpholin-2-yl-phenyl)-amine

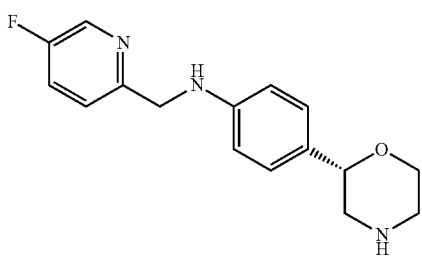 [SMILES: Fc1ccc(CNc2ccc([C@H]3CNCCO3)cc2)nc1]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 5-fluoropicolinaldehyde instead of 4-chlorobenzaldehyde in step (a). Yellow oil. MS (ISP): 288.2 ([M+H]$^+$).

Example 38

(5-Chloro-pyridin-2-yl)-((S)-4-morpholin-2-yl-phenyl)-amine

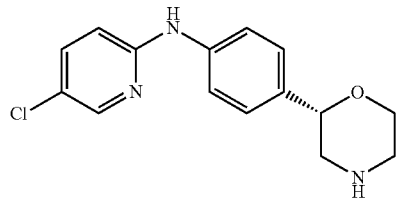 [SMILES: Clc1ccc(Nc2ccc([C@H]3CNCCO3)cc2)nc1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester in step (a). Yellow solid. MS (ISP): 292.1 ([{$^{37}$Cl}M+H]$^+$), 290.1 ([{$^{35}$Cl}M+H]$^+$).

Example 39

(S)-4-Methoxy-N-(4-(morpholin-2-yl)phenyl)pyridin-2-amine

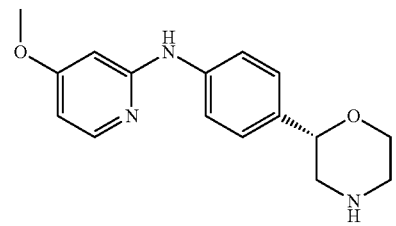 [SMILES: COc1ccnc(Nc2ccc([C@H]3CNCCO3)cc2)c1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-4-methoxypyridine (CAS 17228-69-2) instead of 2,5-dichloropyridine in step (a). Yellow amorphous solid. MS (ISP): 286.2 ([M+H]$^+$).

Example 40

(S)-6-Chloro-5-fluoro-N-(4-(morpholin-2-yl)phenyl)pyridin-3-amine

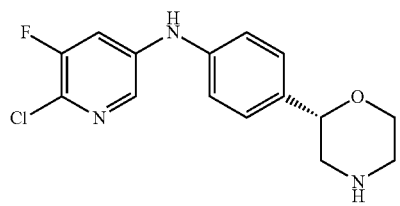 [SMILES: Fc1cc(Nc2ccc([C@H]3CNCCO3)cc2)cnc1Cl]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 5-bromo-2-chloro-3-fluoropyridine (CAS 831203-13-5) instead of 2,5-dichloropyridine in step (a). White solid. MS (ISP): 310.1 ([{$^{37}$Cl}M+H]$^+$), 308.1 ([{$^{35}$Cl}M+H]$^+$).

Example 41

(S)—N-(4-(Morpholin-2-yl)phenyl)-3-(trifluoromethyl)pyridin-2-amine

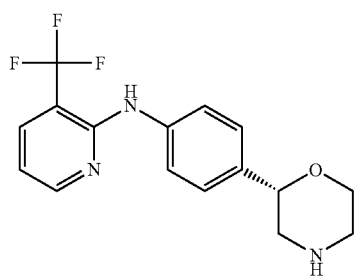 [SMILES: FC(F)(F)c1cccnc1Nc1ccc([C@H]2CNCCO2)cc1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-3-(trifluoromethyl)pyridine (CAS 65753-47-1) instead of 2,5-dichloropyridine in step (a). Colourless oil. MS (ISP): 324.1 ([M+H]$^+$).

Example 42

(S)—N-(4-(Morpholin-2-yl)phenyl)-4-(trifluoromethyl)pyridin-2-amine

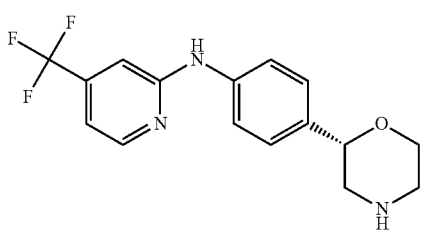 [SMILES: FC(F)(F)c1ccnc(Nc2ccc([C@H]3CNCCO3)cc2)c1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-4-(trifluoromethyl)pyridine (CAS 81565-18-6) instead of 2,5-dichloropyridine in step (a). White solid. MS (ISP): 324.1 ([M+H]$^+$).

Example 43

(S)-5-Fluoro-N-(4-(morpholin-2-yl)phenyl)pyridin-3-amine

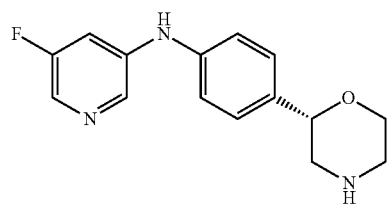 [SMILES: Fc1cncc(Nc2ccc([C@H]3CNCCO3)cc2)c1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 3-bromo-5-fluoropyridine (CAS 407-20-5) instead of 2,5-dichloropyridine in step (a). White solid. MS (ISP): 274.1 ([M+H]$^+$).

Example 44

((S)-4-Morpholin-2-yl-phenyl)-naphthalen-2-yl-amine

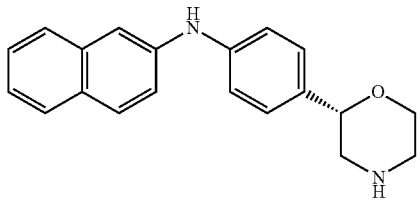 [SMILES: c1ccc2cc(Nc3ccc([C@H]4CNCCO4)cc3)ccc2c1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-bromonaphthalene (CAS 580-13-2) instead of 2,5-dichloropyridine in step (a). Orange gum. MS (ISP): 305.3 ([M+H]$^+$).

Example 45

(4-Bromo-benzyl)-((S)-4-morpholin-2-yl-phenyl)-amine

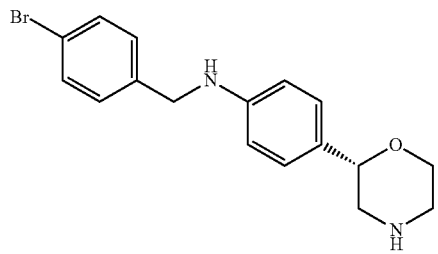 [SMILES: Brc1ccc(CNc2ccc([C@H]3CNCCO3)cc2)cc1]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 4-bromo-benzaldehyde instead of 4-chlorobenzaldehyde in step (a). White solid. MS (ISP): 349.2 ([{$^{81}$Br}M+H]$^+$), 347.1 ([{$^{79}$Br}M+H]$^+$).

Example 46

((S)-4-Morpholin-2-yl-phenyl)-quinolin-2-yl-amine

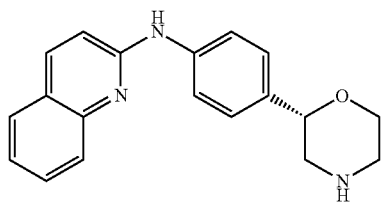 [SMILES: c1ccc2nc(Nc3ccc([C@H]4CNCCO4)cc3)ccc2c1]

The title compound was obtained in analogy to example 19 using 2-aminoquinoline (CAS 580-22-3) instead of 5-trifluoromethyl-pyrimidin-2-ylamine in step (a). Light yellow solid. MS (ISP): 306.3 ([M+H]$^+$).

Example 47

(S)-6-Chloro-N-(4-(morpholin-2-yl)phenyl)quinolin-2-amine

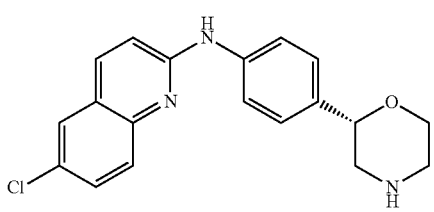 [SMILES: Clc1ccc2nc(Nc3ccc([C@H]4CNCCO4)cc3)ccc2c1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2,6-dichloroquinoline (CAS 1810-72-6) instead of 2,5-dichloropyridine in step (a). White solid. MS (ISP): 342.1 ([{$^{37}$Cl}M+H]$^+$), 340.1 ([{$^{35}$Cl}M+H]$^+$).

Example 48

(S)-2-Methyl-N-(4-(morpholin-2-yl)phenyl)quinolin-8-amine

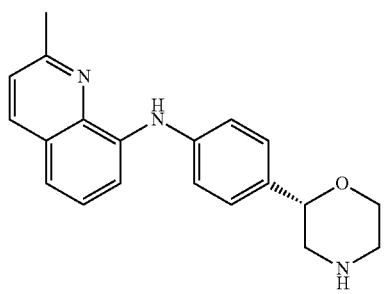 [SMILES: Cc1ccc2cccc(Nc3ccc([C@H]4CNCCO4)cc3)c2n1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 8-bromo-2-methylquinoline (CAS 61047-43-6) instead of 2,5-dichloropyridine in step (a). Yellow amorphous solid. MS (ISP): 320.2 ([M+H]$^+$).

Example 49

(S)—N-(4-(Morpholin-2-yl)phenyl)-2,8-bis(trifluoromethyl)quinolin-4-amine

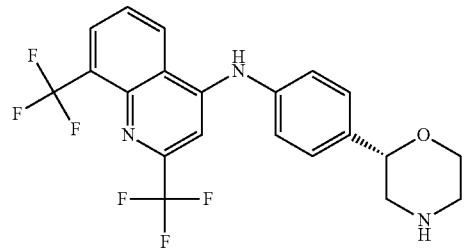 [SMILES: FC(F)(F)c1cc(Nc2ccc([C@H]3CNCCO3)cc2)c2cccc(C(F)(F)F)c2n1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 4-bromo-2,8-bis(trifluoromethyl)quinoline (CAS 35853-45-3) instead of 2,5-dichloropyridine in step (a). White solid. MS (ISP): 442.1 ([M+H]$^+$).

Example 50

(S)-6-Chloro-N-(4-(morpholin-2-yl)phenyl)quinazolin-4-amine

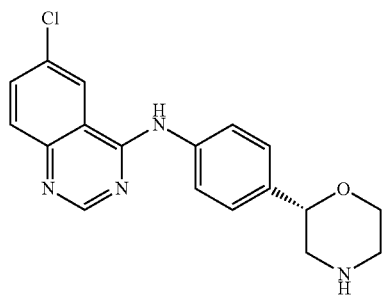 [SMILES: Clc1ccc2ncnc(Nc3ccc([C@H]4CNCCO4)cc3)c2c1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 4,6-dichloroquinazoline (CAS 7253-22-7) instead of 2,5-dichloropyridine in step (a). White solid. MS (ISP): 343.1 ([{$^{37}$Cl}M+H]$^+$), 341.1 ([{$^{35}$Cl}M+H]$^+$).

Example 51

(S)—N-((2-Chloroquinolin-3-yl)methyl)-4-(morpholin-2-yl)aniline

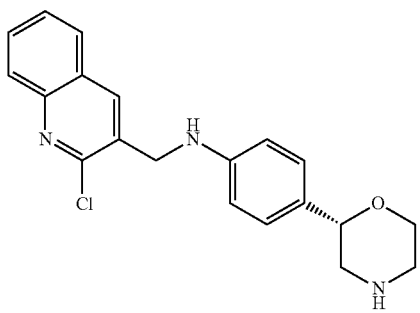 [SMILES: Clc1nc2ccccc2cc1CNc1ccc([C@H]2CNCCO2)cc1]

The title compound was obtained in analogy to example 9 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloroquinoline-3-carbaldehyde instead of 4-chlorobenzaldehyde in step (a). White solid. MS (ISP): 356.1 ([$\{^{37}Cl\}$M+H]$^+$), 354.1 ([$\{^{35}Cl\}$M+H]$^+$).

Example 52

(S)-8-Chloro-N-(4-(morpholin-2-yl)phenyl)quinolin-2-amine

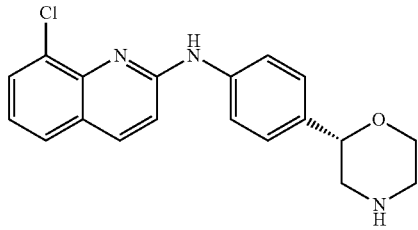 [SMILES: Clc1cccc2ccc(Nc3ccc([C@H]4CNCCO4)cc3)nc12]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2,8-dichloroquinoline (CAS 4470-83-1) instead of 2,5-dichloropyridine in step (a). White solid. MS (ISP): 342.1 ([$\{^{37}Cl\}$M+H]$^+$), 340.1 ([$\{^{35}Cl\}$M+H]$^+$).

Example 53

(S)-5-Bromo-N-(4-(morpholin-2-yl)phenyl)quinolin-2-amine

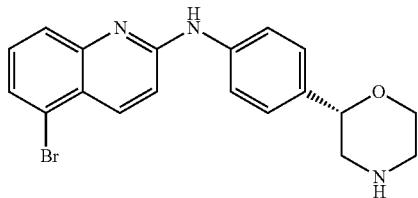 [SMILES: Brc1cccc2nc(Nc3ccc([C@H]4CNCCO4)cc3)ccc12]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 5-bromo-2-chloroquinoline (CAS 99455-13-7) instead of 2,5-dichloropyridine in step (a). Yellow solid. MS (ISP): 386.1 ([$\{^{81}Br\}$M+H]$^+$), 384.1 ([$\{^{79}Br\}$M+H]$^+$).

Example 54

(S)-4-Chloro-N-(4-(morpholin-2-yl)phenyl)quinolin-2-amine

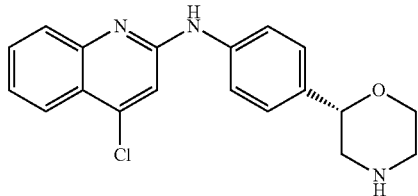 [SMILES: Clc1cc(Nc2ccc([C@H]3CNCCO3)cc2)nc2ccccc12]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2,4-dichloroquinoline (CAS 703-61-7) instead of 2,5-dichloropyridine in step (a). White solid. MS (ISP): 342.1 ([$\{^{37}Cl\}$M+H]$^+$), 340.1 ([$\{^{35}Cl\}$M+H]$^+$).

Example 55

(2-Fluoro-pyridin-3-yl)-((S)-4-morpholin-2-yl-phenyl)-amine

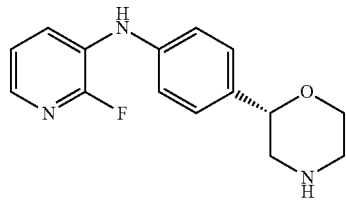 [SMILES: Fc1ncccc1Nc1ccc([C@H]2CNCCO2)cc1]

The title compound was obtained in analogy to example 19 using 3-amino-2-fluoropyridine (CAS 1597-33-7) instead of 5-trifluoromethyl-pyrimidin-2-ylamine in step (a). Orange gum. MS (ISP): 274.3 ([M+H]$^+$).

Example 56

(S)-5-Bromo-3-methyl-N-(4-(morpholin-2-yl)phenyl)pyridin-2-amine

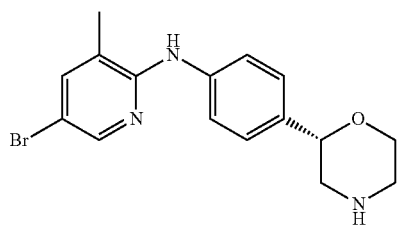 [SMILES: Cc1cc(Br)cnc1Nc1ccc([C@H]2CNCCO2)cc1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2,5-dibromo-3-methylpyridine (CAS 3430-18-0) instead of 2,5-dichloropyridine in step (a). White solid. MS (ISP): 350.1 ([$\{^{81}Br\}$M+H]$^+$), 348.1 ([$\{^{79}Br\}$M+H]$^+$).

Example 57

(S)-5-Bromo-3-fluoro-N-(4-(morpholin-2-yl)phenyl)pyridin-2-amine

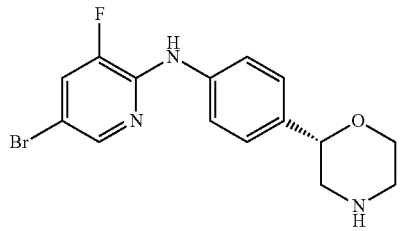 [SMILES: Fc1cc(Br)cnc1Nc1ccc([C@H]2CNCCO2)cc1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2,5-dibromo-3-fluoropyridine (CAS 156772-60-0) instead of 2,5-dichloropyridine in step (a). White solid. MS (ISP): 354.0 ([$\{^{81}Br\}$M+H]$^+$), 352.0 ([$\{^{79}Br\}$M+H]$^+$).

Example 58

(S)-3,5-Dichloro-N-(4-(morpholin-2-yl)phenyl)pyridin-2-amine

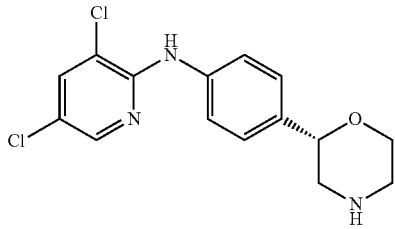 [SMILES: Clc1cnc(Nc2ccc([C@H]3CNCCO3)cc2)c(Cl)c1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2,3,5-trichloropyridine (CAS 16063-70-0) instead of 2,5-dichloropyridine in step (a). White amorphous solid. MS (ISP): 328.1 ([{$^{37}$Cl}M+H]$^+$), 326.1 ([{$^{37}$Cl$^{35}$Cl}M+H]$^+$), 324.1 ([{35Cl}M+H]$^+$).

Example 59

(S)-4-Chloro-2-fluoro-N-(4-(morpholin-2-yl)phenyl)aniline

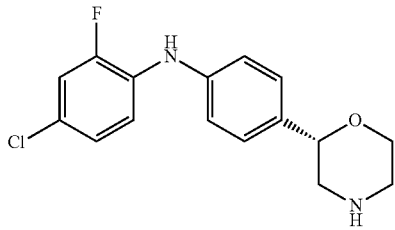 [SMILES: Fc1cc(Cl)ccc1Nc1ccc([C@H]2CNCCO2)cc1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 4-chloro-2-fluoro-1-iodobenzene (CAS 6797-79-1) instead of 2,5-dichloropyridine in step (a). White solid. MS (ISP): 309.1 ([{$^{37}$Cl}M+H]$^+$), 307.1 ([{$^{35}$Cl}M+H]$^+$).

Example 60

(4-Chloro-phenyl)-methyl-((S)-4-morpholin-2-yl-phenyl)-amine

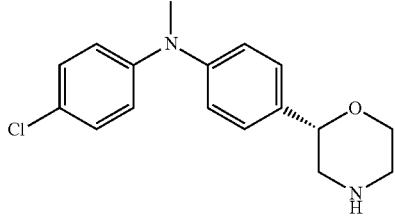 [SMILES: CN(c1ccc(Cl)cc1)c1ccc([C@H]2CNCCO2)cc1]

a) (S)-2-[4-(4-Chloro-phenylamino)-phenyl]-morpholine-4-carboxylic acid tert-butyl ester The title compound was obtained in analogy to example 5 step (a) using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 1-bromo-4-chlorobenzene (CAS 106-39-8) instead of 2,5-dichloropyridine. Yellow viscous oil. MS (ISP): 391.3 ([{$^{37}$Cl}M+H]$^+$), 389.3 ([{$^{35}$Cl}M+H]$^+$).

b) (S)-2-{4-[(4-Chloro-phenyl)-methyl-amino]-phenyl}-morpholine-4-carboxylic acid tert-butyl ester To a stirred solution of (S)-2-[4-(4-chloro-phenylamino)-phenyl]-morpholine-4-carboxylic acid tert-butyl ester (60 mg) in DMF (2 ml) was added sodium hydride (6.2 mg) and stirring was continued at room temperature for 15 min. Iodomethane (24.3 mg) was then added dropwise. The reaction mixture was stirred at room temperature for 1 h. TLC at t=1 h showed the reaction was incomplete with some starting material remaining A second portion of sodium hydride (6.2 mg) was added. After stirring at room temperature for 15 min, iodomethane (24.3 mg) was added. Stirring was continued for a further hour. TLC then showed the reaction was complete. The reaction mixture was poured into sat. aq. NaCl and extracted twice with EtOAc. The combined organic layers were dried over Na$_2$SO$_4$ and concentrated in vacuo. The crude material was purified by flash column chromatography (silica gel; gradient: 0% to 50% EtOAc in heptane) to afford (S)-2-{4-[(4-chloro-phenyl)-methyl-amino]-phenyl}-morpholine-4-carboxylic acid tert-butyl ester (49 mg, 79%) as a colourless gum. MS (ISP): 405.4 ([{$^{37}$Cl}M+H]$^+$), 403.4 ([{$^{35}$Cl}M+H]$^+$).

c) (4-Chloro-phenyl)-methyl-((S)-4-morpholin-2-yl-phenyl)-amine

To a stirred solution of trifluoroacetic acid (51.3 µl) in water (4 ml) was added a solution of (S)-2-{4-[(4-chloro-phenyl)-methyl-amino]-phenyl}-morpholine-4-carboxylic acid tert-butyl ester (45 mg) in acetonitrile (2 ml). The reaction mixture was then capped and the mixture was shaken at 80° C. for 2 h. The reaction mixture was then cooled to room temperature and poured into 1 M aq. NaOH and the resulting mixture was extracted twice with EtOAc. The organic layers were dried over Na2SO4 and concentrated in vacuo. The crude material was purified by flash column chromatography (Isolute® Flash-NH$_2$ from Separtis; gradient: 0% to 100% EtOAc in heptane, then 0% to 10% MeOH in EtOAc) to afford (4-chloro-phenyl)-methyl-((S)-4-morpholin-2-yl-phenyl)-amine (9 mg, 27%) as a colourless gum. MS (ISP): 305.3 ([{$^{37}$Cl}M+H]$^+$), 303.3 ([{$^{35}$Cl}M+H]$^+$).

Example 61

(S)-3,5-Dibromo-N-(4-(morpholin-2-yl)phenyl)pyridin-2-amine

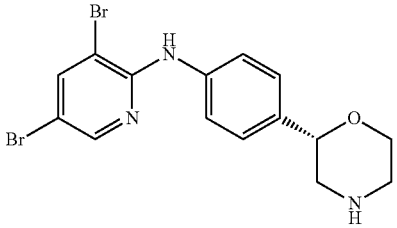 [SMILES: Brc1cnc(Nc2ccc([C@H]3CNCCO3)cc2)c(Br)c1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2,3,5-tribromopyridine (CAS 75806-85-8) instead of 2,5-dichloropyridine in step (a). White amorphous solid. MS (ISP): 415.8 ([{$^{81}$Br}M+H]$^+$), 413.9 ([{$^{81}$Br$^{79}$Br}M+H]$^+$), 412.0 ([{$^{79}$Br}M+H]$^+$).

Example 62

(S)-5-Bromo-4-methyl-N-(4-(morpholin-2-yl)phenyl)pyridin-2-amine

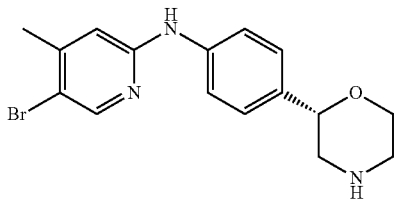 [SMILES: Cc1cc(Nc2ccc([C@H]3CNCCO3)cc2)ncc1Br]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2,5-dibromo-4-methylpyridine (CAS 3430-26-0) instead of 2,5-dichloropyridine in step (a). White solid. MS (ISP): 350.2 ([{$^{81}$Br}M+H]$^+$), 348.0 ([{$^{79}$Br}M+H]$^+$).

Example 63

(S)-2,5-Dichloro-N-(4-(morpholin-2-yl)phenyl)pyridin-4-amine

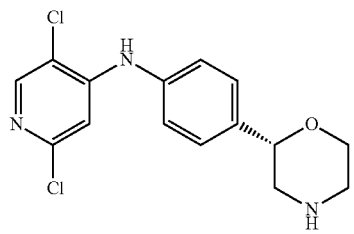 [SMILES: Clc1cc(Nc2ccc([C@H]3CNCCO3)cc2)c(Cl)cn1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 4-bromo-2,5-dichloropyridine (CAS 1184917-16-5) instead of 2,5-dichloropyridine in step (a). White amorphous solid. MS (ISP): 328.1 ([{$^{37}$Cl}M+H]$^+$), 326.1 ([{$^{37}$Cl$^{35}$Cl}M+H]$^+$), 324.2 ([{$^{35}$Cl}M+H]$^+$).

Example 64

(S)-4-Bromo-5-methyl-N-(4-(morpholin-2-yl)phenyl)pyridin-2-amine

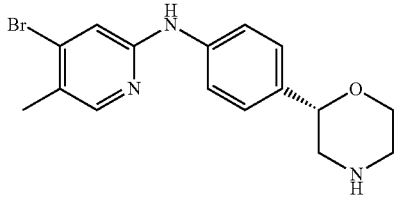 [SMILES: Cc1cnc(Nc2ccc([C@H]3CNCCO3)cc2)cc1Br]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 4-bromo-2-chloro-5-methylpyridine (CAS 867279-13-8) instead of 2,5-dichloropyridine in step (a). White solid. MS (ISP): 350.1 ([{$^{81}$Br}M+H]$^+$), 348.2 ([{$^{79}$Br}M+H]$^+$).

Example 65

(S)—N-(4-(Morpholin-2-yl)phenyl)benzo[d][1,3]dioxol-5-amine

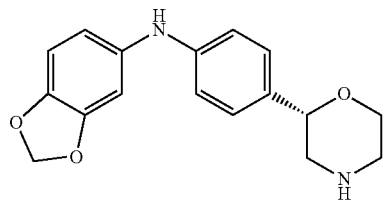 [SMILES: c1cc([C@H]2CNCCO2)ccc1Nc1ccc2c(c1)OCO2]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 5-iodobenzo[d][1,3]dioxole (CAS 5876-51-7) instead of 2,5-dichloropyridine in step (a). Brown amorphous solid. MS (ISP): 299.1 ([M+H]$^+$).

Example 66

(S)-5-Bromo-N-(4-(morpholin-2-yl)phenyl)quinolin-8-amine

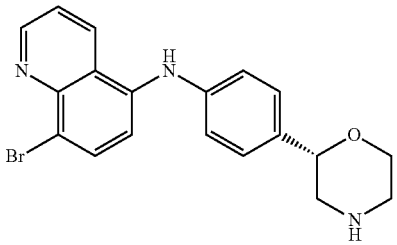 [SMILES: Brc1ccc(Nc2ccc([C@H]3CNCCO3)cc2)c2cccnc12]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 5,8-dibromoquinoline (CAS 81278-86-6) instead of 2,5-dichloropyridine in step (a). Yellow amorphous solid. MS (ISP): 386.1 ([{$^{81}$Br}M+H]$^+$), 384.1 ([{$^{79}$Br}M+H]$^+$).

Example 67

(R)-6-Chloro-N-(4-(morpholin-2-yl)phenyl)pyridin-3-amine

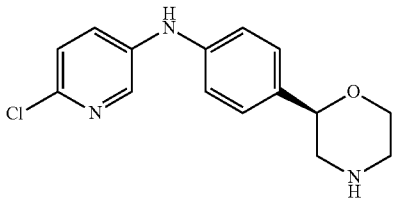 [SMILES: Clc1ccc(Nc2ccc([C@@H]3CNCCO3)cc2)cn1]

The title compound was obtained in analogy to example 5 using (R)-2-(4-amino-phenyl)-morpholine-4-carboxylic acid tert-butyl ester (CAS 1260220-42-5) in place of (RS)-2-(4-amino-phenyl)-morpholine-4-carboxylic acid tert-butyl ester and 5-bromo-2-chloropyridine (CAS 53939-30-3) instead of 2,5-dichloropyridine in step (a). Yellow amorphous solid. MS (ISP): 292.1 ([{$^{37}$Cl}M+H]$^+$), 290.1 ([{$^{35}$Cl}M+H]$^+$).

Example 68

(R)-5-Ethyl-N-(4-(morpholin-2-yl)phenyl)pyrimidin-2-amine

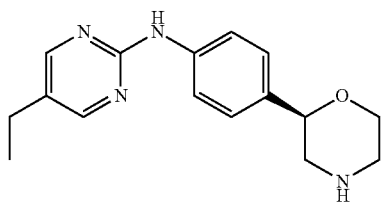 [SMILES: CCc1cnc(Nc2ccc([C@@H]3CNCCO3)cc2)nc1]

The title compound was obtained in analogy to example 5 using (R)-2-(4-amino-phenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-5-ethylpyrimidine (CAS 111196-81-7) instead of 2,5-dichloropyridine in step (a). White solid. MS (ISP): 285.2 ([M+H]$^+$).

Example 69

(R)-5-Chloro-N-(4-(morpholin-2-yl)phenyl)pyridin-2-amine

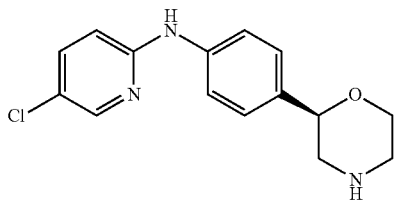 [SMILES: Clc1ccc(Nc2ccc([C@@H]3CNCCO3)cc2)nc1]

The title compound was obtained in analogy to example 5 using (R)-2-(4-amino-phenyl)-morpholine-4-carboxylic acid tert-butyl ester (CAS 1260220-42-5) in place of (RS)-2-(4-amino-phenyl)-morpholine-4-carboxylic acid tert-butyl ester and 2,5-dichloropyridine (CAS 16110-09-1) instead of 2,5-dichloropyridine in step (a). Yellow amorphous solid. MS (ISP): 292.1 ([{$^{37}$Cl}M+H]$^+$), 290.1 ([{$^{35}$Cl}M+H]$^+$).

Example 70

[(RS)-1-(4-Chloro-phenyl)-ethyl]-((S)-4-morpholin-2-yl-phenyl)-amine

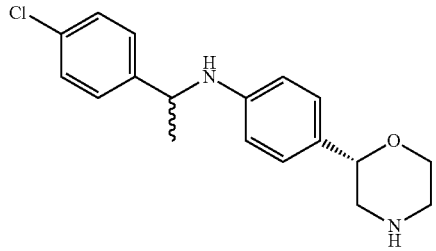 [SMILES: CC(Nc1ccc([C@H]2CNCCO2)cc1)c1ccc(Cl)cc1]

The title compound was obtained in analogy to example 19 using (RS)-1-(4-chlorophenyl)-ethylamine (CAS 6299-02-1)

instead of 5-trifluoromethyl-pyrimidin-2-ylamine in step (a). Colourless gum. MS (ISP): 319.2 ([{$^{37}$Cl}M+H]$^+$), 317.2 ([{$^{35}$Cl}M+H]$^+$).

Example 71

(S)-6-Chloro-5-ethoxy-N-(4-(morpholin-2-yl)phenyl)pyridin-3-amine

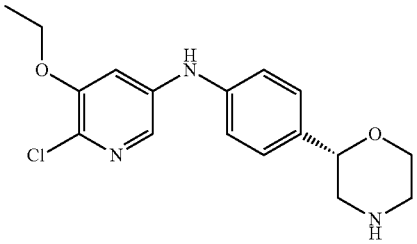 [SMILES: CCOc1cc(Nc2ccc([C@H]3CNCCO3)cc2)cnc1Cl]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 5-bromo-2-chloro-3-ethoxypyridine (CAS 1241752-29-3) instead of 2,5-dichloropyridine in step (a). Yellow solid. MS (ISP): 336.1 ([{$^{37}$Cl}M+H]$^+$), 334.1 ([{$^{35}$Cl}M+H]$^+$).

Example 72

(5-Ethyl-4-methyl-pyrimidin-2-yl)-((S)-4-morpholin-2-yl-phenyl)-amine

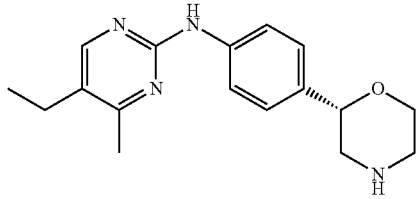 [SMILES: CCc1cnc(Nc2ccc([C@H]3CNCCO3)cc2)nc1C]

The title compound was obtained in analogy to example 19 using 2-amino-5-ethyl-4-methyl-pyrimidine (CAS 861031-36-9) instead of 5-trifluoromethyl-pyrimidin-2-ylamine in step (a). Light yellow gum. MS (ISP): 299.4 ([M+H]$^+$).

Example 73

(5-Isopropyl-4-methyl-pyrimidin-2-yl)-((S)-4-morpholin-2-yl-phenyl)-amine

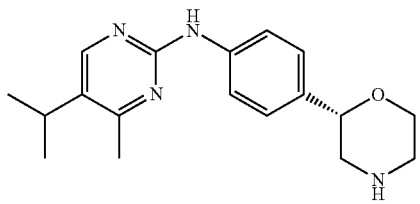

The title compound was obtained in analogy to example 19 using 4-methyl-5-(1-methylethyl)-pyrimidine (CAS 1071763-86-4) instead of 5-trifluoromethyl-pyrimidin-2-ylamine in step (a). Light yellow gum. MS (ISP): 313.3 ([M+H]⁺).

Example 74

((S)-4-Morpholin-2-yl-phenyl)-(5,6,7,8-tetrahydroquinazolin-2-yl)-amine

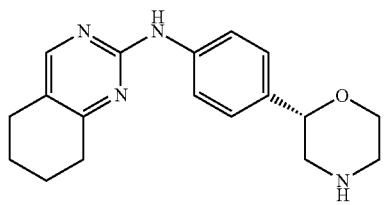 [SMILES: c1cc([C@H]2CNCCO2)ccc1Nc1ncc2c(n1)CCCC2]

The title compound was obtained in analogy to example 19 using 2-amino-5,6,7,8-tetrahydro-quinazoline (CAS 2305-85-3) instead of 5-trifluoromethyl-pyrimidin-2-ylamine in step (a). White solid. MS (ISP): 311.4 ([M+H]⁺).

Example 75

((S)-4-Morpholin-2-yl-phenyl)-(5-nitro-pyrimidin-2-yl)-amine

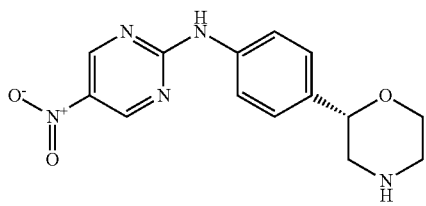 [SMILES: O=[N+]([O-])c1cnc(Nc2ccc([C@H]3CNCCO3)cc2)nc1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-5-nitro-pyrimidine (CAS 10320-42-0) instead of 2,5-dichloropyridine in step (a). Yellow solid. MS (ISP): 302.3 ([M+H]⁺).

Example 76

(RS)-5-Bromo-N-(2-methyl-4-(morpholin-2-yl)phenyl)pyridin-2-amine

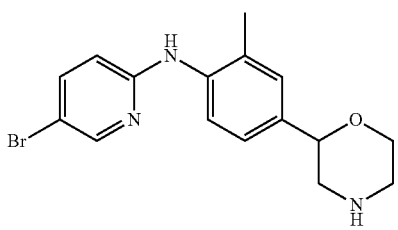 [SMILES: Cc1cc(C2CNCCO2)ccc1Nc1ccc(Br)cn1]

a) 2-Bromo-1-(3-methyl-4-nitrophenyl)ethanone & 2-Chloro-1-(3-methyl-4-nitrophenyl)ethanone To a stirred solution of 3-methyl-4-nitrobenzoyl chloride (5.85 g, CAS 35675-46-8) in acetonitrile (70 ml) and THF (70ml) at 0-5° C. was added dropwise (trimethylsilyl)diazomethane (16.5 ml, 2 M solution in hexane). The reaction mixture was stirred at room temperature for 1 hour. TLC analysis showed the reaction was complete. Hydrobromic acid (9.29 g) was then added dropwise at 0-5° C. and the reaction mixture was stirred at room temperature for 30 min. The reaction mixture was then poured into EtOAc and extracted sequentially with aq. Na₂CO₃ solution, water and saturated brine. The organic layer was then dried over Na₂SO₄ and concentrated in vacuo to afford a ca 1:1 mixture of 2-bromo-1-(3-methyl-4-nitrophenyl)ethanone and 2-chloro-1-(3-methyl-4-nitrophenyl)ethanone (6.23 g) as a brown solid which was used in the next step without further purification. MS (EI): 163.9 ([M₁-CH₂Cl]⁺ & [M₂-CH₂Br]⁺).

b) (RS)-2-(3-Methyl-4-nitrophenyl)oxirane

To a stirred suspension of the mixture of 2-bromo-1-(3-methyl-4-nitrophenyl)ethanone and 2-chloro-1-(3-methyl-4-nitrophenyl)ethanone (6.23 g) in ethanol (100 ml) at 5° C. was added portionwise over 5 min NaBH₄ (913 mg). The reaction mixture was then stirred at room temperature for 1 hour to afford a dark yellow solution. TLC analysis showed the reaction was complete. Sodium methoxide (652 mg) was then added and the reaction mixture was stirred at room temperature overnight. TLC analysis showed a small amount of starting material remaining and so the reaction mixture was stirred at 40° C. for 1 h. The reaction mixture was then poured into EtOAc and extracted with saturated brine. The organic layer was dried over Na₂SO₄ and concentrated in vacuo to afford (RS)-2-(3-methyl-4-nitrophenyl)oxirane (4.63 g, 94% over 2 steps) as a yellow oil. MS (EI): 179 (M⁺), 164 ([M-CH₃]⁺), 162 [M-OH]⁺), 132 [M-OH—NO]⁺), 103, 77.

c) (RS)-2-(2-Hydroxyethylamino)-1-(3-methyl-4-nitrophenyl)ethanol

To a stirred solution of (RS)-2-(3-methyl-4-nitrophenyl)oxirane (4.63 g) in THF (15 ml) was added 2-aminoethanol (15.5 ml) and the mixture was stirred at room temperature overnight. The reaction mixture was then poured into EtOAc/THF (1:1) and extracted with saturated brine. The organic layer was dried over Na₂SO₄ and concentrated in vacuo to afford (RS)-2-(2-hydroxyethylamino)-1-(3-methyl-4-nitrophenyl)ethanol (6.84 g, quant.) as a brown oil which was used in the next step without further purification. MS (ISP): 241.1 ([M+H]⁺).

d) tert-Butyl (RS)-2-hydroxy-2-(3-methyl-4-nitrophenyl)ethyl(2-hydroxyethyl)carbamate To a stirred solution of (RS)-2-(2-hydroxyethylamino)-1-(3-methyl-4-nitrophenyl)ethanol (6.84 g) in THF (50 ml) was added Boc₂O (6.52 g) and the mixture was stirred at room temperature overnight. The reaction mixture was then concentrated in vacuo and the residue was purified by flash column chromatography (silica gel; gradient: heptane/CH₂Cl₂/MeOH) to afford tert-butyl (RS)-2-hydroxy-2-(3-methyl-4-nitrophenyl)ethyl(2-hydroxyethyl)carbamate (6.55 g, 74% over 2 steps) as a yellow oil. MS (ISP): 385.2 ([M+HCOO⁻]⁻).

e) tert-Butyl (RS)-2-(3-methyl-4-nitrophenyl)morpholine-4-carboxylate

To a stirred solution of tert-butyl (RS)-2-hydroxy-2-(3-methyl-4-nitrophenyl)ethyl(2-hydroxyethyl)carbamate (6.55 g) and triethylamine (3.22 ml) in THF (50 ml) at 0-5° C. was added dropwise methanesulfonyl chloride (1.65 ml). The reaction mixture was then stirred at room temperature for 30 min to afford a yellow suspension. TLC analysis showed a small amount of starting material remaining and so further aliquots of triethylamine (0.5 ml) and methanesulfonyl chloride (0.2 ml) were added. The reaction mixture was stirred at room temperature for a further 20 min and was then filtered to remove triethylamine hydrochloride, washing the filter with THF (20 ml). The filtrate was cooled to 0-5° C. and potassium 2-methyl-2-butoxide (17.0 ml, 1.7 M solution in toluene) was added. The reaction mixture was stirred at room temperature for 30 min and then poured into EtOAc and extracted sequentially with water and with saturated brine. The organic layer was dried over $Na_2SO_4$ and concentrated in vacuo.

The residue was purified by flash column chromatography (silica gel; gradient: 0% to 70% EtOAc in hexanes) to afford tert-butyl (RS)-2-(3-methyl-4-nitrophenyl)morpholine-4-carboxylate (2.21 g, 36%) as a yellow oil. MS (ISP): 223.1 ([M+H—$C_5H_8O_2$]$^+$).

f) tert-Butyl (RS)-2-(4-amino-3-methylphenyl)morpholine-4-carboxylate

To a stirred solution of tert-butyl (RS)-2-(3-methyl-4-nitrophenyl)morpholine-4-carboxylate (2.21 g) in methanol (100 ml) was added ammonium formate (6.48 g). The reaction mixture was degassed by bubbling argon into the mixture for several minutes. 10% Palladium on activated charcoal (219 mg) was then added and the reaction mixture was stirred at 60° C. for 1 hour. The reaction mixture was then filtered through celite and concentrated in vacuo. The residue was taken up in EtOAc and extracted sequentially with water and with saturated brine. The organic layer was dried over $Na_2SO_4$ and concentrated in vacuo to afford tert-butyl (RS)-2-(4-amino-3-methylphenyl)morpholine-4-carboxylate (1.99 g, 99%) as a colourless oil. MS (EI): 292 (M$^+$), 235 ([M-$C_4H_9$]$^+$), 219 ([M-$C_4H_9O$]$^+$), 191, 136, 57 ([$C_4H_9$]$^+$).

g) tert-butyl (RS)-2-(4-(5-bromopyridin-2-ylamino)-3-methylphenyl)morpholine-4-carboxylate tert-butyl (RS)-2-(4-amino-3-methylphenyl)morpholine-4-carboxylate (60 mg), 2,5-dibromopyridine (48.6 mg, CAS 624-28-2) and cesium carbonate (100 mg) were combined with dioxane (2 ml) to give a yellow suspension. The mixture was degassed by bubbling argon into the mixture for several minutes. Xantphos (7.12 mg) and tris(dibenzylideneacetone) dipalladium chloroform complex (6.37 mg) were then added. The reaction mixture was then capped and stirred at 80° C. for 1 hour. The crude reaction mixture was cooled to room temperature and filtered. The filtrate was concentrated in vacuo and the residue was purified by flash column chromatography (silica gel; gradient: 0% to 80% EtOAc in hexanes) to afford tert-butyl (RS)-2-(4-(5-bromopyridin-2-ylamino)-3-methylphenyl)morpholine-4-carboxylate (40 mg, 44%) as a colourless amorphous solid. MS (ISP): 450.2 ([$\{^{81}Br\}$M+H]$^+$), 448.1 ([$\{^{79}Br\}$M+H]$^+$), 394.3 ([$\{^{81}Br\}$M+H—$C_4H_8$]$^+$), 392.1 ([$\{^{79}Br\}$M+H—$C_4H_8$]$^+$).

h) (RS)-5-Bromo-N-(2-methyl-4-(morpholin-2-yl)phenyl)pyridin-2-amine

To a stirred solution of trifluoroacetic acid (67.0 μl) in water (6 ml) was added a solution of tert-butyl (RS)-2-(4-(5-bromopyridin-2-ylamino)-3-methylphenyl)morpholine-4-carboxylate (39 mg) in acetonitrile (2 ml). The reaction mixture was then capped and the mixture was shaken at 80° C. for 2 h. The reaction mixture was then cooled to room temperature and poured into EtOAc/THF (1:1) and washed with 1 M aq. NaOH. The organic layer was dried over $Na_2SO_4$ and concentrated in vacuo. The crude material was purified by flash column chromatography (Isolute® Flash-$NH_2$ from Separtis; gradient: heptane/EtOAc/MeOH) to afford (RS)-5-bromo-N-(2-methyl-4-(morpholin-2-yl)phenyl)pyridin-2-amine (17 mg, 56%) as a light yellow amorphous solid. MS (ISP): 350.1 ([$\{^{81}Br\}$M+H]$^+$), 348.2 ([$\{^{79}Br\}$M+H]$^+$).

Example 77

(S)-5-Chloro-3-fluoro-N-(4-(morpholin-2-yl)phenyl)pyridin-2-amine

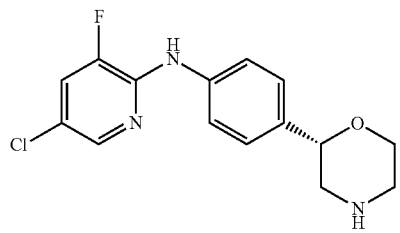 [SMILES: Fc1cc(Cl)cnc1Nc1ccc([C@H]2CNCCO2)cc1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2,5-dichloro-3-fluoropyridine (CAS 103999-77-5) instead of 2,5-dichloropyridine in step (a). Yellow amorphous solid. MS (ISP): 310.2 ([$\{^{37}Cl\}$M+H]$^+$), 308.2 ([$\{^{35}Cl\}$M+H]$^+$).

Example 78

(5-Methanesulfonyl-pyrimidin-2-yl)-((S)-4-morpholin-2-yl-phenyl)-amine

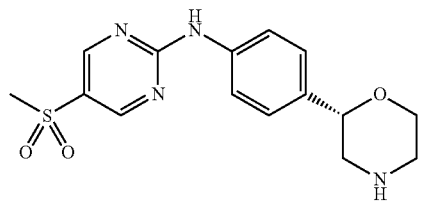 [SMILES: CS(=O)(=O)c1cnc(Nc2ccc([C@H]3CNCCO3)cc2)nc1]

a) (S)-2-[4-(5-Methylsulfanyl-pyrimidin-2-ylamino)-phenyl]-morpholine-4-carboxylic acid tert-butyl ester The title compound was obtained in analogy to example 5 step (a) using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-5-methylsulfanylpyrimidine (CAS 115581-36-7) instead of 2,5-dichloropyridine. Yellow solid. MS (ISP): 403.3 ([M+H]$^+$), 347.1 ([M+H—$C_4H_8$]$^+$).

b) (S)-2-[4-(5-Methanesulfonyl-pyrimidin-2-ylamino)-phenyl]-morpholine-4-carboxylic acid tert-butyl ester To a stirred solution of (S)-2-[4-(5-methylsulfanyl-pyrimidin-2-ylamino)-phenyl]-morpholine-4-carboxylic acid tert-butyl ester (72 mg) in dichloromethane (5 ml) was added 3-chloroperoxybenzoic acid (77.2 mg). The reaction mixture was stirred at room temperature for 1 h. The reaction mixture was then poured into saturated aq. Na$_2$SO$_3$ solution and extracted twice with dichloromethane. The combined organic layers were dried over Na$_2$SO$_4$ and concentrated in vacuo to afford (S)-2-[4-(5-methanesulfonyl-pyrimidin-2-ylamino)-phenyl]-morpholine-4-carboxylic acid tert-butyl ester (84 mg, quant.) as a light brown foam which was used in the next step without further purification. MS (ISP): 435.2 ([M+H]$^+$), 379.2 ([M+H—C$_4$H$_8$]$^+$).

c) (5-Methanesulfonyl-pyrimidin-2-yl)-((S)-4-morpholin-2-yl-phenyl)-amine

The title compound was obtained in analogy to example 60 step (c) using (S)-2-[4-(5-methanesulfonyl-pyrimidin-2-ylamino)-phenyl]-morpholine-4-carboxylic acid tert-butyl ester in place of (S)-2-{4-[(4-chloro-phenyl)-methyl-amino]-phenyl}-morpholine-4-carboxylic acid tert-butyl ester. Off-white solid. MS (ISP): 335.3 ([M+H]$^+$).

Example 79

(RS)-(4-Chloro-phenyl)-(2-methyl-4-morpholin-2-yl-phenyl)-amine

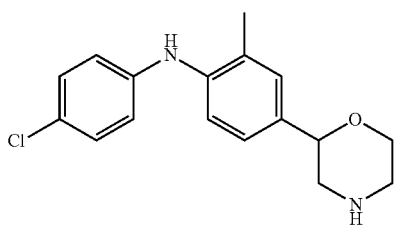 [SMILES: Cc1cc(C2CNCCO2)ccc1Nc1ccc(Cl)cc1]

The title compound was obtained in analogy to example 76 using 1-bromo-4-chlorobenzene (CAS 106-39-8) instead of 2,5-dibromopyridine in step (g). Light yellow gum. MS (ISP): 305.3 ([{$^{37}$Cl}M+H]$^+$), 303.3 ([{$^{35}$Cl}M+H]$^+$).

Example 80

(RS)-(5-Chloro-pyridin-2-yl)-(2-methyl-4-morpholin-2-yl-phenyl)-amine

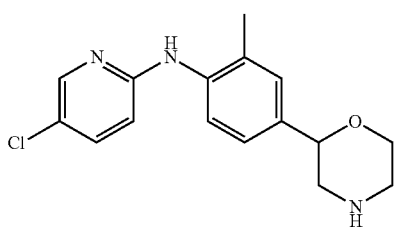 [SMILES: Cc1cc(C2CNCCO2)ccc1Nc1ccc(Cl)cn1]

The title compound was obtained in analogy to example 76 using 2-bromo-5-chloropyridine (CAS 40473-01-6) instead of 2,5-dibromopyridine in step (g). Light yellow gum. MS (ISP): 306.2 ([{$^{37}$Cl}M+H]$^+$), 304.2 ([{$^{35}$Cl}M+H]$^+$).

Example 81

(RS)-(5-Chloro-pyrimidin-2-yl)-(2-methyl-4-morpholin-2-yl-phenyl)-amine

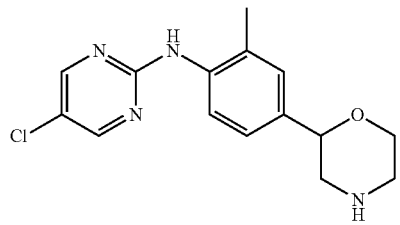 [SMILES: Cc1cc(C2CNCCO2)ccc1Nc1ncc(Cl)cn1]

The title compound was obtained in analogy to example 76 using 2,5-dichloropyrimidine (CAS 22536-67-0) instead of 2,5-dibromopyridine in step (g). Colourless gum. MS (ISP): 307.2 ([{$^{37}$Cl}M+H]$^+$), 305.2 ([{$^{35}$Cl}M+H]$^+$).

Example 82

(S)-5-Chloro-N-(4-(morpholin-2-yl)phenyl)-4-(trifluoromethyl)pyridin-2-amine

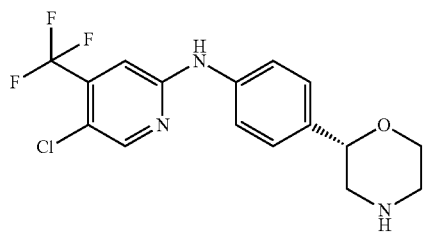 [SMILES: FC(F)(F)c1cc(Nc2ccc([C@H]3CNCCO3)cc2)ncc1Cl]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2,5-dichloro-4-(trifluoromethyl)pyridine (CAS 89719-92-6) instead of 2,5-dichloropyridine in step (a). Light yellow solid. MS (ISP): 360.1 ([{$^{37}$Cl}M+H]$^+$), 358.1 ([{$^{35}$Cl}M+H]$^+$).

Example 83

(S)-5-Chloro-4-methyl-N-(4-(morpholin-2-yl)phenyl)pyridin-2-amine

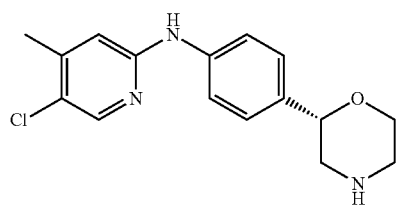 [SMILES: Cc1cc(Nc2ccc([C@H]3CNCCO3)cc2)ncc1Cl]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2,5-dichloro-4-methylpyridine (CAS 886365-00-0) instead of 2,5-dichloropyridine in step (a). White solid. MS (ISP): 306.1 ([{$^{37}$Cl}M+H]$^+$), 304.1 ([{$^{35}$Cl}M+H]$^+$).

Example 84

(RS)-5-Chloro-4-methyl-N-(2-methyl-4-(morpholin-2-yl)phenyl)pyridin-2-amine

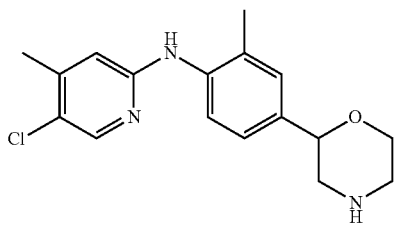 [SMILES: Cc1cc(Nc2ccc(C3CNCCO3)cc2C)ncc1Cl]

The title compound was obtained in analogy to example 76 using 2,5-dichloro-4-methylpyridine (CAS 886365-00-0) instead of 2,5-dibromopyridine in step (g). Colourless amorphous solid. MS (ISP): 320.1 ([{$^{37}$Cl}M+H]$^+$), 318.1 ([{$^{35}$Cl}M+H]$^+$).

Example 85

(RS)-5-Bromo-4-methyl-N-(2-methyl-4-(morpholin-2-yl)phenyl)pyridin-2-amine

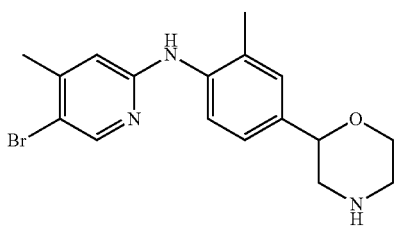

The title compound was obtained in analogy to example 76 using 2,5-dibromo-4-methylpyridine (CAS 3430-26-0) instead of 2,5-dibromopyridine in step (g). Light yellow amorphous solid. MS (ISP): 364.1 ([{$^{81}$Br}M+H]$^+$), 362.1 ([{$^{79}$Br}M+H]$^+$).

Example 86

(5-Cyclopropyl-pyrimidin-2-yl)-((R)-4-morpholin-2-yl-phenyl)-amine

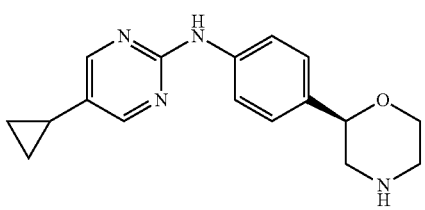 [SMILES: c1cc([C@@H]2CNCCO2)ccc1Nc1ncc(C2CC2)cn1]

The title compound was obtained in analogy to example 5 using (R)-2-(4-amino-phenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-5-cyclopropylpyrimidine (CAS 166740-44-9) instead of 2,5-dichloropyridine in step (a). White solid. MS (ISP): 297.4 ([M+H]$^+$).

Example 87

(RS)-5-Cyclopropyl-N-(2-methyl-4-(morpholin-2-yl)phenyl)pyrimidin-2-amine

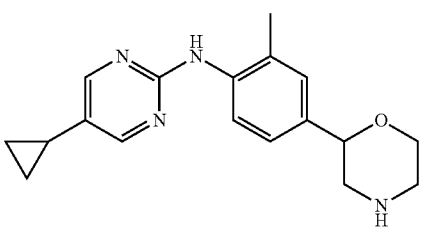 [SMILES: Cc1cc(C2CNCCO2)ccc1Nc1ncc(C2CC2)cn1]

The title compound was obtained in analogy to example 76 using 2-chloro-5-cyclopropylpyrimidine (CAS 166740-44-9) instead of 2,5-dibromopyridine in step (g). Colourless oil. MS (ISP): 311.2 ([M+H]$^+$).

Example 88

(RS)-5-Ethyl-N-(2-methyl-4-(morpholin-2-yl)phenyl)pyrimidin-2-amine

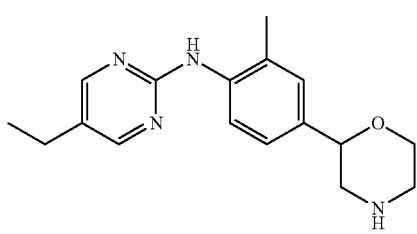 [SMILES: CCc1cnc(Nc2ccc(C3CNCCO3)cc2C)nc1]

The title compound was obtained in analogy to example 76 using 2-chloro-5-ethylpyrimidine (CAS 111196-81-7) instead of 2,5-dibromopyridine in step (g). Yellow oil. MS (ISP): 299.2 ([M+H]$^+$).

Example 89

(RS)-5-Bromo-N-(2-methyl-4-(morpholin-2-yl)phenyl)pyrimidin-2-amine

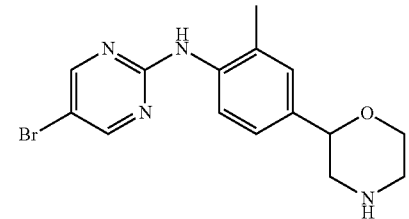

The title compound was obtained in analogy to example 76 using 2,5-dibromopyrimidine (CAS 32779-37-6) instead of 2,5-dibromopyridine in step (g). Off-white amorphous solid. MS (ISP): 351.1 ([{$^{81}$Br}M+H]$^+$), 349.2 ([{$^{79}$Br}M+H]$^+$).

Example 90

(RS)-5-Chloro-N-(5-(morpholin-2-yl)pyridin-2-yl)pyridin-2-amine

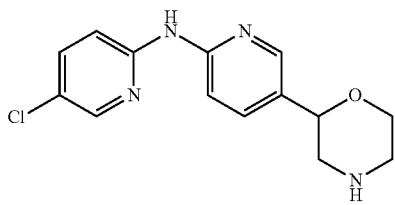 [SMILES: Clc1ccc(Nc2ccc(C3CNCCO3)cn2)nc1]

a) 2-Bromo-1-(6-chloropyridin-3-yl)ethanone & 2-Chloro-1-(6-chloropyridin-3-yl)ethanone To a stirred solution of 6-chloronicotinoyl chloride (5.83 g, CAS 58757-38-3) in acetonitrile (70 ml) and THF (70 ml) at 0-5° C. was added dropwise (trimethylsilyl)diazomethane (15.9 ml, 2 M solution in diethyl ether). The reaction mixture was stirred at room temperature for 1 hour. TLC analysis showed the reaction was complete. Hydrobromic acid (5.98 ml) was then added dropwise at 0-5° C. and the reaction mixture was stirred at room temperature for 30 min. The reaction mixture was then poured into EtOAc and extracted sequentially with aq. $Na_2CO_3$ solution, water and saturated brine. The organic layer was then dried over $Na_2SO_4$ and concentrated in vacuo to afford a ca 1:1 mixture of 2-bromo-1-(6-chloropyridin-3-yl)ethanone and 2-chloro-1-(6-chloropyridin-3-yl)ethanone (5.6 g) as a brown solid which was used in the next step without further purification. MS (EI): 142 ($[\{^{37}Cl\}M_1\text{-}CH_2Cl]^+$ & $[\{^{37}Cl\}M_2\text{-}CH_2Br]^+$), 140 ($[\{^{35}Cl\}M_1\text{-}CH_2Cl]^+$ & $[\{^{35}Cl\}M_2\text{-}CH_2Br]^+$), 114 ($[\{^{37}Cl\}M_1\text{-}CH_2Cl\text{—}CO]^+$ & $[\{^{37}Cl\}M_2\text{-}CH_2Br\text{—}CO]^+$), 112 ($[\{^{35}Cl\}M_1\text{-}CH_2Cl\text{—}CO]^+$ & $[\{^{35}Cl\}M_2\text{-}CH_2Br\text{—}CO]^+$).

b) (RS)-2-Chloro-5-(oxiran-2-yl)pyridine

To a stirred solution of the mixture of 2-bromo-1-(6-chloropyridin-3-yl)ethanone and 2-chloro-1-(6-chloropyridin-3-yl)ethanone (5.6 g) in ethanol (100 ml) at 5° C. was added portionwise over 5 min $NaBH_4$ (904 mg). The reaction mixture was then stirred at room temperature for 1 hour to afford a light yellow solution. TLC analysis showed the reaction was complete. Sodium methoxide (645 mg) was then added and the reaction mixture was stirred at room temperature overnight. TLC analysis showed a small amount of starting material remaining and so the reaction mixture was stirred at 50° C. for 1 h. The reaction mixture was then poured into EtOAc and washed with saturated brine. The organic phase was dried over $Na_2SO_4$ and concentrated in vacuo to afford (RS)-2-chloro-5-(oxiran-2-yl)pyridine (4.04 g) as a yellow oil which was used in the next step without further purification. MS (ISP): 158.0 ($[\{^{37}Cl\}M+H]^+$), 156.0 ($[\{^{35}Cl\}M+H]^+$).

c) (RS)-1-(6-Chloropyridin-3-yl)-2-(2-hydroxyethylamino)ethanol

To a stirred solution of (RS)-2-chloro-5-(oxiran-2-yl)pyridine (4.0 g) in THF (15 ml) was added 2-aminoethanol (15.4 ml) and the mixture was stirred at room temperature overnight. The reaction mixture was then poured into EtOAc/THF (1:1) and the mixture was washed with saturated brine. The organic layer was dried over $Na_2SO_4$ and concentrated in vacuo to afford (RS)-1-(6-chloropyridin-3-yl)-2-(2-hydroxyethylamino)ethanol (5.05 g) as a yellow solid which was used in the next step without further purification. MS (ISP): 219.3 ($[\{^{37}Cl\}M+H]^+$), 217.2 ($[\{^{35}Cl\}M+H]^+$), 201.3 ($[\{^{37}Cl\}M+H\text{—}H_2O]^+$), 199.1 ($[\{^{35}Cl\}M+H\text{—}H_2O]^+$).

d) tert-Butyl(RS)-2-(6-chloropyridin-3-yl)-2-hydroxyethyl(2-hydroxyethyl)carbamate To a stirred solution of (RS)-1-(6-chloropyridin-3-yl)-2-(2-hydroxyethylamino)ethanol (5.05 g) in THF (50 ml) was added $Boc_2O$ (5.34 g) and the mixture was stirred at room temperature overnight. The reaction mixture was then poured into water and extracted with dichloromethane. The organic layer was washed sequentially with 1 M aq. HCl, sat. aq. $NaHCO_3$ solution and saturated brine, then dried over Na2SO4 and concentrated in vacuo. The residue was purified by flash column chromatography (silica gel; gradient: MeOH/dichloromethane/heptane) to afford tert-butyl (RS)-2-(6-chloropyridin-3-yl)-2-hydroxyethyl(2-hydroxyethyl)carbamate (4.68 g, 45% over 4 steps) as a yellow oil. MS (ISP): MS (ISP): 319.1 ($[\{^{37}Cl\}M+H]^+$), 317.1 ($[\{^{35}Cl\}M+H]^+$), 263.1 ($[\{^{37}Cl\}M+H\text{—}C_4H_8]^+$), 261.1 ($[\{^{35}Cl\}M+H\text{—}C_4H_8]^-$).

e) tert-Butyl (RS)-2-(6-chloropyridin-3-yl)morpholine-4-carboxylate

To a stirred solution of tert-butyl (RS)-2-(6-chloropyridin-3-yl)-2-hydroxyethyl(2-hydroxyethyl)carbamate (4.68 g) and triethylamine (3.5 ml) in THF (50 ml) at 0-5° C. was added dropwise methanesulfonyl chloride (1.84 ml). The reaction mixture was then stirred at room temperature for 2.5 hours to afford a yellow suspension. The reaction mixture was then filtered to remove triethylamine hydrochloride, washing the filter with THF (10 ml). The filtrate was cooled to 0-5° C. and potassium 2-methyl-2-butoxide (15.6 ml, 1.7 M solution in toluene) was added. The reaction mixture was stirred at room temperature for 15 min and then poured into EtOAc and washed sequentially with water and with saturated brine. The organic phase was dried over $Na_2SO_4$ and concentrated in vacuo. The residue was purified by flash column chromatography (silica gel; gradient: 0% to 70% EtOAc in hexanes) to afford tert-butyl (RS)-2-(6-chloropyridin-3-yl)morpholine-4-carboxylate (1.16 g, 26%) as a yellow solid. MS (ISP): 301.2 ($[\{^{37}Cl\}M+H]^+$), 299.1 ($[\{^{35}Cl\}M+H]^+$), 245.2 ($[\{^{37}Cl\}M+H\text{—}C_4H_8]^+$), 243.2 ($[\{^{35}Cl\}M+H\text{—}C_4H_8]^+$).

f) tert-Butyl (RS)-2-(6-(diphenylmethyleneamino)pyridin-3-yl)morpholine-4-carboxylate To a stirred solution of tert-butyl (RS)-2-(6-chloropyridin-3-yl)morpholine-4-carboxylate (1.16 g) and benzophenone imine (977 μl) in toluene (35 ml) was added sodium tert-butoxide (597 mg). The reaction mixture was purged with argon for 10 min. (R)-(+)-2,2'-bis(diphenylphosphino)-1,1'-binaphthyl (242 mg) and tris(dibenzylideneacetone)dipalladium(0) (107 mg) were added and the reaction mixture was heated at 100° C. overnight. The reaction mixture was then cooled to room temperature, poured into water and extracted twice with EtOAc. The organic layers were dried over Na2SO4 and concentrated in vacuo. The residue was purified by flash column chromatography (silica gel; gradient: 0% to 30% EtOAc in hexanes) to afford tert-butyl (RS)-2-(6-(diphenylmethyleneamino)pyridin-3-yl)morpholine-4-carboxylate (374 mg, 22%) as a yellow oil. MS (ISP): 444.2 ([M+H]$^+$).

g) tert-Butyl (RS)-2-(6-aminopyridin-3-yl)morpholine-4-carboxylate

To a stirred solution of tert-butyl (RS)-2-(6-(diphenylmethyleneamino)pyridin-3-yl)morpholine-4-carboxylate (370 mg) in methanol (20 ml) was added ammonium formate (789 mg). The reaction mixture was degassed by bubbling argon into the mixture for several minutes. 10% Palladium on activated charcoal (44 mg) was then added and the reaction mixture was stirred at 60° C. for 1 hour. The reaction mixture was then filtered through celite and the filtrate was concentrated in vacuo. The residue was taken up in EtOAc and the mixture was washed sequentially with water and with saturated brine. The organic layer was dried over Na$_2$SO$_4$ and concentrated in vacuo. The residue was purified by flash column chromatography (silica gel; gradient: heptane/dichloromethane/MeOH) to afford tert-butyl (RS)-2-(6-aminopyridin-3-yl)morpholine-4-carboxylate (171 mg, 73%) as a light yellow oil. MS (ISP): 280.2 ([M+H]$^+$).

h) tert-Butyl 2-(6-(5-chloropyridin-2-ylamino)pyridin-3-yl)morpholine-4-carboxylate tert-Butyl (RS)-2-(6-aminopyridin-3-yl)morpholine-4-carboxylate (55 mg), 2,5-dichloropyridine (29 mg, CAS 16110-09-1) and cesium carbonate (96 mg) were combined with dioxane (2 ml) to give a yellow suspension. The mixture was degassed by bubbling argon into the mixture for several minutes. Xantphos (6.84 mg) and tris(dibenzylideneacetone) dipalladium chloroform complex (6.11 mg) were then added. The reaction mixture was then capped and stirred at 100° C. overnight. The crude reaction mixture was cooled to room temperature and filtered. The filtrate was concentrated in vacuo and the residue was purified by flash column chromatography (silica gel; gradient: 0% to 80% EtOAc in hexanes) to afford tert-butyl 2-(6-(5-chloropyridin-2-ylamino)pyridin-3-yl)morpholine-4-carboxylate (22 mg, 29%) as a yellow solid. MS (ISP): 393.2 ([{$^{37}$Cl}M+H]$^+$), 391.2 ([{$^{35}$Cl}M+H]$^+$).

i) (RS)-5-Chloro-N-(5-(morpholin-2-yl)pyridin-2-yl)pyridin-2-amine

To a stirred solution of tert-butyl 2-(6-(5-chloropyridin-2-ylamino)pyridin-3-yl)morpholine-4-carboxylate (22 mg) in acetonitrile (1.5 ml) and water (4.5 ml) was added trifluoroacetic acid (43 μl). The reaction mixture was then capped and the mixture was shaken at 80° C. for 3 h. The reaction mixture was then cooled to room temperature and poured into EtOAc/THF (1:1) and washed with 1 M aq. NaOH. The organic layer was dried over Na$_2$SO$_4$ and concentrated in vacuo. The crude material was purified by flash column chromatography (Isolute® Flash-NH$_2$ from Separtis; gradient: heptane/EtOAc/MeOH) to afford (RS)-5-chloro-N-(5-(morpholin-2-yl)pyridin-2-yl)pyridin-2-amine (15 mg, 92%) as a colourless amorphous solid. MS (ISP): 293.1 ([{$^{37}$Cl}M+H]$^+$), 291.1 ([{$^{35}$Cl}M+H]$^+$).

Example 91

(RS)-5-Bromo-N-(5-(morpholin-2-yl)pyridin-2-yl)pyridin-2-amine

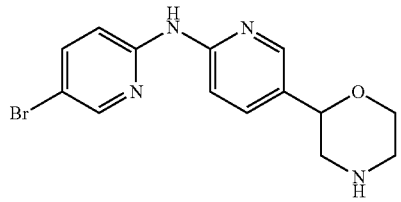

The title compound was obtained in analogy to example 90 using 2,5-dibromopyridine (CAS 624-28-2) instead of 2,5-dichloropyridine in step (h). Light yellow solid. MS (ISP): 337.1 ([{$^{81}$Br}M+H]$^+$), 335.1 ([{$^{79}$Br}M+H]$^+$).

Example 92

(RS)-5-Cyclopropyl-N-(5-(morpholin-2-yl)pyridin-2-yl)pyrimidin-2-amine

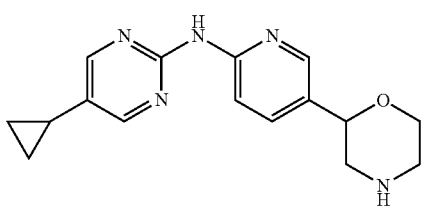 [SMILES: c1nc(Nc2ccc(C3CNCCO3)cn2)ncc1C1CC1]

The title compound was obtained in analogy to example 90 using 2-chloro-5-cyclopropylpyrimidine (CAS 166740-44-9) instead of 2,5-dichloropyridine in step (h). White. MS (ISP): 298.2 ([M+H]$^+$).

Example 93

((R)-4-Morpholin-2-yl-phenyl)-(5-propyl-pyrimidin-2-yl)-amine

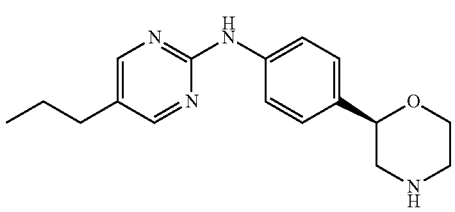 [SMILES: CCCc1cnc(Nc2ccc([C@@H]3CNCCO3)cc2)nc1]

The title compound was obtained in analogy to example 5 using (R)-2-(4-amino-phenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-5-propylpyrimidine (CAS 219555-98-3) instead of 2,5-dichloropyridine in step (a). Off-white solid. MS (ISP): 299.4 ([M+H]$^+$).

Example 94

(5-Bromo-pyrimidin-2-yl)-((R)-4-morpholin-2-yl-phenyl)-amine

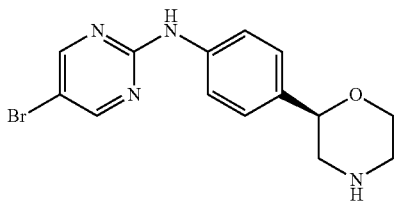

The title compound was obtained in analogy to example 5 using (R)-2-(4-amino-phenyl)-morpholine-4-carboxylic acid tert-butyl ester (CAS 1260220-42-5) in place of (RS)-2-(4-amino-phenyl)-morpholine-4-carboxylic acid tert-butyl ester and 2,5-dibromopyrimidine (CAS 32779-37-6) instead of 2,5-dichloropyridine in step (a). White solid. MS (ISP): 337.3 ([$\{^{81}$Br$\}$M+H]$^+$), 335.3 ([$\{^{79}$Br$\}$M+H]$^+$).

Example 95

((R)-4-Morpholin-2-yl-phenyl)-(5-trifluoromethyl-pyrimidin-2-yl)-amine

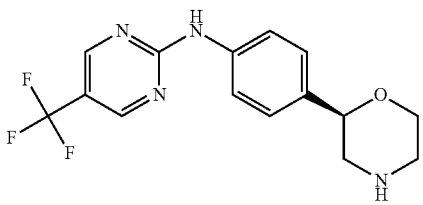 [SMILES: FC(F)(F)c1cnc(Nc2ccc([C@@H]3CNCCO3)cc2)nc1]

The title compound was obtained in analogy to example 19 using (R)-2-(4-bromo-phenyl)-morpholine-4-carboxylic acid tert-butyl ester instead of (S)-2-(4-bromo-phenyl)-morpholine-4-carboxylic acid tert-butyl ester in step (a). White solid. MS (ISP): 325.3 ([M+H]$^+$).

Example 96

(RS)-5-Chloro-N-(2-fluoro-4-(morpholin-2-yl)phenyl)pyrimidin-2-amine

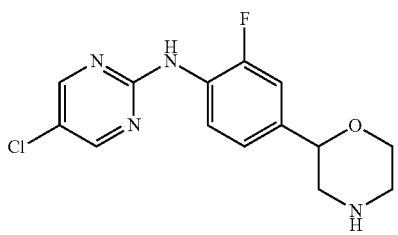 [SMILES: Fc1cc(C2CNCCO2)ccc1Nc1ncc(Cl)cn1]

a) 2-Bromo-1-(4-bromo-3-fluoro-phenyl)-ethanone & 2-Chloro-1-(4-bromo-3-fluoro-phenyl)-ethanone To a stirred solution of 4-bromo-3-fluorobenzoyl chloride (5.4 g, CAS 695188-21-7) in acetonitrile (60 ml) and THF (60ml) at 0-5° C. was added dropwise (trimethylsilyl)diazomethane (13.6 ml, 2 M solution in diethyl ether). The reaction mixture was stirred at room temperature for 30 min. TLC analysis showed the reaction was complete. Hydrobromic acid (5.15 ml) was then added dropwise at 0-5° C. and the reaction mixture was stirred at room temperature for 1 hour. The reaction mixture was then poured into EtOAc and extracted sequentially with aq. Na$_2$CO$_3$ solution, water and saturated brine. The organic layer was then dried over Na$_2$SO$_4$ and concentrated in vacuo to afford a ca 1:1 mixture of 2-bromo-1-(4-bromo-3-fluoro-phenyl)-ethanone and 2-chloro-1-(4-bromo-3-fluoro-phenyl)-ethanone (6.16 g) as a light yellow solid which was used in the next step without further purification. MS (EI): 203.2 ([$\{^{81}$Br$\}$M$_1$-CH$_2$Cl]$^+$ & [$\{^{81}$Br$\}$M$_2$-CH$_2$Br]$^+$), 201.2 ([$\{^{79}$Br$\}$M$_1$-CH$_2$Cl]$^+$ & [$\{^{79}$Br$\}$M$_2$-CH$_2$Br]$^+$).

b) (RS)-2-(4-Bromo-3-fluoro-phenyl)-oxirane

To a stirred solution of the mixture of 2-bromo-1-(4-bromo-3-fluoro-phenyl)-ethanone and 2-chloro-1-(4-bromo-3-fluoro-phenyl)-ethanone (6.16 g) in ethanol (100 ml) at 5° C. was added portionwise over 5 min NaBH$_4$ (788 mg). The reaction mixture was then stirred at room temperature for 1 hour to afford a light yellow solution. TLC analysis showed the reaction was complete. Sodium methoxide (562 mg) was then added and the reaction mixture was stirred at room temperature overnight. TLC analysis showed a small amount of starting material remaining and so the reaction mixture was stirred at 40° C. for 1 h. The reaction mixture was then poured into water and extracted twice with EtOAc. The combined organic layers were washed with saturated brine, then dried over Na$_2$SO$_4$ and concentrated in vacuo to afford (RS)-2-(4-bromo-3-fluoro-phenyl)-oxirane (4.69 g) as a yellow oil which was used in the next step without further purification.

c) (RS)-1-(4-Bromo-3-fluoro-phenyl)-2-(2-hydroxy-ethylamino)-ethanol

To a stirred solution of (RS)-2-(4-bromo-3-fluoro-phenyl)-oxirane (4.69 g) in THF (11 ml) was added 2-aminoethanol (13.2 ml) and the mixture was stirred at room temperature overnight. The reaction mixture was then poured into brine and extracted twice with EtOAc. The combined organic layers was dried over Na$_2$SO$_4$ and concentrated in vacuo to afford (RS)-1-(4-bromo-3-fluoro-phenyl)-2-(2-hydroxy-ethylamino)-ethanol (5.37 g) as a yellow viscous oil which was used in the next step without further purification. MS (ISP): 280.2 ([$\{^{81}$Br$\}$M+H]$^+$), 278.1 ([$\{^{79}$Br$\}$M+H]$^+$).

d) (RS)-[2-(4-Bromo-3-fluoro-phenyl)-2-hydroxy-ethyl]-(2-hydroxy-ethyl)-carbamic acid tert-butyl ester To a stirred solution of (RS)-1-(4-bromo-3-fluoro-phenyl)-2-(2-hydroxy-ethylamino)-ethanol (5.37 g) in dichloromethane (60 ml) was added Boc$_2$O (4.00 g) and the mixture was stirred at room temperature overnight. The reaction mixture was then poured into water and extracted with dichloromethane. The organic layer was washed sequentially with 1 M aq. HCl, sat. aq. NaHCO$_3$ solution and saturated brine, then dried over Na2SO4 and concentrated in vacuo. The residue was purified by flash column chromatography (silica gel; gradient: 0% to 10% MeOH in dichloromethane) to afford (RS)-[2-(4-bromo-3-fluoro-phenyl)-2-hydroxy-ethyl]-(2-hydroxy-ethyl)-carbamic acid tert-butyl ester (3.89 g, 45% over 4 steps) as a light yellow viscous oil. MS (ISP): 380.1 ([{$^{81}$Br}M+H]$^+$), 378.2 ([{$^{79}$Br}M+H]$^+$).

e) (RS)-2-(4-Bromo-3-fluoro-phenyl)-morpholine-4-carboxylic acid tert-butyl ester To a stirred solution of (RS)-[2-(4-bromo-3-fluoro-phenyl)-2-hydroxy-ethyl]-(2-hydroxy-ethyl)-carbamic acid tert-butyl ester (3.88 g) and triethylamine (1.71 ml) in THF (40 ml) at 0-5° C. was added dropwise methanesulfonyl chloride (873 µl). The reaction mixture was then stirred at room temperature for 30 min to afford a white suspension. The reaction mixture was then filtered to remove triethylamine hydrochloride, washing the filter with THF (6 ml). The filtrate was cooled to 0-5° C. and potassium 2-methyl-2-butoxide (9.05 ml, 1.7 M solution in toluene) was added. The reaction mixture was stirred at room temperature for 1 hour and then poured into water and extracted twice with EtOAc. The combined organic phases were dried over $Na_2SO_4$ and concentrated in vacuo. The residue was purified by flash column chromatography (silica gel; gradient: 0% to 30% EtOAc in hexanes) to afford (RS)-2-(4-bromo-3-fluoro-phenyl)-morpholine-4-carboxylic acid tert-butyl ester (1.73 g, 47%) as an orange viscous oil. MS (ISP): 306.1 ([{$^{81}$Br}M+H—$C_4H_8$]$^+$), 304.1 ([{$^{79}$Br}M+H—$C_4H_8$]$^+$), 262.0 ([{$^{81}$Br}M+H—$C_4H_8$—$CO_2$]$^+$), 260.1 ([{$^{79}$Br}M+H—$C_4H_8$—$CO_2$]$^+$).

f) (RS)-2-[4-(Benzhydrylidene-amino)-3-fluoro-phenyl]-morpholine-4-carboxylic acid tert-butyl ester To a stirred solution of (RS)-2-(4-bromo-3-fluoro-phenyl)-morpholine-4-carboxylic acid tert-butyl ester (1.57 g) and benzophenone imine (1.15 ml) in toluene (40 ml) was added sodium tert-butoxide (691 mg). The reaction mixture was purged with argon for 10 min. (R)-(+)-2,2'-bis(diphenylphosphino)-1,1'-binaphthyl (280 mg) and tris(dibenzylideneacetone)dipalladium(0) (120 mg) were added and the reaction mixture was heated to 100° C. and stirred for 1 h. The reaction mixture was poured into water and extracted twice with EtOAc. The organic layers were dried over Na2SO4 and concentrated in vacuo. The residue was purified by flash column chromatography (silica gel; gradient: 0% to 30% EtOAc in hexanes) to afford (RS)-2-[4-(benzhydrylidene-amino)-3-fluoro-phenyl]-morpholine-4-carboxylic acid tert-butyl ester (2.215 g, quant.) as a yellow viscous oil. MS (ISP): 461.3 ([M+H]$^+$), 405.4 ([M+H—$C_4H_8$]$^+$), 361.3 ([M+H—$C_4H_8$—$CO_2$]$^+$).

g) (RS)-2-(4-Amino-3-fluoro-phenyl)-morpholine-4-carboxylic acid tert-butyl ester To a stirred solution of tert-butyl (RS)-2-[4-(benzhydrylidene-amino)-3-fluoro-phenyl]-morpholine-4-carboxylic acid tert-butyl ester (2.21 g) in methanol (40 ml) was added ammonium formate (4.54 g). The reaction mixture was degassed by bubbling argon into the mixture for several minutes. 10% Palladium on activated charcoal (255 mg) was then added and the reaction mixture was stirred at 60° C. for 1 hour. The reaction mixture was then filtered through celite and the filtrate was poured into 1 M aq. NaOH and extracted twice with EtOAc. The combined organic layers were dried over Na2SO4 and concentrated in vacuo. The residue was purified by flash column chromatography (silica gel; gradient: 0% to 30% EtOAc in hexanes) to afford (RS)-2-(4-amino-3-fluoro-phenyl)-morpholine-4-carboxylic acid tert-butyl ester (1.42 g, 74%) as a white solid. MS (ISP): 319.2 ([M+Na]$^+$), 297.3 ([M+H]$^+$), 241.2 ([M+H—$C_4H_8$]$^+$), 197.2 ([M+H—$C_4H_8$—$CO_2$]$^+$).

h) tert-Butyl (RS)-2-(4-(5-chloropyrimidin-2-ylamino)-3-fluorophenyl)morpholine-4-carboxylate (RS)-2-(4-Amino-3-fluoro-phenyl)-morpholine-4-carboxylic acid tert-butyl ester (60 mg), 2,5-dichloropyrimidine (30.2 mg, CAS 22536-67-0) and cesium carbonate (99 mg) were combined with dioxane (2 ml) to give a yellow suspension. The mixture was degassed by bubbling argon into the mixture for several minutes. Xantphos (7.03 mg) and tris (dibenzylideneacetone)dipalladium chloroform complex (6.29 mg) were then added. The reaction mixture was then capped and stirred at 120° C. for 2 hours. The crude reaction mixture was cooled to room temperature and filtered. The filtrate was concentrated in vacuo and the residue was purified by flash column chromatography (silica gel; gradient: 0% to 80% EtOAc in hexanes) to afford tert-butyl (RS)-2-(4-(5-chloropyrimidin-2-ylamino)-3-fluorophenyl)morpholine-4-carboxylate (26 mg, 31%) as a colourless amorphous solid. MS (ISP): 411.3 ([{$^{37}$Cl}M+H]$^+$), 409.2 ([{$^{35}$Cl}M+H]$^+$), 355.3 ([{$^{37}$Cl}M+H—$C_4H_8$]$^+$), 353.3 ([{$^{35}$Cl}M+H—$C_4H_8$]$^+$).

i) (RS)-5-Chloro-N-(2-fluoro-4-(morpholin-2-yl)phenyl)pyrimidin-2-amine

To a stirred solution of tert-butyl (RS)-2-(4-(5-chloropyrimidin-2-ylamino)-3-fluorophenyl)morpholine-4-carboxylate (26 mg) in acetonitrile (1.5 ml) and water (4.5 ml) was added trifluoroacetic acid (49.0 µl). The reaction mixture was then capped and the mixture was shaken at 80° C. for 3 h. The reaction mixture was then cooled to room temperature and poured into EtOAc/THF (1:1) and washed with 1 M aq. NaOH. The organic layer was dried over $Na_2SO_4$ and concentrated in vacuo. The crude material was purified by flash column chromatography (Isolute® Flash-NH$_2$ from Separtis; gradient: heptane/EtOAc/MeOH) to afford (RS)-5-chloro-N-(2-fluoro-4-(morpholin-2-yl)phenyl)pyrimidin-2-amine (14 mg, 71%) as a white solid. MS (ISP): 311.1 ([{$^{37}$Cl}M+H]$^+$), 309.1 ([{$^{35}$Cl}M+H]$^+$).

Example 97

(RS)-5-Ethyl-N-(2-fluoro-4-(morpholin-2-yl)phenyl)pyrimidin-2-amine

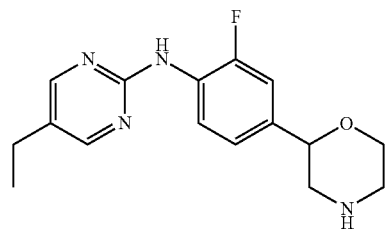 [SMILES: CCc1cnc(Nc2ccc(C3CNCCO3)cc2F)nc1]

The title compound was obtained in analogy to example 96 using 2-chloro-5-ethylpyrimidine (CAS 111196-81-7) instead of 2,5-dichloropyrimidine in step (h). White solid. MS (ISP): 303.2 ([M+H]+).

Example 98

(RS)-5-Cyclopropyl-N-(2-fluoro-4-(morpholin-2-yl)phenyl)pyrimidin-2-amine

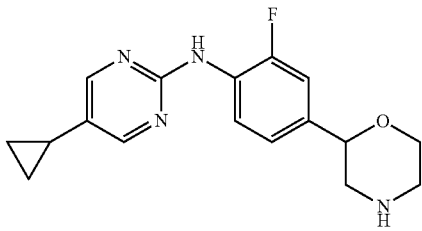 [SMILES: Fc1cc(C2CNCCO2)ccc1Nc1ncc(C2CC2)cn1]

The title compound was obtained in analogy to example 96 using 2-chloro-5-cyclopropylpyrimidine (CAS 166740-44-9) instead of 2,5-dichloropyrimidine in step (h). White solid. MS (ISP): 315.2 ([M+H]+).

Example 99

(RS)-5-Chloro-N-(2-fluoro-4-(morpholin-2-yl)phenyl)pyridin-2-amine

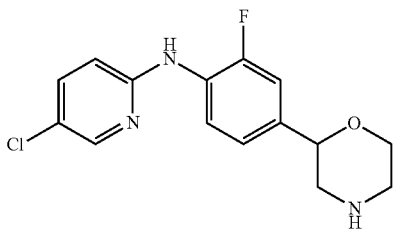 [SMILES: Fc1cc(C2CNCCO2)ccc1Nc1ccc(Cl)cn1]

The title compound was obtained in analogy to example 96 using 2,5-dichloropyridine (CAS 16110-09-1) instead of 2,5-dichloropyrimidine in step (h). Off-white solid. MS (ISP): 310.1 ([{37Cl}M+H]+), 308.1 ([{35Cl}M+H]+).

Example 100

(RS)-(5-Ethoxy-pyrimidin-2-yl)-(2-fluoro-4-morpholin-2-yl-phenyl)-amine

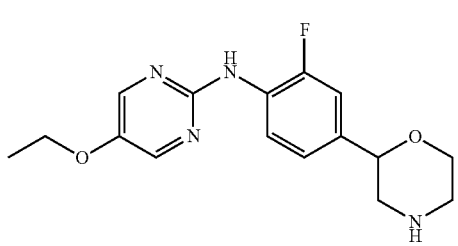 [SMILES: CCOc1cnc(Nc2ccc(C3CNCCO3)cc2F)nc1]

a) (RS)-2-[4-(5-Ethoxy-pyrimidin-2-ylamino)-3-fluoro-phenyl]-morpholine-4-carboxylic acid tert-butyl ester To a 10 ml glass vial was added (RS)-2-(4-bromo-3-fluoro-phenyl)-morpholine-4-carboxylic acid tert-butyl ester (70 mg, Example 96(e)) and 5-ethoxy-2-pyrimidinamine (40.6 mg, CAS 39268-74-1) in dioxane (2 ml). The reaction mixture was purged with argon for 5 min. 2-Di-tert-butylphosphino-2',4',6'-triisopropylbiphenyl (13.6 mg), tris(dibenzylideneacetone)dipalladium(0) (7.12 mg) and sodium tert-butoxide (21.0 mg) were then added. The vial was capped and heated at 120° C. for 16 h. The reaction mixture was then filtered through sintered glass and the filtrate was concentrated in vacuo. The residue was purified by flash column chromatography (silica gel; gradient: 0% to 50% EtOAc in hexanes) to afford (RS)-2-[4-(5-ethoxy-pyrimidin-2-ylamino)-3-fluoro-phenyl]-morpholine-4-carboxylic acid tert-butyl ester (15 mg, 18%) as a yellow gum. MS (ISP): 441.4 ([M+Na]+), 419.3 ([M+H]+).

b) (RS)-(5-Ethoxy-pyrimidin-2-yl)-(2-fluoro-4-morpholin-2-yl-phenyl)-amine

To a stirred solution of (RS)-2-[4-(5-ethoxy-pyrimidin-2-ylamino)-3-fluoro-phenyl]-morpholine-4-carboxylic acid tert-butyl ester (12 mg) in acetonitrile (1.5 ml) and water (3 ml) was added trifluoroacetic acid (22.0 µl). The reaction mixture was then capped and the mixture was shaken at 80° C. for 3.5 h. The reaction mixture was then cooled to room temperature and poured into EtOAc and washed with 1 M aq. NaOH. The organic layer was dried over Na2SO4 and concentrated in vacuo. The crude material was purified by flash column chromatography (Isolute® Flash-NH2 from Separtis; gradient: heptane/EtOAc/MeOH) to afford (RS)-(5-ethoxy-pyrimidin-2-yl)-(2-fluoro-4-morpholin-2-yl-phenyl)-amine (10 mg, quant.) as an off-white solid. MS (ISP): 319.2 ([M+H]+).

Example 101

(RS)-(2-Fluoro-4-morpholin-2-yl-phenyl)-(5-propyl-pyrimidin-2-yl)-amine

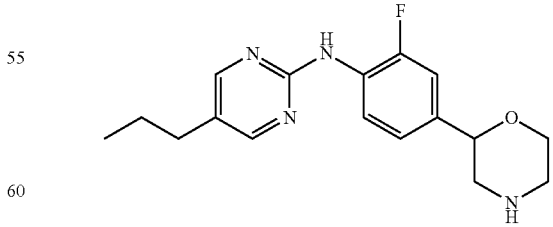

The title compound was obtained in analogy to example 96 using 2-chloro-5-propylpyrimidine (CAS 219555-98-3) instead of 2,5-dichloropyrimidine in step (h). Off-white solid. MS (ISP): 317.2 ([M+H]+).

Example 102

(RS)-(5-Bromo-pyrimidin-2-yl)-(2-fluoro-4-morpholin-2-yl-phenyl)-amine

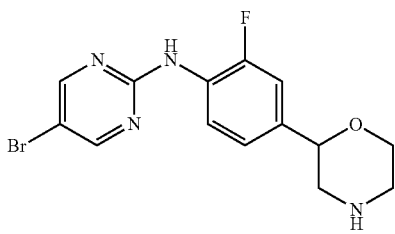

The title compound was obtained in analogy to example 96 using 2,5-dibromopyrimidine (CAS 32779-37-6) instead of 2,5-dichloropyrimidine in step (h). Off-white solid. MS (ISP): 355.3 ([$\{^{81}Br\}M+H$]$^+$), 353.1 ([$\{^{79}Br\}M+H$]$^+$).

Example 103

(R)-5-Chloro-N-(4-(morpholin-2-yl)phenyl)pyrimidin-2-amine

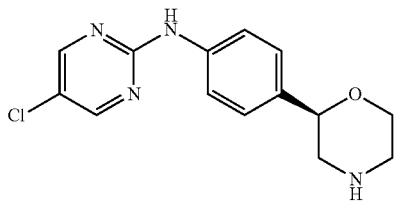 [SMILES: Clc1cnc(Nc2ccc([C@@H]3CNCCO3)cc2)nc1]

The title compound was obtained in analogy to example 5 using (R)-2-(4-amino-phenyl)-morpholine-4-carboxylic acid tert-butyl ester (CAS 1260220-42-5) in place of (RS)-2-(4-amino-phenyl)-morpholine-4-carboxylic acid tert-butyl ester and 2,5-dichloropyrimidine (CAS 22536-67-0) instead of 2,5-dichloropyridine in step (a). White solid. MS (ISP): 293.1 ([$\{^{37}Cl\}M+H$]$^+$), 291.1 ([$\{^{35}Cl\}M+H$]$^+$).

Example 104

(S)-5-Chloro-N-(4-(morpholin-2-yl)phenyl)pyrimidin-2-amine

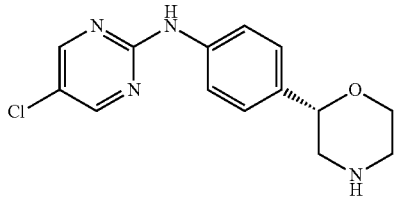 [SMILES: Clc1cnc(Nc2ccc([C@H]3CNCCO3)cc2)nc1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2,5-dichloropyrimidine (CAS 22536-67-0) instead of 2,5-dichloropyridine in step (a). Off-white solid. MS (ISP): 293.0 ([$\{^{37}Cl\}M+H$]$^+$), 291.1 ([$\{^{35}Cl\}M+H$]$^+$).

Example 105

(5-Ethoxy-pyrimidin-2-yl)-((R)-4-morpholin-2-yl-phenyl)-amine

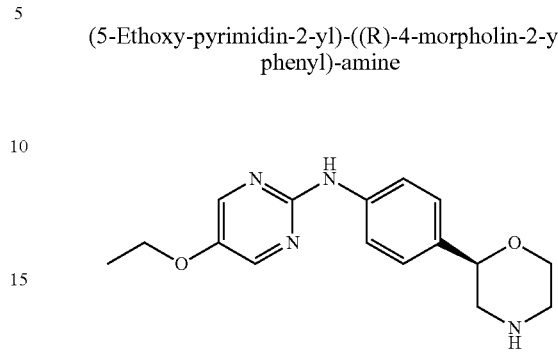

The title compound was obtained in analogy to example 19 using (R)-2-(4-bromo-phenyl)-morpholine-4-carboxylic acid tert-butyl ester instead of (S)-2-(4-bromo-phenyl)-morpholine-4-carboxylic acid tert-butyl ester and 5-ethoxy-2-pyrimidinamine (CAS 39268-74-1) instead of 5-trifluoromethyl-pyrimidin-2-ylamine in step (a). White solid. MS (ISP): 301.3 ([M+H]$^+$).

Example 106

(5-Ethyl-pyrimidin-2-yl)-((R)-2-methyl-4-morpholin-2-yl-phenyl)-amine

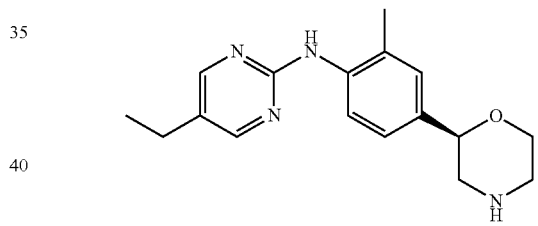

a) (R)-tert-Butyl 2-(4-amino-3-methylphenyl)morpholine-4-carboxylate & (S)-tert-Butyl 2-(4-amino-3-methylphenyl)morpholine-4-carboxylate The enantiomers of tert-butyl (RS)-2-(4-amino-3-methylphenyl)morpholine-4-carboxylate (1.18 g, Example 76(f)) were separated using chiral HPLC (column: Chiralpak AD, 5×50 cm; eluent: 5% isopropanol/heptane; pressure: 18 bar; flow rate: 35 ml/min) affording:
(+)-(R)-tert-Butyl 2-(4-amino-3-methylphenyl)morpholine-4-carboxylate (453 mg, yellow oil) Retention time=120 min
(−)-(S)-tert-Butyl 2-(4-amino-3-methylphenyl)morpholine-4-carboxylate (464 mg, yellow oil) Retention time=152 min b) (5-Ethyl-pyrimidin-2-yl)-((R)-2-methyl-4-morpholin-2-yl-phenyl)-amine The title compound was obtained in analogy to example 76 (g)-(h) using (+)-(R)-tert-butyl 2-(4-amino-3-methylphenyl) morpholine-4-carboxylate in place of (RS)-tert-butyl 2-(4-amino-3-methylphenyl)morpholine-4-carboxylate and 2-chloro-5-ethylpyrimidine (CAS 111196-81-7) instead of 2,5-dibromopyridine in step (g). Light brown viscous oil. MS (ISP): 299.4 ([M+H]⁺).

Example 107

(5-Ethyl-pyrimidin-2-yl)-((S)-2-methyl-4-morpholin-2-yl-phenyl)-amine

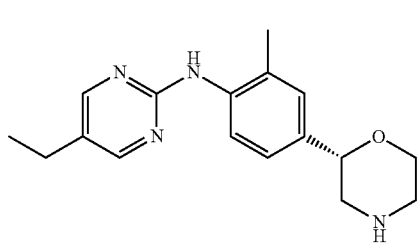

The title compound was obtained in analogy to example 106 using (−)-(S)-tert-butyl 2-(4-amino-3-methylphenyl)morpholine-4-carboxylate in place of (+)-(R)-tert-butyl 2-(4-amino-3-methylphenyl)morpholine-4-carboxylate in step (b). Orange viscous oil. MS (ISP): 299.4 ([M+H]⁺).

Example 108

(R)-5-Bromo-N-(5-(morpholin-2-yl)pyridin-2-yl)pyridin-2-amine

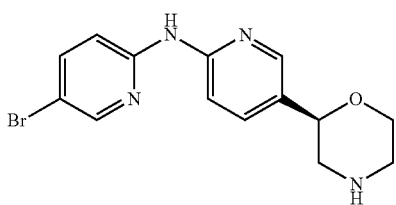 [SMILES: Brc1ccc(Nc2ccc([C@@H]3CNCCO3)cn2)nc1]

a) (R)-tert-Butyl 2-(6-aminopyridin-3-yl)morpholine-4-carboxylate & (S)-tert-Butyl 2-(6-aminopyridin-3-yl)morpholine-4-carboxylate The enantiomers of (RS)-tert-butyl 2-(6-aminopyridin-3-yl)morpholine-4-carboxylate (430 mg, Example 90(g)) were separated using chiral HPLC (column: Chiralpak AD, 5×50 cm; eluent: 5% isopropanol/heptane; pressure: 18 bar; flow rate: 35 ml/min) affording:
(+)-(R)-tert-Butyl 2-(6-aminopyridin-3-yl)morpholine-4-carboxylate (157 mg, light yellow amorphous solid) Retention time=93 min
(−)-(S)-tert-Butyl 2-(6-aminopyridin-3-yl)morpholine-4-carboxylate (157 mg, light yellow amorphous solid) Retention time=112 min b) (R)-5-Bromo-N-(5-(morpholin-2-yl)pyridin-2-yl)pyridin-2-amine The title compound was obtained in analogy to example 90 (h)-(i) using (+)-(R)-tert-butyl 2-(6-aminopyridin-3-yl)morpholine-4-carboxylate in place of (RS)-tert-butyl 2-(6-aminopyridin-3-yl)morpholine-4-carboxylate and 2,5-dibromopyridine (CAS 32779-37-6) instead of 2,5-dichloropyridine in step (h). Yellow amorphous solid. MS (ISP): 337.0 ([{⁸¹Br}M+H]⁺), 335.1 ([{⁷⁹Br}M+H]⁺).

Example 109

(S)-5-Bromo-N-(5-(morpholin-2-yl)pyridin-2-yl)pyridin-2-amine

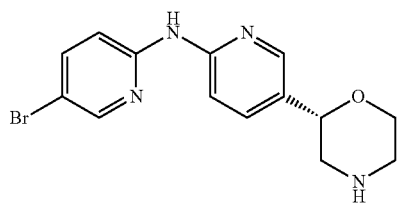

The title compound was obtained in analogy to example 108 using (−)-(S)-tert-butyl 2-(6-aminopyridin-3-yl)morpholine-4-carboxylate in place of (+)-(R)-tert-butyl 2-(6-aminopyridin-3-yl)morpholine-4-carboxylate in step (b). Yellow amorphous solid. MS (ISP): 337.0 ([{⁸¹Br}M+H]⁺), 335.1 ([{⁷⁹Br}M+H]⁺).

Example 110

(5-Cyclopropyl-pyrimidin-2-yl)-((R)-2-methyl-4-morpholin-2-yl-phenyl)-amine

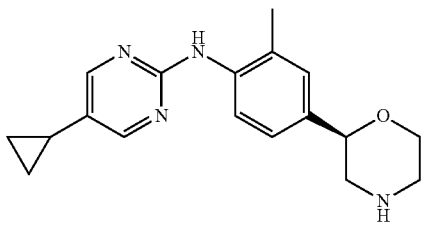 [SMILES: Cc1cc([C@@H]2CNCCO2)ccc1Nc1ncc(C2CC2)cn1]

The title compound was obtained in analogy to example 106 using (+)-(R)-tert-butyl 2-(4-amino-3-methylphenyl)morpholine-4-carboxylate and 2-chloro-5-cyclopropylpyrimidine (CAS 166740-44-9) instead of 2-chloro-5-ethylpyrimidine in step (b). White solid. MS (ISP): 311.4 ([M+H]⁺).

Example 111

(5-Cyclopropyl-pyrimidin-2-yl)-((S)-2-methyl-4-morpholin-2-yl-phenyl)-amine

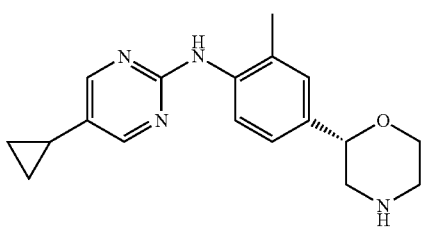 [SMILES: Cc1cc([C@H]2CNCCO2)ccc1Nc1ncc(C2CC2)cn1]

The title compound was obtained in analogy to example 106 using (−)-(S)-tert-butyl 2-(4-amino-3-methylphenyl)

morpholine-4-carboxylate instead of (+)-(R)-tert-butyl 2-(4-amino-3-methylphenyl)morpholine-4-carboxylate and 2-chloro-5-cyclopropylpyrimidine (CAS 166740-44-9) instead of 2-chloro-5-ethylpyrimidine in step (b). White solid. MS (ISP): 311.4 ([M+H]⁺).

Example 112

(5-Ethyl-pyrimidin-2-yl)-((S)-4-piperidin-3-yl-phenyl)-amine

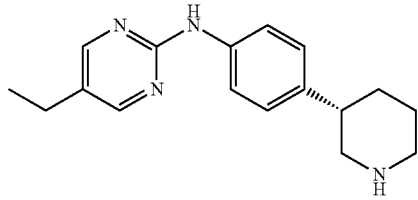 [SMILES: CCc1cnc(Nc2ccc([C@@H]3CCCNC3)cc2)nc1]

The title compound was obtained in analogy to example 5 using (S)-4-(4-amino-phenyl)-piperidine-1-carboxylicacid tert-butyl ester (CAS 1171197-20-8) in place of (RS)-2-(4-amino-phenyl)-morpholine-4-carboxylic acid tert-butyl ester and 2-chloro-5-ethylpyrimidine (CAS 111196-81-7) instead of 2,5-dichloropyridine in step (a). Off-white solid. MS (ISP): 283.4 ([M+H]⁺).

Example 113

(S)—N-(4-(Morpholin-2-yl)phenyl)-5-phenyl-1H-pyrazol-3-amine

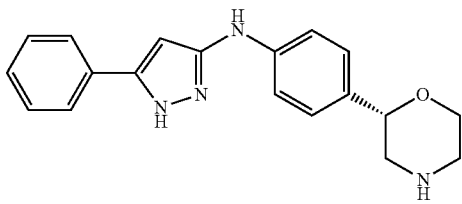 [SMILES: c1ccc(-c2cc(Nc3ccc([C@H]4CNCCO4)cc3)n[nH]2)cc1]

The title compound was obtained in analogy to example 19 using 5-phenyl-1H-pyrazol-3-amine (CAS 1572-10-7) instead of 5-trifluoromethyl-pyrimidin-2-ylamine in step (a). Orange solid. MS (ISP): 321.1 ([M+H]⁺).

Example 114

(5-Ethoxy-pyrimidin-2-yl)-((S)-4-piperidin-3-yl-phenyl)-amine

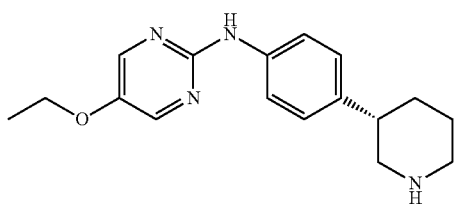 [SMILES: CCOc1cnc(Nc2ccc([C@@H]3CCCNC3)cc2)nc1]

The title compound was obtained in analogy to example 5 using (S)-4-(4-amino-phenyl)-piperidine-1-carboxylicacid tert-butyl ester (CAS 1171197-20-8) in place of (RS)-2-(4-amino-phenyl)-morpholine-4-carboxylic acid tert-butyl ester and 2-chloro-5-ethoxypyrimidine (CAS 82153-68-2) instead of 2,5-dichloropyridine in step (a). Off-white solid. MS (ISP): 299.3 ([M+H]⁺).

Example 115

(S)—N-(4-(Morpholin-2-yl)phenyl)-5-phenyl-1,3,4-oxadiazol-2-amine

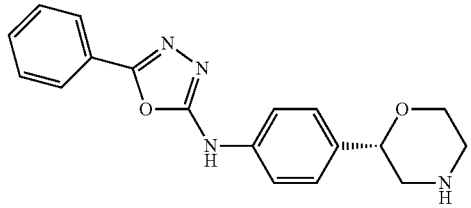 [SMILES: c1ccc(-c2nnc(Nc3ccc([C@H]4CNCCO4)cc3)o2)cc1]

The title compound was obtained in analogy to example 19 using 5-phenyl-1,3,4-oxadiazol-2-amine (CAS 1612-76-6) instead of 5-trifluoromethyl-pyrimidin-2-ylamine in step (a). Off-white solid. MS (ISP): 323.3 ([M+H]⁺).

Example 116

(5-Ethyl-pyrimidin-2-yl)-((R)-2-fluoro-4-morpholin-2-yl-phenyl)-amine

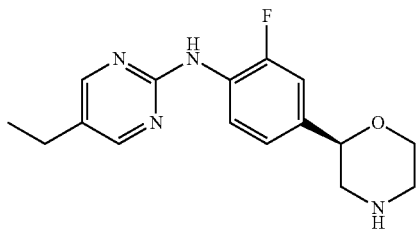 [SMILES: CCc1cnc(Nc2ccc([C@@H]3CNCCO3)cc2F)nc1]

a) (+)-(R)-2-(4-Amino-3-fluoro-phenyl)-morpholine-4-carboxylic acid tert-butyl ester & (−)-(S)-2-(4-Amino-3-fluoro-phenyl)-morpholine-4-carboxylic acid tert-butyl ester The enantiomers of (RS)-2-(4-amino-3-fluoro-phenyl)-morpholine-4-carboxylic acid tert-butyl ester (520 mg, Example 96(g)) were separated using chiral HPLC (column: Chiralpak AD, 5×50 cm; eluent: 10% isopropanol/heptane; pressure: 18 bar; flow rate: 35 ml/min) affording:
(+)-(R)-2-(4-Amino-3-fluoro-phenyl)-morpholine-4-carboxylic acid tert-butyl ester (146 mg, light yellow solid) Retention time=62 min
(−)-(S)-2-(4-Amino-3-fluoro-phenyl)-morpholine-4-carboxylic acid tert-butyl ester (153 mg, off-white solid) Retention time=74 min b) (5-Ethyl-pyrimidin-2-yl)-((R)-2-fluoro-4-morpholin-2-yl-phenyl)-amine The title compound was obtained in analogy to example 96 (h)-(i) using (+)-(R)-2-(4-amino-3-fluoro-phenyl)-morpholine-4-carboxylic acid tert-butyl ester in place of (RS)-2-(4-amino-3-fluoro-phenyl)-morpholine-4-carboxylic acid tert-butyl ester and 2-chloro-5-ethylpyrimidine (CAS 111196-81-7) instead of 2,5-dichloropyrimidine in step (h). White solid. MS (ISP): 303.3 ([M+H]+).

Example 117

(5-Ethyl-pyrimidin-2-yl)-((S)-2-fluoro-4-morpholin-2-yl-phenyl)-amine

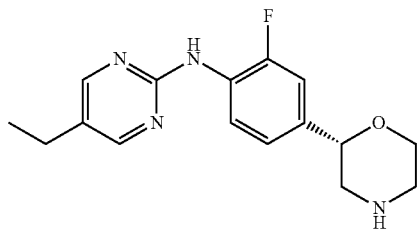 [SMILES: CCc1cnc(Nc2ccc([C@H]3CNCCO3)cc2F)nc1]

The title compound was obtained in analogy to example 116 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester in step (b). Off-white solid. MS (ISP): 303.3 ([M+H]+).

Example 118

(5-Cyclopropyl-pyrimidin-2-yl)-((R)-2-fluoro-4-morpholin-2-yl-phenyl)-amine

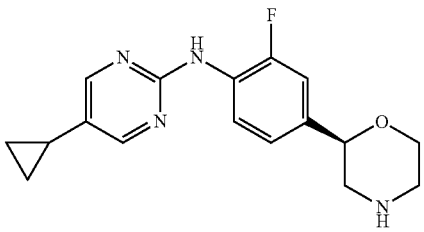 [SMILES: Fc1cc([C@@H]2CNCCO2)ccc1Nc1ncc(C2CC2)cn1]

The title compound was obtained in analogy to example 116 using (+)-(R)-2-(4-amino-3-fluoro-phenyl)-morpholine-4-carboxylic acid tert-butyl ester and 2-chloro-5-cyclopropylpyrimidine (CAS 166740-44-9) in place of 2-chloro-5-ethylpyrimidine in step (b). White solid. MS (ISP): 315.1 ([M+H]+).

Example 119

(5-Cyclopropyl-pyrimidin-2-yl)-((S)-2-fluoro-4-morpholin-2-yl-phenyl)-amine

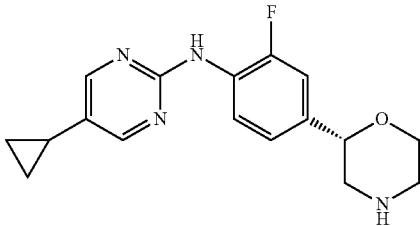 [SMILES: Fc1cc([C@H]2CNCCO2)ccc1Nc1ncc(C2CC2)cn1]

The title compound was obtained in analogy to example 116 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 2-chloro-5-cyclopropylpyrimidine (CAS 166740-44-9) in place of 2-chloro-5-ethylpyrimidine in step (b). White solid. MS (ISP): 315.1 ([M+H]+).

Example 120

(RS)—N-(5-Bromopyridin-2-yl)-3-methyl-5-(morpholin-2-yl)pyridin-2-amine

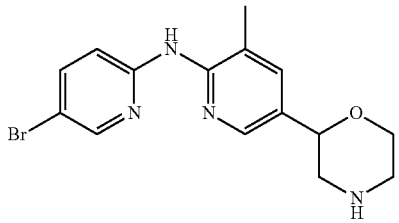 [SMILES: Cc1cc(C2CNCCO2)cnc1Nc1ccc(Br)cn1]

a) (RS)-2-Bromo-3-methyl-5-(oxiran-2-yl)pyridine

To a stirred suspension of sodium hydride (1.01 g) in THF (20 ml) was added dropwise over 5 min a solution of trimethylsulfonium iodide (4.69 g) in DMSO (20 ml). The reaction mixture was stirred for 5 min and then cooled to 0° C. A solution of 6-bromo-5-methylnicotinaldehyde (4.6 g, CAS 885167-81-7) in THF (15 ml) was added dropwise. The reaction mixture was stirred at 0° C. for 30 min and then at room temperature overnight. The mixture was then poured into EtOAc/Et2O (1:1) and washed with saturated brine. The organic layer was dried over $Na_2SO_4$ and concentrated in vacuo. The residue was purified by flash column chromatography (silica gel; gradient: 0% to 50% EtOAc in hexanes) to afford (RS)-2-bromo-3-methyl-5-(oxiran-2-yl)pyridine (1.26 g, 26%) as a colourless oil. MS (ISP): 216.1 ([$\{^{81}Br\}$M+H]+), 214.1 ([$\{^{79}Br\}$M+H]+).

b) (RS)-1-(6-Bromo-5-methylpyridin-3-yl)-2-(2-hydroxyethylamino)ethanol

To a stirred solution of (RS)-2-bromo-3-methyl-5-(oxiran-2-yl)pyridine (1.4 g) in THF (6 ml) was added 2-aminoethanol (3.92 ml) and the mixture was stirred at room temperature overnight. The reaction mixture was then poured into EtOAc/THF (1:1) and the mixture was washed with saturated brine. The organic layer was dried over $Na_2SO_4$ and concentrated in vacuo to afford (RS)-1-(6-bromo-5-methylpyridin-3-yl)-2-(2-hydroxyethylamino)ethanol (1.76 g) as an off-white solid which was used in the next step without further purification. MS (ISP): 277.0 ([$\{^{81}Br\}$M+H]+), 275.0 ([$\{^{79}Br\}$M+H]+), 258.9 ([$\{^{81}Br\}$M+H—$H_2O$]+), 257.0 ([$\{^{79}Br\}$M+H—$H_2O$]+).

c) tert-Butyl (RS)-2-(6-bromo-5-methylpyridin-3-yl)-2-hydroxyethyl(2-hydroxyethyl)carbamate To a stirred solution of (RS)-1-(6-bromo-5-methylpyridin-3-yl)-2-(2-hydroxyethylamino)ethanol (1.76 g) in THF (20 ml) was added $Boc_2O$ (1.54 g) and the mixture was stirred at room temperature for 7 hours. The reaction mixture was then poured into EtOAc and the mixture was washed sequentially with dilute aq. NaOH and saturated brine. The organic layer was dried over $Na_2SO_4$ and concentrated in vacuo to afford tert-butyl (RS)-2-(6-bromo-5-methylpyridin-3-yl)-2-hydroxyethyl(2-hydroxyethyl)carbamate (2.57 g) as a colourless oil which was used in the next step without further purification. MS (ISP): MS (ISP): 377.2 ([$\{^{81}Br\}$M+H]+), 375.2 ([$\{^{79}Br\}$M+H]+), 321.0 ([$\{^{81}Br\}$M+H—$C_4H_8$]+), 319.0 ([$\{^{79}Br\}$M+H—$C_4H_8$]+).

d) tert-Butyl (RS)-2-(6-bromo-5-methylpyridin-3-yl)morpholine-4-carboxylate

To a stirred solution of tert-butyl (RS)-2-(6-bromo-5-methylpyridin-3-yl)-2-hydroxyethyl(2-hydroxyethyl)carbamate (2.57 g) and triethylamine (1.51 ml) in THF (30 ml) at 0-5° C. was added dropwise methanesulfonyl chloride (546 •l). The reaction mixture was then stirred at room temperature for 15 min to afford a white suspension. The reaction mixture was then filtered to remove triethylamine hydrochloride, washing the filter with THF (10 ml). The filtrate was cooled to 0-5° C. and potassium 2-methyl-2-butoxide (5.62 ml, 1.7 M solution in toluene) was added. The reaction mixture was stirred at room temperature for 10 min and then poured into EtOAc and washed sequentially with water and with saturated brine. The organic phase was dried over $Na_2SO_4$ and concentrated in vacuo. The residue was purified by flash column chromatography (silica gel; gradient: 0% to 70% EtOAc in hexanes) to afford tert-butyl (RS)-2-(6-bromo-5-methylpyridin-3-yl)morpholine-4-carboxylate (1.7 g, 73% over 3 steps) as a colourless oil. MS (ISP): 359.0 ($[\{^{81}Br\}M+H]^+$), 357.0 ($[\{^{79}Br\}M+H]^+$), 303.0 ($[\{^{81}Br\}M+H—C_4H_8]^+$), 301.0 ($[\{^{79}Br\}M+H—C_4H_8]^+$).

e) tert-Butyl (RS)-2-(6-(diphenylmethyleneamino)-5-methylpyridin-3-yl)morpholine-4-carboxylate To a stirred solution of tert-butyl (RS)-2-(6-bromo-5-methylpyridin-3-yl)morpholine-4-carboxylate (1.7 g) and benzophenone imine (1.2 ml) in toluene (20 ml) was added sodium tert-butoxide (732 mg). The reaction mixture was purged with argon for 10 min. (R)-(+)-2,2'-bis(diphenylphosphino)-1,1'-binaphthyl (296 mg) and tris(dibenzylideneacetone)dipalladium(0) (131 mg) were added and the reaction mixture was heated at 100° C. overnight. The reaction mixture was then cooled to room temperature, poured into water and extracted twice with EtOAc. The organic layers were dried over $Na_2SO_4$ and concentrated in vacuo. The residue was purified by flash column chromatography (silica gel; gradient: 0% to 75% EtOAc in hexanes) to afford tert-butyl (RS)-2-(6-(diphenylmethyleneamino)-5-methylpyridin-3-yl)morpholine-4-carboxylate (1.01 g, 46%) as a yellow foam. MS (ISP): 458.3 ($[M+H]^+$).

f) tert-Butyl (RS)-2-(6-amino-5-methylpyridin-3-yl)morpholine-4-carboxylate

To a stirred solution of tert-butyl (RS)-2-(6-(diphenylmethyleneamino)-5-methylpyridin-3-yl)morpholine-4-carboxylate (1.0 g) in ethanol (100 ml) was added ammonium formate (14 g). The reaction mixture was degassed by bubbling argon into the mixture for several minutes. 10% Palladium on activated charcoal (2.56 mg) was then added and the reaction mixture was stirred at 80° C. for 2 hours. The reaction mixture was then filtered through celite and the filtrate was concentrated in vacuo. The residue was taken up in EtOAc and the mixture was washed sequentially with water and with saturated brine. The organic layer was dried over $Na_2SO_4$ and concentrated in vacuo. The residue was purified by flash column chromatography (silica gel; gradient: heptane/dichloromethane/MeOH) to afford tert-butyl (RS)-2-(6-amino-5-methylpyridin-3-yl)morpholine-4-carboxylate (246 mg, 38%) as a colourless oil. MS (ISP): 294.2 ($[M+H]^+$).

g) tert-Butyl (RS)-2-(6-(5-bromopyridin-2-ylamino)-5-methylpyridin-3-yl)morpholine-4-carboxylate tert-Butyl (RS)-2-(6-amino-5-methylpyridin-3-yl)morpholine-4-carboxylate (60 mg), 2,5-dibromopyridine (72.7 mg, CAS 624-28-2) and cesium carbonate (100 mg) were combined with dioxane (2 ml) to give a yellow suspension. The mixture was degassed by bubbling argon into the mixture for several minutes. Xantphos (14.1 mg) and tris(dibenzylideneacetone)dipalladium chloroform complex (12.6 mg) were then added. The reaction mixture was then capped and stirred at 100° C. overnight and then at 120° C. for 2 hours. The crude reaction mixture was cooled to room temperature and filtered. The filtrate was concentrated in vacuo and the residue was purified by flash column chromatography (silica gel; gradient: 0% to 100% EtOAc in hexanes) to afford tert-butyl (RS)-2-(6-(5-bromopyridin-2-ylamino)-5-methylpyridin-3-yl)morpholine-4-carboxylate (26 mg, 28%) as a yellow amorphous solid. MS (ISP): 451.1 ($[\{^{81}Br\}M+H]^+$), 449.1 ($[\{^{79}Br\}M+H]^+$).

h) (RS)—N-(5-Bromopyridin-2-yl)-3-methyl-5-(morpholin-2-yl)pyridin-2-amine

To a stirred solution of tert-butyl (RS)-2-(6-(5-bromopyridin-2-ylamino)-5-methylpyridin-3-yl)morpholine-4-carboxylate (26 mg) in acetonitrile (1.5 ml) and water (4.5 ml) was added trifluoroacetic acid (45 µl). The reaction mixture was then capped and the mixture was shaken at 80° C. for 3 h. The reaction mixture was then cooled to room temperature and poured into EtOAc/THF (1:1) and washed with 1 M aq. NaOH. The organic layer was dried over $Na_2SO_4$ and concentrated in vacuo. The crude material was purified by flash column chromatography (Isolute® Flash-$NH_2$ from Separtis; gradient: heptane/EtOAc/MeOH) to afford (RS)—N-(5-bromopyridin-2-yl)-3-methyl-5-(morpholin-2-yl)pyridin-2-amine (11 mg, 54%) as a colourless amorphous solid. MS (ISP): 351.1 ($[\{^{81}Br\}M+H]^+$), 349.1 ($[\{^{79}Br\}M+H]^+$).

Example 121

(RS)-(2-Fluoro-4-morpholin-2-yl-phenyl)-(5-trifluoromethyl-pyrimidin-2-yl)-amine

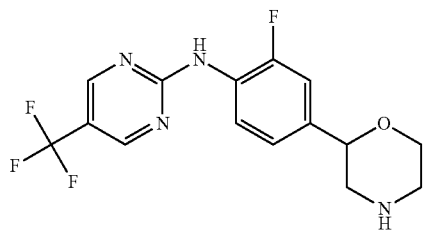 [SMILES: Fc1cc(C2CNCCO2)ccc1Nc1ncc(C(F)(F)F)cn1]

a) (RS)-2-[3-Fluoro-4-(5-trifluoromethyl-pyrimidin-2-ylamino)-phenyl]-morpholine-4-carboxylic acid tert-butyl ester To a 20 ml glass vial was added (RS)-2-(4-bromo-3-fluorophenyl)-morpholine-4-carboxylic acid tert-butyl ester (200 mg, example 96(e)) and 5-trifluoromethyl-pyrimidin-2-ylamine (145 mg, CAS 69034-08-8) in dioxane (5 ml). The reaction mixture was purged with argon for 5 min. 2-Di-tert-butylphosphino-2',4',6'-triisopropylbiphenyl (38.9 mg), tris(dibenzylideneacetone)dipalladium(0) (20.3 mg) and sodium tert-butoxide (59.9 mg) were then added. The vial was capped and heated at 120° C. for 16 h. The reaction mixture was then filtered through sintered glass and the filtrate was concentrated in vacuo. The residue was purified by flash column chromatography (silica gel; gradient: 0% to 50% EtOAc in heptane) to afford (RS)-2-[3-fluoro-4-(5-trifluoromethyl-pyrimidin-2-ylamino)-phenyl]-morpholine-4-carboxylic acid tert-butyl ester (115 mg, 47%) as a yellow gum. MS (ISP): 441.4 ([M–H]⁻).

b) (RS)-(2-Fluoro-4-morpholin-2-yl-phenyl)-(5-trifluoromethyl-pyrimidin-2-yl)-amine To a stirred solution of (RS)-2-[3-fluoro-4-(5-trifluoromethyl-pyrimidin-2-ylamino)-phenyl]-morpholine-4-carboxylic acid tert-butyl ester (110 mg) in acetonitrile (2 ml) and water (4 ml) was added trifluoroacetic acid (190 µl). The reaction mixture was then capped and the mixture was shaken at 80° C. for 4 h. The reaction mixture was then cooled to room temperature and poured into 1 M aq. NaOH and extracted twice with EtOAc. The combined organic layers were dried over Na₂SO₄ and concentrated in vacuo. The crude material was purified by flash column chromatography (Isolute® Flash-NH₂ from Separtis; gradient: heptane/EtOAc) to (RS)-(2-fluoro-4-morpholin-2-yl-phenyl)-(5-trifluoromethyl-pyrimidin-2-yl)-amine (23 mg, 27%) as a white solid. MS (ISP): 343.1 ([M+H]⁺).

Example 122

(5-Isopropoxy-pyrimidin-2-yl)-((S)-4-morpholin-2-yl-phenyl)-amine

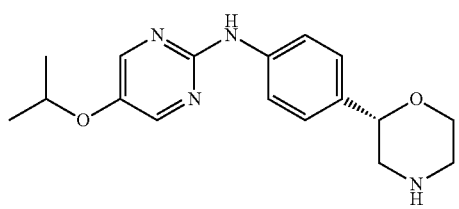 [SMILES: CC(C)Oc1cnc(Nc2ccc([C@H]3CNCCO3)cc2)nc1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-5-(1-methylethoxy)-pyrimidine (CAS 169677-67-2) instead of 2,5-dichloropyridine in step (a). White solid. MS (ISP): 315.1 ([M+H]⁺).

Example 123

(5-Isopropoxy-pyrimidin-2-yl)-((R)-4-morpholin-2-yl-phenyl)-amine

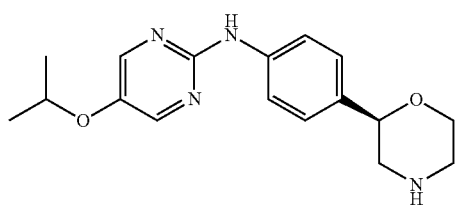 [SMILES: CC(C)Oc1cnc(Nc2ccc([C@@H]3CNCCO3)cc2)nc1]

The title compound was obtained in analogy to example 5 using (R)-2-(4-amino-phenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-5-(1-methylethoxy)-pyrimidine (CAS 169677-67-2) instead of 2,5-dichloropyridine in step (a). White solid. MS (ISP): 315.1 ([M+H]⁺).

Example 124

(S)-5-(Cyclopropylmethoxy)-N-(4-(morpholin-2-yl)phenyl)pyrimidin-2-amine

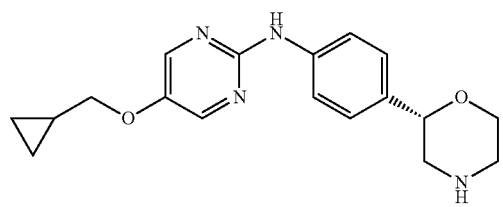 [SMILES: c1cc([C@H]2CNCCO2)ccc1Nc1ncc(OCC2CC2)cn1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-5-(cyclopropylmethoxy)-pyrimidine (CAS 169677-66-1) instead of 2,5-dichloropyridine in step (a). White solid. MS (ISP): 327.2 ([M+H]⁺).

Example 125

(R)-5-(Cyclopropylmethoxy)-N-(4-(morpholin-2-yl)phenyl)pyrimidin-2-amine

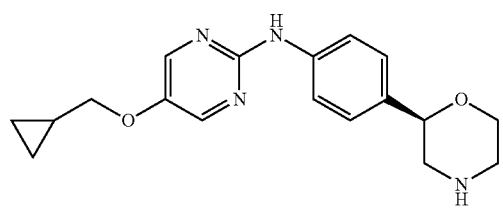 [SMILES: c1cc([C@@H]2CNCCO2)ccc1Nc1ncc(OCC2CC2)cn1]

The title compound was obtained in analogy to example 5 using (R)-2-(4-amino-phenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-5-(cyclopropylmethoxy)-pyrimidine (CAS 169677-66-1) instead of 2,5-dichloropyridine in step (a). White solid. MS (ISP): 327.2 ([M+H]⁺).

Example 126

(5-Bromo-pyrimidin-2-yl)-((R)-2-fluoro-4-morpholin-2-yl-phenyl)-amine

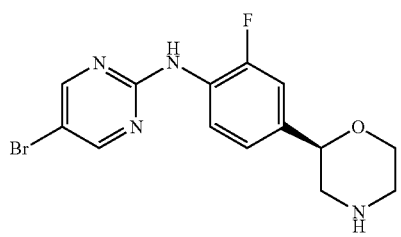

The title compound was obtained in analogy to example 116 using (+)-(R)-2-(4-amino-3-fluoro-phenyl)-morpholine-4-carboxylic acid tert-butyl ester and 2,5-dibromopyrimidine (CAS 32779-37-6) in place of 2-chloro-5-ethylpyrimidine in step (b). White solid. MS (ISP): 355.0 ([{$^{81}$Br}M+H]$^+$), 353.0 ([{$^{79}$Br}M+H]$^+$).

Example 127

(5-Bromo-pyrimidin-2-yl)-((S)-2-fluoro-4-morpholin-2-yl-phenyl)-amine

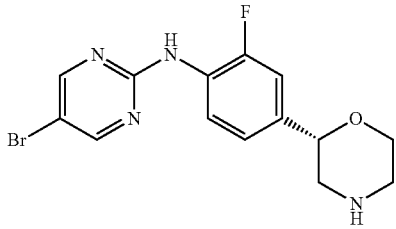

The title compound was obtained in analogy to example 116 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 2,5-dibromopyrimidine (CAS 32779-37-6) in place of 2-chloro-5-ethylpyrimidine in step (b). White solid. MS (ISP): 355.0 ([{$^{81}$Br}M+H]$^+$), 353.0 ([{$^{79}$Br}M+H]$^+$).

Example 128

((R)-2-Fluoro-4-morpholin-2-yl-phenyl)-(5-propyl-pyrimidin-2-yl)-amine

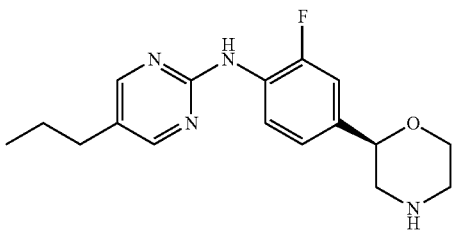 [SMILES: CCCc1cnc(Nc2ccc([C@@H]3CNCCO3)cc2F)nc1]

The title compound was obtained in analogy to example 116 using (+)-(R)-2-(4-amino-3-fluoro-phenyl)-morpholine-4-carboxylic acid tert-butyl ester and 2-chloro-5-n-propylpyrimidine (CAS 219555-98-3) in place of 2-chloro-5-ethylpyrimidine in step (b). White solid. MS (ISP): 317.2 ([M+H]$^+$).

Example 129

((S)-2-Fluoro-4-morpholin-2-yl-phenyl)-(5-propyl-pyrimidin-2-yl)-amine

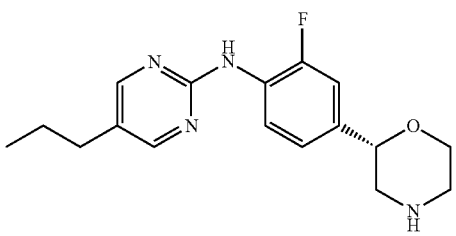 [SMILES: CCCc1cnc(Nc2ccc([C@H]3CNCCO3)cc2F)nc1]

The title compound was obtained in analogy to example 116 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 2-chloro-5-n-propylpyrimidine (CAS 219555-98-3) in place of 2-chloro-5-ethylpyrimidine in step (b). White solid. MS (ISP): 317.3 ([M+H]$^+$).

Example 130

(5-Chloro-pyrimidin-2-yl)-((R)-2-fluoro-4-morpholin-2-yl-phenyl)-amine

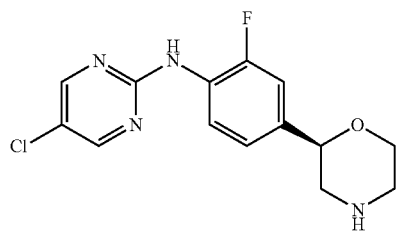

The title compound was obtained in analogy to example 116 using (+)-(R)-2-(4-amino-3-fluoro-phenyl)-morpholine-4-carboxylic acid tert-butyl ester and 2,5-dichloropyrimidine (CAS 22536-67-0) in place of 2-chloro-5-ethylpyrimidine in step (b). White solid. MS (ISP): 309.3 ([M+H]$^+$).

Example 131

(5-Chloro-pyrimidin-2-yl)-((S)-2-fluoro-4-morpholin-2-yl-phenyl)-amine

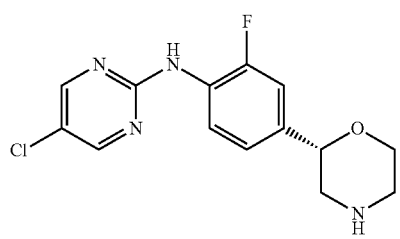

The title compound was obtained in analogy to example 116 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 2,5-dichloropyrimidine (CAS 22536-67-0) in place of 2-chloro-5-ethylpyrimidine in step (b). Off-white solid. MS (ISP): 309.3 ([M+H]$^+$).

Example 132

(5-Ethoxy-pyrimidin-2-yl)-((R)-2-fluoro-4-morpholin-2-yl-phenyl)-amine

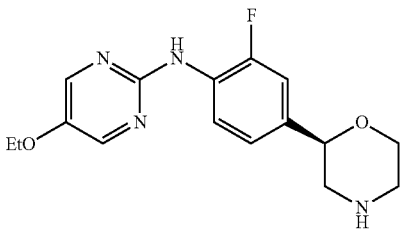 [SMILES: CCOc1cnc(Nc2ccc([C@@H]3CNCCO3)cc2F)nc1]

The title compound was obtained in analogy to example 116 using (+)-(R)-2-(4-amino-3-fluoro-phenyl)-morpholine- 4-carboxylic acid tert-butyl ester and 2-chloro-5-ethoxypyrimidine (CAS 82153-68-2) in place of 2-chloro-5-ethylpyrimidine in step (b). White solid. MS (ISP): 319.2 ([M+H]+).

Example 133

(5-Ethoxy-pyrimidin-2-yl)-((S)-2-fluoro-4-morpholin-2-yl-phenyl)-amine

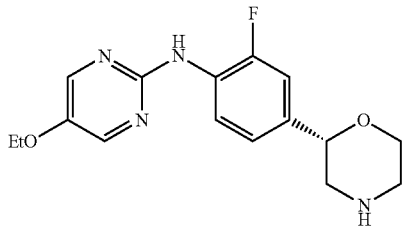 [SMILES: CCOc1cnc(Nc2ccc([C@H]3CNCCO3)cc2F)nc1]

The title compound was obtained in analogy to example 116 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 2-chloro-5-ethoxypyrimidine (CAS 82153-68-2) in place of 2-chloro-5-ethylpyrimidine in step (b). Off-white solid. MS (ISP): 319.2 ([M+H]+).

Example 134

((R)-2-Fluoro-4-morpholin-2-yl-phenyl)-(5-trifluoromethyl-pyrimidin-2-yl)-amine

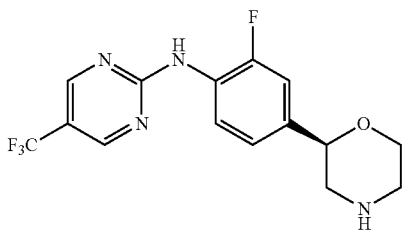 [SMILES: Fc1cc([C@@H]2CNCCO2)ccc1Nc1ncc(C(F)(F)F)cn1]

The title compound was obtained in analogy to example 116 using (+)-(R)-2-(4-amino-3-fluoro-phenyl)-morpholine-4-carboxylic acid tert-butyl ester and 2-chloro-5-(trifluoromethyl)-pyrimidine (CAS 69034-12-4) in place of 2-chloro-5-ethylpyrimidine in step (b). Yellow solid. MS (ISP): 343.1 ([M+H]+).

Example 135

((S)-2-Fluoro-4-morpholin-2-yl-phenyl)-(5-trifluoromethyl-pyrimidin-2-yl)-amine

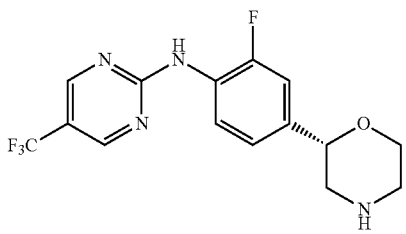 [SMILES: Fc1cc([C@H]2CNCCO2)ccc1Nc1ncc(C(F)(F)F)cn1]

The title compound was obtained in analogy to example 116 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 2-chloro-5-(trifluoromethyl)-pyrimidine (CAS 69034-12-4) in place of 2-chloro-5-ethylpyrimidine in step (b). Yellow solid. MS (ISP): 343.1 ([M+H]+).

Example 136

((S)-4-Morpholin-2-yl-phenyl)-[5-(2,2,2-trifluoroethoxy)-pyrimidin-2-yl]-amine

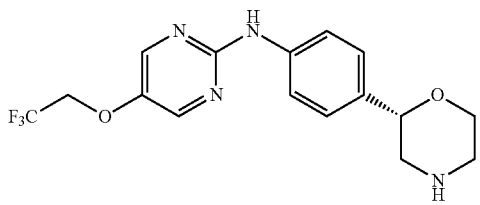 [SMILES: FC(F)(F)COc1cnc(Nc2ccc([C@H]3CNCCO3)cc2)nc1]

The title compound was obtained in analogy to example 5 using (S)-2-(4-amino-phenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-5-(2,2,2-trifluoroethoxy)-pyrimidine (CAS 145948-01-2) instead of 2,5-dichloropyridine in step (a). White solid. MS (ISP): 355.2 ([M+H]+).

Example 137

((R)-4-Morpholin-2-yl-phenyl)-[5-(2,2,2-trifluoroethoxy)-pyrimidin-2-yl]-amine

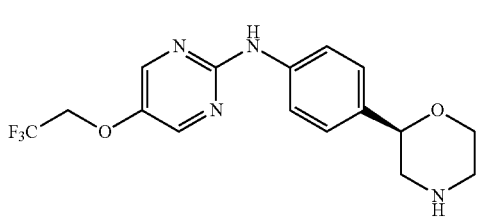 [SMILES: FC(F)(F)COc1cnc(Nc2ccc([C@@H]3CNCCO3)cc2)nc1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-5-(2,2,2-trifluoroethoxy)-pyrimidine (CAS 145948-01-2) instead of 2,5-dichloropyridine in step (a). White solid. MS (ISP): 355.2 ([M+H]+).

Example 138

[5-(2-Methoxy-ethoxy)-pyrimidin-2-yl](S)-4-morpholin-2-yl-phenyl)-amine

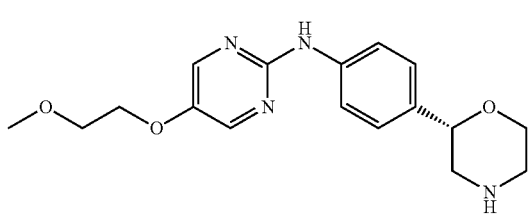 [SMILES: COCCOc1cnc(Nc2ccc([C@H]3CNCCO3)cc2)nc1]

The title compound was obtained in analogy to example 5 using (S)-2-(4-aminophenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-5-(2-methoxyethoxy)pyrimidine (CAS 61533-68-4) instead of 2,5-dichloropyridine in step (a). White solid. MS (ISP): 331.2 ([M+H]+).

Example 139

[5-(2-Methoxy-ethoxy)-pyrimidin-2-yl]-(R)-4-morpholin-2-yl-phenyl)-amine

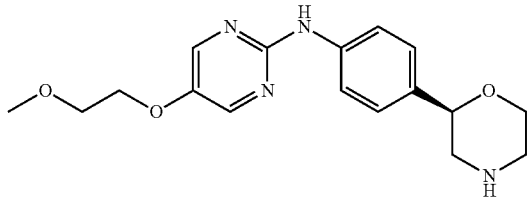 [SMILES: COCCOc1cnc(Nc2ccc([C@@H]3CNCCO3)cc2)nc1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-5-(2-methoxyethoxy)pyrimidine (CAS 61533-68-4) instead of 2,5-dichloropyridine in step (a). White solid. MS (ISP): 331.2 ([M+H]+).

Example 140

(RS)-(1-Methyl-1H-pyrazol-3-yl)-(4-morpholin-2-yl-phenyl)-amine

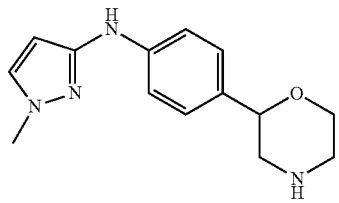 [SMILES: Cn1ccc(Nc2ccc(C3CNCCO3)cc2)n1]

The title compound was obtained in analogy to example 19 using (RS)-2-(4-bromo-phenyl)-morpholine-4-carboxylic acid tert-butyl ester instead of (S)-2-(4-bromo-phenyl)-morpholine-4-carboxylic acid tert-butyl ester and 3-amino-1-methylpyrazole (CAS 1904-31-0) instead of 5-trifluoromethyl-pyrimidin-2-ylamine in step (a). Off-white solid. MS (ISP): 259.2 ([M+H]+).

Example 141

[5-(3,4-Dimethoxy-phenyl)-pyrimidin-2-yl]-(S)-4-morpholin-2-yl-phenyl)-amine

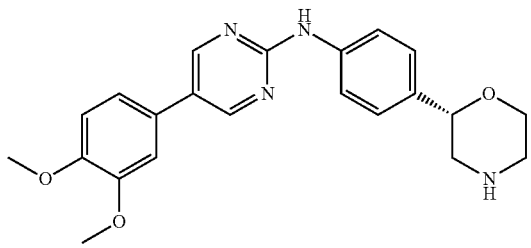 [SMILES: COc1ccc(-c2cnc(Nc3ccc([C@H]4CNCCO4)cc3)nc2)cc1OC]

The title compound was obtained in analogy to example 5 using (S)-2-(4-aminophenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-5-(3,4-dimethoxyphenyl)pyrimidine (CAS 76972-10-6) instead of 2,5-dichloropyridine in step (a). White solid. MS (ISP): 393.2 ([M+H]+).

Example 142

[5-(3,4-Dimethoxy-phenyl)-pyrimidin-2-yl](R)-4-morpholin-2-yl-phenyl)-amine

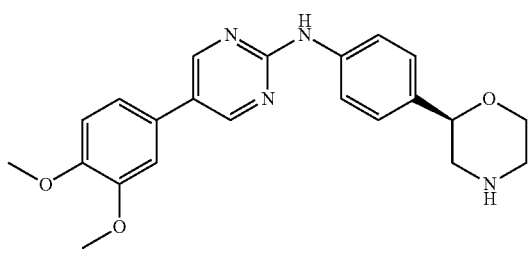 [SMILES: COc1ccc(-c2cnc(Nc3ccc([C@@H]4CNCCO4)cc3)nc2)cc1OC]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-5-(3,4-dimethoxyphenyl)pyrimidine (CAS 76972-10-6) instead of 2,5-dichloropyridine in step (a). White solid. MS (ISP): 393.2 ([M+H]+).

Example 143

(RS)-(4-Bromo-1-methyl-1H-pyrazol-3-yl)-(4-morpholin-2-yl-phenyl)-amine

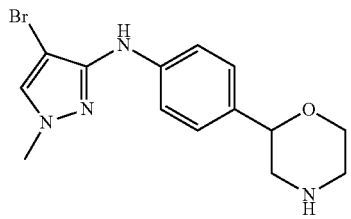 [SMILES: Cn1cc(Br)c(Nc2ccc(C3CNCCO3)cc2)n1]

The title compound was obtained in analogy to example 19 using (RS)-2-(4-bromo-phenyl)-morpholine-4-carboxylic acid tert-butyl ester instead of (S)-2-(4-bromo-phenyl)-morpholine-4-carboxylic acid tert-butyl ester and 3-amino-4-bromo-1-methylpyrazole (CAS 146941-72-2) instead of 5-trifluoromethyl-pyrimidin-2-ylamine in step (a). Off-white solid. MS (ISP): 339.1 ([{81Br}M+H]+), 337.2 ([{81Br}M+H]+).

Example 144

((R)-2-Fluoro-4-morpholin-2-yl-phenyl)-[5-(2,2,2-trifluoro-ethoxy)-pyrimidin-2-yl]-amine

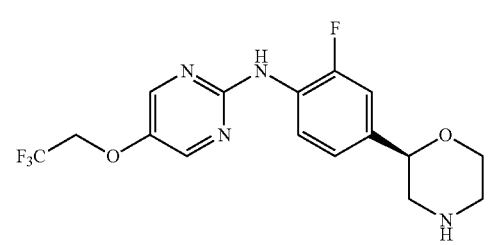

The title compound was obtained in analogy to example 116 using (+)-(R)-2-(4-amino-3-fluoro-phenyl)-morpholine- 4-carboxylic acid tert-butyl ester and 2-chloro-5-(2,2,2-trifluoroethoxy)-pyrimidine (CAS 145948-01-2) in place of 2-chloro-5-ethylpyrimidine in step (b). White solid. MS (ISP): 373.1 ([M+H]⁺).

Example 145

((S)-2-Fluoro-4-morpholin-2-yl-phenyl)-[5-(2,2,2-trifluoro-ethoxy)-pyrimidin-2-yl]-amine

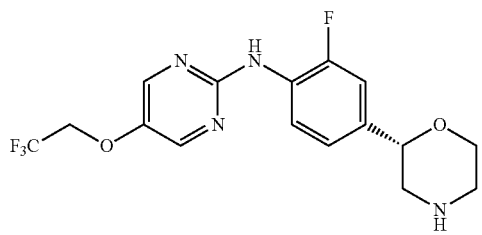 [SMILES: Fc1cc([C@H]2CNCCO2)ccc1Nc1ncc(OCC(F)(F)F)cn1]

The title compound was obtained in analogy to example 116 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 2-chloro-5-(2,2,2-trifluoroethoxy)-pyrimidine (CAS 145948-01-2) in place of 2-chloro-5-ethylpyrimidine in step (b). White solid. MS (ISP): 373.1 ([M+H]⁺).

Example 146

(RS)-(1-Cyclopropylmethyl-1H-pyrazol-3-yl)-(4-morpholin-2-yl-phenyl)-amine

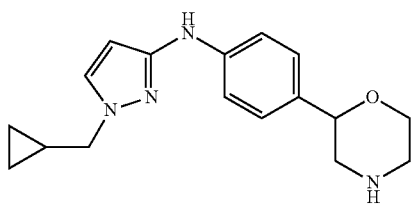 [SMILES: c1cc(C2CNCCO2)ccc1Nc1ccn(CC2CC2)n1]

The title compound was obtained in analogy to example 19 using (RS)-2-(4-bromo-phenyl)-morpholine-4-carboxylic acid tert-butyl ester instead of (S)-2-(4-bromo-phenyl)-morpholine-4-carboxylic acid tert-butyl ester and [1-(cyclopropylmethyl)-1H-pyrazol-3-yl]amine (CAS 899899-07-1) instead of 5-trifluoromethyl-pyrimidin-2-ylamine in step (a). Off-white solid. MS (ISP): 299.3 ([M+H]⁺).

Example 147

(5-Furan-2-yl-pyrimidin-2-yl)-((S)-4-morpholin-2-yl-phenyl)-amine

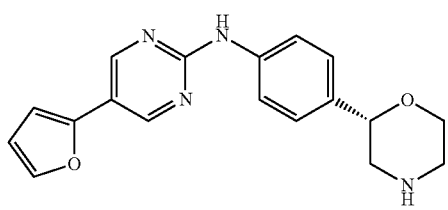 [SMILES: c1coc(-c2cnc(Nc3ccc([C@H]4CNCCO4)cc3)nc2)c1]

The title compound was obtained in analogy to example 5 using (S)-2-(4-aminophenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-5-(2-furanyl)-pyrimidine (CAS 63558-66-7) instead of 2,5-dichloropyridine in step (a). White solid. MS (ISP): 323.2 ([M+H]⁺).

Example 148

(5-Furan-2-yl-pyrimidin-2-yl)-((R)-4-morpholin-2-yl-phenyl)-amine

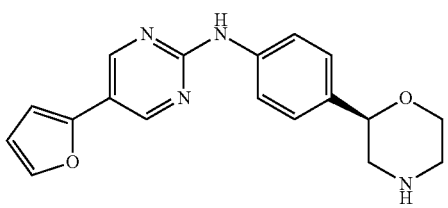 [SMILES: c1coc(-c2cnc(Nc3ccc([C@@H]4CNCCO4)cc3)nc2)c1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-5-(2-furanyl)-pyrimidine (CAS 63558-66-7) instead of 2,5-dichloropyridine in step (a). White solid. MS (ISP): 323.2 ([M+H]⁺).

Example 149

(RS)—N-(2-Chloro-4-(morpholin-2-yl)phenyl)-5-cyclopropylpyrimidin-2-amine

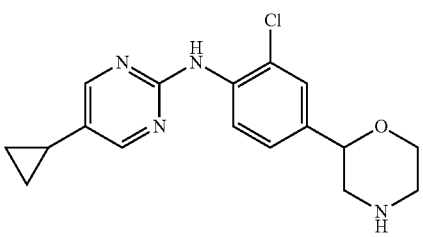 [SMILES: Clc1cc(C2CNCCO2)ccc1Nc1ncc(C2CC2)cn1]

a) 2-Bromo-1-(4-bromo-3-chlorophenyl)ethanone & 2-Chloro-1-(4-bromo-3-chlorophenyl)ethanone To a stirred solution of 4-bromo-3-chlorobenzoyl chloride (16.4 g, CAS 21900-32-3) in acetonitrile (80 ml) and THF (120 ml) at 0-5° C. was added dropwise (trimethylsilyl)diazomethane (38.8 ml, 2 M solution in diethyl ether). The reaction mixture was stirred at room temperature for 30 min. TLC analysis showed the reaction was complete. Hydrobromic acid (14.6 ml) was then added dropwise at 0-5° C. and the reaction mixture was stirred at room temperature for 30 min. The reaction mixture was then poured into EtOAc and extracted sequentially with aq. $Na_2CO_3$ solution, water and saturated brine. The organic layer was then dried over $Na_2SO_4$ and concentrated in vacuo to afford a ca 1:1 mixture of 2-bromo-1-(4-bromo-3-chlorophenyl)ethanone and 2-chloro-1-(4-bromo-3-chlorophenyl)ethanone (18.4 g) as a brown solid which was used in the next step without further purification.

b) (RS)-2-(4-Bromo-3-chloro-phenyl)-oxirane

To a stirred solution of the mixture of 2-bromo-1-(4-bromo-3-chlorophenyl)ethanone and 2-chloro-1-(4-bromo- 3-chlorophenyl)ethanone (18.4 g) in ethanol (200 ml) at 5° C. was added portionwise over 5 min NaBH$_4$ (2.23 g). The reaction mixture was then stirred at room temperature for 90 min to afford a yellow solution. TLC analysis showed the reaction was complete. Sodium methoxide (1.59 g) was then added and the reaction mixture was stirred at 50° C. for 4 h. TLC analysis showed the reaction was complete. The reaction mixture was then poured into TBME and washed with saturated brine. The organic layer was separated, then dried over Na$_2$SO$_4$ and concentrated in vacuo to afford (RS)-2-(4-bromo-3-chloro-phenyl)-oxirane (15.2 g) as a brown oil which was used in the next step without further purification.

c) (RS)-1-(4-bromo-3-chlorophenyl)-2-(2-hydroxyethylamino)ethanol

To a stirred solution of (RS)-2-(4-bromo-3-chloro-phenyl)-oxirane (15.2 g) in THF (40 ml) was added 2-aminoethanol (35.1 ml) and the mixture was stirred at room temperature for 7 hours. The reaction mixture was then poured into EtOAc/THF (1:1) and washed with saturated brine. The organic layer was separated and was then dried over Na$_2$SO$_4$ and concentrated in vacuo to afford (RS)-1-(4-bromo-3-chlorophenyl)-2-(2-hydroxyethylamino)ethanol (19.0 g) as a yellow oil which was used in the next step without further purification. MS (ISP): 298.1 ($[\{^{81}Br^{37}Cl\}M+H]^+$), 296.0 ($[\{^{81}Br^{35}Cl$ or $^{79}Br^{37}Cl\}M+H]^+$), 293.9 ($[\{^{79}Br^{35}Cl\}M+H]$).

d) tert-Butyl (RS)-2-(4-bromo-3-chlorophenyl)-2-hydroxyethyl(2-hydroxyethyl)carbamate To a stirred solution of (RS)-1-(4-bromo-3-chlorophenyl)-2-(2-hydroxyethylamino)ethanol (19.0 g) in dichloromethane (200 ml) at 0° C. was added Boc$_2$O (14.1 g) and the mixture was then stirred at room temperature overnight. The reaction mixture was then poured into EtOAc and the mixture was washed sequentially with dilute aq. sodium hydroxide and with saturated brine. The organic phase was separated and then dried over Na$_2$SO$_4$ and concentrated in vacuo. The residue was purified by flash column chromatography (silica gel; gradient: MeOH/dichloromethane 20/1) to afford tert-butyl (RS)-2-(4-bromo-3-chlorophenyl)-2-hydroxyethyl(2-hydroxyethyl)carbamate (12.7 g, 50% over 4 steps) as a yellow oil. MS (ISP): 398.0 ($[\{^{81}Br^{37}Cl\}M+H]^+$), 395.9 ($[\{^{81}Br^{35}Cl$ or $^{79}Br^{37}Cl\}M+H]^+$), 393.9 ($[\{^{79}Br^{35}Cl\}M+H]^+$).

e) tert-Butyl (RS)-2-(4-bromo-3-chlorophenyl)morpholine-4-carboxylate

To a stirred solution of tert-butyl (RS)-2-(4-bromo-3-chlorophenyl)-2-hydroxyethyl(2-hydroxyethyl)carbamate (12.7 g) and triethylamine (6.72 ml) in THF (150 ml) at 0-5° C. was added dropwise methanesulfonyl chloride (2.76 ml). The reaction mixture was then stirred at room temperature for 60 min to afford a white suspension. The reaction mixture was then filtered to remove triethylamine hydrochloride, washing the filter with THF (20 ml). The filtrate was cooled to 0-5° C. and potassium 2-methyl-2-butoxide (28.4 ml, 1.7 M solution in toluene) was added. The reaction mixture was stirred at room temperature for 30 min and then poured into EtOAc and washed sequentially with dilute aq. HCl, water and saturated brine. The organic phase was separated and was then dried over Na$_2$SO$_4$ and concentrated in vacuo. The residue was purified by flash column chromatography (silica gel; gradient: 0% to 50% EtOAc in hexanes) to afford tert-butyl (RS)-2-(4-bromo-3-chlorophenyl)morpholine-4-carboxylate (9.32 g, 77%) as a yellow oil. MS (ISP): 324.0 ($[\{^{81}Br^{37}Cl\}M+H-C_4H_8]^+$), 321.9 ($[\{^{81}Br^{35}Cl$ or $^{79}Br^{37}Cl\}M+H-C_4H_8]^+$), 319.9 ($[\{^{79}Br^{35}Cl\}M+H-C_4H_8]^+$), 279.9 ($[\{^{81}Br^{37}Cl\}M+H-C_4H_8-CO_2]^+$), 277.9 ($[\{^{81}Br^{35}Cl$ or $^{79}Br^{37}Cl\}M+H]-C_4H_8]-CO_2]^+$), 276.0 ($[\{^{79}Br^{35}Cl\}M+H-C_4H_8-CO_2]^+$).

f) tert-Butyl (RS)-2-(3-chloro-4-(diphenylmethyleneamino)phenyl)morpholine-4-carboxylate To a stirred solution of afford tert-butyl (RS)-2-(4-bromo-3-chlorophenyl)morpholine-4-carboxylate (0.50 g) and benzophenone imine (253 mg) in toluene (5 ml) was added sodium tert-butoxide (204 mg). The reaction mixture was purged with argon for 10 min. (R)-(+)-2,2'-bis(diphenylphosphino)-1,1'-binaphthyl (82.7 mg) and tris(dibenzylideneacetone)dipalladium(0) (36.5 mg) were added and the reaction mixture was heated to 90° C. and stirred for 16 h. The reaction mixture was poured into EtOAc and washed sequentially with dilute aq. HCl, water and saturated brine. The organic phase was separated and was then dried over Na2SO4 and concentrated in vacuo. The residue was purified by flash column chromatography (silica gel; gradient: 0% to 50% EtOAc in hexanes) to afford tert-butyl (RS)-2-(3-chloro-4-(diphenylmethyleneamino)phenyl)morpholine-4-carboxylate (639 mg, quant.) as a yellow oil. MS (ISP): 479.1 ($[\{^{37}Cl\}M+H]^+$), 477.1 ($[\{^{35}Cl\}M+H]^+$).

g) tert-Butyl (RS)-2-(4-amino-3-chlorophenyl)morpholine-4-carboxylate

To a stirred solution of tert-butyl (RS)-2-(3-chloro-4-(diphenylmethyleneamino)phenyl)morpholine-4-carboxylate (0.63 g) in methanol (8 ml) were added sodium acetate (325 mg) and hydroxylamine hydrochloride (202 mg). The reaction mixture was stirred at room tempearture for 16 hours and then at 60° C. for 1 hour. The reaction mixture was then cooled to room temperature and concentrated in vacuo. The residue was purified by flash column chromatography (silica gel; gradient: 0% to 70% EtOAc in hexanes) to afford tert-butyl (RS)-2-(4-amino-3-chlorophenyl)morpholine-4-carboxylate (345 mg, 84%) as a white solid. MS (ISP): 337.2 ($[\{^{37}Cl\}M+Na]^+$), 335.1 ($[\{^{35}Cl\}M+Na]^+$), 314.9 ($[\{^{37}Cl\}M+H]^+$), 313.0 ($[\{^{35}Cl\}M+H]^+$), 259.1 ($[\{^{37}Cl\}M+H-C_4H_8]^+$), 257.1 ($[\{^{35}Cl\}M+H-C_4H_8]^+$), 215.3 ($[\{^{37}Cl\}M+H-C_4H_8-CO_2]^+$), 213.0 ($[\{^{35}Cl\}M+H-C_4H_8-CO_2]^+$).

h) tert-Butyl (RS)-2-(3-chloro-4-(5-cyclopropylpyrimidin-2-ylamino)phenyl)morpholine-4-carboxylate tert-Butyl (RS)-2-(4-amino-3-chlorophenyl)morpholine-4-carboxylate (70 mg), 2-chloro-5-cyclopropylpyrimidine (45.0 mg, CAS 166740-44-9) and cesium carbonate (109 mg) were combined with dioxane (2 ml) to give a yellow suspension. The mixture was degassed by bubbling argon into the mixture for several minutes. Xantphos (7.77 mg) and tris (dibenzylideneacetone)dipalladium chloroform complex (6.95 mg) were then added. The reaction mixture was then capped and stirred at 120° C. for 16 hours. The crude reaction mixture was cooled to room temperature and filtered. The filtrate was concentrated in vacuo and the residue was purified by flash column chromatography (silica gel; gradient: 0% to 75% EtOAc in hexanes) to afford tert-butyl (RS)-2-(3-chloro-4-(5-cyclopropylpyrimidin-2-ylamino)phenyl)morpholine- 4-carboxylate (48 mg, 50%) as a colourless amorphous solid. MS (ISP): 433.2 ([{$^{37}$Cl}M+H]$^+$), 431.2 ([{$^{35}$Cl}M+H]$^+$).

i) (RS)—N-(2-Chloro-4-(morpholin-2-yl)phenyl)-5-cyclopropylpyrimidin-2-amine

To a stirred solution of tert-butyl (RS)-2-(3-chloro-4-(5-cyclopropylpyrimidin-2-ylamino)phenyl)morpholine-4-carboxylate (35 mg) in acetonitrile (1.5 ml) and water (4.5 ml) was added trifluoroacetic acid (77.3 µl). The reaction mixture was then capped and the mixture was shaken at 80° C. for 3 h. The reaction mixture was then cooled to room temperature and poured into EtOAc/THF (1:1) and washed with 1 M aq. NaOH. The organic layer was dried over Na$_2$SO$_4$ and concentrated in vacuo. The crude material was purified by flash column chromatography (Isolute® Flash-NH$_2$ from Separtis; gradient: heptane/EtOAc/MeOH) to afford (RS)—N-(2-chloro-4-(morpholin-2-yl)phenyl)-5-cyclopropylpyrimidin-2-amine (28 mg, 76%) as a white solid. MS (ISP): 333.1 ([{$^{37}$Cl}M+H]$^+$), 331.1 ([{$^{35}$Cl}M+H]$^+$).

Example 150

(RS)-[1-(2,2-Difluoro-ethyl)-1H-pyrazol-3-yl]-(4-morpholin-2-yl-phenyl)-amine

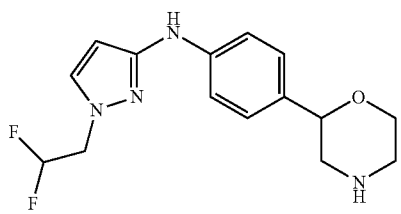 [SMILES: FC(F)Cn1ccc(Nc2ccc(C3CNCCO3)cc2)n1]

The title compound was obtained in analogy to example 19 using (RS)-2-(4-bromo-phenyl)-morpholine-4-carboxylic acid tert-butyl ester instead of (S)-2-(4-bromo-phenyl)-morpholine-4-carboxylic acid tert-butyl ester and 1-(2,2-difluoro-ethyl)-1H-pyrazol-3-ylamine (CAS 1006462-38-9) instead of 5-trifluoromethyl-pyrimidin-2-ylamine in step (a). Off-white solid. MS (ISP): 309.4 ([M+H]$^+$).

Example 151

((R)-2-Fluoro-4-morpholin-2-yl-phenyl)-[5-(2-methoxy-ethoxy)-pyrimidin-2-yl]-amine

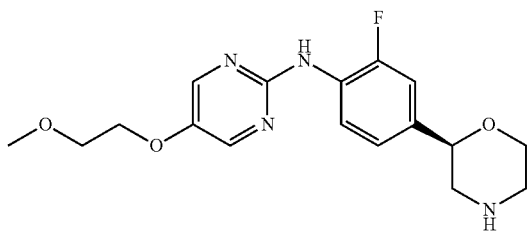 [SMILES: COCCOc1cnc(Nc2ccc([C@@H]3CNCCO3)cc2F)nc1]

The title compound was obtained in analogy to example 116 using (+)-(R)-2-(4-amino-3-fluoro-phenyl)-morpholine-4-carboxylic acid tert-butyl ester and 2-chloro-5-(2-methoxyethoxy)pyrimidine (CAS 61533-68-4) in place of 2-chloro-5-ethylpyrimidine in step (b). Colourless gum. MS (ISP): 349.2 ([M+H]$^+$).

Example 152

((S)-2-Fluoro-4-morpholin-2-yl-phenyl)-[5-(2-methoxy-ethoxy)-pyrimidin-2-yl]-amine

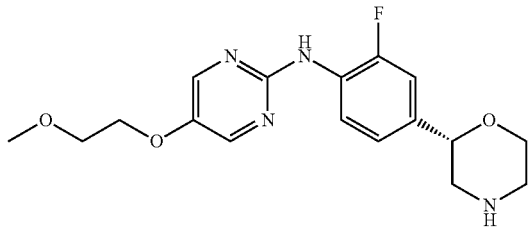 [SMILES: COCCOc1cnc(Nc2ccc([C@H]3CNCCO3)cc2F)nc1]

The title compound was obtained in analogy to example 116 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 2-chloro-5-(2-methoxyethoxy)pyrimidine (CAS 61533-68-4) in place of 2-chloro-5-ethylpyrimidine in step (b). Colourless gum. MS (ISP): 349.2 ([M+H]$^+$).

Example 153

((S)-4-Morpholin-2-yl-phenyl)-(2-trifluoromethyl-pyrimidin-5-yl)-amine

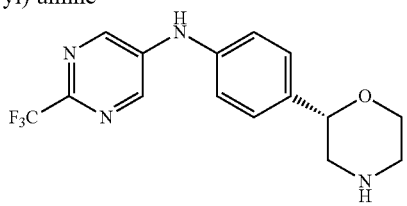

The title compound was obtained in analogy to example 5 using (S)-2-(4-aminophenyl)-morpholine-4-carboxylic acid tert-butyl ester (CAS 1260220-43-6) in place of (RS)-2-(4-amino-phenyl)-morpholine-4-carboxylic acid tert-butyl ester and 5-chloro-2-trifluoromethylpyrimidine (CAS 845618-08-8) instead of 2,5-dichloropyridine in step (a). White solid. MS (ISP): 325.3 ([M+H]$^+$).

Example 154

((R)-4-Morpholin-2-yl-phenyl)-(2-trifluoromethyl-pyrimidin-5-yl)-amine

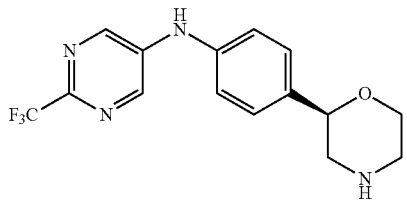 [SMILES: FC(F)(F)c1ncc(Nc2ccc([C@@H]3CNCCO3)cc2)cn1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 5-chloro-2-trifluoromethylpyrimidine (CAS 845618-08-8) instead of 2,5-dichloropyridine in step (a). White solid. MS (ISP): 325.3 ([M+H]+).

Example 155

(RS)-(4-Morpholin-2-yl-phenyl)-(1H-pyrazol-3-yl)-amine

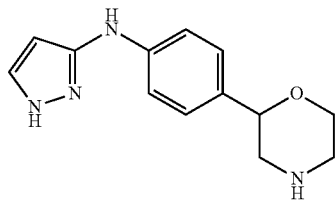 [SMILES: c1cc(Nc2ccc(C3CNCCO3)cc2)n[nH]1]

The title compound was obtained in analogy to example 19 using (RS)-2-(4-bromo-phenyl)-morpholine-4-carboxylic acid tert-butyl ester instead of (S)-2-(4-bromo-phenyl)-morpholine-4-carboxylic acid tert-butyl ester and 3-aminopyrazole-1-carboxylic acid tert-butyl ester (CAS 863504-84-1) instead of 5-trifluoromethylpyrimidin-2-ylamine in step (a). Orange gum. MS (ISP): 245.3 ([M+H]+).

Example 156

(5-Methyl-pyrazin-2-yl)-((S)-4-morpholin-2-yl-phenyl)-amine

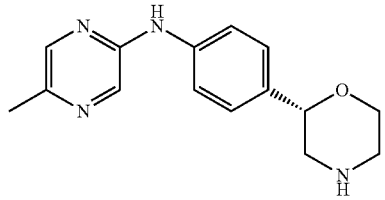 [SMILES: Cc1cnc(Nc2ccc([C@H]3CNCCO3)cc2)cn1]

The title compound was obtained in analogy to example 5 using (S)-2-(4-aminophenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-5-methylpyrazine (CAS 59303-10-5) instead of 2,5-dichloropyridine in step (a). White solid. MS (ISP): 271.4 ([M+H]+).

Example 157

(5-Methyl-pyrazin-2-yl)-((R)-4-morpholin-2-yl-phenyl)-amine

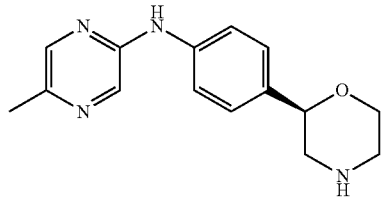 [SMILES: Cc1cnc(Nc2ccc([C@@H]3CNCCO3)cc2)cn1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-5-methylpyrazine (CAS 59303-10-5) instead of 2,5-dichloropyridine in step (a). White solid. MS (ISP): 271.4 ([M+H]+).

Example 158

2-((S)-4-Morpholin-2-yl-phenylamino)-pyrimidine-5-carboxylic acid methylamide

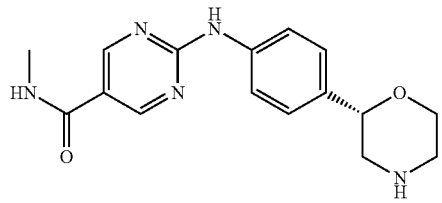 [SMILES: CNC(=O)c1cnc(Nc2ccc([C@H]3CNCCO3)cc2)nc1]

The title compound was obtained in analogy to example 5 using (S)-2-(4-aminophenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-N-methylpyrimidine-5-carboxamide instead of 2,5-dichloropyridine in step (a). White solid. MS (ISP): 314.2 ([M+H]+).

Example 159

2-((R)-4-Morpholin-2-yl-phenylamino)-pyrimidine-5-carboxylic acid methylamide

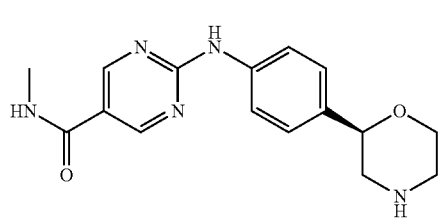 [SMILES: CNC(=O)c1cnc(Nc2ccc([C@@H]3CNCCO3)cc2)nc1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-N-methylpyrimidine-5-carboxamide instead of 2,5-dichloropyridine in step (a). White solid. MS (ISP): 314.2 ([M+H]+).

Example 160

(6-Methyl-pyridazin-3-yl)-((S)-4-morpholin-2-yl-phenyl)-amine

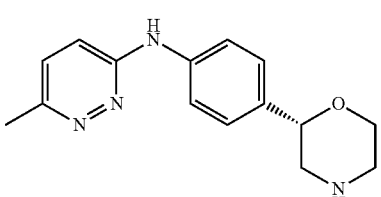

The title compound was obtained in analogy to example 5 using (S)-2-(4-aminophenyl)-morpholine-4-carboxylic acid tert-butyl ester (CAS 1260220-43-6) in place of (RS)-2-(4- amino-phenyl)-morpholine-4-carboxylic acid tert-butyl ester and 3-chloro-6-methylpyridazine (CAS 1121-79-5) instead of 2,5-dichloropyridine in step (a). Off-white solid. MS (ISP): 271.4 ([M+H]+).

Example 161

(1-Benzyl-1H-pyrazol-3-yl)-((S)-4-morpholin-2-yl-phenyl)-amine

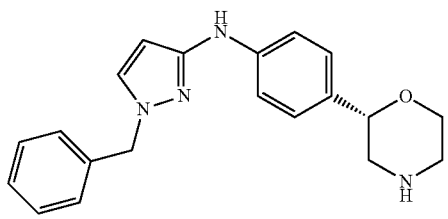 [SMILES: c1ccc(Cn2ccc(Nc3ccc([C@H]4CNCCO4)cc3)n2)cc1]

The title compound was obtained in analogy to example 19 using 1-benzyl-1H-pyrazol-3-ylamine (CAS 21377-09-3) instead of 5-trifluoromethyl-pyrimidin-2-ylamine in step (a). Off-white solid. MS (ISP): 335.4 ([M+H]+).

Example 162

(1-Benzyl-1H-pyrazol-3-yl)-((R)-4-morpholin-2-yl-phenyl)-amine

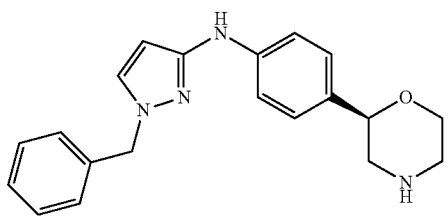 [SMILES: c1ccc(Cn2ccc(Nc3ccc([C@@H]4CNCCO4)cc3)n2)cc1]

The title compound was obtained in analogy to example 19 using (R)-2-(4-bromo-phenyl)-morpholine-4-carboxylic acid tert-butyl ester instead of (S)-2-(4-bromo-phenyl)-morpholine-4-carboxylic acid tert-butyl ester and 1-benzyl-1H-pyrazol-3-ylamine (CAS 21377-09-3) instead of 5-trifluoromethyl-pyrimidin-2-ylamine in step (a). Off-white solid. MS (ISP): 335.4 ([M+H]+).

Example 163

((S)-4-Morpholin-2-yl-phenyl)-(1-phenyl-1H-pyrazol-3-yl)-amine

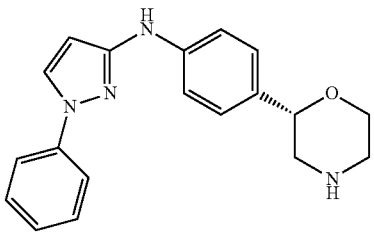 [SMILES: c1ccc(-n2ccc(Nc3ccc([C@H]4CNCCO4)cc3)n2)cc1]

The title compound was obtained in analogy to example 19 using 1-phenyl-1H-pyrazol-3-ylamine (CAS 1128-56-9) instead of 5-trifluoromethyl-pyrimidin-2-ylamine in step (a). Off-white solid. MS (ISP): 321.2 ([M+H]+).

Example 164

((R)-4-Morpholin-2-yl-phenyl)-(1-phenyl-1H-pyrazol-3-yl)-amine

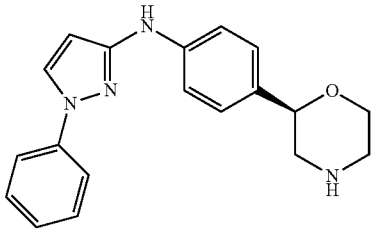 [SMILES: c1ccc(-n2ccc(Nc3ccc([C@@H]4CNCCO4)cc3)n2)cc1]

The title compound was obtained in analogy to example 19 using (R)-2-(4-bromo-phenyl)-morpholine-4-carboxylic acid tert-butyl ester instead of (S)-2-(4-bromo-phenyl)-morpholine-4-carboxylic acid tert-butyl ester and 1-phenyl-1H-pyrazol-3-ylamine (CAS 1128-56-9) instead of 5-trifluoromethyl-pyrimidin-2-ylamine in step (a). Light yellow solid. MS (ISP): 321.2 ([M+H]+).

Example 165

((S)-4-Morpholin-2-yl-phenyl)-(5-oxetan-3-yl-pyridin-2-yl)-amine

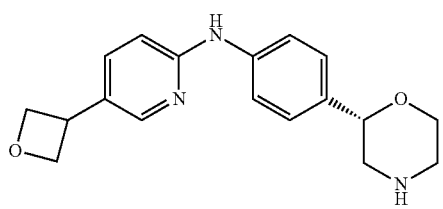 [SMILES: c1cc([C@H]2CNCCO2)ccc1Nc1ccc(C2COC2)cn1]

a) 2-Chloro-5-oxetan-3-yl-pyridine

To a solution of 2-chloropyridine-5-boronic acid (315 mg, CAS 444120-91-6) in isopropanol (2 ml) in a 10 mL microwave vial were added nickel iodide (18.8 mg), trans-2-aminocyclohexanol hydrochloride (9.21 mg) and sodium bis(trimethylsilyl)amide (387 mg). Argon was bubbled into the reaction mixture for 5 min. A solution of 3-iodo-oxetane (190 mg, CAS 26272-85-5) in isopropanol (0.25 ml) was then added. The vial was then capped and heated in the microwave at 80° C. for 20 min. TLC at t=20 min showed the reaction was complete. The reaction mixture was diluted with EtOH and filtered through celite. The filter cake was washed with EtOH and the filtrate was concentrated in vacuo. The crude material was purified by flash chromatography (silica gel; gradient: 0% to 50% EtOAc in heptane) to afford 2-chloro-5-oxetan-3-yl-pyridine (40 mg, 24%) as a white solid.

b) ((S)-4-Morpholin-2-yl-phenyl)-(5-oxetan-3-yl-pyridin-2-yl)-amine

The title compound was obtained in analogy to example 5 using (S)-2-(4-aminophenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-5-oxetan-3-yl-pyridine instead of 2,5-dichloropyridine in step (a). Light brown solid. MS (ISP): 312.3 ([M+H]⁺).

Example 166

((R)-2-Methyl-4-morpholin-2-yl-phenyl)-(5-trifluoromethyl-pyrimidin-2-yl)-amine

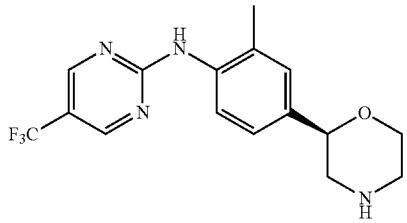 [SMILES: Cc1cc([C@@H]2CNCCO2)ccc1Nc1ncc(C(F)(F)F)cn1]

The title compound was obtained in analogy to example 106 using (+)-(R)-tert-butyl 2-(4-amino-3-methylphenyl)morpholine-4-carboxylate and 2-chloro-5-(trifluoromethyl)-pyrimidine (CAS 69034-12-4) instead of 2-chloro-5-ethylpyrimidine in step (b). White solid. MS (ISP): 339.3 ([M+H]⁺).

Example 167

((S)-2-Methyl-4-morpholin-2-yl-phenyl)-(5-trifluoromethyl-pyrimidin-2-yl)-amine

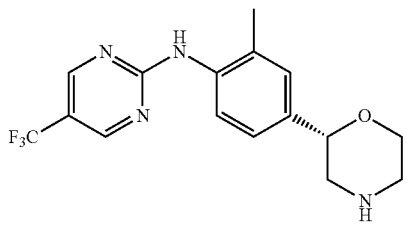 [SMILES: Cc1cc([C@H]2CNCCO2)ccc1Nc1ncc(C(F)(F)F)cn1]

The title compound was obtained in analogy to example 106 using (−)-(S)-tert-butyl 2-(4-amino-3-methylphenyl)morpholine-4-carboxylate instead of (+)-(R)-tert-butyl 2-(4-amino-3-methylphenyl)morpholine-4-carboxylate and 2-chloro-5-(trifluoromethyl)-pyrimidine (CAS 69034-12-4) instead of 2-chloro-5-ethylpyrimidine in step (b). White solid. MS (ISP): 339.3 ([M+H]⁺).

Example 168

((R)-2-Chloro-4-morpholin-2-yl-phenyl)-(5-trifluoromethyl-pyrimidin-2-yl)-amine

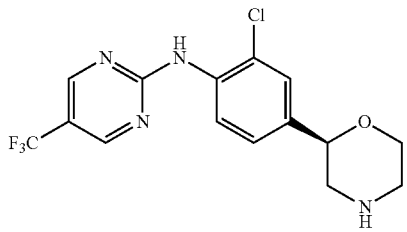

a) (RS)-2-[3-Chloro-4-(5-trifluoromethyl-pyrimidin-2-ylamino)-phenyl]-morpholine-4-carboxylic acid tert-butyl ester The title compound was obtained in analogy to example 149 step (h) using 2-chloro-5-(trifluoromethyl)-pyrimidine (CAS 69034-12-4) instead of 2-chloro-5-cyclopropylpyrimidine. Colourless gum. MS (ISP): 461.3 ([{³⁷Cl}M+H]⁺), 459.3 ([{³⁵Cl}M+H]⁺), 405.3 ([{³⁷Cl}M+H—C₄H₈]⁺), 403.2 ([{³⁵Cl}M+H—C₄H₈]⁺).

b) (+)-(R)-2-[3-Chloro-4-(5-trifluoromethyl-pyrimidin-2-ylamino)-phenyl]-morpholine-4-carboxylic acid tert-butyl ester & (−)-(S)-2-[3-Chloro-4-(5-trifluoromethyl-pyrimidin-2-ylamino)-phenyl]-morpholine-4-carboxylic acid tert-butyl ester The enantiomers of (RS)-2-[3-chloro-4-(5-trifluoromethyl-pyrimidin-2-ylamino)-phenyl]-morpholine-4-carboxylic acid tert-butyl ester (130 mg) were separated using chiral HPLC (column: Chiralpak AD, 5×50 cm; eluent: 30% isopropanol/heptane; pressure: 18 bar; flow rate: 35 ml/min) affording:

(+)-(R)-2-[3-Chloro-4-(5-trifluoromethyl-pyrimidin-2-ylamino)-phenyl]-morpholine-4-carboxylic acid tert-butyl ester (35 mg, white solid) Retention time=62 min (−)-(S)-2-[3-Chloro-4-(5-trifluoromethyl-pyrimidin-2-ylamino)-phenyl]-morpholine-4-carboxylic acid tert-butyl ester (33 mg, white solid) Retention time=92 min c) ((R)-2-Chloro-4-morpholin-2-yl-phenyl)-(5-trifluoromethyl-pyrimidin-2-yl)-amine The title compound was obtained in analogy to example 149 step (i) using (+)-(R)-2-[3-chloro-4-(5-trifluoromethyl-pyrimidin-2-ylamino)-phenyl]-morpholine-4-carboxylic acid tert-butyl ester in place of (RS)-2-[3-chloro-4-(5-trifluoromethylpyrimidin-2-ylamino)-phenyl]-morpholine-4-carboxylic acid tert-butyl ester. White solid. MS (ISP): 361.1 ([{³⁷Cl}M+H]⁺), 359.1 ([{³⁵Cl}M+H]⁺).

Example 169

((S)-2-Chloro-4-morpholin-2-yl-phenyl)-(5-trifluoromethyl-pyrimidin-2-yl)-amine

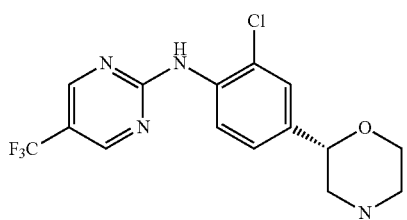

The title compound was obtained in analogy to example 168 using (−)-(S)-2-[3-chloro-4-(5-trifluoromethyl-pyrimidin-2-ylamino)-phenyl]-morpholine-4-carboxylic acid tert-butyl ester in place of (+)-(R)-2-[3-Chloro-4-(5-trifluoromethyl-pyrimidin-2-ylamino)-phenyl]-morpholine-4-carboxylic acid tert-butyl ester in step (c). Colourless gum. MS (ISP): 361.1 ([{³⁷Cl}M+H]⁺), 359.1 ([{³⁵Cl}M+H]⁺).

Example 170

(R)—N-(2-Chloro-4-(morpholin-2-yl)phenyl)-5-cyclopropylpyrimidin-2-amine

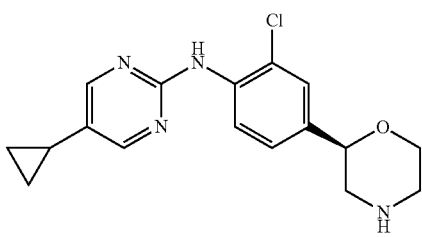

a) (+)-(R)-tert-Butyl 2-(4-amino-3-chlorophenyl)morpholine-4-carboxylate & (−)-(S)-tert-Butyl 2-(4-amino-3-chlorophenyl)morpholine-4-carboxylate The enantiomers of (RS)-tert-butyl 2-(4-amino-3-chlorophenyl)morpholine-4-carboxylate (2.0 g, Example 149(g)) were separated using chiral HPLC (column: Chiralpak AD, 5×50 cm; eluent: 10% isopropanol/heptane; pressure: 18 bar; flow rate: 35 ml/min) affording:
(+)-(R)-tert-Butyl 2-(4-amino-3-chlorophenyl)morpholine-4-carboxylate (894 mg, white solid) Retention time=60 min
(−)-(S)-tert-Butyl 2-(4-amino-3-chlorophenyl)morpholine-4-carboxylate (934 mg, white solid) Retention time=76 min b) (R)—N-(2-Chloro-4-(morpholin-2-yl)phenyl)-5-cyclopropylpyrimidin-2-amine The title compound was obtained in analogy to example 149 (h)-(i) using (+)-(R)-tert-butyl 2-(4-amino-3-chlorophenyl)morpholine-4-carboxylate in place of (RS)-tert-butyl 2-(4-amino-3-chlorophenyl)morpholine-4-carboxylate in step (h). White solid. MS (ISP): 333.1 ([{$^{37}$Cl}M+H]$^+$), 331.1 ([{$^{35}$Cl}M+H]$^+$).

Example 171

(S)—N-(2-Chloro-4-(morpholin-2-yl)phenyl)-5-cyclopropylpyrimidin-2-amine

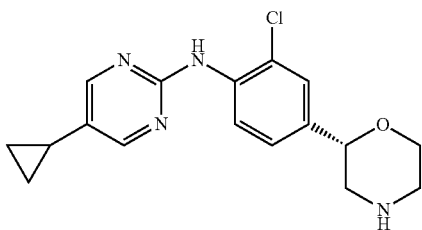 [SMILES: Clc1cc([C@H]2CNCCO2)ccc1Nc1ncc(C2CC2)cn1]

The title compound was obtained in analogy to example 170 using (−)-(S)-tert-butyl 2-(4-amino-3-chlorophenyl)morpholine-4-carboxylate in place of (+)-(R)-tert-butyl 2-(4-amino-3-chlorophenyl)morpholine-4-carboxylate in step (b). Off-white solid. MS (ISP): 333.1 ([{$^{37}$Cl}M+H]$^+$), 331.1 ([{$^{35}$Cl}M+H]$^+$).

Example 172

((R)-4-Morpholin-2-yl-phenyl)-[4-(2,2,2-trifluoroethoxy)-pyrimidin-2-yl]-amine

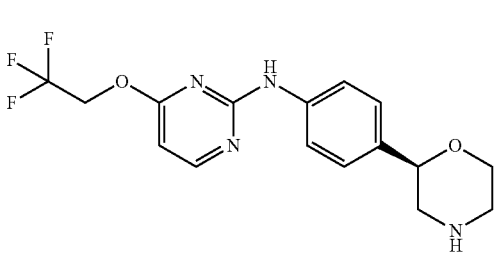 [SMILES: FC(F)(F)COc1ccnc(Nc2ccc([C@@H]3CNCCO3)cc2)n1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-4-(2,2,2-trifluoroethoxy)-pyrimidine (CAS 935252-67-8) instead of 2,5-dichloropyridine in step (a). Off-white solid. MS (ISP): 355.1 ([M+H]$^+$).

Example 173

(R)—N-(4-(Morpholin-2-yl)phenyl)-4-(trifluoromethyl)pyrimidin-2-amine

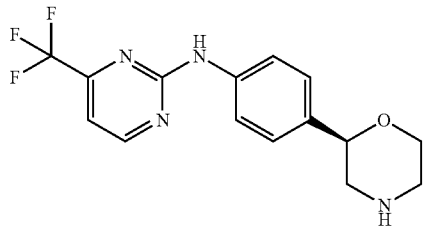 [SMILES: FC(F)(F)c1ccnc(Nc2ccc([C@@H]3CNCCO3)cc2)n1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-4-trifluoromethylpyrimidine (CAS 33034-67-2) instead of 2,5-dichloropyridine in step (a). Off-white solid. MS (ISP): 325.1 ([M+H]$^+$).

Example 174

(R)-5-(5-(Difluoromethoxy)pyrimidin-2-yloxy)-N-(4-(morpholin-2-yl)phenyl)pyrimidin-2-amine

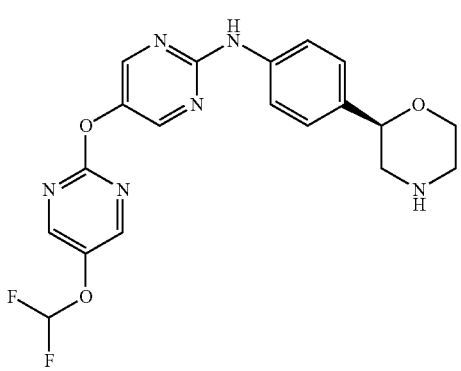 [SMILES: FC(F)Oc1cnc(Oc2cnc(Nc3ccc([C@@H]4CNCCO4)cc3)nc2)nc1]

a) 2-Chloro-5-(5-(difluoromethoxy)pyrimidin-2-yloxy)pyrimidine

2-Chloropyrimidin-5-ol (0.5 g) was combined with DMF (5 ml) to give a colourless solution. $K_2CO_3$ (582 mg) and ethyl 2-chloro-2,2-difluoroacetate (534 μl) were then added. The reaction mixture was stirred at 70° C. overnight to afford a brown suspension. The reaction mixture was then poured into EtOAc and washed sequentially with water and with saturated brine. The organic layer was separated, dried over Na2SO4 and concentrated in vacuo. The crude material was purified by flash chromatography (silica gel; gradient: 0% to 60% EtOAc in hexanes) to afford 2-chloro-5-(5-(difluoromethoxy)pyrimidin-2-yloxy)pyrimidine (154 mg, 15%) as a yellow solid. MS (ISP): 277.0 ($[\{^{37}Cl\}M+H]^+$), 275.0 ($[\{^{35}Cl\}M+H]^+$).

b) (R)-5-(5-(Difluoromethoxy)pyrimidin-2-yloxy)-N-(4-(morpholin-2-yl)phenyl)pyrimidin-2-amine The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-5-(5-(difluoromethoxy)pyrimidin-2-yloxy)pyrimidine instead of 2,5-dichloropyridine in step (a). White solid. MS (ISP): 417.1 ($[M+H]^+$).

Example 175

(R)—N-(2-Chloro-4-(morpholin-2-yl)phenyl)-5-(5-(difluoromethoxy)pyrimidin-2-yloxy)pyrimidin-2-amine

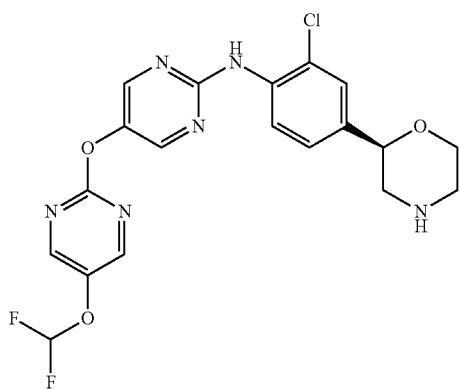 [SMILES: FC(F)Oc1cnc(Oc2cnc(Nc3ccc([C@@H]4CNCCO4)cc3Cl)nc2)nc1]

The title compound was obtained in analogy to example 170 using 2-chloro-5-(5-(difluoromethoxy)pyrimidin-2-yloxy)pyrimidine (Example 174(a)) in place 2-chloro-5-cyclopropylpyrimidine in step (b). Colourless amorphous solid. MS (ISP): 453.1 ($[\{^{37}Cl\}M+H]^+$), 451.1 ($[\{^{35}Cl\}M+H]^+$).

Example 176

(R)—N-(4-(Morpholin-2-yl)phenyl)pyrimidin-2-amine

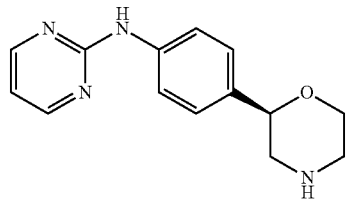 [SMILES: c1cnc(Nc2ccc([C@@H]3CNCCO3)cc2)nc1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-pyrimidine (CAS 1722-12-9) instead of 2,5-dichloropyridine in step (a). White solid. MS (ISP): 257.1 ($[M+H]^+$).

Example 177

((R)-4-Morpholin-2-yl-phenyl)-quinazolin-2-yl-amine

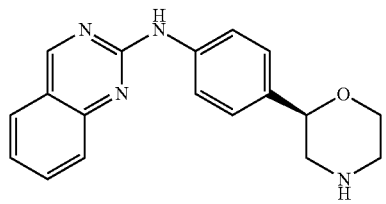 [SMILES: c1ccc2nc(Nc3ccc([C@@H]4CNCCO4)cc3)ncc2c1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloroquinazoline (CAS 6141-13-5) instead of 2,5-dichloropyridine in step (a). Light yellow solid. MS (ISP): 307.2 ($[M+H]^+$).

Example 178

(4-Methyl-6-trifluoromethyl-pyrimidin-2-yl)-((R)-4-morpholin-2-yl-phenyl)-amine

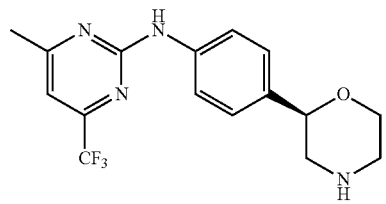 [SMILES: Cc1cc(C(F)(F)F)nc(Nc2ccc([C@@H]3CNCCO3)cc2)n1]

The title compound was obtained in analogy to example 19 using (R)-2-(4-bromo-phenyl)-morpholine-4-carboxylic acid tert-butyl ester instead of (S)-2-(4-bromo-phenyl)-morpholine-4-carboxylic acid tert-butyl ester and 4-methyl-6-(trifluoromethyl)pyrimidin-2-amine (CAS 5734-63-4) instead of 2,5-dichloropyridine in step (a). White solid. MS (ISP): 339.1 ([M+H]$^+$).

Example 179

(R)-5-(Difluoromethoxy)-N-(4-(morpholin-2-yl)phenyl)pyrimidin-2-amine

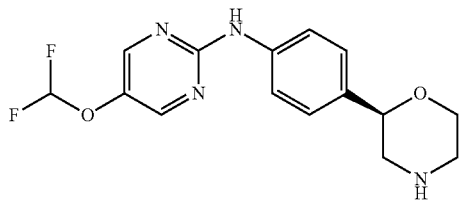 [SMILES: FC(F)Oc1cnc(Nc2ccc([C@@H]3CNCCO3)cc2)nc1]

a) (R)-tert-Butyl 2-(4-(5-(benzyloxy)pyrimidin-2-ylamino)phenyl)morpholine-4-carboxylate The title compound was obtained in analogy to example 5 using ®-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-5-(phenylmethoxy)-pyrimidine (CAS 138274-14-3) instead of 2,5-dichloropyridine in step (a). Off-white solid. MS (ISP): 463.2 ([M+H]$^+$), 407.3 ([M+H—C$_4$H$_8$]$^+$).

b) (R)-tert-Butyl 2-(4-(5-hydroxypyrimidin-2-ylamino)phenyl)morpholine-4-carboxylate (R)-tert-Butyl 2-(4-(5-(benzyloxy)pyrimidin-2-ylamino)phenyl)morpholine-4-carboxylate (0.36 g) was combined with MeOH (15 ml) and THF (5 ml) to give a light brown solution. The mixture was degassed by bubbling through argon for several minutes. Palladium on charcoal (41.4 mg, 10%) was added. The reaction mixture was then stirred under a balloon filled with argon overnight. The reaction mixture was then filtered through celite and concentrated in vacuo to afford (R)-tert-butyl 2-(4-(5-hydroxypyrimidin-2-ylamino)phenyl)morpholine-4-carboxylate (311 mg, quant.) as a light brown foam which was used in the next step without further purification. MS (ISP): 373.2 ([M+H]$^+$).

c) (R)-tert-Butyl 2-(4-(5-(difluoromethoxy)pyrimidin-2-ylamino)phenyl)morpholine-4-carboxylate (R)-tert-Butyl 2-(4-(5-hydroxypyrimidin-2-ylamino)phenyl)morpholine-4-carboxylate (0.24 g) and K$_2$CO$_3$ (124 mg) were combined with DMF (2 ml) to give a brown solution. Ethyl 2-chloro-2,2-difluoroacetate (152 mg) was then added. The reaction mixture was stirred at 80° C. for 1.5 h to afford a dark brown suspension. TLC & HPLC showed the reaction was complete. The reaction mixture was poured into EtOAc and washed sequentially with water and with saturated brine. The organic layer was separated, dried over Na2SO4 and concentrated in vacuo. The crude material was purified by flash chromatography (silica gel; gradient: 0% to 70% EtOAc in hexanes) to afford (R)-tert-butyl 2-(4-(5-(difluoromethoxy)pyrimidin-2-ylamino)phenyl)morpholine-4-carboxylate (60 mg, 24%) as a yellow oil. MS (ISP): 423.1 ([M+H]$^+$), 367.0 ([M+H—C$_4$H$_8$]$^+$).

d) (R)-5-(Difluoromethoxy)-N-(4-(morpholin-2-yl)phenyl)pyrimidin-2-amine (R)-tert-Butyl 2-(4-(5-(difluoromethoxy)pyrimidin-2-ylamino)phenyl)morpholine-4-carboxylate (58 mg) was combined with acetonitrile (2 ml) and water (6 ml). Trifluoroacetic acid (138 µl) was added. The vial was capped and shaken at 80° C. for 4 hours. The reaction mixture was then poured into EtOAc/THF (1:1) and washed with 1 M aq. NaOH. The organic layer was separated, dried over Na$_2$SO$_4$ and concentrated in vacuo. The crude material was purified by flash column chromatography (Isolute® Flash-NH$_2$ from Separtis; gradient: heptane/EtOAc/MeOH) to afford (R)-5-(difluoromethoxy)-N-(4-(morpholin-2-yl)phenyl)pyrimidin-2-amine (31 mg, 70%) as a white solid. MS (ISP): 323.1 ([M+H]$^+$).

Example 180

(4-Chloro-6-methoxy-pyrimidin-2-yl)-((R)-4-morpholin-2-yl-phenyl)-amine

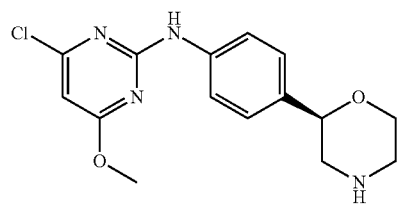 [SMILES: COc1cc(Cl)nc(Nc2ccc([C@@H]3CNCCO3)cc2)n1]

The title compound was obtained in analogy to example 19 using (R)-2-(4-bromo-phenyl)-morpholine-4-carboxylic acid tert-butyl ester instead of (S)-2-(4-bromo-phenyl)-morpholine-4-carboxylic acid tert-butyl ester and 2-amino-4-chloro-6-methoxypyrimidine (CAS 5734-64-5) instead of 2,5-dichloropyridine in step (a). White solid. MS (ISP): 323.3 ([{$^{37}$Cl}M+H]$^+$), 321.2 ([{$^{35}$Cl}M+H]$^+$).

Example 181

2-((R)-4-Morpholin-2-yl-phenylamino)-pyrimidine-4-carbonitrile

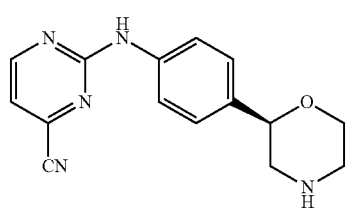 [SMILES: N#Cc1ccnc(Nc2ccc([C@@H]3CNCCO3)cc2)n1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloropyrimidine-4-carbonitrile (CAS 75833-38-4) instead of 2,5-dichloropyridine in step (a). Light yellow solid. MS (ISP): 282.2 ([M+H]+).

Example 182

(4,6-Dimethyl-pyrimidin-2-yl)-((R)-4-morpholin-2-yl-phenyl)-amine

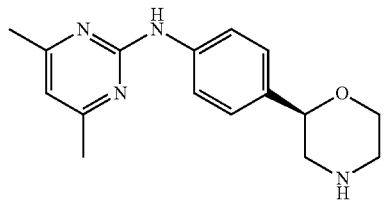 [SMILES: Cc1cc(C)nc(Nc2ccc([C@@H]3CNCCO3)cc2)n1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-4,6-dimethylpyrimidine (CAS 4472-44-0) instead of 2,5-dichloropyridine in step (a). White solid. MS (ISP): 285.1 ([M+H]+).

Example 183

(4,6-Dimethoxy-pyrimidin-2-yl)-((R)-4-morpholin-2-yl-phenyl)-amine

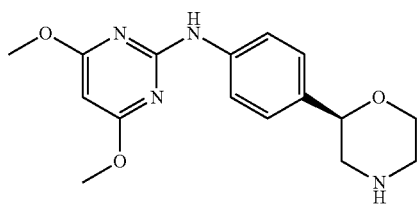 [SMILES: COc1cc(OC)nc(Nc2ccc([C@@H]3CNCCO3)cc2)n1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-4,6-dimethoxypyrimidine (CAS 13223-25-1) instead of 2,5-dichloropyridine in step (a). White solid. MS (ISP): 317.1 ([M+H]+).

Example 184

((R)-2-Chloro-4-morpholin-2-yl-phenyl)-[5-(2,2,2-trifluoro-ethoxy)-pyrimidin-2-yl]-amine

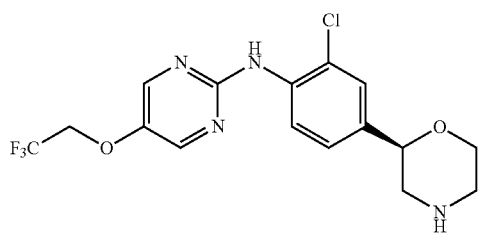 [SMILES: FC(F)(F)COc1cnc(Nc2ccc([C@@H]3CNCCO3)cc2Cl)nc1]

The title compound was obtained in analogy to example 170 using 2-chloro-5-(2,2,2-trifluoroethoxy)-pyrimidine (CAS 145948-01-2) in place of 2-chloro-5-cyclopropylpyrimidine in step (b). White solid. MS (ISP): 391.3 ([{37Cl}M+H]+), 389.2 ([{35Cl}M+H]+).

Example 185

(R)-3-Chloro-N-(4-(morpholin-2-yl)phenyl)-5-(trifluoromethyl)pyridin-2-amine

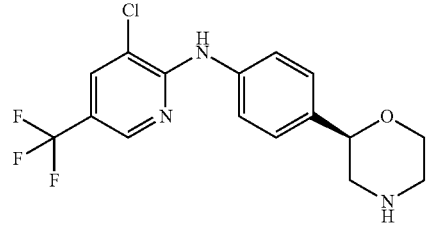 [SMILES: FC(F)(F)c1cnc(Nc2ccc([C@@H]3CNCCO3)cc2)c(Cl)c1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2,3-dichloro-5-(trifluoromethyl)pyridine (CAS 69045-84-7) instead of 2,5-dichloropyridine in step (a). White solid. MS (ISP): 358.1 ([{35Cl}M+H]+), 360.1 ([{37Cl}M+H]+).

Example 186

(S)-2,5-Dichloro-N-(4-(morpholin-2-yl)phenyl)pyrimidin-4-amine

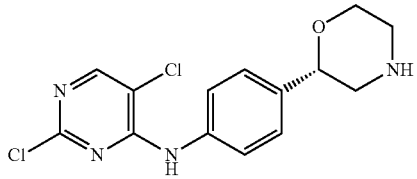 [SMILES: Clc1ncc(Cl)c(Nc2ccc([C@H]3CNCCO3)cc2)n1]

a) (S)-tert-Butyl 2-(4-(2,5-dichloropyrimidin-4-ylamino)phenyl)morpholine-4-carboxylate A mixture of (S)-tert-butyl 2-(4-aminophenyl)morpholine-4-carboxylate (100 mg, 0.36 mmol), 2,4,5-trichloropyrimidine (66 mg, 0.36 mmol) and diisopropylethylamine (70 mg, 0.54 mmol) was dissolved in 2-propanol (1.5 ml) and stirred at 80° C. overnight. For work-up most of the solvent was evaporated, then aqueous ammonium chloride solution was added and the mixture was extracted with ethyl acetate. The aqueous phase was re-extracted with ethyl acetate twice. The combined organic layers were dried (MgSO4) and concentrated in vacuo. The residue was purified by flash chromatography (20 g silica gel, 10 to 30% ethyl acetate in heptane) to yield a white solid (141 mg, 92%). MS (ISP): 425.1 ([{35Cl}M+H]+), 427.1 ([{37Cl}M+H]+).

b) (S)-2,5-Dichloro-N-(4-(morpholin-2-yl)phenyl)pyrimidin-4-amine hydrochloride (S)-tert-Butyl 2-(4-(2,5-dichloropyrimidin-4-ylamino)phenyl)morpholine-4-carboxylate (45 mg, 0.106 mmol) was dissolved in dioxane (0.5 ml) and a solution of HCl in dioxane (4 M, 0.3 ml, 1.27 mmol) was added. The reaction mixture was stirred at 60° C. for 2 hours. After cooling, ether (2 ml) was added and the solid was filtered off. It was washed with ether and dried in vacuo to afford (S)-2,5-dichloro-N-(4-(morpholin-2-yl)phenyl)pyrimidin-4-amine hydrochloride (38 mg, 99%) as a white solid. MS (ISP): 325.1 ([{$^{35}$Cl}M+H]$^+$), 327.1 ([{$^{37}$Cl}M+H]$^+$).

Example 187

((S)-4-Morpholin-2-yl-phenyl)-[4-(2,2,2-trifluoro-ethoxy)-pyrimidin-2-yl]-amine

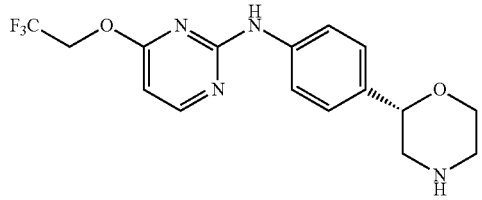 [SMILES: FC(F)(F)COc1ccnc(Nc2ccc([C@H]3CNCCO3)cc2)n1]

The title compound was obtained in analogy to example 5 using (S)-2-(4-aminophenyl)-morpholine-4-carboxylic acid tert-butyl ester (CAS 1260220-43-6) in place of (RS)-2-(4-amino-phenyl)-morpholine-4-carboxylic acid tert-butyl ester and 2-chloro-4-(2,2,2-trifluoroethoxy)-pyrimidine (CAS 935252-67-8) instead of 2,5-dichloropyridine in step (a). White solid. MS (ISP): 355.2 ([M+H]$^+$).

Example 188

[5-Fluoro-4-(2,2,2-trifluoro-ethoxy)-pyrimidin-2-yl]-((R)-4-morpholin-2-yl-phenyl)-amine

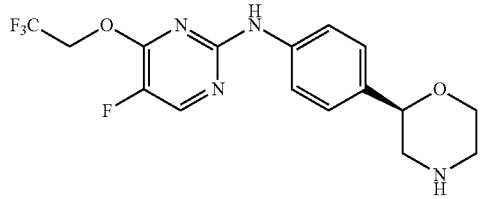 [SMILES: Fc1cnc(Nc2ccc([C@@H]3CNCCO3)cc2)nc1OCC(F)(F)F]

a) 2-Chloro-5-fluoro-4-(2,2,2-trifluoro-ethoxy)-pyrimidine 2,4-Dichloro-5-fluoropyrimidine (100 mg, CAS 2927-71-1) was combined with trifluoroethanol (1.09 ml) to give a colourless solution. Potassium carbonate (82.8 mg) was added. The reaction mixture was stirred at room temperature for 30 min. TLC at t=30 min showed the reaction was complete. The reaction mixture was filtered through sintered glass and concentrated in vacuo. The residue was triturated with diethyl ether, then filtered through sintered glass and dried in vacuo.

b) [5-Fluoro-4-(2,2,2-trifluoro-ethoxy)-pyrimidin-2-yl]-((R)-4-morpholin-2-yl-phenyl)-amine The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-5-fluoro-4-(2,2,2-trifluoro-ethoxy)-pyrimidine instead of 2,5-dichloropyridine in step (a). White solid. MS (ISP): 373.2 ([M+H]$^+$).

Example 189

(4-Cyclopropyl-pyrimidin-2-yl)-((R)-4-morpholin-2-yl-phenyl)-amine

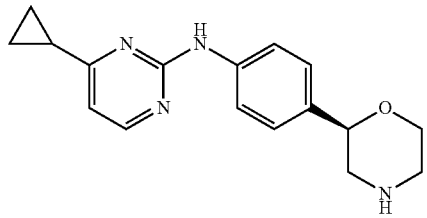 [SMILES: c1cc(C2CC2)nc(Nc2ccc([C@@H]3CNCCO3)cc2)n1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-4-cyclopropylpyrimidine (CAS 954237-31-1) instead of 2,5-dichloropyridine in step (a). Off-white solid. MS (ISP): 297.3 ([M+H]$^+$).

Example 190

(4-Cyclopropyl-5-fluoro-pyrimidin-2-yl)-((R)-4-morpholin-2-yl-phenyl)-amine

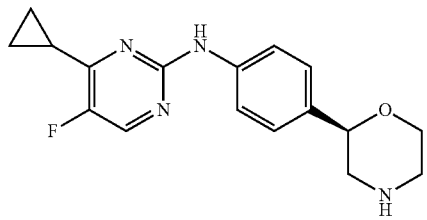 [SMILES: Fc1cnc(Nc2ccc([C@@H]3CNCCO3)cc2)nc1C1CC1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2-chloro-4-cyclopropyl-5-fluoro-pyrimidine (CAS 1312535-71-9) instead of 2,5-dichloropyridine in step (a). Off-white solid. MS (ISP): 315.2 ([M+H]$^+$).

Example 191

(4-Pentalluorosulfanyl-phenyl)-((R)-4-morpholin-2-yl-phenyl)-amine

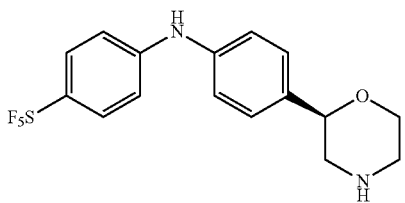

The title compound was obtained in analogy to example 19 using (R)-2-(4-bromo-phenyl)-morpholine-4-carboxylic acid tert-butyl ester instead of (S)-2-(4-bromo-phenyl)-morpholine-4-carboxylic acid tert-butyl ester and 4-(pentafluorosulfanyl)aniline (CAS 2993-24-0) instead of 2,5-dichloropyridine in step (a). White solid. MS (ISP): 381.2 ([M+H]⁺).

Example 192

(R)-5-Cyclopropyl-N-(3-fluoro-4-(morpholin-2-yl)phenyl)pyrimidin-2-amine

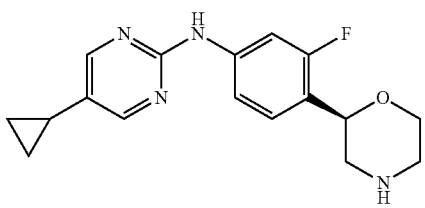 [SMILES: Fc1cc(Nc2ncc(C3CC3)cn2)ccc1[C@@H]1CNCCO1]

a) 1-(4-Bromo-2-fluorophenyl)-2-chloroethanone

To a stirred solution of 4-bromo-2-fluorobenzoyl chloride (33 g, CAS 151982-51-3) in acetonitrile (150 ml) and THF (150 ml) at 0-5° C. was added dropwise (trimethylsilyl)diazomethane (83.4 ml, 2 M solution in hexane). The reaction mixture was stirred at room temperature for 30 min. TLC analysis showed the reaction was complete. 37% Hydrochloric acid (23.2 ml) was then added dropwise at 0-5° C. and the reaction mixture was stirred at room temperature for 1 hour. The reaction mixture was then poured into EtOAc and extracted sequentially with aq. $Na_2CO_3$ solution, water and saturated brine. The organic layer was then dried over $Na_2SO_4$ and concentrated in vacuo to afford a ca 1:1 mixture of 2-bromo-1-(4-bromo-3-fluoro-phenyl)-ethanone and 2-chloro-1-(4-bromo-3-fluoro-phenyl)-ethanone (34.4 g, 98%) as a yellow solid which was used in the next step without further purification. MS (EI): 203 ([{⁸¹Br}M-CH₂Cl]⁺), 201 ([{⁷⁹Br}M-CH₂Cl]⁺).

b) (RS)-2-(4-Bromo-2-fluorophenyl)oxirane

To a stirred solution of 1-(4-bromo-2-fluorophenyl)-2-chloroethanone (5.57 g) in ethanol (100 ml) at 5° C. was added portionwise over 5 min $NaBH_4$ (838 mg). The reaction mixture was then stirred at room temperature for 1 hour to afford a light yellow solution. TLC analysis showed the reaction was complete. Sodium methoxide (2.06 ml, 30% solution in methanol) was then added and the reaction mixture was stirred at room temperature overnight. TLC analysis showed the reaction was complete. The reaction mixture was then poured into water and extracted twice with EtOAc. The combined organic layers were washed with saturated brine, then dried over $Na_2SO_4$ and concentrated in vacuo. The crude product was purified by flash chromatography (silica gel; gradient: 5% to 40% EtOAc in heptane) to afford (RS)-2-(4-bromo-2-fluorophenyl)oxirane (1.35 g, 28%) as a light yellow oil which was used in the next step without further purification. MS (EI): 218 ([{⁸¹Br}M]⁺, 216 ([{⁷⁹Br}M]⁺).

c) (RS)-1-(4-Bromo-2-fluorophenyl)-2-(2-hydroxyethylamino)ethanol

To a stirred solution of (RS)-2-(4-bromo-2-fluorophenyl)oxirane (12.3 g) in THF (40 ml) was added 2-aminoethanol (33.9 ml) and the mixture was stirred at room temperature overnight. The reaction mixture was then poured into EtOAc/THF (3:1) and washed with saturated brine. The organic layer was separated, dried over $Na_2SO_4$ and concentrated in vacuo. The crude product was purified by flash chromatography (silica gel; gradient: 0% to 35% MeOH in dichloromethane containing a few drops of aq. $NH_3$) to afford (RS)-1-(4-bromo-2-fluorophenyl)-2-(2-hydroxyethylamino)ethanol (12.0 g, 76%) as a brown oil. MS (ISP): 280.0 ([{⁸¹Br}M+H]⁻), 278.0 ([{⁷⁹Br}M+H]⁺).

d) (RS)-tert-Butyl 2-(4-bromo-2-fluorophenyl)-2-hydroxyethyl(2-hydroxyethyl)carbamate To a stirred solution of (RS)-1-(4-bromo-2-fluorophenyl)-2-(2-hydroxyethylamino)ethanol (12.0 g) in THF (70 ml) at 0° C. was added $Boc_2O$ (10.4 g) and the mixture was stirred at 0° C. for 1 hour and then at room temperature overnight. The reaction mixture was then poured into EtOAc and the mixture washed sequentially with 1 M aq. NaOH solution and saturated brine, then dried over Na2SO4 and concentrated in vacuo to afford (RS)-tert-butyl 2-(4-bromo-2-fluorophenyl)-2-hydroxyethyl(2-hydroxyethyl)carbamate (15.5 g, 95%) as a yellow oil which was used in the next step without further purification. MS (ISP): 380.0 ([{⁸¹Br}M+H]⁺), 378.0 ([{⁷⁹Br}M+H]⁻).

e) (RS)-tert-Butyl 2-(4-bromo-2-fluorophenyl)morpholine-4-carboxylate

To a stirred solution of (RS)-tert-butyl 2-(4-bromo-2-fluorophenyl)-2-hydroxyethyl(2-hydroxyethyl)carbamate (15.5 g) and triethylamine (9.85 ml) in THF (120 ml) at 0-5° C. was added dropwise methanesulfonyl chloride (3.35 ml). The reaction mixture was then stirred at room temperature for 1 hour to afford a white suspension. The reaction mixture was then filtered to remove triethylamine hydrochloride, washing the filter with THF (20 ml). The filtrate was cooled to 0-5° C. and potassium 2-methyl-2-butoxide (36.2 ml, 1.7 M solution in toluene) was added. The reaction mixture was stirred at room temperature for 20 min and then poured into EtOAc and washed sequentially with 1 M aq. HCl, water and saturated brine. The organic phase was separated, dried over $Na_2SO_4$ and concentrated in vacuo. The residue was purified by flash column chromatography (silica gel; gradient: 0% to 30% EtOAc in hexanes) to afford (RS)-tert-butyl 2-(4-bromo-2-fluorophenyl)morpholine-4-carboxylate (6.46 g, 44%) as a yellow oil. MS (EI): 305 ([{⁸¹Br}M-C₄H₈]⁺), 303 ([{⁷⁹Br}M-C₄H₈]⁺), 260 ([{⁰Br}M-C₄H₈—CO₂H]⁺), 258 ([{⁷⁹Br}M-C₄H₈—CO₂H]⁺).

f) (−)-(S)-tert-Butyl 2-(4-bromo-2-fluorophenyl)morpholine-4-carboxylate & (+)-(R)-tert-Butyl 2-(4-bromo-2-fluorophenyl)morpholine-4-carboxylate The enantiomers of afford (RS)-tert-butyl 2-(4-bromo-2-fluorophenyl)morpholine-4-carboxylate (6.46 g) were separated using chiral HPLC (column: Chiralpak AD, 5×50 cm; eluent: 4% isopropanol/heptane; pressure: 18 bar; flow rate: 35 ml/min) affording:
(−)-(S)-tert-Butyl 2-(4-bromo-2-fluorophenyl)morpholine-4-carboxylate (2.79 g, light yellow solid) Retention time=28 min
(+)-(R)-tert-Butyl 2-(4-bromo-2-fluorophenyl)morpholine-4-carboxylate (2.84 g, white solid) Retention time=35 min g) (R)-tert-Butyl 2-(4-(diphenylmethyleneamino)-2-fluorophenyl)morpholine-4-carboxylate To a stirred solution of (+)-(R)-tert-butyl 2-(4-bromo-2-fluorophenyl)morpholine-4-carboxylate (4.3 g) and benzophenone imine (2.2 ml) in toluene (20 ml) was added sodium tert-butoxide (1.84 g). The reaction mixture was purged with argon for 10 min. (R)-(+)-2,2'-Bis(diphenylphosphino)-1,1'-binaphthyl (743 mg) and tris(dibenzylideneacetone)dipalladium(0) (328 mg) were added and the reaction mixture was heated to 90° C. and stirred for 90 min. The reaction mixture was poured into water and extracted twice with EtOAc. The organic layers were dried over Na2SO4 and concentrated in vacuo. The residue was purified by flash column chromatography (silica gel; gradient: 0% to 40% EtOAc in hexanes) to afford (R)-tert-butyl 2-(4-(diphenylmethyleneamino)-2-fluorophenyl)morpholine-4-carboxylate 5.95 g, quant.) as a yellow amorphous solid. MS (ISP): 461.2 ([M+H]$^+$).

h) (R)-tert-Butyl 2-(4-amino-2-fluorophenyl)morpholine-4-carboxylate

To a stirred solution of (R)-tert-butyl 2-(4-(diphenylmethyleneamino)-2-fluorophenyl)morpholine-4-carboxylate (5.95 g) in methanol (50 ml) were added sodium acetate (2.93 g) and hydroxylamine hydrochloride (1.82 g). The reaction mixture was stirred at 50° C. overnight. The reaction mixture was then filtered through sintered glass and the filtrate was concentrated in vacuo. The residue was purified by flash column chromatography (silica gel; gradient: 0% to 60% EtOAc in hexanes) to afford (R)-tert-butyl 2-(4-amino-2-fluorophenyl)morpholine-4-carboxylate (3.0 g, 85%) as a yellow solid. MS (ISP): 296 ([M]$^+$), 240 ([M-C$_4$H$_8$]$^+$), 195 ([M+H—C$_4$H$_8$—CO$_2$H]$^+$).

i) (R)-tert-Butyl 2-(4-(5-cyclopropylpyrimidin-2-ylamino)-2-fluorophenyl)morpholine-4-carboxylate (R)-tert-Butyl 2-(4-amino-2-fluorophenyl)morpholine-4-carboxylate (300 mg), 2-chloro-5-cyclopropylpyrimidine (188 mg, CAS 166740-44-9) and cesium carbonate (495 mg) were combined with dioxane (8 ml) to give a yellow suspension. The mixture was degassed by bubbling argon into the mixture for several minutes. Xantphos (35.1 mg) and tris(dibenzylideneacetone)dipalladium chloroform complex (31.4 mg) were then added. The reaction mixture was then capped and stirred at 120° C. for 3 hours. The crude reaction mixture was cooled to room temperature and filtered. The filtrate was concentrated in vacuo and the residue was purified by flash column chromatography (silica gel; gradient: 0% to 55% EtOAc in hexanes) to afford (R)-tert-butyl 2-(4-(5-cyclopropylpyrimidin-2-ylamino)-2-fluorophenyl)morpholine-4-carboxylate (180 mg, 43%) as a yellow solid. MS (ISP): 415.2 ([M+H]$^+$).

j) (R)-5-Cyclopropyl-N-(3-fluoro-4-(morpholin-2-yl) phenyl)pyrimidin-2-amine

To a stirred solution of (R)-tert-butyl 2-(4-(5-cyclopropylpyrimidin-2-ylamino)-2-fluorophenyl)morpholine-4-carboxylate (180 mg) in acetonitrile (2 ml) and water (6 ml) was added trifluoroacetic acid (335 µl). The reaction mixture was then capped and the mixture was shaken at 80° C. for 16 h. The reaction mixture was then cooled to room temperature and poured into EtOAc and washed with 4 M aq. NaOH. The organic layer was dried over Na$_2$SO$_4$ and concentrated in vacuo. The crude material was purified by flash column chromatography (silica gel; gradient: CH$_2$Cl$_2$/MeOH/aq. NH$_3$) to afford (R)-5-cyclopropyl-N-(3-fluoro-4-(morpholin-2-yl) phenyl)pyrimidin-2-amine (57 mg, xx %) as an off-white solid. MS (ISP): 315.2 ([M+H]$^+$).

Example 193

((S)-3-Chloro-4-morpholin-2-yl-phenyl)-(5-cyclopropyl-pyrimidin-2-yl)-amine

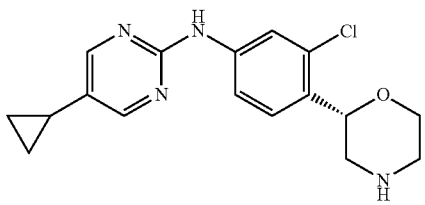 [SMILES: Clc1cc(Nc2ncc(C3CC3)cn2)ccc1[C@H]1CNCCO1]

The title compound was obtained in analogy to example 192 using 4-bromo-2-chlorobenzoyl chloride (CAS 21900-55-0) instead of 4-bromo-2-fluorobenzoyl chloride in step (a) and (−)-(S)-tert-butyl 2-(4-bromo-2-chloro-phenyl)-morpholine-4-carboxylate instead of (+)-(R)-tert-butyl 2-(4-bromo-2-fluorophenyl)morpholine-4-carboxylate in step (g). White solid. MS (ISP): 333.2 ([{$^{37}$Cl}M+H]$^+$), 331.2 ([{$^{35}$Cl}M+H]$^+$).

Example 194

((R)-3-Chloro-4-morpholin-2-yl-phenyl)-(5-cyclopropyl-pyrimidin-2-yl)-amine

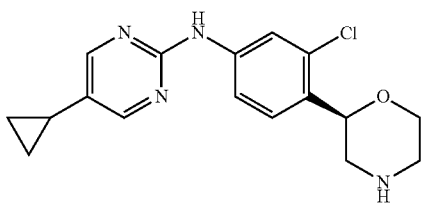 [SMILES: Clc1cc(Nc2ncc(C3CC3)cn2)ccc1[C@@H]1CNCCO1]

The title compound was obtained in analogy to example 192 using 4-bromo-2-chlorobenzoyl chloride (CAS 21900-55-0) instead of 4-bromo-2-fluorobenzoyl chloride in step (a) and (+)-(R)-tert-butyl 2-(4-bromo-2-chloro-phenyl)-morpholine-4-carboxylate instead of (+)-(R)-tert-butyl 2-(4-bromo-2-fluorophenyl)morpholine-4-carboxylate in step (g). White solid. MS (ISP): 333.2 ([{$^{37}$Cl}M+H]$^+$), 331.2 ([{$^{35}$Cl}M+H]$^+$).

Example 195

(S)-5-Cyclopropyl-N-(3-fluoro-4-(morpholin-2-yl) phenyl)pyrimidin-2-amine

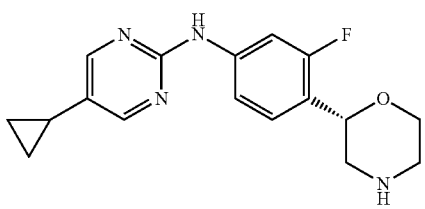 [SMILES: Fc1cc(Nc2ncc(C3CC3)cn2)ccc1[C@H]1CNCCO1]

The title compound was obtained in analogy to example 192 using (−)-(S)-tert-butyl 2-(4-bromo-2-fluorophenyl)morpholine-4-carboxylate instead of (+)-(R)-tert-butyl 2-(4-bromo-2-fluorophenyl)morpholine-4-carboxylate in step (g). White solid. MS (ISP): 315.2 ([M+H]⁺).

Example 196

(R)—N-(3-Fluoro-4-(morpholin-2-yl)phenyl)-5-(trifluoromethyl)pyrimidin-2-amine

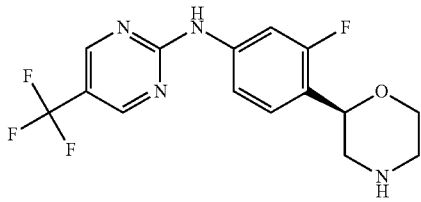

a) (R)-tert-Butyl 2-(2-fluoro-4-(5-(trifluoromethyl)pyrimidin-2-ylamino)phenyl)morpholine-4-carboxylate To a 25 ml glass vial was added (+)-(R)-tert-butyl 2-(4-bromo-2-fluorophenyl)morpholine-4-carboxylate (300 mg, example 192(f)) and 5-trifluoromethyl-pyrimidin-2-ylamine (156 mg, CAS 69034-08-8) in dioxane (5 ml). The reaction mixture was purged with argon for 5 min. 2-Di-tert-butylphosphino-2',4',6'-triisopropylbiphenyl (58.3 mg), tris(dibenzylideneacetone)dipalladium(0) (30.5 mg) and sodium tert-butoxide (89.8 mg) were then added. The vial was capped and heated at 100° C. for 2 h. The reaction mixture was then filtered through sintered glass and the filtrate was concentrated in vacuo. The residue was purified by flash column chromatography (silica gel; gradient: 0% to 60% EtOAc in heptane) to afford (R)-tert-butyl 2-(2-fluoro-4-(5-(trifluoromethyl)pyrimidin-2-ylamino)phenyl)morpholine-4-carboxylate (304 mg, 83%) as an amorphous yellow solid. MS (ISP): 441.2 ([M−H]⁻).

b) (R)—N-(3-Fluoro-4-(morpholin-2-yl)phenyl)-5-(trifluoromethyl)pyrimidin-2-amine To a stirred solution of (R)-tert-butyl 2-(2-fluoro-4-(5-(trifluoromethyl)pyrimidin-2-ylamino)phenyl)morpholine-4-carboxylate (300 mg) in acetonitrile (2 ml) and water (6 ml) was added trifluoroacetic acid (522 µl). The reaction mixture was then capped and the mixture was shaken at 80° C. for 16 h. The reaction mixture was then cooled to room temperature and poured into 4 M aq. NaOH and extracted twice with EtOAc. The combined organic layers were dried over Na₂SO₄ and concentrated in vacuo. The crude material was purified by flash column chromatography (silica gel, CH₂Cl₂/MeOH/aq. NH₃) to afford (R)—N-(3-fluoro-4-(morpholin-2-yl)phenyl)-5-(trifluoromethyl)pyrimidin-2-amine (171 mg, 74%) as an off-white solid. MS (ISP): 343.1 ([M+H]⁺).

Example 197

(S)—N-(3-Fluoro-4-(morpholin-2-yl)phenyl)-5-(trifluoromethyl)pyrimidin-2-amine

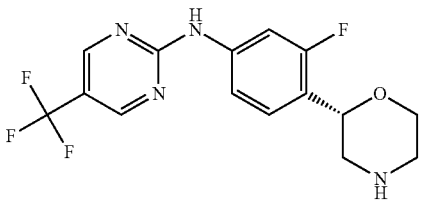 [SMILES: Fc1cc(Nc2ncc(C(F)(F)F)cn2)ccc1[C@H]1CNCCO1]

The title compound was obtained in analogy to example 196 using (−)-(S)-tert-butyl 2-(4-bromo-2-fluorophenyl)morpholine-4-carboxylate instead of (+)-(R)-tert-butyl 2-(4-bromo-2-fluorophenyl)morpholine-4-carboxylate in step (a). White solid. MS (ISP): 343.1 ([M+H]⁺).

Example 198

(R)—N-(4-(Morpholin-2-yl)phenyl)-6-(trifluoromethyl)pyrimidin-4-amine

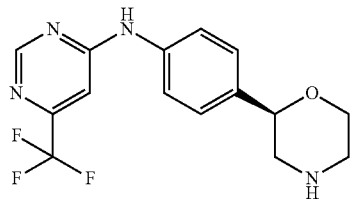 [SMILES: FC(F)(F)c1cc(Nc2ccc([C@@H]3CNCCO3)cc2)ncn1]

a) (R)-tert-Butyl 2-(4-(6-trifluoromethylpyrimidin-4-ylamino)phenyl)morpholine-4-carboxylate A mixture of (S)-tert-butyl 2-(4-aminophenyl)morpholine-4-carboxylate (100 mg, 0.36 mmol), 4-chloro-6-(trifluoromethyl)pyrimidine (72 mg, 0.4 mmol) and diisopropylethylamine (70 mg, 0.54 mmol) was dissolved in dimethylacetamide (1.3 ml) and stirred at 80° C. overnight. For work-up water was added, and the mixture was extracted with ethyl acetate twice. The combined organic layers were dried (MgSO₄) and concentrated in vacuo. The residue was purified by flash chromatography (10 g silica gel, 20 to 40% ethyl acetate in heptane) to yield a white solid (135 mg, 89%). MS (ISP): 425.2 ([M+H]⁺).

b) (R)—N-(4-(Morpholin-2-yl)phenyl)-6-(trifluoromethyl)pyrimidin-4-amine hydrochloride (R)-tert-Butyl 2-(4-(6-trifluoromethylpyrimidin-4-ylamino)phenyl)morpholine-4-carboxylate (130 mg, 0.3 mmol) was dissolved in dioxane (1.2 ml) and a solution of HCl in dioxane (4 M, 1.15 ml, 4.59 mmol) was added. The reaction mixture was stirred at 60° C. for 2 hours. After cooling ether (2 ml) was added and the solid was filtered off. It was washed with ether and dried in vacuo to afford (R)—N-(4-(morpholin-2-yl)phenyl)-6-(trifluoromethyl)pyrimidin-4-amine hydrochloride (96 mg, 87%) as a light yellow solid. MS (ISP): 325.2 ([M+H]⁺).

Example 199

(R)-6-Chloro-N-(4-(morpholin-2-yl)phenyl)pyrimidin-4-amine

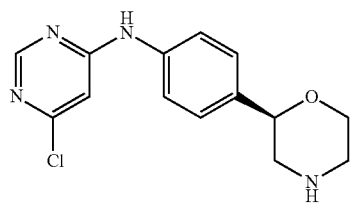 [SMILES: Clc1cc(Nc2ccc([C@@H]3CNCCO3)cc2)ncn1]

The title compound was obtained in analogy to example 198 using 4,6-dichloropyrimidine instead of 4-chloro-6-(trifluoromethyl)pyrimidine in step a). Light yellow solid. MS (ISP): 291.1 ([{$^{35}$Cl}M+H]$^+$), 293.2 ([{$^{37}$Cl}M+H]$^+$).

Example 200

(R)—N-(4-(morpholin-2-yl)phenyl)-2-(trifluoromethyl)pyrimidin-4-amine

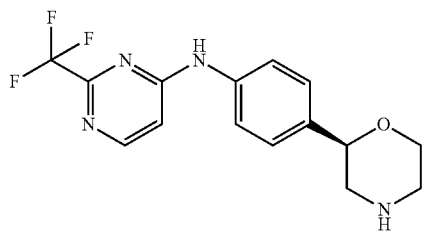 [SMILES: FC(F)(F)c1nccc(Nc2ccc([C@@H]3CNCCO3)cc2)n1]

The title compound was obtained in analogy to example 198 using 4-chloro-6-(trifluoromethyl)-pyrimidine instead of 4-chloro-6-(trifluoromethyl)pyrimidine in step a). Light yellow solid. MS (ISP): 325.2 ([M+H]$^+$).

Example 201

(R)—N-(4-(Morpholin-2-yl)phenyl)-5-(trifluoromethyl)pyrazin-2-amine

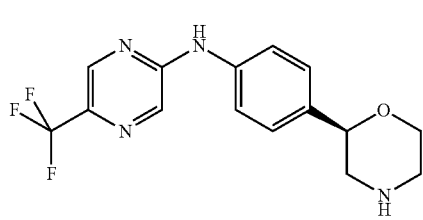 [SMILES: FC(F)(F)c1cnc(Nc2ccc([C@@H]3CNCCO3)cc2)cn1]

The title compound was obtained in analogy to example 198 using 2-chloro-5-(trifluoromethyl)-pyrazine instead of 4-chloro-6-(trifluormethyl)pyrimidine in step a). Off-white solid. MS (ISP): 325.2 ([M+H]$^+$).

Example 202

((R)-3-Chloro-4-morpholin-2-yl-phenyl)-(5-chloro-pyrimidin-2-yl)-amine

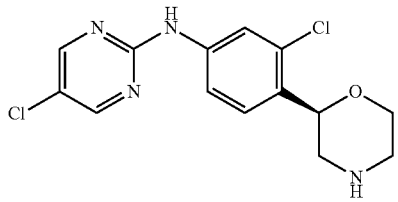 [SMILES: Clc1cnc(Nc2ccc([C@@H]3CNCCO3)c(Cl)c2)nc1]

The title compound was obtained in analogy to example 192 using 4-bromo-2-chlorobenzoyl chloride (CAS 21900-55-0) instead of 4-bromo-2-fluorobenzoyl chloride in step (a), (+)-(R)-tert-butyl 2-(4-bromo-2-chloro-phenyl)-morpholine-4-carboxylate instead of (+)-(R)-tert-butyl 2-(4-bromo-2-fluorophenyl)morpholine-4-carboxylate in step (g), and 2,5-dichloro-pyrimidine (CAS 22536-67-0) instead of 2-chloro-5-cyclopropylpyrimidine in step (i). White solid. MS (ISP): 325.4 ([{$^{37}$Cl$^{35}$Cl}M+H]$^+$), 323.4([{$^{35}$Cl}M+H]$^+$).

Example 203

((R)-3-Chloro-4-morpholin-2-yl-phenyl)-[5-(2,2,2-trifluoro-ethoxy)-pyrimidin-2-yl]-amine

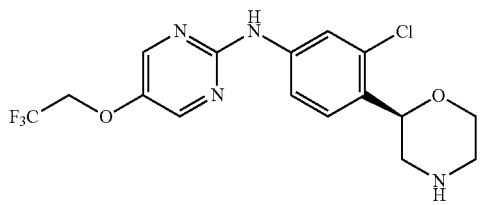 [SMILES: FC(F)(F)COc1cnc(Nc2ccc([C@@H]3CNCCO3)c(Cl)c2)nc1]

The title compound was obtained in analogy to example 192 using 4-bromo-2-chlorobenzoyl chloride (CAS 21900-55-0) instead of 4-bromo-2-fluorobenzoyl chloride in step (a), (+)-(R)-tert-butyl 2-(4-bromo-2-chloro-phenyl)-morpholine-4-carboxylate instead of (+)-(R)-tert-butyl 2-(4-bromo-2-fluorophenyl)morpholine-4-carboxylate in step (g), and 2-chloro-5-(2,2,2-trifluoroethoxy)-pyrimidine (CAS 145948-01-2) instead of 2-chloro-5-cyclopropylpyrimidine in step (i). White solid. MS (ISP): 389.4 ([{$^{37}$Cl}M+H]$^+$), 387.5 ([{$^{35}$Cl}M+H]$^+$).

Example 204

((R)-3-Chloro-4-morpholin-2-yl-phenyl)-(5-trifluoromethyl-pyrimidin-2-yl)-amine

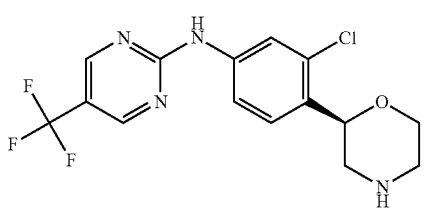 [SMILES: FC(F)(F)c1cnc(Nc2ccc([C@@H]3CNCCO3)c(Cl)c2)nc1]

The title compound was obtained in analogy to example 192 using 4-bromo-2-chlorobenzoyl chloride (CAS 21900-55-0) instead of 4-bromo-2-fluorobenzoyl chloride in step (a), (+)-(R)-tert-butyl 2-(4-bromo-2-chloro-phenyl)-morpholine-4-carboxylate instead of (+)-(R)-tert-butyl 2-(4-bromo-2-fluorophenyl)morpholine-4-carboxylate in step (g), and 2-chloro-5-(trifluoromethyl)pyrimidine (CAS 69034-12-4) instead of 2-chloro-5-cyclopropylpyrimidine in step (i). Light yellow solid. MS (ISP): 359.4 ([{$^{37}$Cl}M+H]$^+$), 357.4 ([{$^{35}$Cl}M+H]$^+$).

Example 205

(R)-5-Chloro-N-(4-(morpholin-2-yl)phenyl)pyrazin-2-amine

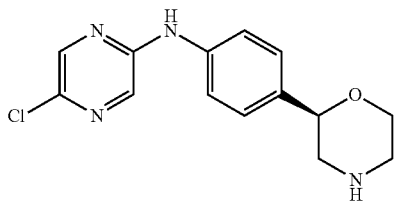 [SMILES: Clc1cnc(Nc2ccc([C@@H]3CNCCO3)cc2)cn1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2,5-dichloro-pyrazine instead of 2,5-dichloropyridine in step (a). Light yellow. MS (ISP): 291.4 ([{$^{35}$Cl}M+H]$^+$), 293.4 ([{$^{37}$Cl}M+H]$^+$).

Example 206

(R)-6-Chloro-N-(4-(morpholin-2-yl)phenyl)pyrazin-2-amine

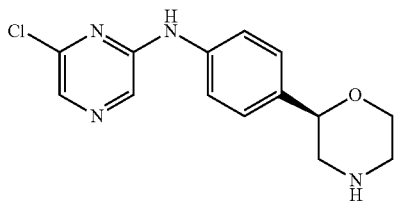 [SMILES: Clc1cncc(Nc2ccc([C@@H]3CNCCO3)cc2)n1]

The title compound was obtained in analogy to example 5 using (R)-2-(4-aminophenyl)-morpholine-4-carboxylic acid tert-butyl ester (CAS 1260220-42-5) in place of (RS)-2-(4-amino-phenyl)-morpholine-4-carboxylic acid tert-butyl ester and 2,6-dichloro-pyrazine instead of 2,5-dichloropyridine in step (a). Orange solid. MS (ISP): 291.4 ([{$^{35}$Cl}M+H]$^+$), 293.4 ([{$^{37}$Cl}M+H]$^+$).

Example 207

(R)—N-(3-Fluoro-4-(morpholin-2-yl)phenyl)-5-(2,2,2-trifluoroethoxy)pyrimidin-2-amine

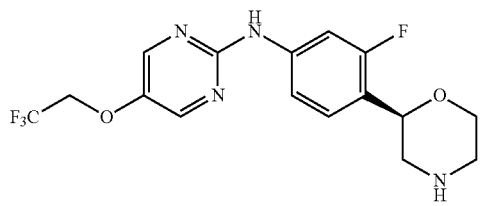 [SMILES: Fc1cc(Nc2ncc(OCC(F)(F)F)cn2)ccc1[C@@H]1CNCCO1]

The title compound was obtained in analogy to example 192 using 2-chloro-5-(2,2,2-trifluoroethoxy)-pyrimidine (CAS 145948-01-2) instead of 2-chloro-5-cyclopropylpyrimidine in step (i). White solid. MS (ISP): 373.1 ([M+H]$^+$).

Example 208

(R)—N-(3-Fluoro-4-(morpholin-2-yl)phenyl)-4-(2,2,2-trifluoroethoxy)pyrimidin-2-amine

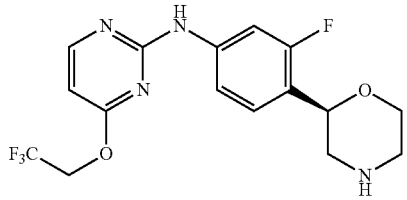 [SMILES: Fc1cc(Nc2nccc(OCC(F)(F)F)n2)ccc1[C@@H]1CNCCO1]

The title compound was obtained in analogy to example 192 using 2-chloro-4-(2,2,2-trifluoroethoxy)-pyrimidine (CAS 935252-67-8) instead of 2-chloro-5-cyclopropylpyrimidine in step (i). White solid. MS (ISP): 373.1 ([M+H]$^+$).

Example 209

(R)-5-Fluoro-N-(3-fluoro-4-(morpholin-2-yl)phenyl)-4-(2,2,2-trifluoroethoxy)pyrimidin-2-amine

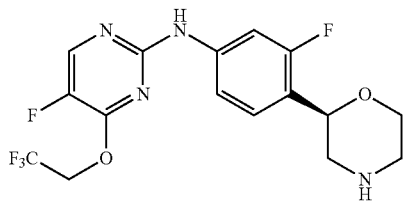 [SMILES: Fc1cc(Nc2ncc(F)c(OCC(F)(F)F)n2)ccc1[C@@H]1CNCCO1]

The title compound was obtained in analogy to example 192 using 2-chloro-5-fluoro-4-(2,2,2-trifluoro-ethoxy)-pyrimidine (Example 188(a)) instead of 2-chloro-5-cyclopropylpyrimidine in step (i). White solid. MS (ISP): 391.1 ([M+H]$^+$).

Example 210

(R)-5-Chloro-N-(3-fluoro-4-(morpholin-2-yl)phenyl)pyrimidin-2-amine

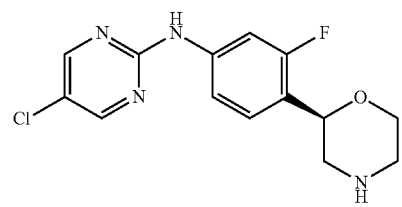 [SMILES: Fc1cc(Nc2ncc(Cl)cn2)ccc1[C@@H]1CNCCO1]

The title compound was obtained in analogy to example 192 using 2,5-dichloropyrimidine (CAS 22536-67-0) instead of 2-chloro-5-cyclopropylpyrimidine in step (i). White solid. MS (ISP): 311.1 ([{$^{37}$Cl}M+H]$^+$), 309.1 ([{$^{37}$Cl}M+H]$^+$).

Example 211

((R)-3-Chloro-4-morpholin-2-yl-phenyl)-[4-(2,2,2-trifluoro-ethoxy)-pyrimidin-2-yl]-amine

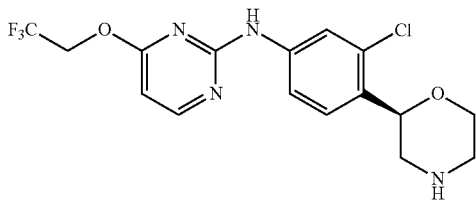 [SMILES: FC(F)(F)COc1ccnc(Nc2ccc([C@@H]3CNCCO3)c(Cl)c2)n1]

The title compound was obtained in analogy to example 192 using 4-bromo-2-chlorobenzoyl chloride (CAS 21900-55-0) instead of 4-bromo-2-fluorobenzoyl chloride in step (a), (+)-(R)-tert-butyl 2-(4-bromo-2-chloro-phenyl)-morpholine-4-carboxylate instead of (+)-(R)-tert-butyl 2-(4-bromo-2-fluorophenyl)morpholine-4-carboxylate in step (g), and 2-chloro-4-(2,2,2-trifluoroethoxy)-pyrimidine (CAS 935252-67-8) instead of 2-chloro-5-cyclopropylpyrimidine in step (i). White solid. MS (ISP): 389.5 ($[\{^{37}Cl\}M+H]^+$), 387.6 ($[\{^{35}Cl\}M+H]^+$).

The compounds of formula I and their pharmaceutically usable addition salts possess valuable pharmacological properties. Specifically, it has been found that the compounds of the present invention have a good affinity to the trace amine associated receptors (TAARs), especially TAAR1. The compounds were investigated in accordance with the test given hereinafter.

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM $Mg^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC #CRL-1573) were cultured essentially as described by Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Radioligand Binding Assay on Rat TAAR1
Membrane Preparation and Radioligand Binding HEK-293 cells stably expressing rat TAAR1 were maintained at 37° C. and 5% $CO_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without $Ca^{2+}$ and $Mg^{2+}$), pelleted at 1,000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (Kd) was determined via a saturation curve. The TAAR1 radioligand $^3$[H]-(S)-4-[(ethyl-phenylamino)-methyl]-4,5-dihydro-oxazol-2-ylamine (described in WO 2008/098857) was used at a concentration equal to the calculated Kd value, that was usually around 2.3 nM, resulting in the binding of approximately 0.2% of the radioligand and a specific binding representing approximately 85% of the total binding. Nonspecific binding was defined as the amount of $^3$[H]-(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 µl/well) were transferred into a 96 deep well plate (TreffLab), and 180 µl of HEPES-NaOH (20 mM, pH 7.4) containing $MgCl_2$ (10 mM) and $CaCl_2$ (2 mM) (binding buffer), 300 µl of the radioligand $^3$[H]-(S)-4-[(ethyl-phenyl-amino)-methyl]-4,5-dihydro-oxazol-2-ylamine at a concentration of 3.3× Kd in nM and 500 µl of the membranes (resuspended at 50 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the ratioactivity counted using a TopCount Microplate Scintillation Counter (Packard Instrument Company).

Radioligand Binding Assay on Mouse TAAR1
Membrane Preparation and Radioligand Binding.

HEK-293 cells stably expressing mouse TAAR1 were maintained at 37° C. and 5% $CO_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without $Ca^{2+}$ and $Mg^{2+}$), pelleted at 1,000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (Kd) was determined via a saturation curve. The TAAR1 radioligand $^3$[H]-(S)-4-[(ethyl-phenyl-amino)-methyl]-4,5-dihydro-oxazol-2-ylamine (described in WO 2008/098857) was used at a concentration equal to the calculated Kd value, that was usually around 0.7 nM, resulting in the binding of approximately 0.5% of the radioligand and a specific binding representing approximately 70% of the total binding. Nonspecific binding was defined as the amount of $^3$[H]-(S)-4-[(ethylphenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 µl/well) were transferred into a 96 deep well plate (TreffLab), and 180 µl of HEPES-NaOH (20 mM, pH 7.4) containing MgCl$_2$ (10 mM) and CaCl$_2$ (2 mM) (binding buffer), 300 µl of the radioligand $^3$[H]-(S)-4-[(ethyl-phenyl-amino)-methyl]-4,5-dihydro-oxazol-2-ylamine at a concentration of 3.3×Kd in nM and 500 µl of the membranes (resuspended at 60 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the ratioactivity counted using a TopCount Microplate Scintillation Counter (Packard Instrument Company).

The preferred compounds show a Ki value (µM) in mouse or rat on TAAR1 in the range of <0.1 µM. In the table below are shown the data of examples 1-211.

| Example | Ki (µM) mouse/rat | Example | Ki (µM) mouse/rat | Example | Ki (µM) mouse/rat |
|---|---|---|---|---|---|
| 1 | 0.074/1.5108 | 72 | 0.0171/0.22 | 143 | 0.4185/0.2836 |
| 2 | 4.2857/3.5145 | 73 | 0.0096/0.035 | 144 | 0.0042/0.0049 |
| 3 | 0.0157/0.0251 | 74 | 0.0059/0.0295 | 145 | 0.0034/0.0067 |
| 4 | 0.1223/0.0785 | 75 | 0.0141/0.228 | 146 | 0.0046/0.1404 |
| 5 | 0.0011/0.029 | 76 | 0.0024/0.045 | 147 | 0.0009/0.0197 |
| 6 | 0.0133/0.2322 | 77 | 0.0053/0.1304 | 148 | 0.0017/0.0083 |
| 7 | 0.0033/0.0425 | 78 | 0.11/3.1921 | 149 | 0.0011/0.0014 |
| 8 | 0.0005/0.0325 | 79 | 0.0047/0.0716 | 150 | 0.0134/0.1486 |
| 9 | 0.0181/0.0893 | 80 | 0.0026/0.0626 | 151 | 0.048/0.0954 |
| 10 | 0.0015/0.0337 | 81 | 0.0162/0.2027 | 152 | 0.0196/0.2677 |
| 11 | 0.0015/0.0233 | 82 | 0.0008/0.0101 | 153 | 0.007/0.8397 |
| 12 | 0.0055/0.2588 | 83 | 0.0006/0.0222 | 154 | 0.0096/0.8627 |
| 13 | 0.0266/0.1085 | 84 | 0.0015/0.057 | 155 | 0.6002/— |
| 14 | 0.0122/0.504 | 85 | 0.0014/0.0194 | 156 | 0.0093/0.8327 |
| 15 | 0.0028/0.0466 | 86 | 0.0024/0.009 | 157 | 0.0132/>10 |
| 16 | 0.0276/0.4483 | 87 | 0.0071/0.037 | 158 | 1.0168/1.8542 |
| 17 | 0.0017/0.0131 | 88 | 0.008/0.0874 | 159 | 1.3362/1.7562 |
| 18 | 0.0054/0.3133 | 89 | 0.0139/0.1767 | 160 | 0.0061/2.749 |
| 19 | 0.0056/0.0236 | 90 | 0.0196/0.2324 | 161 | 0.0016/0.2229 |
| 20 | 0.0453/0.7641 | 91 | 0.0081/0.1233 | 162 | 0.002/0.1273 |
| 21 | 0.002/0.0245 | 92 | 0.0229/0.2748 | 163 | 0.0026/0.0332 |
| 22 | 0.0375/0.468 | 93 | 0.005/0.0222 | 164 | 0.0006/0.025 |
| 23 | 0.0514/1.644 | 94 | 0.0035/0.0489 | 165 | 0.011/0.3395 |
| 24 | 0.0119/0.149 | 95 | 0.0057/0.0223 | 166 | 0.0301/0.1589 |
| 25 | 0.0124/0.0705 | 96 | 0.0062/0.0216 | 167 | 0.1115/1.3539 |
| 26 | 0.002/0.0083 | 97 | 0.0029/0.0056 | 168 | 0.0077/0.0065 |
| 27 | 0.0438/0.8083 | 98 | 0.0028/0.0033 | 169 | 0.0243/0.0397 |
| 28 | 0.2762/0.561 | 99 | 0.0008/0.0185 | 170 | 0.0016/0.0012 |
| 29 | 0.0042/0.1555 | 100 | 0.0053/0.0164 | 171 | 0.0008/0.0011 |
| 30 | 0.0051/0.0417 | 101 | 0.0032/0.0041 | 172 | 0.0035/0.0162 |
| 31 | 0.0452/0.2222 | 102 | 0.0047/0.0126 | 173 | 0.0044/0.0625 |
| 32 | 0.0357/1.2375 | 103 | 0.0044/0.05 | 174 | 0.0088/0.0628 |
| 33 | 0.047/0.5444 | 104 | 0.0041/0.1048 | 175 | 0.006/0.0066 |
| 34 | 0.0042/0.0181 | 105 | 0.0116/0.1265 | 176 | 0.1516/>10 |
| 35 | 0.0096/0.1883 | 106 | 0.0086/0.0814 | 177 | 0.0028/0.0299 |
| 36 | 0.0288/0.1633 | 107 | 0.005/0.0877 | 178 | 0.0043/0.0298 |
| 37 | 0.1292/1.1738 | 108 | 0.0122/0.2157 | 179 | 0.0047/0.0517 |
| 38 | 0.0011/0.0544 | 109 | 0.0077/0.3624 | 180 | 0.0058/0.033 |
| 39 | 0.004/0.2514 | 110 | 0.0026/0.0306 | 181 | 0.0084/0.3981 |
| 40 | 0.0026/0.1882 | 111 | 0.0044/0.0322 | 182 | 0.0144/0.4465 |
| 41 | 0.2704/1.0809 | 112 | 0.0038/0.1966 | 183 | 0.0094/0.1737 |
| 42 | 0.0023/0.0518 | 113 | 0.0011/0.0877 | 184 | 0.002/0.002 |
| 43 | 0.0269/0.6484 | 114 | 0.0212/0.9959 | 185 | 0.0549/0.0888 |
| 44 | 0.0007/0.0118 | 115 | 0.0079/0.2349 | 186 | 0.138/1.1018 |
| 45 | 0.0061/0.1261 | 116 | 0.0039/0.007 | 187 | 0.0021/0.01 |
| 46 | 0.0008/0.0643 | 117 | 0.0034/0.0104 | 188 | 0.0016/0.0033 |
| 47 | 0.0012/0.0067 | 118 | 0.0038/0.003 | 189 | 0.1089/0.0605 |
| 48 | 0.1218/0.2336 | 119 | 0.0025/0.0051 | 190 | 0.0031/0.0422 |
| 49 | 0.0266/0.1038 | 120 | 0.0058/0.0364 | 191 | 0.001/0.0032 |
| 50 | 0.005/0.0608 | 121 | 0.0058/0.0096 | 192 | 0.0025/0.0026 |
| 51 | 0.0363/0.2803 | 122 | 0.0079/0.0847 | 193 | 0.0038/0.0196 |
| 52 | 0.0005/0.0084 | 123 | 0.0174/0.0796 | 194 | 0.0021/0.0011 |
| 53 | 0.0012/0.0045 | 124 | 0.0036/0.0348 | 195 | 0.0017/0.0252 |
| 54 | 0.0008/0.0138 | 125 | 0.0045/0.0278 | 196 | 0.0049/0.004 |
| 55 | 0.7376/1.9843 | 126 | 0.004/0.0096 | 197 | 0.0031/0.0315 |
| 56 | 0.0372/0.211 | 127 | 0.003/0.0165 | 198 | 0.0419/0.1628 |
| 57 | 0.0023/0.0866 | 128 | 0.0049/0.0039 | 199 | 0.0231/0.056 |
| 58 | 0.0704/0.5844 | 129 | 0.0043/0.0068 | 200 | 0.0089/0.0588 |
| 59 | 0.0049/0.2073 | 130 | 0.0051/0.0199 | 201 | 0.008/0.0626 |
| 60 | 0.0222/0.7582 | 131 | 0.0028/0.0379 | 202 | 0.0032/0.0065 |
| 61 | 0.0591/0.5024 | 132 | 0.0047/0.0182 | 203 | 0.0022/0.0017 |
| 62 | 0.0005/0.0094 | 133 | 0.0052/0.0387 | 204 | 0.0038/0.0021 |
| 63 | 0.3728/1.4897 | 134 | 0.0069/0.0079 | 205 | 0.0026/0.1621 |
| 64 | 0.0027/0.101 | 135 | 0.0057/0.0198 | 206 | 0.005/0.0963 |
| 65 | 0.0131/0.6291 | 136 | 0.0051/0.0494 | 207 | 0.0043/0.0102 |
| 66 | 0.2169/0.2569 | 137 | 0.0037/0.0026 | 208 | 0.003/0.0035 |
| 67 | 0.0074/0.2917 | 138 | 0.0641/1.3566 | 209 | 0.0032/0.0025 |
| 68 | 0.0094/0.0751 | 139 | 0.0667/1.0607 | 210 | 0.0047/0.0266 |
| 69 | 0.0014/0.0438 | 140 | 0.0386/5.251 | 211 | 0.0042/0.0011 |
| 70 | 0.5235/4.0665 | 141 | 0.0027/0.0129 | | |
| 71 | 0.0118/0.168 | 142 | 0.0027/0.0146 | | |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety and attention deficit hyperactivity disorder (ADHD).

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.

2. Dry the granules at 50° C.

3. Pass the granules through suitable milling equipment.

4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.

2. Add items 4 and 5 and mix for 3 minutes.

3. Fill into a suitable capsule.

The invention claimed is:

1. A compound of formula I

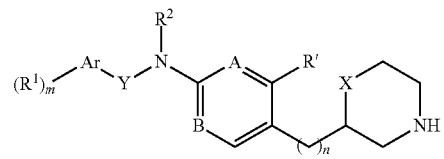

wherein $R^1$ is hydrogen, lower alkyl, halogen, lower alkyl substituted by halogen, lower alkoxy,
lower alkoxy substituted by halogen, cyano, nitro, $C_{3-6}$-cycloalkyl, —$CH_2$—$C_{3-6}$-cycloalkyl, —O—$CH_2$—$C_{3-6}$-cycloalkyl, —O—$(CH_2)_2$—O-lower alkyl, $S(O)_2CH_3$, $SF_5$, —C(O)NH-lower alkyl, phenyl, —O-pyrimidinyl, optionally substituted by lower alkoxy substituted by halogen, or is benzyl, oxetanyl or furanyl;

m is 1 or 2;

Ar is aryl or heteroaryl, selected from the group consisting of naphthyl, pyrimidinyl, benzothiazolyl, quinolinyl, quinazolinyl, benzo[d][1.3]dioxolyl, 5,6,7,8-tetrahydro-quinazolinyl, pyrazolyl, pyrazinyl, pyridazinyl, and 1,3,4-oxadiazolyl;

Y is a bond, —$CH_2$—, —$CH_2CH_2$—, —$CH(CF_3)$— or —$CH(CH_3)$—;

$R^2$ is hydrogen or lower alkyl;

A is CR or N; and R is hydrogen, cyano, halogen or lower alkyl;

R' is hydrogen or halogen; with the proviso that when R' is halogen, A is CH;

B is CH or N;

n is o, 1 or 2; and

X is a bond, —$CH_2$— or —O—;

or a pharmaceutical active acid addition salt thereof.

2. The compound of claim 1, having formula IA

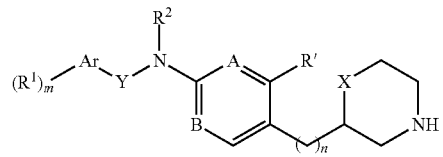

wherein $R^1$ is hydrogen, lower alkyl, halogen, lower alkyl substituted by halogen, lower alkoxy, lower alkoxy substituted by halogen, cyano, nitro, $C_{3-6}$-cycloalkyl, $S(O)_2CH_3$ or phenyl;

m is 1 or 2;

Ar is aryl or heteroaryl, selected from the group consisting of naphthyl, pyrimidinyl, benzothiazolyl, quinolinyl, quinazolinyl, benzo[d][1.3]dioxolyl, 5,6,7,8-tetrahydro-quinazolinyl, pyrazolyl and 1,3,4-oxadiazolyl;

Y is a bond, —$CH_2$—, —$CH_2CH_2$—, —$CH(CF_3)$— or —$CH(CH_3)$—;

$R^2$ is hydrogen or lower alkyl;

A is CR or N; and R is hydrogen, cyano, halogen or lower alkyl;

B is CH or N;

n is o, 1 or 2; and

X is a bond, —CH$_2$— or —O—;

or a pharmaceutical active acid addition salt thereof.

3. The compound of claim 1, wherein A is CR, and B is CH.

4. The compound of claim 3, wherein Y is a bond and Ar is naphthyl.

5. The compound of claim 4, wherein said compound is ((S)-4-Morpholin-2-yl-phenyl)-naphthalen-2-yl-amine or a pharmaceutical active acid addition salt thereof.

6. The compound of claim 3, wherein Y is a bond and Ar is pyrimidinyl, pyrazolyl, benzothiazolyl, quinolinyl, quinazolinyl, benzo[d][1.3]dioxolyl, 5,6,7,8-tetrahydroquinazolinyl, pyrazinyl, pyridazinyl or 1,3,4-oxadiazolyl.

7. The compound of claim 6, selected from the group consisting of (RS)-(4,6-Dimethyl-pyrimidin-2-yl)-(4-pyrrolidin-3-yl-phenyl)-amine; hydrochloride;

(RS)-(5-Chloro-pyrimidin-2-yl)-(4-morpholin-2-yl-phenyl)-amine;

(RS)-(5-Bromo-pyrimidin-2-yl)-(4-morpholin-2-yl-phenyl)-amine;

(5-Methoxy-pyrimidin-2-yl)-((S)-4-morpholin-2-yl-phenyl)-amine;

(5-Fluoro-pyrimidin-2-yl)-((S)-4-morpholin-2-yl-phenyl)-amine;

(5-Ethyl-pyrimidin-2-yl)-((S)-4-morpholin-2-yl-phenyl)-amine; and 2-((S)-4-Morpholin-2-yl-phenylamino)-pyrimidine-5-carbonitrile, or a pharmaceutical active acid addition salt thereof.

8. The compound of claim 6, selected from the group consisting of (5-Cyclopropyl-pyrimidin-2-yl)-((S)-4-morpholin-2-yl-phenyl)-amine;

(5-Methyl-pyrimidin-2-yl)-((S)-4-morpholin-2-yl-phenyl)-amine;

((S)-4-Morpholin-2-yl-phenyl)-(5-trifluoromethyl-pyrimidin-2-yl)-amine;

((S)-4-Morpholin-2-yl-phenyl)-(5-propyl-pyrimidin-2-yl)-amine;

(6-Chloro-benzothiazol-2-yl)-((S)-4-morpholin-2-yl-phenyl)-amine; and (5-Ethoxy-pyrimidin-2-yl)-((S)-4-morpholin-2-yl-phenyl)-amine;

or a pharmaceutical active acid addition salt thereof.

9. The compound of claim 6, selected from the group consisting of ((S)-4-Morpholin-2-yl-phenyl)-quinolin-2-yl-amine;

(S)-6-Chloro-N-(4-(morpholin-2-yl)phenyl)quinolin-2-amine;

(S)-2-Methyl-N-(4-(morpholin-2-yl)phenyl)quinolin-8-amine;

(S)—N-(4-(Morpholin-2-yl)phenyl)-2,8-bis(trifluoromethyl)quinolin-4-amine;

(S)-6-Chloro-N-(4-(morpholin-2-yl)phenyl)quinazolin-4-amine;

(S)-8-Chloro-N-(4-(morpholin-2-yl)phenyl)quinolin-2-amine;

(S)-5-Bromo-N-(4-(morpholin-2-yl)phenyl)quinolin-2-amine; and (S)-4-Chloro-N-(4-(morpholin-2-yl)phenyl)quinolin-2-amine;

or a pharmaceutical active acid addition salt thereof.

10. The compound of claim 6, selected from the group consisting of (S)—N-(4-(Morpholin-2-yl)phenyl)benzo[d][1,3]dioxol-5-amine; and (S)-5-Bromo-N-(4-(morpholin-2-yl)phenyl)quinolin-8-amine;

or a pharmaceutical active acid addition salt thereof.

11. The compound of claim 6, selected from the group consisting of (R)-5-Ethyl-N-(4-(morpholin-2-yl)phenyl)pyrimidin-2-amine;

(5-Ethyl-4-methyl-pyrimidin-2-yl)-((S)-4-morpholin-2-yl-phenyl)-amine;

(5-Isopropyl-4-methyl-pyrimidin-2-yl)-((S)-4-morpholin-2-yl-phenyl)-amine;

((S)-4-Morpholin-2-yl-phenyl)-(5,6,7,8-tetrahydroquinazolin-2-yl)-amine; and ((S)-4-Morpholin-2-yl-phenyl)-(5-nitro-pyrimidin-2-yl)-amine;

or a pharmaceutical active acid addition salt thereof.

12. The compound of claim 6, selected from the group consisting of (5-Methanesulfonyl-pyrimidin-2-yl)-((S)-4-morpholin-2-yl-phenyl)-amine;

(RS)-(5-Chloro-pyrimidin-2-yl)-(2-methyl-4-morpholin-2-yl-phenyl)-amine;

(5-Cyclopropyl-pyrimidin-2-yl)-((R)-4-morpholin-2-yl-phenyl)-amine;

(RS)-5-Cyclopropyl-N-(2-methyl-4-(morpholin-2-yl)phenyl)pyrimidin-2-amine; and (RS)-5-Ethyl-N-(2-methyl-4-(morpholin-2-yl)phenyl)pyrimidin-2-amine;

or a pharmaceutically suitable acid addition salt thereof.

13. The compound of claim 6, selected from the group consisting of (RS)-5-Bromo-N-(2-methyl-4-(morpholin-2-yl)phenyl)pyrimidin-2-amine;

((R)-4-Morpholin-2-yl-phenyl)-(5-propyl-pyrimidin-2-yl)-amine;

(5-Bromo-pyrimidin-2-yl)-((R)-4-morpholin-2-yl-phenyl)-amine;

((R)-4-Morpholin-2-yl-phenyl)-(5-trifluoromethyl-pyrimidin-2-yl)-amine;

(RS)-5-Chloro-N-(2-fluoro-4-(morpholin-2-yl)phenyl)pyrimidin-2-amine;

(RS)-5-Ethyl-N-(2-fluoro-4-(morpholin-2-yl)phenyl)pyrimidin-2-amine;

(RS)-5-Cyclopropyl-N-(2-fluoro-4-(morpholin-2-yl)phenyl)pyrimidin-2-amine;

(RS)-(5-Ethoxy-pyrimidin-2-yl)-(2-fluoro-4-morpholin-2-yl-phenyl)-amine; and (RS)-(2-Fluoro-4-morpholin-2-yl-phenyl)-(5-propyl-pyrimidin-2-yl)-amine;

or a pharmaceutically suitable acid addition salt thereof.

14. The compound of claim 6, selected from the group consisting of (RS)-(5-Bromo-pyrimidin-2-yl)-(2-fluoro-4-morpholin-2-yl-phenyl)-amine;

(R)-5-Chloro-N-(4-(morpholin-2-yl)phenyl)pyrimidin-2-amine;

(S)-5-Chloro-N-(4-(morpholin-2-yl)phenyl)pyrimidin-2-amine;

(5-Ethoxy-pyrimidin-2-yl)-((R)-4-morpholin-2-yl-phenyl)-amine;

(5-Ethyl-pyrimidin-2-yl)-((R)-2-methyl-4-morpholin-2-yl-phenyl)-amine;

(5-Ethyl-pyrimidin-2-yl)-((S)-2-methyl-4-morpholin-2-yl-phenyl)-amine;

(5-Cyclopropyl-pyrimidin-2-yl)-((R)-2-methyl-4-morpholin-2-yl-phenyl)-amine;

(5-Cyclopropyl-pyrimidin-2-yl)-((S)-2-methyl-4-morpholin-2-yl-phenyl)-amine;
(5-Ethyl-pyrimidin-2-yl)-((S)-4-piperidin-3-yl-phenyl)-amine; and
(S)—N-(4-(Morpholin-2-yl)phenyl)-5-phenyl-1H-pyrazol-3-amine;
or a pharmaceutically suitable acid addition salt thereof.

15. The compound of claim 6, selected from the group consisting of
(5-Ethoxy-pyrimidin-2-yl)-((S)-4-piperidin-3-yl-phenyl)-amine;
(S)—N-(4-(Morpholin-2-yl)phenyl)-5-phenyl-1,3,4-oxadiazol-2-amine;
(5-Ethyl-pyrimidin-2-yl)-((R)-2-fluoro-4-morpholin-2-yl-phenyl)-amine;
(5-Ethyl-pyrimidin-2-yl)-((S)-2-fluoro-4-morpholin-2-yl-phenyl)-amine;
(5-Cyclopropyl-pyrimidin-2-yl)-((R)-2-fluoro-4-morpholin-2-yl-phenyl)-amine;
(5-Cyclopropyl-pyrimidin-2-yl)-((S)-2-fluoro-4-morpholin-2-yl-phenyl)-amine;
(RS)-(2-Fluoro-4-morpholin-2-yl-phenyl)-(5-trifluoromethyl-pyrimidin-2-yl)-amine;
(5-Isopropoxy-pyrimidin-2-yl)-((S)-4-morpholin-2-yl-phenyl)-amine;
(5-Isopropoxy-pyrimidin-2-yl)-((R)-4-morpholin-2-yl-phenyl)-amine; and
(S)-5-(Cyclopropylmethoxy)-N-(4-(morpholin-2-yl)phenyl)pyrimidin-2-amine;
or a pharmaceutically suitable acid addition salt thereof.

16. The compound of claim 6, selected from the group consisting of
(R)-5-(Cyclopropylmethoxy)-N-(4-(morpholin-2-yl)phenyl)pyrimidin-2-amine;
(5-Bromo-pyrimidin-2-yl)-((R)-2-fluoro-4-morpholin-2-yl-phenyl)-amine;
(5-Bromo-pyrimidin-2-yl)-((S)-2-fluoro-4-morpholin-2-yl-phenyl)-amine;
((R)-2-Fluoro-4-morpholin-2-yl-phenyl)-(5-propyl-pyrimidin-2-yl)-amine;
((S)-2-Fluoro-4-morpholin-2-yl-phenyl)-(5-propyl-pyrimidin-2-yl)-amine;
(5-Chloro-pyrimidin-2-yl)-((R)-2-fluoro-4-morpholin-2-yl-phenyl)-amine; (5-Chloro-pyrimidin-2-yl)-((S)-2-fluoro-4-morpholin-2-yl-phenyl)-amine;
(5-Ethoxy-pyrimidin-2-yl)-((R)-2-fluoro-4-morpholin-2-yl-phenyl)-amine;
(5-Ethoxy-pyrimidin-2-yl)-((S)-2-fluoro-4-morpholin-2-yl-phenyl)-amine; and
((R)-2-Fluoro-4-morpholin-2-yl-phenyl)-(5-trifluoromethyl-pyrimidin-2-yl)-amine;
or a pharmaceutically suitable acid addition salt thereof.

17. The compound of claim 6, selected from the group consisting of
((S)-2-Fluoro-4-morpholin-2-yl-phenyl)-(5-trifluoromethyl-pyrimidin-2-yl)-amine;
((S)-4-Morpholin-2-yl-phenyl)-[5-(2,2,2-trifluoro-ethoxy)-pyrimidin-2-yl]-amine;
((R)-4-Morpholin-2-yl-phenyl)-[5-(2,2,2-trifluoro-ethoxy)-pyrimidin-2-yl]-amine;
[5-(2-Methoxy-ethoxy)-pyrimidin-2-yl]-((S)-4-morpholin-2-yl-phenyl)-amine;
[5-(2-Methoxy-ethoxy)-pyrimidin-2-yl]-((R)-4-morpholin-2-yl-phenyl)-amine;
(RS)-(1-Methyl-1H-pyrazol-3-yl)-(4-morpholin-2-yl-phenyl)-amine;
(RS)-(4-Bromo-1-methyl-1H-pyrazol-3-yl)-(4-morpholin-2-yl-phenyl)-amine;
((R)-2-Fluoro-4-morpholin-2-yl-phenyl)-[5-(2,2,2-trifluoro-ethoxy)-pyrimidin-2-yl]-amine;
((S)-2-Fluoro-4-morpholin-2-yl-phenyl)-[5-(2,2,2-trifluoro-ethoxy)-pyrimidin-2-yl]-amine; and
(RS)-(1-Cyclopropylmethyl-1H-pyrazol-3-yl)-(4-morpholin-2-yl-phenyl)-amine;
or a pharmaceutically suitable acid addition salt thereof.

18. The compound of claim 6, selected from the group consisting of
(5-Furan-2-yl-pyrimidin-2-yl)-((S)-4-morpholin-2-yl-phenyl)-amine;
(5-Furan-2-yl-pyrimidin-2-yl)-((R)-4-morpholin-2-yl-phenyl)-amine;
(RS)—N-(2-Chloro-4-(morpholin-2-yl)phenyl)-5-cyclopropylpyrimidin-2-amine;
(RS)-[1-(2,2-Difluoro-ethyl)-1H-pyrazol-3-yl]-(4-morpholin-2-yl-phenyl)-amine;
((R)-2-Fluoro-4-morpholin-2-yl-phenyl)-[5-(2-methoxy-ethoxy)-pyrimidin-2-yl]-amine;
((S)-2-Fluoro-4-morpholin-2-yl-phenyl)-[5-(2-methoxy-ethoxy)-pyrimidin-2-yl]-amine;
((S)-4-Morpholin-2-yl-phenyl)-(2-trifluoromethyl-pyrimidin-5-yl)-amine;
((R)-4-Morpholin-2-yl-phenyl)-(2-trifluoromethyl-pyrimidin-5-yl)-amine;
(RS)-(4-Morpholin-2-yl-phenyl)-(1H-pyrazol-3-yl)-amine; and
(5-Methyl-pyrazin-2-yl)-((S)-4-morpholin-2-yl-phenyl)-amine;
or a pharmaceutically suitable acid addition salt thereof.

19. The compound of claim 6, selected from the group consisting of
(5-Methyl-pyrazin-2-yl)-((R)-4-morpholin-2-yl-phenyl)-amine;
2-((S)-4-Morpholin-2-yl-phenylamino)-pyrimidine-5-carboxylic acid methylamide;
2-((R)-4-Morpholin-2-yl-phenylamino)-pyrimidine-5-carboxylic acid methylamide;
(6-Methyl-pyridazin-3-yl)-((S)-4-morpholin-2-yl-phenyl)-amine;
(1-Benzyl-1H-pyrazol-3-yl)-((S)-4-morpholin-2-yl-phenyl)-amine;
(1-Benzyl-1H-pyrazol-3-yl)-((R)-4-morpholin-2-yl-phenyl)-amine;
((S)-4-Morpholin-2-yl-phenyl)-(1-phenyl-1H-pyrazol-3-yl)-amine;
((R)-4-Morpholin-2-yl-phenyl)-(1-phenyl-1H-pyrazol-3-yl)-amine; and
((R)-2-Methyl-4-morpholin-2-yl-phenyl)-(5-trifluoromethyl-pyrimidin-2-yl)-amine;
or a pharmaceutically suitable acid addition salt thereof.

20. The compound of claim 6, selected from the group consisting of
((S)-2-Methyl-4-morpholin-2-yl-phenyl)-(5-trifluoromethyl-pyrimidin-2-yl)-amine;
((R)-2-Chloro-4-morpholin-2-yl-phenyl)-(5-trifluoromethyl-pyrimidin-2-yl)-amine;
((S)-2-Chloro-4-morpholin-2-yl-phenyl)-(5-trifluoromethyl-pyrimidin-2-yl)-amine;
(R)—N-(2-Chloro-4-(morpholin-2-yl)phenyl)-5-cyclopropylpyrimidin-2-amine;
(S)—N-(2-Chloro-4-(morpholin-2-yl)phenyl)-5-cyclopropylpyrimidin-2-amine;
((R)-4-Morpholin-2-yl-phenyl)-[4-(2,2,2-trifluoro-ethoxy)-pyrimidin-2-yl]-amine;

(R)—N-(4-(Morpholin-2-yl)phenyl)-4-(trifluoromethyl) pyrimidin-2-amine;
(R)-5-(5-(Difluoromethoxy)pyrimidin-2-yloxy)-N-(4-(morpholin-2-yl)phenyl)pyrimidin-2-amine; and
(R)—N-(2-Chloro-4-(morpholin-2-yl)phenyl)-5-(5-(difluoromethoxy)pyrimidin-2-yloxy)pyrimidin-2-amine;
or a pharmaceutically suitable acid addition salt thereof.

21. The compound of claim 6, selected from the group consisting of
(R)—N-(4-(Morpholin-2-yl)phenyl)pyrimidin-2-amine;
((R)-4-Morpholin-2-yl-phenyl)-quinazolin-2-yl-amine;
(4-Methyl-6-trifluoromethyl-pyrimidin-2-yl)-((R)-4-morpholin-2-yl-phenyl)-amine;
(R)-5-(Difluoromethoxy)-N-(4-(morpholin-2-yl)phenyl) pyrimidin-2-amine;
(4-Chloro-6-methoxy-pyrimidin-2-yl)-((R)-4-morpholin-2-yl-phenyl)-amine;
2-((R)-4-Morpholin-2-yl-phenylamino)-pyrimidine-4-carbonitrile;
(4,6-Dimethyl-pyrimidin-2-yl)-((R)-4-morpholin-2-yl-phenyl)-amine;
(4,6-Dimethoxy-pyrimidin-2-yl)-((R)-4-morpholin-2-yl-phenyl)-amine; and
((R)-2-Chloro-4-morpholin-2-yl-phenyl)-[5-(2,2,2-trifluoro-ethoxy)-pyrimidin-2-yl]-amine;
or a pharmaceutically suitable acid addition salt thereof.

22. The compound of claim 6, selected from the group consisting of
(S)-2,5-Dichloro-N-(4-(morpholin-2-yl)phenyl)pyrimidin-4-amine;
((S)-4-Morpholin-2-yl-phenyl)-[4-(2,2,2-trifluoro-ethoxy)-pyrimidin-2-yl]-amine;
[5-Fluoro-4-(2,2,2-trifluoro-ethoxy)-pyrimidin-2-yl]-((R)-4-morpholin-2-yl-phenyl)-amine;
(4-Cyclopropyl-pyrimidin-2-yl)-((R)-4-morpholin-2-yl-phenyl)-amine;
(4-Cyclopropyl-5-fluoro-pyrimidin-2-yl)-((R)-4-morpholin-2-yl-phenyl)-amine;
(R)-5-Cyclopropyl-N-(3-fluoro-4-(morpholin-2-yl)phenyl)pyrimidin-2-amine;
((S)-3-Chloro-4-morpholin-2-yl-phenyl)-(5-cyclopropyl-pyrimidin-2-yl)-amine;
((R)-3-Chloro-4-morpholin-2-yl-phenyl)-(5-cyclopropyl-pyrimidin-2-yl)-amine; and
(S)-5-Cyclopropyl-N-(3-fluoro-4-(morpholin-2-yl)phenyl)pyrimidin-2-amine;
or a pharmaceutically suitable acid addition salt thereof.

23. The compound of claim 6, selected from the group consisting of (R)—N-(3-Fluoro-4-(morpholin-2-yl)phenyl)-5-(trifluoromethyl)pyrimidin-2-amine;
(S)—N-(3-Fluoro-4-(morpholin-2-yl)phenyl)-5-(trifluoromethyl)pyrimidin-2-amine;
(R)—N-(4-(Morpholin-2-yl)phenyl)-6-(trifluoromethyl) pyrimidin-4-amine;
(R)-6-Chloro-N-(4-(morpholin-2-yl)phenyl)pyrimidin-4-amine;
(R)—N-(4-(morpholin-2-yl)phenyl)-2-(trifluoromethyl) pyrimidin-4-amine;
(R)—N-(4-(Morpholin-2-yl)phenyl)-5-(trifluoromethyl) pyrazin-2-amine;
((R)-3-Chloro-4-morpholin-2-yl-phenyl)-(5-chloro-pyrimidin-2-yl)-amine;
((R)-3-Chloro-4-morpholin-2-yl-phenyl)-[5-(2,2,2-trifluoro-ethoxy)-pyrimidin-2-yl]-amine;
((R)-3-Chloro-4-morpholin-2-yl-phenyl)-(5-trifluoromethyl-pyrimidin-2-yl)-amine;
(R)-5-Chloro-N-(4-(morpholin-2-yl)phenyl)pyrazin-2-amine; and
a pharmaceutical active acid addition salt thereof.

24. The compound of claim 6, selected from the group consisting of
(R)-6-Chloro-N-(4-(morpholin-2-yl)phenyl)pyrazin-2-amine;
(R)—N-(3-Fluoro-4-(morpholin-2-yl)phenyl)-5-(2,2-trifluoroethoxy)pyrimidin-2-amine;
(R)—N-(3-Fluoro-4-(morpholin-2-yl)phenyl)-4-(2,2,2-trifluoroethoxy)pyrimidin-2-amine;
(R)-5-Fluoro-N-(3-fluoro-4-(morpholin-2-yl)phenyl)-4-(2,2,2-trifluoroethoxy)pyrimidin-2-amine;
(R)-5-Chloro-N-(3-fluoro-4-(morpholin-2-yl)phenyl)pyrimidin-2-amine; and
((R)-3-Chloro-4-morpholin-2-yl-phenyl)-[4-(2,2,2-trifluoro-ethoxy)-pyrimidin-2-yl]-amine;
or a pharmaceutically suitable acid addition salt thereof.

25. The compound of claim 3, wherein Y is —CH$_2$—, —CH$_2$CH$_2$—, —CH(CF$_3$)— or —CH(CH$_3$)— and Ar is pyrimidinyl, pyrazolyl, benzothiazolyl, quinolinyl, quinazolinyl, benzo[d][1.3]dioxolyl, 5,6,7,8-tetrahydro-quinazolinyl or 1,3,4-oxadiazolyl.

26. The compound of claim 25, wherein said compound is (S)—N-((2-Chloroquinolin-3-yl)methyl)-4-(morpholin-2-yl)aniline;
or a pharmaceutically suitable acid addition salt thereof.

27. The compound of claim 1, wherein A is N, B is CH, Y is a bond and Ar is pyrimidinyl.

28. The compound of claim 27, wherein said compound is (RS)-5-Cyclopropyl-N-(5-(morpholin-2-yl)pyridin-2-yl) pyrimidin-2-amine.

29. A pharmaceutical composition comprising a therapeutically effective amount of a compound of formula I

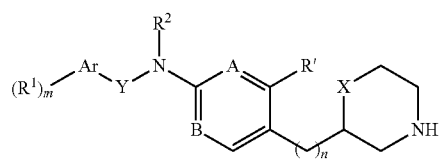

wherein
R$^1$ is hydrogen, lower alkyl, halogen, lower alkyl substituted by halogen, lower alkoxy, lower alkoxy substituted by halogen, cyano, nitro, C$_{3-6}$-cycloalkyl, —CH$_2$—C$_{3-6}$-cycloalkyl, —O—CH$_2$—C$_{3-6}$-cycloalkyl, —O—(CH$_2$)$_2$—O-lower alkyl, S(O)$_2$CH$_3$, SF$_5$, —C(O)NH-lower alkyl, phenyl, —O-pyrimidinyl, optionally substituted by lower alkoxy substituted by halogen, or is benzyl, oxetanyl or furanyl;
m is 1 or 2;
Ar is aryl or heteroaryl, selected from the group consisting of naphthyl, pyrimidinyl, benzothiazolyl, quinolinyl, quinazolinyl, benzo[d][1.3]dioxolyl, 5,6,7,8-tetrahydro-quinazolinyl, pyrazolyl, pyrazinyl, pyridazinyl, and 1,3,4-oxadiazolyl;
Y is a bond, —CH$_2$—, —CH$_2$CH$_2$—, —CH(CF$_3$)— or —CH(CH$_3$)—;
R$^2$ is hydrogen or lower alkyl;
A is CR or N; and R is hydrogen, cyano, halogen or lower alkyl;
R' is hydrogen or halogen; with the proviso that when R$^1$ is halogen, A is CH;

B is CH or N;
n is o, 1 or 2; and
X is a bond, —CH$_2$— or —O—;
or a pharmaceutical active acid addition salt thereof
and a pharmaceutically acceptable carrier.

30. The compound of claim 23 wherein said compound is N-(4-(morpholin-2-yl)phenyl)-5-(trifluoromethyl)pyrazin-2-amine or a pharmaceutical active acid addition salt thereof.

* * * * *